US010174293B1

(12) United States Patent
Gruszka et al.

(10) Patent No.: US 10,174,293 B1
(45) Date of Patent: Jan. 8, 2019

(54) RECOMBINANT PB1 BACTERIOPHAGES AND USES THEREOF

(71) Applicant: Charles Stark Draper Laboratory, Inc., Cambridge, MA (US)

(72) Inventors: Sarah Gruszka, Cambridge, MA (US); Parker Dow, Boston, MA (US); Jason Holder, Swampscott, MA (US)

(73) Assignee: THE CHARLES STARK DRAPER LABORATORY, INC., Cambridge, MA (US)

(*) Notice: Subject to any disclaimer, the term of this patent is extended or adjusted under 35 U.S.C. 154(b) by 0 days.

(21) Appl. No.: 15/908,140

(22) Filed: Feb. 28, 2018

(51) Int. Cl.

| | |
|---|---|
| ***A61K 39/145*** | (2006.01) |
| ***A61K 39/00*** | (2006.01) |
| ***C07K 14/005*** | (2006.01) |
| ***C12N 7/00*** | (2006.01) |
| ***A61K 39/12*** | (2006.01) |
| ***C12N 15/78*** | (2006.01) |
| ***C12Q 1/02*** | (2006.01) |
| ***C12Q 1/04*** | (2006.01) |

(52) U.S. Cl.
CPC ............... *C12N 7/00* (2013.01); *C12N 15/78* (2013.01); *C12Q 1/025* (2013.01); *C12Q 1/04* (2013.01); *C12N 2795/00021* (2013.01); *C12N 2795/00043* (2013.01)

(58) Field of Classification Search
CPC ........ C07K 14/005; C12N 7/00; C12N 15/86; A61K 39/12; A61K 39/145
See application file for complete search history.

*Primary Examiner* — Barry A Chestnut
(74) *Attorney, Agent, or Firm* — Christopher J. McKenna; Foley & Lardner LLP

(57) ABSTRACT

The present disclosure provides compositions including recombinant PB1 bacteriophages, methods for making the same, and uses thereof. The recombinant PB1 bacteriophages disclosed herein are useful for the identification and/or antibiotic susceptibility profiling of specific bacterial strains/species present in a sample.

24 Claims, 39 Drawing Sheets

Specification includes a Sequence Listing.

Figure 6

>Bsu36I_nanoluciferase_insert (SEQ ID NO: 2)

CGGACTAAAGGCGGCATGATTGCCTAAAAGGAGATTCAACATGGTCTTCACACTCGAAGATTTCGTTGGGGACTG
GCGACAGACAGCCGGCTACAACCTGGACCAAGTCCTTGAACAGGGAGGTGTGTCCAGTTTGTTTCAGAATCTCGG
GGTGTCCGTAACTCCGATCCAAAGGATTGTCCTGAGCGGTGAAAATGGGCTGAAGATCGACATCCATGTCATCAT
CCCGTATGAAGGTCTGAGCGGCGACCAAATGGGCCAGATCGAAAAAATTTTTAAGGTGGTGTACCCTGTGGATGA
TCATCACTTTAAGGTGATCCTGCACTATGGCACACTGGTAATCGACGGGGTTACGCCGAACATGATCGACTATTTC
GGACGGCCGTATGAAGGCATCGCCGTGTTCGACGGCAAAAAGATCACTGTAACAGGGACCCTGTGGAACGGCAA
CAAAATTATCGACGAGCGCCTGATCAACCCCGACGGCTCCCTGCTGTTCCGAGTAACCATCAACGGAGTGACCGG
CTGGCGGCTGTGCGAACGCATTCTGGCGTAATAAGGAGAATTTCATGGCTAGT

Figure 7A

>Pseudomonas phage PB1_nanoluc recombinant, complete genome (SEQ ID NO: 3)

CCTTCTCTTCGTCCCAGCAGAGGCTATCTGCTATCGGCCAGAACTTTCGAAACTGGGAGGTGCTGACGCTTACATCCACTAGGACGATTTCTGCTTCACCCACGA
CTTCGAGCTTGAACTTGACGTCACCGTCGATGCTGTTGAAAGGGATTGGCTTGGACACGACAATTCTCCTGTGAATGGCGCGACCAACCGGCCGCGCCTGATGA
TTACTCTTCGCCTTCGTCCGCGCTCAGCCACTCTTCGAAGGCGAAATTGACCTTAGACTCGACCCAATCTTGAAGCTCATCGGCGAACTCGTCACTGTCGATGTCC
ATCGGAATGCCCAGAGTCTCTTCGTTCCACAGTTCGGCATTCAGTTCGAACTGGATAGCCGGTTCGCCATCCACATTCAGCAGGATGCGGTCTGCGACTTCATAG
TCGTCGACATCGAAGAGGAAACCGCCGCTGATGATGTGCTGGATGAAAGCTTCGTCGAAGTTGCTGACGCCGATATTGATCTGCTTAGTCATTTTTCTGGCCCCT
TATTTGGCGAGTTTGTACTGAGCTTTGAGGGTGGTCAGCTTAGCTTTCAGGGCGATCATAGCCTGGCCGCGCAGGCCTTCCATTTCTGCCTCGCTGATGGCGATC
TTGGCGGAGCGGATTTGATCGTTGATCTGGGATTTGGTCATTTCTGCGTTCCTCTGTTTTGGAGTGTTTCGCGTTTCGATGAAGAGATTATGACGCTATTCAGAAT
GGAAGTAAAGCAGAATTGTGAAATATTTCTCAAAGTGGACGAGCGGTCTGTTCGTCAGGAATATTTCCTCCCATGGAAGGCGTGTCCGCATCCGAAGACTGACA
GGTATCCGTTGACTTCGGATTGTCTCTTTTCGGAGTCGATTTCGATTCTTAGCATTTCCAGCTCATACCGGGCCAGGCCGCCCCACTCCCTTTCGATGCGTTCATAC
TCGGCTTCTAATCGGCGCAGACGTTCAATCATGGGAATCTCCTTTGGATTGTTATAGCTAGCATCATTACGGACAAACAGTCTTTCGTTTCGCTGAAGAGATTATG
CCGTTGGTCAGAATGGAAGTAAAGTGTATTAACAATAAAATTATGTTCACCGACGAACGGTTGTGCTCGACCGTCTGTTGCGGCGTCGATATACTCGACCTATTG
CTGACACCGGATTGATTAGAATGTACAAACTCAACCCTGCACTGCGAGCGGTCTGGCGAACTCGCGCCCGTTACAAAGTCATTTATGGCGGCCGGGCGTCTTCG
AAGTCACACGACGCAGGCGGTATCGCCGTTTACCTCGCGGCCAACTATAGACTCAAGTTCCTCTGTGCTCGCCAGTTTCAGAACCGCATCAGCGAATCGGTCTAC
ACGTTGATCAAGGACAAGATTGAGAATTCTGAGTACAACGGCGAGTTCATTTTCACGAAGAACTCGATCAAGCACAAGAGGACAGGATCAGAATTCTTATTCTA
TGGGATCGCCCGTAACCTGTCGGAAATCAAGTCCACCGAAGGCATTGACATTCTCTGGCTTGAGGAAGCTCACTACCTTACCCAGGAACAGTGGGAAGTCATTG
AGCCGACCATTCGGAAAGAGAACTCAGAAATCTGGATCATCTTCAACCCGAACGAAGTAACAGACTTCGTGTATCAGAACTTCGTGGTGAAGCCACCCAAAGAC
GCCTTCGTCAAGATGATCAACTGGAACGAAAATCCGTTTCTCAGTGAGACGATGCTCAAGGTCATCCACGAAGCTTATGAGCGCGACAAGGACCAGGCCGAGC
ACATATATGGAGGGATTCCGAAGACGGGCGGCGACAAATCCGTCATCAACCTCAAGTTCATCCTTGCTGCCATTGATGCCCACAAAAAACTCGGCTGGGAGCCG
GCCGGGTCGAAGCGCATCGGCTTCGACGTTGCGGATGACGGCGAGGATGCGAACGCCACGACTCTCATGCACGGCAACGTCATCATGGAAGTGGACGAATGG
GATGGTCTGGAAGATGAGTTGCTCAAGTCGTCCAGTCGCGTTTACAATCTGGCAAAGATGAAAGGCGCCTCGGTCACTTATGACTCCATCGGCGTCGGCGCTCA
CGTCGGGTCTAAGTTCGCCGAATTGAATGACTCCAGCCCAGACTTCAAACTGACCTATGATCCATTCAACGCGGGCGGCGCTGTAGATAAGCCTGATGATATTTA
CATGAAGCTGCCGCACACTACGATCAAGAACAAAGATCACTTTAGCAACATCAAGGCGCAAAAGTGGGAAGAAGTCGCGACAAGATTCCGGAAGACTTACGAG
GCGGTTGTCCATGGAAAGGTTTATCCATTCGACGAATTGATTTCGATCAACTCTGAAACAATTCACCCGGACAAACTAAATCAGCTATGTATCGAGCTTTCCTCGC
CGCGCAAAGACTTGGATATGAACGGCCGATTCAAAGTCGAGTCCAAGAAGGATATGCGCGAGAAGCGTAAGATCAAGTCGCCGAACATCGCTGATTCGGTGAT
CATGTCGGCCATTCTGCCGATCAGGAAGCCCAAAGGTTTCTTCGACTTCTAAACACAGAAAAGCCCGGAGCGATCCGGGCTTCTGGTCTTACTCGGTGCGGTTCC
TGGCGCTGAGTGTCGACGCAACGGCCTCGCCGACTTCCAGAGCTTTCTGGCCTGCTGCGAGCGCTTCGGTTTCCGACTCGACGATGAAGTCATCGCCTTGTCCGT
CGCCGGGCGGCACCTCGACCAGCACGGCTTCTTCGCCCTCGAAACGCAGGTCATAAGTCTTCTCGACGGACAGGCCGTAACGGGCGTTGAGCGCATCCCATAG
CTGAGCTTCATAGGTTCGAAGGTCTTGCAGAGATTTCTGGTGACTGAGCATCGCCATGTCGACGGCCCGTTGCAGGGTTTCGTCCAGGACGTTGAGTCGCATGC
GAAGAGAACGAATCCGCTCGACGACTTCCGCATCCACAATGTGTCTTTCGATCATCGCTTTTCACCTTTGCTGAATGTTACGTTATAGCCGTTATCGGCCAAATAG
GTCAGGGCACCTTCGAATGAAGTTCCGACGAGGTGCCTGAGCTGCATTTCGCGTTGCGCAGCGATCCAAAATGCAGTTCCGGAGAACTCTGCGCGGCCTTCCGA
CAGAACCTTTCCGTCAGGTCCGTCGATTCGAACGTGAACGGAAGATAGCTTCAGAGTCATTAGTGAATCCCTCCACTGGCTTGCGACGGCATTCTTTCTGCGCGA
GCGGATGCGCAGTCCGGGCACGGGCAGGCCTGGCGGACGCGCTCCAACTCGTCGGCGTCCATGACATAGAGCTTCCCATCGGAAGTGTCGTGCGCCATGGCG
ATGTTCGGGAAGTCGGTGGCACTCAGGCCGGCGACAGCGCGGATTTCGCCCCAGAGCGCTTCATTCTCGGCATTCAGACGAGCGGCGAGCGCTTCGTGCTCTTT
CGCTACACGCGCCATGAACTCGTCCATCCGGAATGCGAATTCCGCATCGATGGCGCGGGCCGAGGCCATAGAGCTGAGGTGAATCGGTTCTTTCTTCATGGTAA
TTCTCTTTTGGCTGGGGGTTTGTGGTCTACCCAGGCCTATTCAAAGCCTGGTCGTCTTGATGAAGATGAACAAGAAGACTGCAAACGCCAATAGCGTTCCAGCCA
ACATAAATACTGCAAATGCCAATAGCGTTCCTGAGAGCATGCTCGCTTGATTCTGCAGCTCAGCGTACTCCTTGGTTGACAGCCCTTGCTGCGCCGCCTCGGCCG
CGAAGCGGGTTTTCGCCTCGATAACTTCCGGGCGCAGCGACAGGACATATTCTAAGGCCTCTTCCCGCGCTTTTTCGGCCTCGACCAACCTAGGGTCGCGGGCC
GAGACTTCGCTGTGCCCTGGCCTCGCGGGATGGGCCTGCAGCGATGGAGGAAGTTCGGCGGCCACGACTCCATAGTCGGAGCAGGCCCAAGCGATCCCGATG
AGGATCGCGAGGATGGACTGGACGATTCGCAGCATCACTTTGTCGCTAGGAAGACTCATGGTTAATCCTCCACCGACCGAACGATTTCCATATTGCGTCCGGCA
TTGGTTCCGGCAGCGTAGGCGCGCCGACCGTCACTGTCTTCCAGACGCATGAGTTTGGTAACATTAGACTTCTTGTAACCCGGATCGCCGAAATGTTCGTGGACC
GCAGCTTCCTTAACCACCACCAGAGACGTTCCGGCCGAAGAAACCAGCTCCATACGTTTCCGGGTGATGGATCTGAGGCGATAGCTGATTTCCTGGGTCGCGGC
GAGCTTAAATTGCGCGGCGACCTTGACGTTGAACCGCTCGAAACCTTGAGCCTTCTGATATTCCCGGCACAGACGGTCTACTGCCTCGACCAGGGAGTTGAACA
TGTTCACCGCTAGCTCAACGTCAGATTTGTAGCCTTTAAAGCGGACGGCATGGCCCCAGCGCTTGGTGGTGCTGCCGTCGCGAGCGCTCCTGGACGCCTTCGCC
GATGCTCGGTGATTGTTGATGCCACCGACGAAATCCATGATGCAATCATTGTACGTCGCCACTGCCACAGAGAAGAACTTCATCCAGTTCGGGATTGCGGAATA
GTAGCGAGTAGCAATTTGCTCGTCGAATTCTTCGCGAATCTCGCCGGTCACTTCGAAGTCGTGAAGGTCATATTTATCCTTCAGCTTCTTCACGCGTTCTGCCGCG
ATGGCAGCTTCGTGCGGACTGGAAGAGTCGGCCGCCATCGCAGTCAGCTTGCGAATGCGATCTTTCGCCTTCTCGATGGCTTCAGGAGTGAATTCGTTCTGGTC
GGTCATGGTCGGTTCCTTTTGTCTGAAGGTTTCGCGTTTCGATGGAGCTATTCTGCCTTCATCCAGAATGGAAGTAAAGCATTTTCTTCCACTATTTCGGAAGAGC
CTGGAAATAGCTCCAGATCCAATCGCCTGCGGCCAGGACAACGATGAGAACTGCGAAGAACACGACTGCAGAGACCAATTGCGCGCCAGGCTTCAGCTTGGGA
TGACTGAGTTTGTGCTCTACCGGATTCGCCGGGGCGCTGGCGCTGGGCCCGGCGTCTTCTGGACCAAAGCCGGCGCCGCGCTCGCGTGCCTGGATAGACGCTA
TGGATTTCAAATACTCGGTCTGCTTTTGCGACTCTTCGTAGATGCCGGCGACGGCGAACCAGAGTGCGAACACTACGGCCGTGCAGACGACCCAGGCTCCGGTC
AGAAGGATGGCCAGCGGACCGATGAGGAAGACGGAAGCCGCCAGGATGATGGCGCCGCCCCAGATGATGAAGCCGGCCAGACCATTGGTGATGTCGATACA
GAATTTCTTCATTTTTTTGGTTCCTTCGGTCAAGGGATGGATGGGATTTGGAATTCGGCGCCGCCGAGGACATCAATGACGACCTCCCAGAGCGTCGGAACCGA
CCACTGATAACGGTCGAAGTCGGTTTCAGGATCGACTCCCAGGGTTACATAGGAAGTGGCCGGCCATTTGTGAACGGCGCCTTTTCGCATGAGAGCGGCCACG
CGACCGTCACCGAGCGGATTCGTCCTGTGAGGAACATAAGCCGACATCGAATATTGCTGTCCAGCACCAATGATGAATTCTTGCCTCTGGCGCAGACATACAGA
GCCTACAGGCTCCCAACCGCGACCGCCGCAGGCCTGGCGAGCCGAAGAATGCTCATACCCTTCATGAGTCAATTCACCGAGACGCGCCGAACGGTCCACGTAAT
AATTTGTATTCTCCAGAGACCCAACCAGAACCAAGGACTCGAAATCGAATCGATGATCGTGGATGGAAGAGTGATGGAAACAAAGCCGGCGCGGCAGCTCCGG

Figure 7B

ATGCCACACATGGAGGCGCCCGGCCGGGAGCTGGACCTGGATGAAGCCCAGGCCGTGCAGCGTGATTCTGTCCTTCATCGGATCAGGGACGGTGTCCATGGAT
AATCCTCAGTAGCAGAAGTGGATGGTAAAGGTTACGATGGCCAAGCCGGTCGCCCATAGGAGGGCGAACCAGGCCATGGCTTTGATTGTAAGGTGGATCATCC
GAAGAACTTTCCGGCGCAGATGGGGCCGATGCCCATTTCGATGGATGCGTGATTGGTCAACTCGCGACCGCAGCAGGAGCATTGACCAGTCTTCCGACCGTAG
GCGACTGCCGATTCCATTGGCTTTTCGAACATCTTCAGGATATCGCCATACTCTGTGTCGGTGCAGTCGCGGCTCTTGATGAATTTGCCGTTAGTGATCCGGCCG
AGGTAGATGTCGCCCAGGACATACAGACTCCCGGCGTTCCGGCTGTTAGCGCTAGCCTCTTTGACCACAACGATGAGAGGCTCCTCACCTTCGCCAGCCAGACG
CATTTTCGGGCGCTTGATGCCAGAGTCTTTCGCCTTCTCAAACGCCTTCTCGATTCCGGAAATGTCCAGAGTCGGCGCAGCAGCCTCCTGCGCGGCCACTTTCTCG
CGATGTTTGGCGAGGTTTTCGATAGCTCGTTTCGCAGCAGCGATCTGATTTTCGGTCAAGGAGCCATATCTGTAAAGAGAATCCTTAAGGCTCTGGGCAAAACT
GAAAGAGTTGTCGGTCCACCACTCGATGATGTCCGGGTGAGCGGCTTCGAAAGCCTGAATTTTAAGGCCGCGATATTGCTCGGCCTTCTGGACTTTCTCGATGC
GCTTTTCTGCAGCCTTAGCACGACTCTTGGCGCGTTGCTCCGGGCTGCTCTTGTACTCTTTATATCCAACGCCGCCGCAGGCAAAGCAGGCGCGACCATAAGACG
AAGGACCACGGTACAGGCCAGTGCCTGCGCATTTGGGGCACTTTTCGCGATACAGCTTCGGTTCCTTCCAGGAGTTCGGGCGGGCACCCATGGACACCTCTTCC
AGGGTCTTCGGCGCTTCGTTGTTGACCTCTACGGTAGCGAAGTCATCGCCCAGGTCTTCGAAGCCGTTGAACAGATTCTCTGCTGCGTTCATATCGATTCTCCTGT
TTGGAAAGTTCGTTTCGATGGGTTGACTATACTCCATAAATGGAAACGCGGTAGCACTTCACGCTACCGTTCGTCGGGTTGCTGACGATCAATAAATGTCGCTGC
TGATCTTAAACCCATGCTCAGCGCCGTCGTTGTAGTCATACTCAGCATAGCTGTCGCAGTAGTCATTCAGATGCTGGATGATTCCAAGAACGTCGTTAGCGACCC
TGTGACGCTTCGCCGCGATGGTCTTGGCAATGCTGTCGCCGACTTCCAGAGTTTCGGCGGTCCGGCGATGAATCAGCAAACGGCTCCAAAGATAGAGTCGGAC
CCGGCGAATCATGTCATGATGGCGCCTCAGTCGGCTCTGCAACTTTTCAATTTCGAATTCGCGAGACTTGACTACTCGTCGAAGCTGCTGAACTTCCAATTCCAAA
TCGGCCTTAGTAGCCATATTCACCTCAGAAAGGGAAATCGTCTGAGGCTCCAGGAAGCTCGACAATTGTTGTTGAGCCTGAGCGGTCGAGTATGCACCCGACCG
ATCCTGCCCTATGGGGATAATGCCTGCACGAACCGTAACAAGTAACTTCTTTGACGATTCGCCATGTCGATCCTCCACACCACCTACATGCTGGTGGGCGCTTCG
ACTTCAGTTTTCGTTCGTCCAGGACGGCTCGTCTGTCGCAGGAAAGGCAGCGAGCCTTAACCGACGTAACCATGAGTGTAGTCGATCATGCGAATGAGTTCGTC
ATCCACCGATTCTCTCGACTTCAAACCGTTCAACGAATCCGACTGGCCGTTGCAATTTCCATTAATATCCATGGAAGACAGAAAGCCTGCCGACACCACTGTGAT
GTCAACTTTATCGCCAGCCTTCTTGAAGCCTTCGCATTCGGCGTCGAGGGCCACCAACGCACTCGCGGCCATGTTGACGTGACTGATTAAGTCGGGGAAGATTA
CGGGAACTTCACGAGACATTCCCCGGACCGTCATCTTCATCACTACATATTTCATACTCACTATCCTTTTTGTGTGTGAGGAAAGAATTTGCTGTTTTCCGGATGG
TGGAAACGCTCGGCCGCAGGCGGTCTTTCTTCCGGACACTGAATCGTCGAAGGCGGGAAAACCGCGCTAGAGATTATCGCCGCGAGCAGCGCAGCGGATGTC
GACATCCACAGGGCAGTTTCCAGACTGACCCGCACTTCCGGTCGGCGCGGCTTCATTCGCTCCAACCCCTTCCCGGCTCATAAGACGGGATGCTGCCGCCGCGA
ATCCAACTGTCCCACATATGGTTCAGACCAGTGGGCGGCTGGGGCGGCGGACTGTAAAAGCCGGGAACTTCTGTACTGCTGAGGAAATAAGGCGTGCAAACG
GCCCGAACAACCAGTTGATGTCGCTCCCACATCTTATCAATCGCTCTTAGCATGACGTCTTCGCACTGAGCTTTGCTGTCGAACCGTCTGCTGGTATGATCCGGCA
TCTGGACACAGCCATCGCCAGTACAAAGGAAAGCAGTGGCGATCCATACTGTGATGCTTGCCATTTCTTCACCCTCTTTGGTAGATGAGCAGATTTTATTCCATCT
GCTCTTCAGAAGTAAAGCGCTTTTCGTCGGGATAAATGCCGATGATGTCTGCGTCGAGCATCCAAATGTCCACGGACGGATCGTCGCTATTGATCTGATACAGG
TGGTACAATTCTTTCTCGTCACGCGCCGATTCACCGCGAGGTTCGACAGCCAATATGCGGCCGTGCCCTTCGCCGTGCTCATCGCGATACATGACGTGATCTCCG
ACTTCATAGCACTCTTTTCTGACAAGGCGCGAGCGCGAGCTGTTCGGCGATTCCACTACCCAGGAATCCACAACTGCGTCTTTCACATTGCTGTACCACTTCGCAG
ATTTGTCGCAGTCGAACACGCCCAGAACTTCGCCGTCCTTCAACACGATATGTACGATAGGAAGAAGAGGATTCATGTTAATCTCCATTGGTTGATAATTAGAGT
CTAATCTGCCGAAAAGTTCCCGTAAAGAATTATTTTCTCATAACTGATTAGTTGCGACTGTTAATGTGATGTATCTGTTTGAATCTCTTTTGAACGTTTGATGTTTC
CCCTATAATAAGTGCACACAACCAGCAACCGCATGGAATTAAAATGTTTAAACTTTCCTGGATATTCGGGCGCAAAAAGGAATAATGTTGCCTGTTCTGAATCGG
CGCCGGAGAAAGTCGCACGAATCCCTCAACACGATCCGCTCGACCCTATGATTAAGCTGGGGAAGATTCGCGGCTGGAATGTCGAGCCGGAGAAAGCCCCGGT
CATCCGTAGCGTGAAGGATTTCCTGGAGCCGGGCCTATCCGTCGCAATGGACAGTGCGTATGGTGACGGACCCACCCCAGCCGCGAAAGCTGCCGCTGGCGGC
CAGAATCCCTATGTAGTTCCGACCATGCTGCAGGACTGGTATAACTCCCAAGGATTCATCGGATACCAAGCTTGCGCCATCATTTCTCAACACTGGTTGGTCGAC
AAAGCTTGCTCCATGTCAGGCGAAGACGCCGCGCGGAACGGATGGGAACTCAAATCGGATGGCCGGAAGCTGTCTGATGAACAAAGCGCGCTGATCGCTCGG
CGCGACATGGAGTTTCGCGTCAAAGACAACCTCGTCGAATTGAACCGATTCAAAAACGTCTTCGGCGTTCGAATCGCTCTGTTCGTCGTTGAGTCTGACGATCCG
GACTACTATGAGAAGCCATTCAACCCAGACGGAATAGCGCCCGGCTCGTACAAGGGAATTTCCCAGATAGATCCATATTGGGCAATGCCTCAGCTGACCGCAGA
GTCCACGGCAGACCCGTCTGCCGAACACTTCTATGAGCCCGATTTTTGGATCATCAGCGGGAAGAAGTATCATCGCAGCCATCTGGTGGTCGTTCGTGGGCCGC
AGCCGCCAGATATCCTGAAGCCGACATACATTTTCGGAGGCATCCCGCTCACCCAGCGCATTTACGAGCGCGTGTATGCTGCCGAGCGAACTGCGAACGAAGCG
CCGTTGCTGGCGATGTCGAAGCGAACCAGCACCATTCACGTTGACGTGGAAAAGGCCATCGCGAATGAGGATGCCTTCAACGCCCGTCTGGCGTTCTGGATCG
CCAATCGAGACAACCATGGCGTGAAAGTTATTGGTATTGATGAAACCATGGAGCAGTTCGATACGAACCTGTCCGATTTCGACAGCGTCATCATGAACCAATAT
CAGCTGGTTGCGGCCATCGCCAAGACTCCTGCGACGAAGCTACTCGGCACTTCTCCCAAAGGATTCAACGCGACTGGTGAGCACGAGACGATTTCTTATCACGA
AGAGTTGGAATCGATTCAAGAGCATATATTCGACCCGCTGCTTGAGCGTCATTATTTGCTGCTGGCAAAATCGGAAGCAATCGATGTACAGCTGGAAATCGTCT
GGAACCCTGTGGATTCCACAACCAGCCAGCAACAAGCCGAGCTGAACAACAAGAAGGCTGCTACTGATGAAATTTATATCAATTCCGGCGTCGTGTCTCCGGAT
GAAGTCCGCGAGCGCCTGCGTGATGATCCGCGCTCCGGCTATAATCGACTCACCGACGATCAGGCCGAAACCGAGCCGGGCATGTCTCCGGAAAACCTGGCCG
AACTCGAAAAGGCCGGTGCACAGTCGGCGAAGGCGAAAGGCGAGGCCGAGCGAGCCGAAGCCCAAGCGGGCGCCGTAGAAGGCGCAGGCGACCCAGTTCC
GGCCGCTCCACGCGGTACTAAGCCCCTCGCGAAAGCGGCCGAGGAAGGGGCCGGCGAGGCCGCTACACCGCCGTCGCGGCCGAACCCCAGGGCCGAGCTTCG
GAACCTGCTGTCCGATCTACTGTCGAAACTCGAAGCCCTGGACGACGCGCAGGCTCCGGACGGCGTGGACATAGAGCAGGATGACGCGCCAGGTCTGAAGAG
AACGTCAAAGCCGAGCGTATCGGGTATGGAGCCTTCGGTGTTTTCGTCCAACCGCATCGTCGGCCCTCGTGATCATTCTGAACTCCAGAGGATCAAGGTCAATG
GAATTACTACCTTGATCGAAAATCCGCGCGGAAGTATCCGGCAAGGGAAGGACGGGAGCTGGCGAGTCCAGATGAAGCACCACTATGGATTCATCAAAGGTAC
GAAGGGGGCTGATGGGGATGAGGTCGATTGCTTCGTAGGCCCGAACCTTGGTTCGAAACGGGTCTTCGTCGTCAACCAGGTGAACAAAGATGGGCAATTCGA
CGAGCACAAGTGCATGCTCGGTTTCAACAACATTAACGACGCCAAGTCTGGATATCTGTCTTGCTTCCGTCCGGGCTGGGATGGACTCGGCTCCATCCATGAAGT
TGATCTGCCCGCCTTCCGTCGTTGGCTGGCAAATGGCGACACGACGAAGCCATTTGGAGGCAAGTGATGGCGTTCAAAGCCTCCAAGAAACGCGAACGCCGGG
GGCCTCTTCCAGTCGGAAGAGGCAAGCCCATAATTCCTTCTGCTGGAATCGAAGCCTGGTATCGAAAGCAAATGAAGGATATGGCCAGACTCATGATCGCCGAT
TATCGAAGTGAAATCGAGAAGGCCATATCCCAGCCTGCGGCAGAACGGTTTTTCGCGAAAGACGAATCGGTGAACGTCCTGTTCAAGATGACTCTGCGAAGCCT
TCAGCAGCGATGGAATCGCATCTTTGAAGGTTTCGCGGCCAAGATCGCCCCGGAGTTCGTCAATCGGGCCGACGAAGCCGCGACCGCTGCGACTCTACACAGC
CTGTCGGTGGCCGGCGTCGATCAGCCGCGAGCTTCATACAATGAGAGCGTCAGGAACACCCTGGAAGCCGCGACTACTTACAACCATACCCTCATCACCAACAT
TCAAGAGGAAGTCCACGAGAAAATTTACACATCTGTAATGTTGTCTCTGACTTCCCCAAACCCAGAGGAACAAGGAACTTCTGGAATAACAAATGCACTTCGAG
AAGTCGGAAAGTTTTCTGAAAACCGAATCGAACTCATCGCAAGAGATCAAACCAGTAAACTTTACAGTTCGTTGAGTGATGAGAGAATGGCAGAGAATGGAGT
CGAAGAGTTCGAATGGATGCACTCTTCGGCAGGGAAGACGCCTCGCCATACCCACCTGGAAAAGGACGGGAAAAGATTCAAACTGAATGACCCTAGACTTTGG

Figure 7C

GAAGGTCCAAAGGCCGACCAAGGACCGCCAGGTTGGGCGATTAACTGCCGGTGCAGAAAAATCCCGATCATTTAGTCATCGATAGGAGTGCGATATGCCGTTA
GTCCATGGAACTTCCAATGAAGCCCGTTCTGAAAACATCAAGCGGGAGATTGAAGCAGGGAAAGACCCGAAACAGGCAGTCGCCATAGCCTATTCCGTCCAGC
GCAGCGAGAAAGAGAAGAAGGCGAAAGATTGTTCGCATGAACTCGTCGCTGATCTTCGCGCCCTGGTAGACTCGCTGTCGAGGCTCGTGAAATGAACCGAAAG
ACATGCATACGCCGACTCGCGACCGATGTGATCAAGGCCAATATTAACGGCGGATTCTTCAGCCTGAAGTTTGCCGCAGTTGATCTGGCCATCATCGGCGTCTCA
ATCCTGATTGCTTTCGGCGGATGATGCCGCGAGAATCCGGATTCTGACTAAAAATTCTGGTCCGGATAGCCGCAAATTACCGTTTCTGGGAAATAGCGGTAATTT
GGAAATCCTACTGCCGCAAGGCTTTAACAGGCTAAATTCCTAATTTCCGATTTCGCCGCATGCCGCAAAAGTATATAGCATGGGAAATTAGGAATAACGTTCTAA
TAGAATTCATCTATAAGTAACGTTATAATATAACGTTAATCGATATGCTCTATACGCATTGAAATTCAATTTTTAATCGGTAAATTGGTAATTTGGATTAGTTTAAA
GATTGAAAGTCTTGCGGCAGTAGGCCTAGACAAATCCCGTCAAATTTCCGAAACCAATTTACCAGTTTTCGCGGCTGAGGAAGTCCGGTAATTAGGTCACAATA
CAGATTCTAGTGTAAATTAACAGTCGCGGCTACATCGAATTATTGTTCCGCTTATTTACCCTTAGATGTCCTGCGTATATAATACAGCCATAGTCCACGACTCTTCG
AATTAACGATGGCAAAGTCGAAAAGAAAAATTGACGAAAATGGATATATGACCATCGAGGGCTGTCCAATCAGCTCTTATGGCATTTTCCAATATTCTGCCGGT
CAACTCGGTCTTCCGGGCGATCCGATGCGGATTGTCAACGTGTATCGTCCGGAGTCTGCCGTTAGCGATCCTGAGTACATCGAATCTCTGAAGAATCTCCCGCTG
ATCGACGAGCACGAAATGCTGTCGGGATTCGACGGCGATGACGATGGCGTGGCTCCCGAAGACAAAGGCGTGGAAGGCATCATCACAGCCAACGCCTACTAC
GAAGCTCCATGGGCTCGCGGCGATATCCGCATCTATTCCCGCAACATGCAGAATCAGCTGGAAAGGGGCAAGGAAGATCTGTCCCTAGGCTATAGTTGCCGCT
ACACTGAGCAACCCGGCATCTGGAATGGAACGCCTTATGAAGTCGTCCAGGACAAGATGCGCGGCAACCACATCGCCCTGGTAAAAGAGGGTCGTGTGCCGG
GGGCCAGAGTATTGGATGGTCTGTGCTTTGACCATCTCAGTTTTGATTTCAGACCATCCGATGAGGGTAATGAAATGGGTCTCAAGAAAGCCAAGCAGAAGACT
CCTGTCCAGCGCGCAGGACAAGCTGCTGATTCGGCGGTCGAAGAGTTGCGCGCCCTGTGGCCGAAGCTCTCTGCATCTGTCCAGAAGTTCCTGGGCGAAGAGG
CGCAGGAGCCGGAGCATCAGGAAGGCGCAACCGCTCCGGCCGAACCGACCGACAGCGAGCACATGACCGAGCATCCGACTCTGGAAGGCGCTCAGGAAGAC
GACGAAGAGCACGAAGAAGCGCCGTCCGTTGTCGATCCGGCCGTGGTCGCCGTCGAGCCGGAACAGCAAGAAGGTGCCGCATCCGAAATGTCCGGTGAAGGC
GAAGTCGCCGAACTGATCTCCCAGGTCAAGGCCATTCTGGCTCGACTGGAAGGCACGGTAGCCGAAGAGGCGGACGAAGAACATGGCGAAGGTCAAGATGTC
GTCGAGGGCTTGGAAGAACAGAGCATCCTCTGCGGCGCGCAAACCGCCAGCGACGATGGTGGTGAGGGCAAGGATAACAGCGAGGAACTTCCTGAAATGGC
ACAAAAGAACGCGCAAGATGCTGCAATTCGTGGTCTCTATCGCGACATTGCTGCTAAAGATCGCCTCTACAAGCGTCTTAGTTCCGTGGTTGGTGCGTTCGACCA
CCGAGCTATGGACTCGGCTGAAGTCGCTGTTTACGGCGTGAAGAAGCTGGCGATCAGCTGTGAGAAGGGCCAGGAAGTTCTGGCGCTCGACATGTACCTGAAA
GGCGTCGAAGCTGCTCGTGGCGCGGCCAGCCGTCAATCGAAAGCCCAGGATTCGGCCAGTTCTGCTCCGCAGTGCGCCGAGCTGGACAGTTACCTGAAGGGG
GAGTAACCCATGTTCCAGAAACAAGTCTATCGCCAGTACACTCCTGGTTTTCCTGGTGATCTGATCGAGGACGGCCCGAAGCGTGCGCGGCCGGGTCGGATCAT
GGCGTTGGCATCGGTCACTCCGGCCGCGACTGCCACCGGCCCCAACCGCATCAGTCGCGCGTTTGGTTACGCAGGTGATGTCGGCTCCCTCGGTGAAGGCCAG
CCGAAGACCGTTGCCGCGCGCGCTTCTGAAGTCGTGGTCGGCGGCGCGACCTTCTTCGGCATCCTCGGTCACCCGAAGCATTATGCTCTGTACGGGTCGGCCGG
CGATTCCCTGGCTCCCAGTTATGACCTGCCCGACGGTTCCGAAGGCGAGTTCTTCGACATGGCCACCGGCCTGGTCGTCGAAATCTTCAACGGCGCAGAAGCCG
CTCTGGATTTGAGCTACGGCGATCCGGTGGCATATGTACCGAACAACCTGCCTACCGCCGACAACGCCCTGGGCCTGCCGGCCGGCGCCCTGGTCGGTTTCAAG
GCCGGCGCCATGCCAACCGGCCTGGTTCAAATCCCCAACGCGCGTATCGTCAATGCCATCAGCCTGCCTGCCCAGTCGGCGGGAAATCTGGTAGCTGGCGTTAC
CATCGTCCAGCTCACGCAGTAAGGAGGCGTCATGAGCCATATCAGTAAGACCCATTCGCGCCTCGCAGGCCGTCACGCAAAACCATTCGACCTGAAGAACGTCA
CCCACGAAGCCGTGGCCGCCCTGAGTCGCATCGGCCTGGTATTCGATCACGCCGTCGTCCAGGACCAGATCAAGGCCTTGGCGAAGGCCGGCGCATTCCGTTCC
GGCTCGGCCATGGACAGCAACTTCACCGCCCCGGTGACCACGCCGTCCATCCCGACCCCCATCCAGTTCCTTCAGACCTGGTTGCCTGGGTTCGTGAAGGTCATG
ACCGCCGCGCGGAAAATCGATGAGATCATCGGCATCGACACCGTTGGCTCCTGGGAAGACCAGGAAATCGTTCAGGGTATCGTTGAGCCGGCCGGCACTGCG
GTGGAATACGGTGACCACACCAACATCCCGCTGACCAGCTGGAACGCCAACTTCGAGCGCCGCACCATCGTTCGTGGTGAGCTGGGTCTGCTCGTGGGTACTCT
GGAAGAGGGCCGCGCTTCGGCCATTCGCCTGAACAGCGCAGAGGCCAAGCGTCAGCAGGCGGCCATCGGTCTGGAAATCTTCCGCAACGCCATCGGTTTTTAC
GGCTGGCAGAGCGGCCTGGGCAACCGCACCTATGGTTTCCTGAATGACCCCAACCTGCCGCCATTCCAGACTCCGCCGAGCCAGGGCTGGGCCACTGCCGACT
GGGCAGGCATCATCGGCGATATCCGTGAGGCCGTCCGCCAGCTGCGCATCCAGAGCCAAGACCAGATCGACCCGAAGGCCGAGAAGATCACCATGGCCCTGG
CCACCAGCAAAGTGGACTACCTGTCGGTGACCACGCCTTACGGCATTTCGGTTTCTGACTGGATCGAACAGACCTATCCGAAGATGCGGATCGTGTCGGCTCCG
GAGCTGTCCGGCGTCCAGATGCAGGGCCAAACGCCGGAAGACGCCCTGGTCCTCTTCGTCGAAGAAGTGGACGCGTCCGTCGATGGCAGCACCGATGGCGGC
AGCGTGTTCAGCCAGCTGGTTCAGAGCAAGTTCATCACCCTTGGCGTCGAAAAGCGGGCGAAGTCGTATGTGGAGGATTTCTCCAACGGCACCGCCGGTGCTCT
TTGCAAACGCCCTTGGGCTGTGGTGCGCTACCTCGGCATCTAACCGATGCTGACTCACCAAAGGCCGGGCTTCCGGCCTTTGTTCACTCTGACTCTGACTCGGTT
GTAGGGGCCGGTTAGGGCATAATTAATAGGACTACGCCAATGACTGTTTACATCGTTTCCGCAATGACTCAATCCGTGTCTTACAATGCGTATGACACCTCTGAT
CCGTCCAATCCTCGCCTCCAGAGAAAGGTGCTGATTCGCGGCCGCGCTGGTATCGCATCCGAAACCTCCGGCTTCGGCGACATGATTTCCGACGCATCCGGGCG
CCCGATCTGGACGCCGCAGGGCGATTGCACGGCGGTGAGCGATTCCGATTTCGAACTGCTTCAGTCCAACAAAATCTTCATGCGACACATGGAGAAGGGATAT
CTGCGAGTCGTGAAAACCGACATCACCAATGACCACCAGCGGATTGCGAAAGAGACTCGCACCATGGAGCGCGATGGCTTCCAACCTCTGGATTCTACTCGCCT
GAAGCAGAAGATCAAAGTGACTACTGCCAGCGCTTCCCAGGAACAAGAGTTCCGGGTTTAACCGAGGGTTTCGGTATGGTAATTTTCGACGAGCAAAAGTTTC
GAACGCTGTTTCCGGAGTTTACTGATCCGGCTTCCTATCCGGATGTGCGCCTGCAGCTGTACTTCGACATTGCGTGCGAATTCATTTCTGATCGGGATTCTCCATA
CCGAATTCTCAATGGCAAAGCCTTGGAGGCCTGTCTGTATCTGCTGACGGCCCACCTCCTTTCGCTGTCGACGATGCAAGTTCAGGGCGCGGCCGGTGGCGGGG
TCACAGCAGGCGGGACTCAAGGCGGTTTCATCACTAGCGCTACGGTCGGCGAGGTCAGCGTTGCCAAGCTCGCGCCCCCTGCCAAGAACGGTTGGCAGTGGTG
GCTTTCCGGGACGCCTTACGGTCAGGAACTGTGGGCGCTCCTGAGTGTCAAGGCAGTTGGCGGATTCTACATCGGCGGCCTTCCAGAACGTCGAGGATTCCGTA
AGGTTGGAGGGACGTTCTGGTGATCCCTGGAGCGAATCTGCTGCGTATGGCATTTAGCGTCATAGGAACGCAGTTCGTTCAGTATCGCAAATTCGAGCAGAGG
ACGAAGAATAGCCAGGCGCAGTACGTTTCTGTGTTTGGCGAGCCATTCCAATTGGCCGCTTCCATCCAAAGGGTTCGTCGCGATCAGTATGTCCAGTTCAATCTG
GAGTTTCAACGAAATTACGTCATGATCTTTGCCAACTTTGAGATGGTTGACTTGGATCGAGATTTGGCCGGCGACCAGTTCATCTGGACCGGAAGAGTTTTTCAA
CTAGAGTCTCAAGGCTCTTGGTTTTATCAGGACGGCTGGGGAGTCTGCTTAGCCGTGGATATCGGTACAGCCAAACTAGCTGAAGACGGAACCCTGACTTTCTA
GGTGGCTTATGTTCGACGGCGAACTGATAGAAAAATTGGTGGTCGAGCTTACTTCCGCCATGACGTCAGCCAAAGAAACTTTGCAGTTTCCTGATTTTGAGGTT
GTGCAGAAAGCCCAGCCGACCCAACAGGGCACGTCAACCAAGCCTACCATCTTCTTCCAGAAGCTATTTGACATCCCTCGCGGCTGGCCGGCAACCGATTGGTA
TCTGGACAACGTCGCCAGAAAATATGTAGAAATTACTCGACAGCATGTCGAGACGACTTTTCAGATAAGTTCCCTTCATTGGCAGAATCCTGAGATGGATCACGT
AGTCACGGCAGCCGATATCGCCAATTACGTGAGAGCTTATTTCCAGGCTCGGTCCACCATTCAGCGAGTCAAGGAACTGGACTTCCTTATCCTTCGCGTGTCTCA
TATATCCAACGAGGCATTCGAAAATGACAATCATCAGTTCGAATTCCACCCAAGTTTTGACATGGTTGTAACTTACAATCAGTATATTCGTCTGCACGAAAACGCA
GCATATTCAGCCGATGGGGCGCTGATAGGCATATGATCCTGAGACGCGATTCAGAACTGATCGCCGCGCACCTGCAGATGTTAAGAGCCATGCGCGGCAGGTC
CGTTTCGGCCGGATGGTATTCCACCGCTCGATATCCTGATAAGGCGGGCGGATCGGTCGGAATACAAGTCGCGAGAATCGCGCGCCTCAATGAGTACGGCGGA

Figure 7D

ACTATCGACCATCCGGGCGGGACCAGGTATATTAGGGACGCCATTGTTCGGGGTCGGTTTGTTGGCGTTCGGTTCGTCAGAAACGATTTTCCGGGAGAAACCG
AGGTAACAAAACCTCACAGGATTACAATCCCGGCTCGACCGTTTATGCGATATGCTTGGAACTTATTTTCCGCAGATCGCGCCGCAATCCAGAATCGAATAGCCA
TGAGGCTGGCCAGAGGACAAATCACGCCGGATCAAGCGCTTGCCCAGATCGGCCTGGCGTTGGAAGGATACATAGCCAGAAGCATAAGGACCGGGCCATGGG
TGGCTAACTCAGCATCTACGGTCAGGAGAAAGGGTTTCAACAGACCGCTGGTCGATACGGCTCACATGCTCCAGTCGATTAGCAGCAGAGTAACATAAACCAG
GAGATCATCCAGTGATCAGTCAGAGCCGTTATATCCGGATCATTTCCGGCGTAGGCGCAGGCGCTCCGGTCGCAGGCCGAAAGCTGATTCTGCGCGTCATGACC
ACCAACAACGTCATTCCGCCTGGAATCGTCATCGAGTTCGACAATGCCAACGCGGTGATGTCTTACTTCGGCGCCCAGTCTGAAGAATATCAGCGCGCTGCGGC
CTACTTCAAGTTCATCAGCAAGAGCGTCAATTCCCCGTCCAGCATCAGCTTCGCTCGCTGGGTCAACACCGCCATCGCGCCGATGGTAGTTGGCGACAACCTGCC
GAAGACCATCGCCGATTTCGCCGGCTTTTCCGCAGGCGTTCTGACCATCATGGTCGGCGCGTCTGAGCAGAACATCACGGCCATCGATACGTCCGCCGCGACCT
CCATGGACAACGTGGCGTCGATCATTCAGACCGAAATCCGCAAGAATACCGATCCGCAGTTGGCCCAAGCCACCGTCACCTGGAATCCGAATACCAACCAGTTC
ACCTTGGTCGGCGCTACCATCGGCACCGGCGTTCTGGCCGTGGCGAAATCGGCCGATCCGCAGGACATGTCCACCGCCCTCGGCTGGTCCACCTCCAACGTCGT
GAACGTCGCCGGTCAGGCTGCCGACCTCCCAGACGCGGCCGTGGCCAAGAGCACCAATGTCAGCAACAACTTCGGCTCGTTCCTGTTCGCCGGGGCGACCCTC
GACAACGATCAGATCAAGGCCGTGTCGGCCTGGAACGCGGCTCAGAACAACCAGTTCATCTATACGGTTGCGACCTCTCTGGCGAATCTCGGCGCTCTTTTCGA
CTTGGTGAAGGGCAACTCCGGAACCGCGCTGAACGTTCTGTCTGCGACTGCCTCCAACGACTTCGTTGAGCAGTGTCCCAGCGAAATCCTGGCCGCCACCAACT
ATGACGAGCCGGGCGCTTCGCAGAACTACATGTACTATCAGTTCCCTGGCCGCAACATCACCGTGTCCGACGATACCGTTGCGAACACCGTCGACAAGAGCCGG
GGCAACTACATCGGCGTCACCCAGGCCAACGGCCAACAGCTCGCGTTCTACCAGCGCGGCATTCTGTGCGGCGGTCCGACCGATGCGGTGGACATGAACGTCT
ACGCCAACGAAATCTGGCTGAAGTCCGCCATCGCCCAGGCCCTTCTGGATCTGTTCTTGAACGTGAACGCCGTTCCGGCCAGCATGGTCGGCGAAGCGATGACT
CTGGCCGTCCTCCAGCCGGTTCTGGACAAGGCGACTTCCAACGGCACTTTCACCTATGGCAAGGACATCAGCGCCGTCCAACAGCAGTACATCACCCAAATCACC
GGTGATCGTCGCGCCTGGCGTCAAGTCCAAACCTTGGGTTATTGGATCAACATCACCTTCTCCAGCTATACCAACAGCAACACCGGCTTGACCGAGTGGAAGGC
CAACTACACCCTGATCTATTCGAAGGGCGACGCAATCCGCTTCGTCGAAGGATCGGATGTAATGATCTAACGGTTTGCGGCGGACTCGACCGCCGCAACCTTCC
ATGAATGGAGTGAGGAATAAGCAATGATCAACATTTCTGCGTTCGGCTCGATTGCCCAATTCACGGCAAGCAGAACCTTCCCGAACGGATTCACGGTGACCGAG
TTCGCTGATGATGCGGACCCCATCGACAGCCCGCCGTTCACTGCGGCTGATACCGGCGTCGGCCTCAATGGCGATATGGTGGTTTGGAACCGGGCCAACATCCT
GGAAGTCGTCGTCAACGTCATCCCGAACACCGAGGGTGAGCGCAACTTGGCCGTCCTGCTGGATGCCAACCGCACCGGAAAAGACAAGTCGGGTGCTCGTGAT
GTCATCGGTCTGGTCGTGGCGATGCCGGACGGTAGCAAAATCACCTGTACCAACGGCACTCCCATCGACGGCGTTCTGATCAATGCGGTGGCGAGCGTTGGCC
GCCTGAAGACGAAGCCGTATCGATTCCGTTTCGAGAAAGTAGTCAAAGCCGGTACTAGCTGATGAAGAAGATTCCGCTGACAGCAGTCCCGAATCAGGCGATC
TCATTTAACGCCGGCAGCAGCTATTGGAAGATTCGTCTGTACCAGAATCTGGATATGATGAATGCCGATATCAGCCGCGACGGCGTGATCGTTTGTCATGGGGT
CCGCTGCTTCGGCGGAATTCCGCTTCTCCAGTATAGCCACCAGTATCGACCCGACTATGGCAATTTCGTTTTCGACCGTGACGCCGATTGGACGTTGTTCGGCGA
CGGCATAAACCTGTTCTATCTGGACGGTGTCGAGTTCGCAGAATATCAGGCGCTGGCCACGAGGAAAGAATGAGCACATCAACGATCAGAACCGGGGTGAACA
ATGACATCCTTTTGGACGACAATGGAAACATGGTCATTCTCAGGGATGTAGAAGCGTGCGCCCAGGACGTTCGGGCGGCGATGCTCATGCGCACCGGCGAAAA
CATTTTCGATGTGGACGCCGGTGTGGGATATTTTGAATATATCTTCTCGCCGCAGAAGAGCTATGATGATGCTCGCAAATCCATCGCGGATGCAATTTTGTCATC
GCCGGACGTGACCGGCATCGAGCAACTTGACATCGACATCACCGGTGAAGTCTTCGGCGTCGATGCGAAAGTCATCACCATCCACGGGCCTGTAACTGCAGGA
GTTTGAAATGAGTACCATCCGCATCCAATACGCCAACGGCACCCAACTATTCTTGGACGGCAAAAACCCGCCGCTCCTGGACCCGCTGCCTTCTTTCAACCCGTC
GGTCGAAGACCTGGAAGGCCTGGACCGCGAAAAGAACACTGGCAAGGGCAACTCTTCGTCGGCCGGTATTCCCGTTCCCCCGGTGAACGTCGATCCGAATGTC
GACAACGGCGGTGCCATCCCAGCTCCGGCATCGACCGGCACCCCTGCGGCCGGATCGACCCCGGAAAGCGCCCAGGAAGCCCCTGCAGAGGGCCAAGGCGAC
GAGAAAGGGTCCGAGACGCCCCCGACTACTACCAAGGAAGAAAAGACCGAGGTAGAGGCCTCTGCAGCCGCTAAAGAGGCCACCGCCACTACCAAGCCCACG
GCTCGCAAAACCACCAGCAAGTAAGGACTCGACATGATCAACGTCAGCGGCTTCGGCACGGGAATTGTGATAGTTTCAACCTCGTCGTTCCCGATGGGGTTTTC
CTTGTCGAAGTTCGCTGATGATGAGAGTCCGATATCATCCAAAGAGCTGGAGCCGTTCGGGTATGAGATGCTTTATGATGGCGGTCTGTTTGCCTTCGATAAGG
CGGCCCCTTTGGAAGTGTCCATATCCGTAATCGCAGGGAGCGAAGATGATATTAATCTTCGCATCCTTCTAAATTCCAAAAAGGGATCATTTCGATTCCTTCCAG
GCGTCATTCCAGACATGACGACTCTTGTTGCAACTCTTCCCGATGGCGGCCGCACTGTTCTGTCCAACGGAACTATCATCAAGGGTCCGGCCATAGATACCATCC
AGAACACCGGACGGCGCAAAGGCAACACGTATACTTTTGTTTTCGGCAACTATCTCGGCGCCCAGACTGCGCGTCAAGCTATTTCTAACGTTATTCAATCGGTTC
TGGAGGTGATCTGATGTTAGGGATTTTCACCAGCCTCCTAAGCTCGCGGTCTTTTTCGATTGTAGATCAGAATACAAACCAGCTAGTTGCTGCGGATTTGAGGAT
AAGCCGGGTTAACACCCGGTTTTCTTCTGTAGGGCAGCGCCACATGCTGGAAGACGGTACGACAAAGATGGACTCCAGAACGGTCCATCCTATGGAGATAATC
GTTGAGGTATTCTGCCCTTCAATTGATGTCGTAGATCAGATTAATCAACTGCTCCTGGATCGTGATACGCTGTACAAAGTCATCACTCGCGGCATGGTATTCGAA
CGGATGATGTGTACCAGCGAAGCGCTTAATCAGACGCCAGAAATGATATCGGCAACTCCTGCGCGGCTGACATTTTCCCAAGTGCTCGTTCAGAATCCCAAACC
AATCATGTTCAGGAATGCTGGAGACTCTTCCATAATCGACCGAGGGTTGGCCCTGGCCGAAGACGTTGTGGGCTCGGCCAGTGACCTGTTCGACTACGCAGTGA
ACGGCGTCCAGAACGCCGCAGACTTGTTCTGAGGTGCCAATTGAACTCTTTCCTCAAGGCCATTCTCAACACGCCTACTCTCACCATCCGTGATGATTTAACCAAA
CTTCCCGTTTGGAAGAGTCTCCAAGTCAAGAAAGTGGAAATTTACTCACCGGCTTCCGTAGTGTCGAAGCCTTTGGCGACGAAAGACCAGACGGAAGCTCAGGT
GTATACCGAAGCGCTGGACGTTGATGTGAAGAACGGGAAGATCATTCAGCCAGTGCGGCTTCGCATCAATGCCATCTGTCCAGACTTGTCCACAGTTGAAAGTA
TCATGAATGCTTTTAATGACAATACCTCGACTTTCGCCATCACTTCCAAGTCGATATTGGCTGATAAAATGGCCATCATGACGCTCGATGTAGATCAATCTCCTGA
CATGCTAAATGCGGCTGAGATCAACATGGAATTCGAGCAGGTTGAGCCTCCAGTATTGAATGAATTTGATCCGGCTTTCCCTCAAGATCGCCCAACTTATGGCGT
GCAGATTCAGTCCCTTTCCGATGCAAATTTGCTAGACTTGGGAGCCACCGGCGATTCGATATCTTCGGCCGCAAAATCGCTATATAATCGCGTGACCAGTTATTT
CTGAGGATGTATCATGCTTGAAATCAACCTTCCCGATGGCCGCCAAACTCGCGTACAAATCGAGGCGTGGTCGGCATTGGACGGCTGGGAACTCCAGCGCCGTT
TCGTCGAGTTCGCAGTCAGCAAGGATGCCGACTTCCGCCGCGCTTTCACCATGGAAATCCTGAGCTATGCCAAAGTCATTCTCGGTAACGATGATTCCGAAATTC
CGTTGACTACTGCTGCGGTCATCAACAACCACCTCGGCAACTGGAAGAACGTTGAATTCGTCTTCGATTCCGTCCTCAAGCACAACGGCATCGATCCGACAACGC
ACGCCGACCGCCCGGACTATTGGGAGCAAGCCGGTTCGCAGATGGCAATCGCATTTCTGGCCGAGGCGTCCAAGCTCATTGGGCCAGCTATGAAAATCGCCGA
AGGACTCGCCAGCAAGCCGGAGTAATTCATGTCTAGTGATTTGGATGAATTCATACTTCGGTATGAGGCCGACACGGCCAGAGCCGAACGAAATCTGGAACGT
CTCCAGAATCAGATCAGGCGCGTAAACAGCGCATCGACTAGTGGCCTTCAAGATTTGCGCCACTTCGCAGACGGCGCTGCAACCGAACTCGGCCGCGTGGTTCC
GCAGGTGGACGCCGTAACGAGCGCGATTCGCGGGATGAACGCCCAGCTCGCGATAGGCGCTACTGGCGTGGCCCTGGTCGCGGCCGGCGTCAAGGCGTTCAT
GAACACCAGGGACCAGTACAACCAGCAGCGCATCCAGGCGATGGATATCGGCATCGCCCCGGCGCGGCTGGAAGAGTACCAGCGGAAACTGGCCCGCCAGTC
TGGAGGAACGATCAGCCGCGAGCAGGGCGCGGAAATGACCAAAAATCTGGCCGACACTTTCCGGCGAGCTTATCGCGATATCGGACGGGTCGGCCCAGAGGC
GCGGATTCTGCGCATGGCCGGCGTAGATGTCGGAAGCTTCCAGAAAGGCATGAGGCCGCTCAACGACATCATCACTGAGCTGGCCACGAAGATGGCCAAGTTG
AAACCGGACGAGATTTCGGCATATGCTGATGCCCTCGGCGTCTCGCGGGACTATCTGAGCACCCTGGCGAAGATCGGCCCGGCAATGGGCAAAGTCACTGAGA

Figure 7E

TGACGTCAGAAGAGCTTCAGGCTAGGGTCAGGGGCGAGTCAAACATTCAGAAGTTCAATGATGCTTTGGCAAACCTCAACCAAACGTTCACGACTCTGGAAAA
CCGCGTTGGCGAAAAACTCGCGCCTGCATTCACCAAGTTGATCGAAATCATCGACAAAATTGTCCAGGCCATTCCCAATGAAGTGGAAGAATTCGCCAAGGACA
CGAAAGCCCGCTGGGACGATGGAATCACCGGAAAGGCCACTGTGGGCGGCGATATCCTGTCCCTTCTCAGTCCTGGTGCTCTGCTAGGTCGTCTGGCCTCCTGG
GGCACTCGGCGCGGCATGGAAGAGGCCGGATTAATCGACAAGTCAAAGGTCCCAGGCTCCCAAGGCCAAACCAGCGAAGACCTGGCCAAGAAACAGGAAGAC
CAGGACAAAGCTACGAAGTCCATGAAAGAGCTGGAGAAATTGGCCGACCAGACTACGAAGTCAACGAATGATTTCGCGGTGGCGATCAACATGTTCAGCGGA
GCCGTGTCATCGTTCGCCAATGCCGTTGACGAGCGTCAAGCATGGGCGGCATGGGCGGGGGAAATCGGGCGCGCAGTGGGCATGGGAAGCACCGCACCGACT
TCGCGAGCAACAGGGGTTTATCCGCACGCGATCTACGATCAGTCGAAGAGTGGCGCGGCCGGTCAAGTATTCGGCGAGCCTATTGGCGCCCAGTCTCTGCGAA
ACAGGATGTTCTCGCCGCAGCGCAAGGCCGAGCCGATCAACGTGCCATCGTACATCAATGACATCATCAAAGATGCATCTAAGATGTACAACATTCCTGAGATG
GACATCAAGAAGCTCATATACACTGAAAGCCGATTCAACGCTAGGGCGACCAGCGAAGCCGGGGCGAAAGGCCTCATGCAGCTGATGCCGGAAATTGCCAAG
GCGTATGGAATCACCGATGTGTATGACCCACGCCAAAACATCCTCGGTGGAACGCGCCTATTGCGGAAAACCTGGACCGGGCCAAAGGCGACATGCGATTGG
CGTTGACCTACTACCATGGCGGCCTCGACCCGAAGAACTGGGGGCCAAGGACTCGCGCATATCCTGGTTTGGTGATGAGCGCACCAATTGAACTGATGGAGGA
AGCCCAGCGCAAGCAGAAGGCCGCGGCCATGACGGTCGCCAACGAGACGTTCGCGCCAGAAGGTGGCGACATGGACATTCGCCCCTATGACGGCGGAAGGCT
GGAAGCTCCGGACCAGGGCAGGAAGGAGGATGATCGCCGCGAAGCTCGTCGATATGACGACAGAGTTGTCCGGCCGGAGATTCGCATCATCGACCGCATGCC
AGACCGCAGTGACGGCGAAATTCTTAAAATGTCTCAGCGCCAAGACGCCGACCGGGCGGACTCTGGATTCCGGAAATTCCCGAACCAGGTTCGTGGCGAGACA
AAGCAGAACATCCAGGCCCAACTCACTGCCGGAGCTATTGCCCAAGTCATCGGTGTTAATCCTAACCAAATTATGCGCCGCGAAATCAGCCGTTCCGACTTGCTG
TTCGGATACAACCAGGCCATCTTGGGCAAACAGCAGGAAATCAAAGCCGCTGCGACAGAGGCCAACAATGTATTCCTTTCTCCAGCCAAGCTCGCCGAAGCTAC
TGCCAAGGTTAACGCCGCATCGCGAGAAATGGATATTCTCAGGACGTATGGGGAGAAGCTTCTGAAGAGCGCTCCAGAGCGCGGCCAGGAACTGACAATCGG
TCGAATTGATATGTTGGTAAACGTCACCGGCGCGAATTCTCCAGAAGAGGCTCGCGAAATCTTCAGCAGGCAAACCGCAGAACAGCTGACCACTGCCATCCAGG
ACTCCCAAAACGATTCTGCAACTAAGATACTCTACTGATGAAAAAGAGAATTCTGCGAGTCACATTCAATATGCCCTATGGACCCGAAATCATCCGTGAAGACCT
GGATGTTCGGGTCCGGATTATGAAGGCTGCATTGCGAATTCAAAACCGAGCTACCCTGGAAATCTTTGGACTCACGACGCAATTGCGCGAGTCTCTTCTGTCGC
AGTTCACAGCGTGGAAGCACCGGCAGCGTCAAGTAGGCATGGAAGACGAACTGATGATCAGAGTATCGGTTGAGGCCGGTTATTCCGATCAGGGCCGCGAAC
AAGTTTCCAGAGTATTTGTCGGCGAAGTGGCAATTGTCGATGTCATTTCGCCGCCACCGGATATTGGAATTCGCATCCAATGCTACACAAGGCAAATCGATAGG
ACGAAGACTATTCGAAATATGCCGCCAGCCAACACGACGTTTGTAAAGTTCGTCGAATGGGGCGCAAATGAAATGGGGCTTAACTTCATCTGCGACACCAGCTA
CAATGATCAAGTTTTGAAGAATCCGGGCCGGTCGATCACTGTCGCGTCGGCAATCCTGGCATCGATTCAGGATATGTACATGCCGGATGTGGCCGCGTTCGTCG
ATGATGACATTCTGGTCGTGAAGGACCGGGATAAGGTCATTCGTCCTGATGAAGTTGCCAACATCAACTCATTCGTCGGCATCCCTTCATGGTCGGAATGGGGC
GTGGAATTTCAGTGTCTGTTTGAACCGTCGATTCGCGTGGCTGGCGGTGTCGCGGTCGAATCTCTCATGAATCCAAGCGTCAACGGCAACTATGTGATCACCGCT
CTAGAGTATGATTTGGCCAGCCGGGATCGGCCGTTCTATATCAAAGTCATGGGGAGCCCAGCAGCGTAATGGCCAGGGAAATCAAATCATTCAATATGTTCGGC
GTGCACTACAACTCGCGGCAATTCTCTGCGGTCGATGGACTCAGGATGATGTCGGGAATCCATGATGTTCCTCCGGAAGAATTGCTCAAAGGGACCGACGTGTT
GGCCCATACGGAGGAACAACCGGAAGGCGTTTGGCTTCCCTTGACCGCTGCGAACATAAATCTTTATGTAATTGACCGGGCGAACGTAATAGCTCCCGTACAAG
TGCTTGCGCTTTTGTCTGAACTGGTCATAGATTGGAACTTTGGCTTCCTCAAAGATTGGACAGGGGTCAAAATTCCATCAAGATTTGTAGAAGATATCAAAAGCG
TGAAGACGGCCCATTCGCCTTCCGTGGTCGCAAGTTTGGTGGCGAATGGGTCAGCTTCTATGCGCGAGCTGGAAGAGTATTATTCGACTCAAGATGCCTTTAAG
ATGATTGACATCATGACTGCGAAGAGCGTGAATGAGGCTCTAGCGTCCGAAGCATCACAGAACAGAATCAAAAAGGGATAATTCCTAAGCGAGCCTGGGAAG
GCTATACTAGACCGGCCAAATCAGAGGCTTTCCCATGTCCAATATTCCGCTAACATCCGCAAAATCTACCGACAGAACGCGACTGATCGCCGCTCTTGACGCTCG
GTCGCGGCGGGATGCGCTCGACTTTGAAGTCATGATTCCCGCCCAGGTTGTTCAATATGATCGGGCAGAAAACATCGCTACCATTCAACCTCTCATCACCTGGGT
TGATACGGAACACAATGCCGTCCAGCGGCATCAGCTGGTTGACATCCCGGTGATTTCCATGGGCGCTGGCGGCTTCCACATAAGTTTCCCGATCCAGCAGGGGG
ATATCGGCTGGATTTACGCGGCCGACCGCGATACTTCCCAGTTCTTGGAGTCGCTATCGATGTCGAAGCCGAACACCGGCCGCATCCACAAATTTGAACATGGT
ATGTTCATACCGGACGTATTCCGCCGATACACCATCAATTCTGAAGACTCGGACGCGATGGTCATCCAATCGACTAGTGGAGCGACCAGGATATCCATTCGCGG
AGACAACATCAAGATCACTGCGCCGTCGAATGTAACAGTGGATACTCCGCAGGCGAATTTCACTGGAGATGTGACTATCGCCAACACCCTGGTTGTAAACGGCG
TCAACGTGAACAACCACGGTCACCTCGAAAACAATCCGCCTGATACCCGGACTAAAGGCGGCATGATTGCCTAAAAGGAGATTCAACATGGTCTTCACACTCGA
AGATTTCGTTGGGGACTGGCGACAGACAGCCGGCTACAACCTGGACCAAGTCCTTGAACAGGGAGGTGTGTCCAGTTTGTTTCAGAATCTCGGGGTGTCCGTA
ACTCCGATCCAAAGGATTGTCCTGAGCGGTGAAAATGGGCTGAAGATCGACATCCATGTCATCATCCCGTATGAAGGTCTGAGCGGCGACCAAATGGGCCAGA
TCGAAAAAATTTTTAAGGTGGTGTACCCTGTGGATGATCATCACTTTAAGGTGATCCTGCACTATGGCACACTGGTAATCGACGGGGTTACGCCGAACATGATC
GACTATTTCGGACGGCCGTATGAAGGCATCGCCGTGTTCGACGGCAAAAAGATCACTGTAACAGGGACCCTGTGGAACGGCAACAAAATTATCGACGAGCGCC
TGATCAACCCCGACGGCTCCCTGCTGTTCCGAGTAACCATCAACGGAGTGACCGGCTGGCGGCTGTGCGAACGCATTCTGGCGTAAGGAGAATTTCATGGCTAG
TTTTGATTTTTCTGATTTAACAGCGGGGGGGGGTTGTAATGGCTAATTATGACTACATAGTAGATACTGGAGTCATAGTCGCCGATACTGCTGATATTCTGAAGG
ACGTTGAAGCGGAATTCAGGGCAGCCCTCGGCGCCAATATCAACCTGGCGGCCTCAACGCCCCAGGGAACTCTGGTCGCGGCTGAAACCATTGCGCGTTCTAG
CGTGATGAGGAATGAAGCTCGCATCGCCAATACCATCAACCCAAACGTGTCTTTCGGAACGTTCCTGGACGCCATCTGTGCGCTGATGGGAATCGAGCGCGGCT
CTGATCTTTCGACGTTCGGCTATGGCGTCCAGGTGACCGGCCGCAGCCAGACCCGAATTTCCACCGGGTCGCGTGTGCAGACTCCGGCCGGAGCGATTTTCACG
GTCATGAGTGACGTTCTGATTCCGGCAACCGGAGTCGCCACCATCGACGTAAAATCGCAGGACTATGGAAACATCCCTCTTCCCGTAGGAAATCTGATCATCATC
GATGGAACCATCGGTTGGGCCGGGGCGAAAGTCATCGCTTCAACTCGCGTCGATCCTGGCAGCCGCCAAATGACCGATGCAGAATTGAAGAATGCTCGCGTCA
ATCGTCTGGCGATCCAAGGCCGCAACTCGACTTTGGCCATTAAAGCGTATGTCAGCGCCGTGCCCAACGTTACCTCGGTCAACGTCATCGAAAACAACACCGGC
ACGGTTCAAGTTGTCAACGGCGTATCATTCACCCTTCCGTATGCGGTCTGGGTCTGCGTCGCCGGAAATCCGGATAAGCAGGCTGTCGCAGATGCTCTGTGGGC
GGCCCACAACGGCGGGACTCCCTGGGACTATGGCGCGGCCGACAACGGCGTCCCTGTGGATGGGCCTACTGGCGTTCCTGTTCGCGACCCGGCATCCGGTCGG
AAGTATGTGGTGAAGTGGACTACTCCGATCATGTATGACGGATATGTAAACGTCACCGTTCAGCAAGGCTCTTCCTCGGTCGCTCCGGAAGCAATCCAAAACGC
AGTTGTAAATTACGCCCAGGGGAAAGTGGAGGGCGAAGAGGGATTGGTCGTCGGCGCGAGTCTGTCTGCCTTTGAAGTGGCCGGGGCCATCGCTCGCGAGAT
TCCCGGAATCTACATTAAACTATGCCAGGTGGCTTGCGTCCCGGCTGGATCGCCGGCCCCGGCCCCCGGCGACTTCTCGCCTGAGTACGTCATGAGCGCATTCG
GTCAGGCTACCATTTCGGTTGGCAACGTTAGGGTGACTTTCGTATGACTCTGCCCGCGTACAATTCTGATATTCAACAGGCGCTGAAGTGGCTCCATAACCAGGC
CCCTGGGATCACCGGCTTGGTTCAGCGAAAAGCTCAATGGTATGACCGTTTCAGTCGTCAGTTTTGGGTTAACTGGGAGCGCGACGTTTTCAACCTGAAGACCG
CCAACCCGTTCGGCCTCATGGTGTGGTGCATCATCCTCGGCACGCCGTCGAAAGGATTCGGCCTATATCCAAAAAACAGTTCTTGGGCATTCGGTCGGCTACGCC
AGAACTTCATCTATAGCGGTACACAAGTTCCGCCACCGGCAGACGCATCGCCGGGCGGCAACTTCTACGGTGGCGGCAATGCCGAAATTCTCAACTTGGACGAA
ATCAGGAAAGTGCTTCAGCTAAGATATGTAGCGCTGATTTCGAACGGCTCGATTGCATATATCAATCGCATGCTTCGCTACATATTCAATGATGATGAGCCGTGG

Figure 7F

GACGAGGCGACCGGTCTGTACTTCTATCTCATGGACTCAACCGGCGAGGATGGCCCTGTGGAGAACTTGGCCATATATCGGAAAGATTGGGAAGGTATGGTGC
TGTTGTCCAGTTCGCCCAGAACGAACCATGTGCTGACATCGACCCCTGCCAGCGACGCCGATTGGCCGGGAGTCGATCCGGCCGCGAGCGGTCTTCCGGTAAC
GGTCGAAACGGCGTCCGCTACGGCCCCGGACGGCTCCGCTACGGTGTGCAAGCTTACTAAGCCGGCCGGGAGTACCGCTTACGTCTCCGCGCCGATAGATGGG
CCGCTGGGGTCCGGTAGCACTGTAACGTTCTCGTTCTTCGCGAAAGCCGGCTCCACCCGTTTCATTGCAATTCAGTCGGCTGCCGATTTCCCCAGTCGAGCCGAT
GCCGTTTTCGACCTGGATTCCGGGCACGTGATCAGCGATCAGATGTTGGACAGCAGCGTGGTAAGCGCCCGAATGATTCGTCTGGAGAATGGCTGGTGGCGTT
GCGTTCTCACGACCAAGACCGTCAGCTCTTCGTTCCGCGCGGCTTACATCGCTCCGGCAGAAACCAACTTCAGCTGGATTGATTCGAATTCCAGCGCGGCGATTG
ATGTGCTTATCTGGGGCGCTCAGATCGAACTGGGTGATACTCCAACCGGATACTTGGAGACTACCGGAACGCCCGTAACCATCACCGATTACGTTCTGCAGAGC
GCCCAGACCGGAACGGTCAAGTTCACACAGCCTCTTCCGACCGGAGTAGAAGCGTATTGGACTGGAGACTGGAAAGGTGGGTCTGCGACCGAGCCGGCCAGA
TTCGCAGTAGGGGATGGGACTCAAGATACATTCAATCTGTCCAGCCCTGCATACATCGGCCTACCCACTAGTGGGGCGTTCAAGCTAGAATACAGAGTTGGTCC
GGCGCTTAATTTGTCGCCGCAATTGATCAACCTCATGAATGACCGGGCGGTCGGTATCATGCCGACTTGCGCCGGTTGCGATGTAAAAGTCATTCAGGAGTAAT
GACGTGATCACACCCGAACTGATACCCAGTCCGTTTGCTGCGCAGGGCGACAAAGACCCGATCCCGCAGACCTCTTCCACTGGCTTTGCCAACCTTCGCGACGG
CTACACGCCGGACTACGAAATCAGTCTGGCGTCGAACAACCCGCAGGCCAAAGCGGTCGAGCGGAAAATTCAAAACCAACTCTTCTTCATCGCGACCCAGAACG
CACAGGCTTGGCAGCGGCAAATGGCGCCGCCGTGGTTTCAGGGCATGCCTGGCGGCTACGAACAGAATGCAGAAGTCGTGCGAGTCGGCAATGACGGCATAA
TGCGGCGTTATCGTTCCATGGTGAATGCCAATGCGAGCGACCCTCTCAGCAGCACGACTTGGGAAGAACAACCCGCATGGTCGGTGATGCGCTCCAACATACCG
ATGCCAGCTGGAGGCCCAGGCCTATCTTCTGGCGGAGAAGTCATCACGACCGGCCGCAACTTCAATGACCTGTTGAATGGGACGTGGGAGTTCTTCTCTGATTC
AGTGGTCGTCGCTTCTCAGAACGCCCCCGTATATCCCGCTTCGGCTGGTGCAGCAGCTGGAATGTTGGAGGCGAAATCCTGGATATCCGGGTCCAATACATTCT
GCGTTCAACGCTACACTGACCGCGTCGGGAACGTCGCTGTGCGCGGGCTTAATGCCGGGGCCTGGACCAACTGGATGTACGCAGTAAATGTCATGGCCCTCCA
ACAAGGCCGTGTGACCTATGGGGTCGCGGCTGGCTCGGCGAACGCTTACACGTTGACGCTCGTTCCGCAGCTCCAAGGCGGCCTGGTGGACGGCATGATCCTT
CGGGTCAAGTTCAACACCGTTAACACCGGCGCCTCCACCATCAACGTCTCCGGATTTGGCGCCAAGGCCATCGTCGGCGCGGCAAACTTCCCGTTGACTGGTGG
AGAACTCGGTCAAGGACTCATTGCTGAGCTTGTATTCGACGCCACCGGCGACCGTTGGAGGATTCTCGCAGGCGCGCCGCGCATCCAAGTAGGCAACGCCGAT
CAAGATTATCAGGCTCCCAGCTGGAAACAGGTTAAGGACTATGTCGCGTCCCAAAAGTTGACTGAAGTGGACTGGGCTGACGTCGTCAACAAGCCGAACGTCG
CCATCCAAGACACCACACCGTGGTTCGCCAATCTGGAGTTGTCTGACGCTCGTCCTTTCATCGATTTCCACTTCAACAACAACCGCGCCAAAGACTTCGACTATCG
CTTTATCTCTGAAGCTGATGGGTCGATGGCGTTCTATTCTCGCCAGGGGTCCGCTGGTCCTACCCAGGATATCCTGTTCAGCAGGTCGAATGTTACATTCCTCCA
GCCGCGACTGGATGTTGCGAAAAACCTCGCGTACATCGCGAACTCTGGCCCCCTTTGGCAGAACACAACTGCCGATCAGCCCGGTTGGAAATTCACCTTCGCAC
AAGGTGTGGACGCCAACAACAACGCGGTTATCGCAGTCAATACCACCAACCCGGACGGCTCTTATCGCTCGCAGGTCATGCGATGGGACTGGGCGTCCACGAA
CGTCATATTCAACAATCGCCCTCTGTTTGCTGGACAATATGTTCCGTGGGACTCCGGAAACTTTGATCCGGCCACCAAGCTCACTGTCGGTACTACCAACAATATT
TCGGGGCCGACCGGAATTCGTAATACCACCAGCAATACCGGAAATATGAACACCTGGGGCTCCAGCTCCACAACTGCATCGTATGGAAACGCAGCTCTTCAAAT
CTTCGGTAGAGGGGGTGGCGAGCCTGCGGCCATCTACTTCGACAACTCCCAAACCGGCTGGTATTTGGGAATGGACAAGGACGGCCAATTGAAGCGAGCAGG
CTGGTCGCTCGGCAATAACTCCTATGTGGTCACTGACGAGTCGAATATTCGGAATCACGTCAATGGAATGTCTGGCGCTCCTGTTTGGGGAGGTCAATGGTTCT
GGGGTGAATGGAACTTCAACCCGAACACAAAGCTAACCATCAAAGCCGGCACGCAGGAGACTAGCAGCACTGCGATATTCAGCGGAACCCTGCCGTTTGCACC
AATCGCGTCTCTGTCCGACTATTCCCAGGCGCCCCTGACGATTTATAACTCGCCGACTGGGCCATCTGCTAAGCCTGCTGTGATCGCGTTTATTCGCCCTGGGAAC
TGGGGCGCGTTCTTCGGCATCGATACCGACAACAAGCTGAAATGGGGCGGCGGATCGCTCGGCAACAACTCCAGGGAAATCGCCGATTCCAGCAACATCATGA
ATCTTTGGGCGTCCAACCCGACCGCGCCGTCCTGGAACGGCCAAACCGTCTGGCGATCCGGAAACTTTGATCCGGCGACGAAAGTGGATTTGAACGCCGCGAA
CGCCACCAACGGCAACATGATCTTCAACCGCATTTCGGGTACTGGTAGCGGCATCGCTTCGTCCGGTCGAGTTGGTGCCATCAACCTACAGAATGGCGCGCATT
CAGGGCAAGCGGCCGCAGTCACTTTCGAGCGTGGTGGAAGTATCTTCGTCAACTTCGGCTTGGATACCGACAACGTTCTCAAAGTAGGTGGTGGAAACCTGGG
GGCAAACGCCTACCCAGTCATCCACGCCGGGAACTACAACAACTACATCAACCAGGCGTTGGTTCAGGTCGGTCTGGGCGGAGTCGGTTCCTATGGCATTTTCG
CGGTTCTGGATAATGCCGCTCCAATCGCAACCGTTCAACCCGGAGTGGTAGTGGACGGTTCCATTCTCATCTACTCGTCTTGCGCCGCAAACTACAATAGCGGTC
AAAAACCTGCCGGAACTTGGCGCTGCATGGGATATGTAGTCAACAGAGACGCCAACACCCCTGACTCCGCGACCCTTTTCCAGCGAGTGACGTAAAATGAGATG
GACGCGGATCAGAAACCCACGTTGGCTGGACGCAGTAAACATCCACGCCATGGTGACTTTCGAGGGAATCGGTGAAGTGCCGTTCACCGCCAATCCGCAAGAC
GTGGAGGCCCACGGAAGGGCCATATACGCTGCGATTCTATCTGGGGAGCACGGGCCTATCGCCCCGGTCGATTCGAAGCGGGAGAAGGCCTTGCAGGACGCT
ATACGAGCCAGGGAAAAGCGGGCTATCCTTCGGGATACCCGCTGGCCCATAGATCGTCACGACGAGCAGAGACGGCTGGGTATCGAAACCACGGACGGCCCT
GGGCTGATCGCAGCCCTCGTTCACTGGAGGCAGCAGATTCGCGACTGGAATAGCGGGGATCGGCCGCGACTTCCCATGGCTCTGAAAACAATGTTCAAAAATC
AGGAGTACTGATGAAAATAACGAAGGATATTTTGATCACCGGAACCGGGTGTACCACGGATCGGGCGATCAAGTGGCTGGATGACATCCAGGCGGCCATGGA
TAAATTCCAGATCGAGTCGCCGCGAGCCATCGCGGCTTACCTCGCCAACATCGGTGTCGAATCCGGTGGACTGGTGAGTCTGGTGGAGAATCTCAACTACAGCG
CTCAAGGACTGGCCAACACTTGGCCGCGCCGATATGCCGTGGACCCGCGTGTCCGTCCGTATGTACCGAACGCTCTGGCGAACCGCCTGGCTCGCAATCCGGTC
GCCATCGCCAACAACGTGTACGCTGACCGCATGGGTAATGGATGCGAGCAGGACGGGGACGGCTGGAAGTATCGCGGTCGCGGACTGATTCAGCTGACCGGG
AAATCGAACTATGCCCTGTTTGCCGAAGACTCCGGCATGGACGTTCTGGAGAAGCCGGAGCTGCTGGAAACTCCTGCCGGCGCGTCGATGTCTTCGGCATGGTT
CTTCTGGCGCAATCGCTGCATACCCATGGCGGAATCCAACAACTTCTCTATGGTCGTGAAGACCATCAACGGCGCTGCGCCGAACGATGCGAACCACGGTCAGC
TCCGGATAAACCGATATGTGAAGACCGTCGCCGCGATCAATCAAGGCTCCTGATCTTCTCCGAAAAGAAAGGCCGCTTATTCAGCGGCCTTTTTGCTTTCCGGCT
TTGCCTCTTCAATCTTTCTGACTTCAGTAGGCGCGACGGACTCTTCCTGGGTAACTGAGTCCACATAGTTCCCTAGCGAACTCAAAACGCCGATTAACAGCGCTCT
TACCACTTTATCCTTAACTGTCTCGCCTATGATCTTTGTCAGAACGGATATCAACTCTTCCCGGAGCCTTGGGCTTATTCTTGGCCGAAAGCGCTTGCGATGCTCTT
TGCGTTTCATGTTTAGTCCTCTGTTTGCGGTCTTCTCCTCACCCCGATAATGGCTTGGGGATGCGCTGTGTTAATCGGAAGGGTCGGGCGCTATTATAACTCGAC
GAAAATGCTCGCGCTTAACTGTTTAACGATACGCACCGCGATATTAAATCGCCTTCTTTCTGGCCAAGGAACTCTGGCGGCCGAGTCCGGTCTAAGGCTTAATTT
GTCGACATTAAAACGAGAAAACCCGGATCGCCTTTAGGGTAAGGAGTCCGGGTTTTCTTCGCTCTAGTGTACGCTAGAATCAGTGGCTGGCACCCCATCCGTCC
AGCCAGCAGTCGAAGACAGCGTGTCGTGGCTTATCCTTGGCGCCATGGGAGAAGTGCTTAAATCGGATGACCTGGCGCTTGAGATGTTCCCTGTCATTCCAGAG
CCGTTTTTTCTCGTCGTGGGTCAGGCTGGACGCCGACACATTGAAGGTAACTCCAGGCCACAAAACCTCGTTGCGGCAGACGAATGCTCCAACCATGCCTGATG
GGGCCAGATTTTCCGCATGGCTGGAGCGGGCCGTGCGACCTAGCTCATCCGTGAATGCTTCGTTGTTGTTGTGCATCAGCTCTTCGACGTCAACAATCTCTGCTT
CATCATAGTCATAGCGCTTAACCTTGACACAGTAACCTTCCTTGGCAGTAGAGCGCCCGAACTTGTATGCGCCATCAGCGCGCTTGCCCATGGAGCCTTCGAATC
CAAGTCCTGTGTGGCGACGTTCGACTTCGCTGAACTGTTCGATGGAGGTGACCAGTTCCTGCTCGACTAGGTGAATCCTCTCATAGCCGATGCAGTTCTTCAGAA
AGCTGACGCGCTCGGCAGCTCTGGCCAGTCGCTCTTCGGTCGGCGCGCGCGGATCGGTGAAATCGTCAAACACGTGGAAAGACCAATCCGGTTCACCGTCGCG
ACGGCGAAGGTCGCCGGACGACTTCTGGAATACTTTCGGGTCTCTGATGTCGCCGCAGACCAGTTCGCCATCCAGGCCATCGAACATTGCATCGCTGAGATATT

Figure 7G

CACGGATGGACTGGTTGGTCTGCGGCTTTAGGCTTCGCGTCAAGGCTTCGCCTTCAAATATGAAACAGCGAAAACCATCGATCTTCGGAGAAAAGTACATCGGC
AACTGGCCGTCCAGAAGTTCCGGGTCATAGTTCGATGCGAGCATGGGTTTCATACAGTACTCCAGAAAGAAGCCCGGCGAACCGGGCTGAATGGCGGTAAGCC
GGATCAGATGGTTTCGTTGGCGTGATTCAGCTCGGCCATGATCGATGCATAGCGCTCATCCGACTCCTTGATGAACACGCCGTTGTACATTACGCCCTTGCGATC
CTTGATGGTGTCGTAGGCCGCCTGGTAGCATTCGAGCATGCTGGTGTCGTGCTCTTCTGCCGCGTCGAACAGGGATGCGACTGCCATGACCAAGCTCTTGATGG
CAAGCCACTGATTTCCGCGAGCCAGCGAGCCGGCCAGGTCGCCGAGTAATTTCAGATCTTCGCCGTAGGACGGGCGGCGCTCGACCGCCAAGACGAAGGCTGA
CATATGGTCGAGCAGATTTTCGCCGAGCTGCGCGGCCATGATGGTGGCCACGACCATGACATCGCCGATGCCGTCTTTCACTTCGGCGGTGTCATTCTGGATGT
AGGCTTCGCAAACTTCTGCGAATTCTTCTACCAGCTTGAGAAACTGATCTTTGGCCGAAGAGCCTTTGATCAGGTTACGGTCGGCACCCCATTTTACCACCAGGT
CATGGAGTTCGCTATTCATGATTCGTTCGATGATCATTCTTTCGATTCCTTCTGTATTTGGGATTTGACTGCGTTGATGATGGACGCCGTGCTCTGGCGCGATCCG
TCCTTAGTGGTGCCGAAGTAAAAGGCCATAACAGACTTCAGTTCGGCAAACCAATAGCCGATGATAGTGCCGATGGCGACAGAGGAAGTCGGGTCCATCAGCG
CCTCGCGGCCGAATGTGAAAATTGCGATGATGATGAGAATGGAACCGGTCAGAAGAGCGAAGGTTATCGCCGGGCGAACGAAGTCATTTTGTTGCGCGGCAA
GCCTTCTCGCCGAATCTCTGTCTGCCGCCTCGGCGGCGAACTGGCTGAGTTCGGCCTGGAGCTGGTTCTGCTCAGACTGAAGACGGTTTTGTTCGGCCTGGATG
GCCAGTTCCTGGAGACGAACACGCTCGGCGCTCTGGAGTTCTGCGAGGCGCGCTAGAGCCTCCGGATTCGCGTCTAGAGCGCTCGCGACCGATGCTGGGTCGG
CCTTCGACCCTAGAGCCGTCGCGACGATAGCGCCAACGGCGGCGCCTGCAGGCCCACCCAGGAGCGACCCCAGGGCCGGGGCAGCAGCGCCGATCTTACTACC
TATGTCCTTCCAGTCCATTTTCGATTCCTCAAAAGAAAGGCGCCATTACAGCGCCTTTCTCTGGCCGTTGACGTTAGAACTCTTCGGCTTCGGTAGCGCCGCCAAC
GCCGCCGGTGTCGCCGCGAGGCTGTTCCTGCTTGCTGTAGTCCACCTTCACTTCGCCGCCGACGAACGACTTGTACAGATCGGCCGCAGCCTTGAAGTGATCCG
GGTTTTTCACCAGGCCTTCCAGTTCGAACTGGACGCCGGACCAGCTGCCCTTGTCGTTCGACAGACCGACGGTGGTCATGCGGACCAGGTTGGCGAAAGTCGGC
GGGGTGCGCAGGCCCTGCGGAGTCTGGACTTTCTTCTGGGACAGCGCGGTCATGAGCTTCTTCGAGGCCTTGATCTGCGAAGACGACAGGGAGATCAGGGCCT
GGCCGAAATCGCCGGTTTCCGGATCGATGACGATGACGTAATGGCCACGGGTGTCGGCGAAGTAATCAGATTTCTTGTCGCTTACCGAACCGTCTTCGTTCGGC
GCGTACAGTCGCCCTTCTACTTCCTTCACCTTGGTCGGGTCTTTCATCATTTCCTTGAAGTCTTCGACGCTGATGGACCCTTTGAAACCGCCTTCGGCATCGCGGCC
GGCCCAGCGAATGAACTCGCGACGATACGCGGCCGGGATGATCAGCAGACCGGTTTTGCCGTCGTAAATCTTGCCGGTGACGGTATTCAGGAACATGCCGGCC
TTCGCGCCCTCGATGTATTTCGGGTCGTCTTCATCGACCTGCGGCGACATCTTTTGCAGCACTTGGATGAAGGGAATGGCATAGGAATCTGCGTCAGCCCCTTCG
AAACCAGCGCCGTCATACGCGCCCAGGTCCATGAAGTCGGGAACGTCAGTAGTCGCGACGGCGCCGCCGTTGGCCACTGCAACGGCCTTGGTTTCTTCGGTTGC
TTCGGAAGTCTCGGTTTTCTTGCCAGCCATGTTAGGCTCCTTGTTTGTCGAATTTCAGTTATCGCTAACTGTGGGTTTATAATAACGGAAGTTGCAGCGAAGTAAA
GCAAATTACATGTTAAGATTTGCTCTTTTTCACCTTCGGCTTCGTGATCTTGGCCTCTTTATATTCGTGGACGCCGATGAAATCTGGCAACTCTTCGCCCTTCTCCA
GGTACTCGCGACCGAACGCCTGGAGGGTCTGGTAGTGAACATCGCGGTTGATGGTGGCGTCATAGCCGGCTTCGATGATCGCTTCGGCCGCCTTCTTCGCATCT
TCCATTTCTCCGCGACCGAATTCTGCCAGAACTTTGGTCTTGATGATGCCGTCGTTGTCTGTGTCTTCCAGCCACTTCCAGAACTTCGACTTGTTCTCTTCCTTGAC
GGAAATGATGGCTTTCGGCTCGACTTTTACCGTGCGGCCATCAGCCAGAGTCGTGGTCTTCTGGCCGAGTTCCTCCAGAAGTTCAGGAATGGTATTGCGCTTGA
GGGTCTTCAGCTCTTCTTCTTTTTCGGCCAGCGCCTTTTGCAATTCGAGGATTTCGCCGTCCAGCTGCGAAGCCTTGTCCACCAAGTTCAGCAGTCGATGGCCGAT
GTCGGTAGCTTCGACTGCCATTTCATCCATGACGCCGAAATAGTCAATTTCGCCCGGCGCATTGTCCTTCAGATACTCCGGAACTTCCAATTCTTGCTCGCTCATG
TCAGCCTCCAACTTAGTGATGTTCCCTTACTTGAACTAAGTATTGAGTAGATATTATGCCGCATCTTCCTTGATACGGCTACTGATTTACATATTAAATTTCGTCGC
GAGTGCTAACGTCAGCCTCGAACACTCCATCGACGACATAACTCGCAAGATTGCGCTTCCACTCCAAGCTAACCTGGATTTTCTCGTCGATGGAGTCCAGACAGA
TGAGGTCGAAGTACAGGACAGAGTTGATGGTCCCGATGCGATGGTTTCTGTCTTCGGACTGCATCCGCAACTCGTTGTCTTCGTCGGTCGTGTAGTAAATTGCCA
CGTCTGCGGCAGTGAGCGTGATTCCGATCCCAGCAGCGGCCGGGTTTCCCAGGAAGACTTGGACGCGCTTTGCCTGAAAATCATCGATCAGTTTTTCTCGTTCTG
CCTCTTTGGTCTCGCCATAATAGGCTCCAAACGAAATTCCTTGGGCCTCAAGATACGCAGCGATCTGGCCGATTTCGTGAATCCGCATGGCCCAGATGATGATAG
ACCGTTCCGGGTCTTCCTCCAACAGACCCTCCAGAAGGTCGGTGAATACCGCGAATCGCGGGTTGTCTTCGGGCGGCAGGATCACCGGTTCCCCATAGACGTTG
ATATAGCCGGACGCCACTTGCTTGAGTTTCGAACGCGCTGCTGCTGCATCGAACGATACATCCAGCATGAAATCTTCGTTCTTGAGCACGAAATGGTAGTCCTCT
TCAACGCGCTGATAAATCTTCCTTTGCTCCGGCGACATTTCGAAATATATGCGCTTGTAAACCTTTTCTGGCAGGAATGGCAATGCCTCTTTCTTCGTGACCCGGA
AGCTGTGCGGCTCGATCAGGGACCGCAGTTTGTCAAGATTTCGGAATACTGGTCGCCCAAAATCGTCTTTTTCGACGAGCTGAGGTGGAACAGTGCTCTTCCCA
TCCAATTTGCGCATGATGGCGACCATTCGCGGGTCGTCACTTGGAACCAGAACGGAAAATTCAGCCACGAACGCGCGATAGGATTTCGTCCCCAGAATTCCATC
ACGCAGGAATTGAAACTGCATAAACAAATCCGTAGGCGCTCGCGTCAGAGGCGTACCAGAGAGTATGCGGCGCGCCACGGCCTTCTCGCCCAGCTTTACGATCT
TTTTCGCTCGTTTGGCCTGTGGGTTCTTGATCCTCGTTGATTCATCCACAATTGCGCAGACTTTGAACGTCTTAAGGAATCGCTCCACTTCGTCATAGCCAGACTG
ATGGTTGATGGCATCGACGTTTATGGCAAAGACCCGAAGAACTTTTTCATCAGCGAATGTCTCGGCATACAGACGATCCAGACGCGCCCTGGCCTTTTTGGAAG
TCGGTCGGCCGCGCCAATCCACGCACAGAGTCTTGATAGCAACGTGGGTGGGAATCTCGCGCAGAATCCAGTTCGTGTGTACGCCCTTGGGGGCGACGATGAG
CAGCGCGTCAACCCTTCCTTGCAGGAAGAGCCTAACTGAGTCTGCCAAAGTAGTCCAGGTCTTCCCGGTGCCTTGCTCCATCAGGTATGCGAAATTCCTTTTGTT
AAGGGAAGCCTCCAGGGCATTGAACTGGTGTTGCATCGCCTCGGTCTTCATGCCCTTGACTGGAAAGGTTTTGGCTTTCATTTGTTCTCCAGATCGGCGAGAAAT
TGAATGATGTTGTCCAGTCCTTCTGCATGACTCGCGACTTCCACCAGGTCGCGGCTGTTAAGATCGAACAGATCGAGCATTGGATTCAGGAGCAGCCAATCGGT
TCCGATTTTCACCAGAACGAAGCCGCGACCACCCCAGCCGATCCGCTCCCGAAGGAAAGGGATTTGCCCAGGCTCGAAACAGCGCGCCATTGGGCAGGTAGAG
GTGCGCTTTGGCCAAGCTTCCAGAGCCTTGAACTCGACCCAAAACTGGACACCGTGACGATTCAGGCATATCGAATCGGACATGCCGGACCGGCGCGTCTCCAG
GAAATCGACCAGGATTCTGCCTAGCGAGCGTTGCTTAAACGCATTCGCGGCTTTCGTTTCGCGATCATTCATCGCCATTCCCCTCTTCGGAATCTTTCTCTGCTTGC
GCTGCCAACTTTGCTTTCTCGCGTTCGGTCAATATCCGCTTGACGGCCTTCACGATGAACATATCGATTCCGCTGAGCTTCCATCCTTTGATGAGGAACCAAGAGC
CGGTAGGCGTACCTTCGGCGATATTCTTACCGTACTGAAGATATTTTTCAGGGCGAATCCTGAAACGAATCGGTTGGTCAACCGAGTCATCCACGCACATCAAAT
CGAGGAACTGCGACTGGCCTTTGTACACCGGATTCTTTCCTTGGTCAGCCCTCTTCTTCTGGCGGATCGGTTCATTCTCATCCGACAGAACTTTCTTTACCAGCTTG
ACGATAACTAGGCCATCGTCGCCATCGCGGATATCACGAATGTTCTGAATGGGATTTCCGGAAGTCACCCCAACCAACTCAGGATTGTCATAGGCATGACCCCA
GAGCGTATGAGATTCATTCAAATCCGCGAATTGAACCTCAGAATTCGACAAACTCGCGGCAACTTTCTCCCAATCCTGAAGCGTTTTAAGATGGGAGCCGGCCA
GCTCTTTATATTGCGCCTTCAACTCCTTCAGTTCAGCTTTCAACTCCTTGAGATCAGCTTTGAGTAGCTTCTCCAGTTCTTTGTCTCTGCTTACTTTCGCCGAAAGAA
TCTGGGCTTCCAGCGCGGCAACGTCATCGGCCTTATCCTCTACATCCTGCGCCGAAATCGGGCAATTGGCCAGGGCGATCCTCGCGGCCTTGACTTCCTCGCGAA
GACGCAAGAATCGCTCGGCCTTAGCCGGGCCGAAGCCTTTGGCGTTCATGATGCCGCCGATCAGGCGTCCGTCCGCTACAACCCAGTTGAGTTCGGAATGCTCC
GGGTCCAGGGCCGTATATTCTACGCCTTCTTTGGCCAATTCGCGAAGGATAGACACAGTTTGCTGGTCGTCCTTCGCCGCCCGAAGGCACGCGGCCGCGTATTC
CAGGCGATGATACCGCTTCATGTAGCAAGTCCAGTACGTCACCACGGCATAGCTTACAGAGTGGGAGCGGTTGAATCCCCAGGCGCCGAATGTCACCATTTCCT
GCCAAACTCGGTGAGCGTCTTCCGGGGCGACGCCTATGGTCTTGGCGCCCTCGATGAACAATTCTCGGCGCTTGTTGAAGAACTCTTCGCCCTTCCGCGCCGACA
TCGCTTTCCGGATCGCCGACGTTTGTTCCCAGTCGAACTGACCAATGTCCTTAACAATTGACATGATCTGTTCTTGGTACAGGAACACGCCATACGTCCCCGACAA

Figure 7H

ATACTGCTCGACCTGCGGAATGGTATAGGTCACAGGCTCGCGACCGGCTACGCGCTCGATGTATTTCGTGGCCATGCCCGAAGACAACGGACCCGGACGAGCG
AGCGCCGTGATGTGGTCGATGTTTTCGAACGCGGTGATGTTTATCGCATTGGCGACCGAGCGGACGGCCTGGCCTTCGAACTGGAAGATGCCTGACATCTTGTC
TTCGTTGAGAACATCCAAAACCGCCTTGTCGTTCAGCGGCAAGTCGTACAACTCTTGCGCCGTCACGCAATTCGCATCTTGAATTACGCCCAGCGTTCGAAGACC
TAGCGCGTCAATCTTGAGAAGATTCAAATATTCCGAATCAGGCTTGTCGAGCTGCGCGACGCCTTCAGAAGTAACCGTACAGAAATCGATTACTTCATCGTTGCA
GACCAGGATGCCTGCCGCGTGGACGCCGGAGTGGGATGGGTGAATTTCGAGGTCGCCCATGCAGGCGGACGCAATCTCATACTTTTCGCGGAAGTCGCGGCC
GGGTTGAGTCTTTTCGAAAGTGTCCTCCAATCCTTTTCCATATCGTTCGTCCGCCGAAGTATATTCGATGATCGAGTTTTTGATGTTGTCGGTGTCATGGAATGGA
ATGCCGAAGCGCTTTCCGACGTGAGCGATAACCGACGCGGCCTTTAGTGTGTTGATGTTCCCAAGCTTTACCACGTTCCAAGTGCCGTATTTCTGCTGGAGATAT
TCGAACACTAGATAGCGATGGGTATCGGCGAAGTCGATATCTATATCGGGAAGATCGGAACGGGAAATGTCGATAAAGCGCTGGAAGAGAAGGCGATGCGG
GAGCGGATCGACCTCGGTAATTCCCAGCAGGTAGCAGACCAAAGAGCCGGCCGAAGAGCCGCGAGCCGGACCGACCAGCATATGCTTCTTGGCGAAGGCAAC
CAGATCGGCCACAACCAGAAAGTAGCTGTCGAAGTCTTTCAGCTGAATCTGCTTGATTTCTTCCTGGAACCGATCTTCGTAAACTTGGGTCCATTCCTTGATGTGG
CCGCGACTGAGACGGTAGGCTTGGCCCTCGCGAGCCAGGGCGACGATATCACCATCCAGGTGGATCATCGGCGCTTTCGCCAGCTTTACGTCGACCAGCTGCTC
GACCACCGCATGCGTATTGGCAACGGCTTTGTCGAACTCTTCGCGGGTCATGATATGGCGAAGACGGGCCCACAACTCTTCCTCAGTCGCGATGTGGCGAAGGC
CGACCGATTCCCGAACCTTCCAGGCCGAAGCAAAATCTGCATGGTCGATGGACGGCATGTCGTTGTAGGAGGTAATCACCACAGGCTTGCCGAACGCCCTGGC
CGTCTCCATAGCGCCGTGTGCGGCTACCATCGACGCAGGATTGATGTCAATGTAATCGATTCCGGCCAAGTCCAAGTAGGCATAGGCCTCGCCGGCGAACTTGA
TGACGCCGTCAGCATCCTGGAATTCTTGGGGAGACAATCCTTGATTCTGGACAGTTTTGGACGTCAGGCGATAGAACTTTCTGGTATCTTTGGCTAGCGCCCAGG
CTTTCAGTTTCAGCTCTTTGTCACCATCATCGGCGCATTTGATCGGGATTTCCATGCCGAATCCGCGAGGAAGTTCTGCCTTGGTGGCAGCCTGCTCCCAGCGGA
CGTGGCCCCATGTCCCATCATCGACGATGGCGACAAAGGGCGATTCGATTTCTTTGGCGCGCTCAATGATTTCCGGAAACCTGCCATATGCGGCGCCGTATGAG
TAGCCGGAGCGAACGCGGAGTTGAGGGAAAGACATTATGCGGCCTCCATTGCTTGATATGCTCGATATACTCCCATGCGCTTGCAAACTTCGTGGAGCAGCCGC
ACGTCGTCCAATGCCCGGTGCTTCTGAACATAAGGGCCGCAGTAGTGCTCATACAGATGCTGCAGCCGCATGCGGTGGCCGAACAATGGCGCCGACTCTTCTAC
AGTACAGATATCGAGCGATGGGAAGTTGACTTCTTCCAGGCCGAGCTTTCCGCGAGCCAAATCGCAGGTAAGCATGAATTTATCGAATGGAAGGTTGTGGGCA
ATATTTGCGTCGGCCTTCGAAAAGAAATCGCGAACTTTCTGGCGTTGATCGAGGAACGATGGGTGTTTGATTAAGTCTTCATTCTTCAGGCCTGTGATCTTTGTA
ATGATTTCTTCTATCACAATCCCAGGGTTGCAAATGAACTCGACTTCATCCAAAATCGTCTCGCCATCGGTGATCACTCCGGCGAATTCAATGATCCTCGGTTGCT
TTCTCAGACTTACCCTCTGGTGGAACGGGAGTCCTGTGGTCTCAGTATCCCATACGGCGAATCTCATGTCTGTTCCCTCTTATGTCGAAAGGCCGGCTGCTTTCGC
GACCGGCCTGAAGAGTATACCGCAACGGCGCAGGGTTTATGCCTTCTGTCCGTCTTTCGGCGTGATGCGGCCGGAGTGCATGGTGGCGTGGACGAACGCTGAA
TAGTTGATCAAGTCAAATACCGAATCGTCATCCTCAAACCCACTATTCGCCAGGCGAGTGAGTTTGCCAACTGTATGCATCACGAACAGGGCGAGCCGATGATC
ATCTGCGGTCTTCGCCACCATGCCATTCGGGAAGAGGATTTCCATGATCTTGCCATACATCAGATCATTTCGACCATAAGCGCTCTGGCGGTCGCGGAAAATTTC
TGCGGCTGAGGACAGGTTGTTGAGAACATCCTCCACGAAATCATCGGGATCGGCATCACCGTCACCAGGCCAGGCGGATTCCATGGCGAACGGCGCTGCTGCG
TCTTCGGTCGGCTCTTCGGCCGGCTCTTCGGCTGGCTCTTCGGCCGGTGCTTCGTAGAGCGGAGACGGGGCCTGCGCAAACGCCTCGTCGAGGGTAGGGGCGG
AGTCCGGGGCGACCGGGAACGGCTCGCCTGCTATGTCGTTGGGCGCGCTACCGGGATCGCTATCGGCCGCGACGGCGAAGAACGGCGCATCGCAGCCTTCCA
GGTCCAGGATATAGGCGTCGATGCCCAGGCCCTTGTAGGCGTCGATGATATCCTGGCGGTCATCGAATGCCGCGACGATCTTTGTCAGGCCGTCGATCTTCTTC
AAAATATCTAGCGCGACTGAGCGCTTGAACTCCGGCGCCGGCTGGGTGCTTCCATACTCCCGCATGATGAGCTCATATTCGCGATGTTCGGCGATACCCAGGTC
GCGATGGATTTTCGCCCTGGTCTGGAAATAGTTGTTGTCGGTTCGGCCGGTGATGAAGAAAATCATCAGGTCGGCGTCGATGGCGTTACGGATTCGTGCTACTG
CATGCGGATTGAGCTTGTCCTTGTCGAGGCGGGAATGGTACTCGTCCCATTGCTTTTCCAGGGCGAAGCTTTTACGGTGGCTATCGTCGAAGACGCATCCGTCCA
GATCGAAGATCATGATGCCATTCTTGGGTTTTCGTGCCATATTCAGATTTCCTCGCTTTCTGCTTTCTGGGTGATGGTTTTCTCGATGAAAGCGCCATCGGAAGTT
AGACGGAACAGCTCACCGTTCTGGACCAGATCGAACGATTTCACGTTCATGGTGACGCGAATTGATTCGCCGCCGTTGGTCACTTCGACTTGTGCGACATCACCA
ACCTTCTCGATGATGATCTTCATGCTACATTGACTTCCCATTGACCGCTACAGGATTGGCCTCTTGTTTCTCCGATCCCCAGAACTCGCGGCGCAGCTCTTCCTGCT
CGGCCGAGCGATCCATCCATGGACGATAGAACTTGCACTGATAGATCGGTTTCACCGGCAACTCAACAACAGGAATCTGGCCGGGCTTCGTCTCCAGAGCGGAC
ATGAAGCGGTCACAGGATTGCTCATGAATCTCATCTTCATTCAGAACCTTCGATCCATAGCGCGGGAAGGCACAGGAGCCAGTGGCGACGCAGTGCGGCTGGA
GCAGACTATCGAACATAGGATAGACTTCCAGAACCAGTCGGCGCATTTCGCGGAAGGCTTCCTGATACTCACCTTGCGTACGAACACACAGGCGAACTTTCGCC
ATGTCGCTCAGAGTGCGCAGATTGAATTTGGCCGCGATCTTCGTTTCCATGTTGGAAGGGATGATGGCACGAGCATCCTGAAGCGATGCGCCGGCCTCCAAGA
GCTTCTGGTAACTGGTCTGCGCGTCGGCGATTGCATCATGCCACAGGCGGTTCAGCTCTTCACGAGCGTGATAGGTCGGGTCCGGCTCACCATTGGCCGTAGCC
TTCTCATCGAAATCCCAGCGGAACGCTTCCGGCTGAACAACGGCGCTAACCTCCAGAGCGCGACTGGTTTCCTGCTGGTAAGCCCCGGTCCGAGTCCGAACGAG
TTGATGAGTGAAATTCTTGCTGACGCCCTCGATCTGGAAGATGAAGTCCACGAATTCGAATGGCGAGCGAATGGTGTCCAGCATGTACTTCCAGTGGTCGAGCT
TTTCGGCTTCGGTCATGGTCGCCGGGTCTTGGCCGCGCATGCGGGTGGATTTTGTGCCCAGGAGAAGTTCCCAGGCGTTCTGAGTATAACTGATCAGAGAAATT
TTCATCAGAAATCTTCCGGAATTGGCGTGAAAGTGAATTTCTCCGTCAGCGCAATGGCCAACGCTTGTGCATCTTCCTTGTGTAGACCGTATCTGTCGATCTCTTC
GGCCAGCAATTTGCACGCCTCCAGACGGTCTTCATACTCTTCGGCGTGGCACATGGACGAGAAGATAGTGCCATCAGAGGTCCGGTACACCAGTTCAATGGACA
TTACTGTAATCCTCAGTAGCAGCGGATGATTTCGGCGCGAATATCGCGACGGTCCAGGTAATGCTCAATAATCTTGTCGCGGGCGCGCTCGGCCTCTTCGCGACT
GCCGAACGACAGGTTGAACGAAGTGAAAGGCTTATCGTCCAGGCGTCCATCGCCAATCAGGTACAGGATGCCTACCAGCACGAAAGACGGCGCTGTCTGTCGC
GTTTGCGGCGGGTCGATTTGCATTTCGAGGAAAGACATAGGAACCTCTTCAGGATGGTCTGGTGCGTACATTAATAGCGCTCCTGCTGAGCAGCCACCGTCTCC
GGTTCGTAGATGATCATATCCACGATTTCCGGGCACTGGCTTTTCACCCAGTCGATGGCCGCAACCAACGTTGTAGCGGCGCCGAAGGTGAAAGTGCGGTAAG
ACTCATGGATGTACGGCGCACCCATGGAGTCGCGCTCGGTCGTGCGAGAAATGACTACTTTGATGTTAACGATCCGGCCCATCTTCGGCCTCCACTTTAGCGATG
ATATCGGACAGGCTCAGCTTCTCGCCATTCAGGAAATAACTGGCGCGAAGCTTCCTGTCGCCTTCTGGCCCGACGATCCGGGCCGTTATTGTGAGACTCCCGCCG
CCAAGGGCATCTGTGGCCCTGAAGAAAGCCAGCAGCGCCCGCTTGAGCGCTGCCTCGCGAGGATCGACTGCCATTAACCTATCACATTCCAGCCGTGCTGGGC
GCACCACACCGCGCCAGCTCCCGCAGGAAGGCTGTTAAGAAGGAACACTGGGGTCAGGCGGCCATCCTCGGTCATGTGGATGAAGTAGCGTGCACTTTCACCG
AGCCATTCGGCCTTGGCGATGGCGCGTTCGAGATTGGCCTTGGTGGCGTAGGTCTTGGTGGTGTTTTTGTCGGTGGAGAAGGTTACTTCGCGGGCCATTTTGTC
GATTCCTTTTGGTTGAAGGGTTTCGCGTTTCGATGAGGGAATACTACTCTCACCTGGCTCAGAAGTAAAGCACTTTGTGTAAATTATTTCACGAACATCTTCTTGG
CCTTCTGATAAGACGAAGAAGTCATCAGGCGCTCGATGACGTCCATGTCCGAAACCAGATCGTCCAGAAGGACGTTTCGCCAGGTCGCGAACCGACCGAGCGA
GAAGATGCCGGCTTCATGGGTGAGATTCCAGATCATGGATTCGCGCTCGTCGCGGCCGAGCGGAATGATTTTACCCTTGGTCTGGACGGTCGGCTCGCCGTCCG
GAATGAGATTCTTCTTCCTGATGCCGAAGGCCGAGCAAACTTCATCCAGGTCCCAGTTGCTGTCCCATTCGATGGTTTCGATTTCACCAGCCGCAGTCTCCACGAT
GCCCTTAGTAACGGATTCGACGATAAGGGTGTCGCCGGTGATGGACGCTCGAAACGTTCCCACTTCGGGACCAGGGAAATACACCGTCTGGAAGACATCACAA
GGAATGGAAAGCTTGTACCGACTCACGACGATGGAGGTTCCTTCGCCGAATGACGGGTCGATCCCCAGGTCCAGCCCTGCCGCAGCCAGATTGGCGCGGAATG

Figure 7I

GTGCTGTGCTGATGATATTAACGTGATCATCTTGCCGGCGAAGGAACTGGAAGAAAGAGGCGTCGAAAGGCCTGCCCCAGCTGATGCGATTCGCTAGCTTAGC
GACCAGCTGCTCATAGTAGTCTGCCGGCGCGATCCAACGCTTTTCGGTCGCCATATTCCAGATGGACCGATCCGACAGGCCGCCCGTTACTTTCCTGGAGTACAT
GTTGCAGTAGTCGATGCGCGGCTGGGAAACGAACTCGCCGTCAATGTAGATGGCCTTGTGTACGGTGACTTCGCGGAACGGGATGCCGGTGAGTTGGCCGAT
GACTGGTGAGCGGAACCGCAAGAGCGCGTTGTGGCGTTCCTTGCTCGTCGGCGTCGCCGCGTCGATGATTTGGGCTTGAGGGAAACGATGCGCGGCGATCAG
GCCGGCGAGTCCGGCTCCCACGATGATAACTTTGTGATCAGGAATCATGAGATGTTCCTTATGAGTGTACAGAACTTGGGAGGATAAAAAAGGGACCCATTTTC
ATGAGTCCCTTGAAGAGCTAGACGATTCGGTCTCAGAAGAGCGGCGGCTTACTCTTCTTCACCATCGGAACCGTCGGCGCCCTGACCTTCACCGTCGTGCTCCTG
GCCTTCATCGGCCTTCTCGTCATCGCCCTGGCCAGCTTCGTCTTCCTTCGAAGCGATGGCAACCAGATCGACCCAGCCCATGATTTCCAGCTTGCTCAGGTAGCTG
CGAACCGAGGTGCCGTACAGCAAGTGGGCCACCTTCTCGCCGAAGGATTCGATTTCGACCGGCTCACCAACGGTGCAGTGCTCGTTGATGTAAGCGAACACCTT
GCCGCGAGTCGAGAAGGCCTGCGGGGTTCCATGACCGTCGCCGGTCGGGATGAAGTGGGTGGCACGCGGACGGCGCGAACCATTGGACTTCAGGTCTTCGCG
ACGGGCTTCTGCCTTCGCGCGGCGCTCTTCCTGCTCTTCCTTGCGACGCTTCTTCTCGGCTTCGCGCTCTGCCTTCTTCTCTTCGGCCAGGCGCTTGCGCTCTTCTTC
GCGGGCTGCTTTCTGGGCTTCCTGCGCGGCTTTCTTCTCTTCGGCCTTCCTGGCGCGCTCGGCTTCCTTCTCGGCCTTCTTCTGCTCGCGCTCGGCTTCCTTCGCCT
TGGCCTTCTCGGCCTGCTCAGCTTCCTTGGCCTTGGCCTTTTCAGCACGCTCGGCTTCCTTGGCGGCGGCCTTTTCCTTCGCCTTCTCGGCGCGCTCGGCTTCCTTC
TTCTCGCGCTCGGCCTTGCGCTTCTCTTCGCGCTCGGCTTTCTTCTGCTCGGCTTCCTTGGCCTTGGCCTCGGCCTTCTCGGCGCGCTCGCGCTCTTTACGTTGGCG
CTCAGCGGCCTTCTCGGCCTTGCGCAGGGTAGCTGCTTGTTCCTTGGTCAGCTCTTCGCCTTGGGTCTGTTCGTTCTGGTCCTTCTGTTCCATGTTCTTACTCCGGG
AATGTTCAAAGGGATGGCTTATTGGCCTGTGCGGGGATTATCTCTAAACTAATTGAAGAAGGGAATACCCTTAGCCTGAACTTTCCTAAATATTTTCTTTCGGGA
AAGTCCAAACTCTAGGGAACTTATTTATGTTCGAGAAGTTCCTAGCTTTTACGCAAGAACAGTAAGTATTCGATTGCGCGAGTTATCCCAGTATACATCAACTGA
CTATAAGGGATGGACGGCAAGTTTTCTTCTAACATGGCGACCCGTTTCCATTCTGATCCCTGCGACTTGTGGAACGTCATCGCCCATCCGAAGTCGAATCCGCCA
ATGGCCTTCTGCGCCTCCAGCCGCACGTCTTCCTCGACCGAAAAACTCAGAGGATTGAACTTAACCCAGCGTTCAAAGTTCGTACCGATAATGCGAACTTTGGCG
AACAACATTTCATCAGGCTCGTCATCATCTTCTTGCCCTTCAGGAACCGGCTTGAAGTCCAGCAGAATGGCTTGTTCGCCGTTCATGATTCCATATTCGTGCTGGT
TCCCAGTGCATACCAGCTTCTCGCCGATTCCCGGCTGCGCACCTTTGTAGCCGAGGATTCGGCGAGCGCGTGCGTTCAAGCGACGGCGAGTATTGTTGTAAGCA
CAAAGAATCACGCCATCATCGTCCAGGAACGTCCGCATTTCATCATCCGACATATCGAAGCCGGCCCGGACCAATATGTCGTCATACTCGCGGCAGGGCAGGCG
CTTTCCCTGGCGGACGAACATCGACGCCCGAACGATATTGCCAGCGTTGCGCTCGATTTCGGTCATGATGGTGTCACAGCTGTTCTCGTGGAAAATCTGGACGC
CGCGTACAGGAGGAACTTGGCCAAAGTCGCCAATCTCCAGAACCGGAATTCGGTGCGACAACAGGCGCTCTTCATCCCACTCGCCGATCATGGACGACTCGTCG
AGAACTACCAACTTCGGTTTCTCGTCGAGCGAGTCTTTGTTGGCAAACATGATTTCGCCGTCTTCATCTTCACCAATCGGTCGATAGATAAAGCTGTGAAGAGTC
CGGGCATTGACGCAACCTTTCTCACGAAGCCGCGCGGCGGCCTTTCCGGTCGGCGCGATGAAGACTGTCCAGTCCATCGAGCAGCAAAGTTCGGCGATGATCTT
CGCAATAGAAGTCTTACCAGTTCCTGCAAAACCGGCGAGTCGATAGACCTGACGGCGGTGCGCTCGATCACACCAACCGCGATACCAGTTAACGACGGAATTTA
TCGCGTCGATCTGCTGGCTATTAGGTCGGAAGCCGAATCGCTCTTCGATCTGATCGACGGTGAAGTTAGATGCTGACATATTTGCGTTCTCCAACGCTAGGTTTA
ATTGAATTGAGACTCAGTTTAAGCAGACCGTCCACAGACCACCCAGTATCACGACGATATTTGCGGCCGTGCGGATCGACATAGAAGTTTTTCGTGCGCCGCAA
CAGGACATAGTGCCAAGCAGCACCGAGCGCATGGACCCTTCCTTTATAAGGGAAGGCCTTAAGTTGCTCTGCGGCCTTCTTCGCCCCAGGGAGCCAGCGGACG
GTCGAAAGGACCAAGACCGCACCCTTGACAGCCTGGGAAGCGGCGCGGCCGTCCTGTGGGCTATAGCGATGTCTATCGGGGTCTACCCAGTGGTGGTTGCCAC
GCCGGAGCTTCACCGTCCGGGACCGGCCCTCAAACACCACAGTACCTTCGTGAGTAAAAATATGTTCCGCCATGGAATGTTCCTTATAACGTACAGTTCTGCTTT
ACCTCTGCGCAAGAAGAGTATACTATCAGCTGACTCGTCAAAGCGAGCTAATTTAATCCGACTTTACTTCGGCAGGAAAGTGGCCGATACTAGCGCCGCCGCCT
GTACTGCCCTCCAAAACAGAGGATACATTAAATGCAAGAATGCAAGATTTCCCGCGACCAACTCCCGGTCGGCAATCCGAATCCCAATGTCGACAAGACTCGCG
ACCCGAACCTAAAGCCCGGCTACCTGCGTCGCAGTCGCGAGCTGGACCCGGCTCTGGCCGTTCGCATCCGTCGCGAGCTGATCCATGCGGAAGCCTCCGACTTG
GCCATGGCCGGGTGGGTCAATTCCCAGTCCAGCCTCTATGGATCGAAAGCGTTCCCGCGCCATTCCGTCGTTCGCGTGACTGGGATGGCGGAATCTGAAACGAA
CGTCGGAATGCTCATCGGATTCATCGAGCACCGCAAGCACGGTGAATGGGCAGTTCTGGAAACTGGGACGAAAGAAGGCGGCGCGATCACCATCCCAGTCGA
GAGCATCATGCGTGCGTCATTCGCAGAGGCCGAAGAATTCGCCGAGAAATGGAAGCGTAACCTGGGGTGGCGCCTCCTGCGTCAGCTTCGTGAATGCGGCGCC
CTGGCCGGGACTGAAGACGAATTCCTGCGGCGGATAATCAATCGATATGTTCGCGATCTCACGATACTCGCCCACCACAAAGCCGGCGCAGACAAAAGCTATAC
CGATGCAGTGCTCAAAAGTATCGGCGAAGCATGGCCGCAGATTCCTGCCGGAACATTCGTCGGCCACCGAGTCGCGCAACTCCTGATCAATCACAAACTAGGCC
GAGCTGGCACCATCTTGAATGACCTGGTGGACTTCCTGGAGAGGTTCGCGGCCGGTCGTGATAAAGTGCTCAATATCGCCATTTGTAATTGAGGTTAGTGATAT
GCCAGATTTGATGAAGCTGAGTCATAGGCAAGTTGAAGCTCTGCTAGGGCTGTCTAGGAATTCTTACAATTGGATTCACGGTCCTTCGACTGATTCAACCTTGAA
GGCTCTGAGACGAATGGGACTCGTAAATTTGTCCTGGGATGATTCTGTAGCTGGATACATGTTCGGCAGTCAGCCTTGTTGGAGCATAACTGACGCCGGGAAAA
AACGAATCCTGGCAATGCAGGAAACTCTGACAGAAGAGCCTGAACAGCAATTTAATCCCAGCCCATGCCGCCATGAGCCAGGTAAGTCCGATTCTGATCGACTT
GCTAAGCAACTAGAAACCATCGCTCGTCTGGAAAAGGAACTTGAAGCATCGGAAAAGCGCGGGAGCGAACTGGCAGCAAGCTATTGCGACGGCGTGGTCGGT
GATGAATACGGCCACACTTATTGCCGTTATAAGGCGGAACGCGATACAGCTCTGGCCAGGGTCGCTGAGCTGGAAGGAAAGTTGACTGATTGGGTACACGAAG
GATTCCGGCTCAACGAAGCACTGGCAGCGGCACAGACCGCCCACGAATGTACCATGGGCGTAGGCGACGGCGACGGCAAGTTGCTAGTTCATGGTGACCACG
CCAGCATCAAAGCTGCCCAGAAGATCGTCATAGAGCGCGACGCCGCGTTGGTCAGGATAGCGGAGCTTGAATCTAAGCTTGCGGAGACGCAACCCTACAAACA
ACACCCGCAAATCATAGGGTACGCCCGCAAAAAGGAACTTGCGCCATTGCTCGATCCAAGCCAACCCGGTGGAAGCTACATCTATATTGGACTGGACCATCCGG
CCTGCTGGGCGGAAGAGCCACCTTACGAATTCTTGACCCCTTTGTATACCGGTCCTGTGGCGAGTCACAGCGTGCCGGATGGTTACGCCCTAATTCCGGTTAAG
GAGACTGAGGCGATGCACGATGCCGTAATGGCGCTGTTGTACAACGGCATAGCCCGCACCGATACACAAAAGCTGCTGGATGCGTACATCAACGCCGCGACTA
ACAAGGAGTCCGTGTAATGGAACCGAAGAAACCTTCACCAGTAGATGGAGTCATCATGACCAGCCTCGACGTTCTCAGGAAGGCAAAGCCTGAAGCGCAGGAC
GAGTATGCTCTGTCCATGTTCGCAACGGCGATCCGCCAGAAGTTGCAGCGCTCCCGCGACAAGGGCCGAGGCGGATGGATCGATTGCGACGAAAATGTTCTGC
TGGATGGATTCGCCGAACATGCGCTGAAGGGCAATGAGAACAATCTCCTGGACCTGGCGACGTTCCTGATGTTCATGTGGGTTCGCGGCATCGATGATGCGAA
GATTCCCCCGGCGCTAGAAAAGGCGCGGCAGCACAAGGTCACTGAAGCTTGGGACCAGATCAACGAAGGAAGGACAAGCTATGCCGGTAAGGCCGGCGGCA
AGCGACAATTCGTGGAAGTGCCTCGACGCAAAGGGCGCCCGGAGCGGCTCGCATGAAGCCTCACGAAATAAGATTGGCCCAGGCCGAAGAATTCCTGAGAGA
ACTCGGCCGAGGGATTCCGGAAGACGAACGGGTGATGGTCGGCTACGCTGAAGAGGCCACAGTCCAGACCGACGAAAACGGCCGCAAGCTCAACGCAGGCT
GGTGGCCCGTGCCCTGGAAGGAAGGCAAGTACATCAATTCCAGATCCAACGCTTATGCCTGTATATCGTCATCCATCAAGACGCCCAACCCGAAGACTGGCCAG
ATGCGATACTGGCGCGGCGAGGCCTCTTTCGGCCACGGACTGGCGTTAATGGTCGATGACATCGGCTCCGGCAAAGGGTCCAAGGGCGACTTCAACCGCGACG
AGTTCCGCGAGCGCCTGGAGCCGACCGCGATTGTGGAGACTTCGCCGAACAACTACCAGTTCTGGTATTTCTTCAAAGAGCCGATGTCCCACATGCTCCAGTTTA
AGGCATTGCTCTATTCGTTCGTGGACCAGGTGCTAAAGAAAGGCGGCGACAACACCGTCAAAGACGTAAGCCGTTATGGTCGCATGCCATTCGGCTTCAACAAT
AAGCGCGGGGAAGACGGCAACTTCAAGTATGCCGACGAAAACGGCAAGCCCGAACTCGTGCGTTTGTATCACGCAGACTATTCCAAGCGCTACTCGCCAGAGG

Figure 7J

AAATCGCCCAGGCCTTCGGCGTCCGCATCATCATGCCACAGATGAAGAAGGTGGAGATAAACCGCGACGATTGGGTTTATGACCAGGTGTGGCTAAAGTATGC
CGAGCACATCTGCACGAAATACAAAATGGGCGAGGCAGCGGGCGGCCAAGTCCAACAGAATATGTCCGGTAAATATCGCATCCGCTGCCCATGGGGAGACGA
GCATACAAATGGCGATCCATTTGGCGCCTACTTTCGCGGACCGATCCCTGGAGCCGAGCACGAATATGTGTTCGGTTGCGGCCACGATACCTGCCGCAAAGAGC
ATCGCCGGACGTGGGCGGCCTTCACGGATGAAGTCGTGCTACCCTATATCGTCGAACAATTGGAAAGAATCAACCGCCGTCACATCGGTGAGGAGTAGACAAT
ATGCAAAACGATCCTGGAATCCTGATCACAGCCATTGGCTTGCTGTTCCTCGGCCTTATCATCTTCTTCGAAGGCCTAAAGGGATGGAAAATACAAGTCGCAAAC
TTCCTCGCGTCGCTTCTGTGCTTCTTCTTCGGCCTTTCTGCTTTGACGTTCTGGTTCGTCGTGGCGTTTGACGTATTTTAATCGACGAACGGTACAGAAATTTTCGG
ATGGGGACGGAACTTATTAGCTATGCCGGTTTAGGTAGGAGATAATAGCCGTCCCTTTCGCCTCAATATGTAGAGGCAATGTTGAATCCGATCATGTAAAGCAG
AAGGCGGCAAACCTAACATGATTATCGACGAAGATAATATTTTTGATGATGACGAATCAGGGTCCAGTGAGTTCGATCTCACACAGATAGAAGATGCTGGAATG
GACCCTTTGATGACCGCCGCGAGCAAGGCGGCCGATGATGCGATTGCGAGGAACGAAACGCACCGCGCACAAAAGGCGGCAAGATACGCCGAGGCGTATGC
GGAACCAGACTTGAGAAAGCGAGCGCGATTGTTGATGCTCGACCAGGCGTTCGATCTTCCGGTCAGCCGGGTGGTGAAAGGGCCGTTCGATGACTTCATCACT
AAATACAGCTCGACTTCCGACAGCAACTATCTCGCGGTGTACGATACTTTGTTCTGCAAGGGTGATGGAACCGTCCCGCATCCGCACTTCGACGAGTTTCGCGGA
CGGCTGGTGGACCATCGCGGCGTGGCGTTCAACAACAAGACCCTCGACCCGATTGACCTGATGGGCGCCCTCGCGGCTGCGGCCTTGGACGATCCCTCGATTA
AGAAGACGATTGAGACTTGCTGCGTTTGGGCGCGTCGATACCGCCGCAACTCGCTGATAGAGACGTTCGAGAAGAAGATACCGGAGTGGGACGGCGAAGAGC
GAATTAGCACGTTGCTGATCGATCTTTTTAAGCCATTCGACACCGAATTGAACCGGATGGTGAGCAAGTATTTCTGGCTGAGCCTGTACTGCCGCATCAACTATC
CTGGAATCTCGGCGCCGATCTCGCTGGCGTTGATTGGTGGGCAGGATGCGGGGAAATCCTATTTCGGCCTGCTGATCTGCAAGGAACTGTCGGGCGGTCGCGA
TCTGGCTCCCGTCCAGCTCGACCTGAGCCGACACGACCAGACACCATTCCTGCGCAACATCACCGGCAACTCGGTCATTGCGAACGTCGGGGAAATGTCCGGCT
TCAAAAAGGGCGACATGGAACGCATCAAGGAGTTCTTGGTGCGGTCTTCTGATACATTCGACCAGAAGTTTGAGCCGGGCGAAACGATCAAGCGACAATGGAT
CACCATCATGGACGGCAACGGCTACGATGGACTCCAGCGGGACGACTCTGGTAACCGACGTTTCTATCCTATGTTTGTTGCGCAACTGCCCGATGAGGATGGAA
AGCCGAACTGGGTTAAGCCGGGCGATGGCAATGAACCGTTCAAGGTGGACTTCACCGACTTCGGCCGCAAATTCTGGCAAGCGATGGCTGAATGCCGCGCATG
GATCGAAGAGCACGGCGTCGATGGCTACCTGAATATGGTGTCGGAAGCAAACCGCGAAGTCCAGAACTTCTCTATTTCGGAAATGGAGAATGCGCGCGGCGTG
GTTCGCGACGATACGATTGATATGTATCTGATCAATGTCCTGATCAGTTGTGAGTTCGAAGAGGTTAAGCCTGGTGGGAATTCCAAGACTCCTGGGTGGAGGGC
AGACACCGTTTCCATTCTGAAGTGGTTCGATATTCTCGCCAGGAAGAAGCCGATTTCTCGCCATTTAACTCCACACCTGAAAGCGCTGGGATTCATTCCGAATAA
GAACGGCCTGAATGGATGGTGCCTGCCTGTGGATAAGGTCGCGCCTGACTGGTCGAAGAATATGCAGACGACGCTGCCGCCATTCAATGATGCGCTGGTGTAT
CTGTTGAGAAAGGGCGATCCGGATATGACCGATGAGGCTGCCATGGCAAAAATTCGAGCAGTACGGGCAGAGCGAGCCAAGATATTGGGCGAGGATTTCTGA
TAGGTCGATTGAGTTGGAGTGGATTAGGCCGCCTTCGGGCGGTCTTTTCTTTGTCGCGGAGAACATTAATTTAGCTTGTGAACGGGTGAGGCTTGAAAGCTATG
TGGGAATTAGGTTGGCGTGGCGATGGCGTATTATGGGAAGTTAATAGATTTCGGTATTGGTCTGGAGTGTATGATGGTTGGATTTTGCGTGAAATGTTGAGAA
ATTGTGGGTTTGAGGTGGATTTTTGTGTGGAAATAGCCGCAAATTCCTGGATTGCTATTCTGACTGGGAAGATGGGAGGCCTACTGCCGCGCGGGTTTGCGGCC
ATATTCCCTAATTCCCGGGTTTTTCGAGCATGGTTTAAAACTATTCTACAGCGAAAATCGATTGCACAATCCTAATAGAAAAAATCTATCACGGACGTTACCTATC
TTTAAAATTAATAAAATTAATGGTAATTTGGTAATTTGGAATAGTTTAGTCTTTGAAAGCCTCGCGGCACTAAGCCGGTACACTACCCGTCGAGTTTCCGATTCCA
CTCAACTCGCGGCAGGGTCGCCGGAAACTTCCGTCCTTCCAAACCATGGGCAGCGGCAACACCACGGCGGACTAAGCGGCAGGGGCCAAAACTCGACGAGCG
GAACCGGAAATTTGGTCACAGGGCAGAATCGCTCACCTGGACATATTCCTAACATCCGATTTAACATTCAATCCAAACACTCACCGCCACCATCGCCCGCCACCC
ACCAATCCGACCCTCACCCGCCAGCAGACCGCCCATATAACATCCTATAACACCACCTAACACTCATTCACCATCAAACCCACCCAGACCTACAGGCCACCCACAA
GCAGCCCATAGACGCGCTCCCTGGCCCCATAGTACAATCGCGCCATACTCAGTGTCGCGGCAAGCACCAGGTCCCAGCCACCTACCCAGCCACCGCGACGGTCC
AAGAATCGAACTCCAGGGACGCAGCAACAAATGACCGCCAAATATTACAGCCCCGACGATTTAGTCACGCCACAGGAATTCGCTGATCCGCAGTTCGCGGCGAT
CAACCAGAAGCGTTTCGATCTGTACATCGACCTGCGCGTTCAAGGCTATAGCTCCTGGCGGGTCTTCAGAGCGATCTGGGGCGAAGAGCACATGGATGGCCCG
GCCCAGGCCCGCATCTTCGCGATGGAGTCCAACCCGTACTATCGCAAGCAATTCAAAGCCAAGCTGAATGCGACCAGAACGTCCGATCTATGGAATCCAAAGAC
GGCGCTTCACGAACTTCTCCAGATGGTTCGTGATCCCACCGTCAAGGACTCCAGCCGTCTGTCGGCCATCAAGGAATTGAACGTTCTGGCCGAAATCACGTTCGT
TGACGAGTCTGGTAAGACCAGGGTAGGTCGCGGATTGGCCGACTTCTACGCATCAGAAGCCGAGGCTCAGACCGCCACCGTCGCTGCTGCGGCCGAAGCCAAT
GGCTATGTGCAGGACGGCGAAGAGGGCGATTTCCCGTCCCCGACGCCGGAGCCGACCGAGGAAGACCGCGCCAACCCCATTCAGACATAAAATAACATCGTTC
TAGGCCCGAATCGGACCGAACTAAGGCGACGGTAGCGGGTTGGGACGAAAAACGATTCTAGGGCTGTTCTAGGAAGCCGACCAATAACAATCAGAAACGACA
AAGCCCCGGACTCTAGTTCAGAATCCGGGGCTTTCTTTTTGGGTTTCTTATTCTCCAGCTTCGATGATTTCGAAGTTGTATTTGACGCCTTCGTGCTCGAAAGTCA
ACTTGCCGGCTTCCTTCAGCTGCATGCGGAAGCGGATGTGCTTCGAAGAGGGCAGGCCGAACTCGATGAATGCTGCGTTGGTGGACCGGAACTCACCGCGCTT
GCCTTTGACGGTAACGGCAACTCCATGACGCTGAGTGCGCTTTCTGGAGACTTCCGGGTCTTTCCAGGAGTTGGCGATGGCTGCCGACAGGTCTTTGGCCTCTTT
GGCCTTCTCTGGAGCGTTCTTCGCCTCTTCGCGCATCTTCCTGATTTCTTCCAGCGCTTCCTCTTCGGTGATTTCCTCTTCCGGCTTCAGGCTCTCTTCCTCGGCCTT
CTCTTCTTCCTTCTTCTTGGAAGTGCGGGTTTTGTAAACCTTGGCCGGGGCTTCCTCTTCCTGGAAGGCTTCTTCCTCGGCCGGCAGAGCGTTCAGGATGGCGAG
GCAGCGACGCTCGGCGGTCTTGCGGTCGGAGAAGCGCTTTACAGTCGCATCGGCGTTGTGAGAGTTGTAGAAGGCGACCAGTTCTTTCATTTCTGCGTTCTGGA
TGTCGCCGAAGGTTTTGATGGAGTTGGTCATTTCTGCGATCCTCTGTTTTGGAAGATTTCTTTCGGGCTTCGGTTTGTCGCCCCGTTGAAAGAGATTATGCCTAGA
TCGATGCTGCGTGTCTACATTTATTTTAGCAGAATGATGATGAACCCGACGAACGGTTGTCGGATGTGAAAACACCGCAGGACAGGCTGCGGTGTTTTCTGGAC
GATGGTGCGACGGTCAGAAAGTCGGGACCGTGATCGGCTCGATTGGTAGGTCGCCGGGCTTGTCGTTGTCCGACGCGGGTGACGAACTTGACGGTATGGCTCC
GGACCGAAGACCCAGCGGTTCAGGCCGCCTGCTTACCTGCGGAGGTGGCGGAGCTTTTGGCGCTTTCGGAACTGGAGGTACTGGAGGCGCCGGCGGAGACAT
CGGCCCTTCTGGAAGATCGGGAAGGCTCGGCGCTTTCGGTTCGTGGTAAACCGTCGTGTCGTTGCCTGGTTCTGCGGGATCGACGCCCATGAATGGAGTGGTG
ACGCAGCGCATGTTCGGATAGTTCGGCAGCGTTTTCAAAGCGATGGAGTCTGCCCAGACATACGGATTCTTGTGATTACCAGGGCCGTGGCTGATGATCTCGGC
AGGCATGTGGCCGTTGAGGTTCAGCCACTCCGCCGCCCCTTGCCGAGACAGCGGGCTTACCACGATCTGGCCAGTGGCCTCTTCGGCAACAGCGAACAGATCG
CCGAGTTTGAATCCGATGATCAAATAGTTGGACCTGGCCTCGCCGACGAATGCGACAGTTTCAGTGCCGTGATGGATATCTTGATCTTCCCATATGTATAGCATG
ATGCGCCCTCAGTAAGGTTGCTTGATGTGATCGACCAGGGACATTCCGGCCGGAATTTTGAAGCGTATGTACTCGATCATAATCGCAGTTCGGCGACGATTCGT
TCCTGCCTCGTCATTCACGAAGAGTTCGCACTGGTTCGGAATGACTCGCGTCACCAGAGCTTCGCCTTTCGAGCCGTAGAACTTGATGTAGGCTGCGACGCCTCG
CGTCATGTTCAGTTGGATCGTTTCGCAGAGTCGCTGCGCGGCCGACGCGCTGGACAGATCTGTCGGACTGACCGTCACCCAGTAATGAGCATTTGCTGTTTGTTC
TTTGTCAGACATCAATGGTCTCCAGTGAGAAAGCCCTGCCGAGTCGCAGAGGCTGGTTGCTGTTAGTCGCGCTTCAACAGAACGACTTTGTCATATGCGCGATA
TTTACCGCGCCAGTCTTCCCAGTAGTCGCCGGCCGGGCAGGTGAGCTCCAGGGTGATTTCGTCGCGCCAGCATTCGACAGAAAGTACAATAGCCTTGTTCCTTG
CTGCGGCATCTGCTCTGAGCTTAATCAGAATTTCGTCGCCAGTTTTCAGCTCATCAACTCTCACAACTTTGGCCATGACACACTCCTGTTTGAAGAGGCGCGACCG
GAACCAACCCAGCCGCGCCGATGGATTAACGTTTGTGAAGGATGGACACGGCGTCCACGTCGAGGATGCTGATGGTACGGCGACGGCGCGGATTGCTGCGTT

Figure 7K

CATGGATGCGAATCAGGTCAGCAGATGTAGCTTCGTGCACCACCCATACATCTTCTGGCTTCTGCGTCCGGAGCAGGATCGTTACCTCTGTGTTCTGGGCGAGG
CCGTTGCAGATGAACGTGAACTTGGACGAGGGAGTTCTGTACATTTCTAGATTCCTTTTTGGACTTTGGGTCCGACTTCTCAGCCGGTGAAGAGATTATGCCCTT
ATTTTGGCCGCCGAGTAAAGCATTTGTGTATCAATTCTCCCGTCAGGTGGAACCAAAGTGCGGTATCGCTTATGGCTACGCTACCGCGCCATGGCCCTTCTTGCT
CGCACACTGCGAACCACAGGCTGATTTCCATCCTTGCCAGGACTCGGCCGAAAGATTCGAACCTGCGCCGACTGGACAGGATGTCGACATTCACTCGTCGATTG
ACCTCGTACCGGCGACCGTTGATGACGAAGACCAGCCGCAGGGTTTGTCCGTCAAGACACTCCCAGTATCTGGTTTCATATCGGAGCCAATAGCGCTTGCCTGT
CGGCCCTACCATAGTCATCCTTCTATGCTCCTGGCCGCTCCACGGGGACCGGGCGGTGGAGTCGGATCGAATCGACCCAGGATGTAATCGGGCCGACGCGCTTC
CTGCGGACAAACGGCGAGAAGGCGCCATCCTGCGTCCAGGGCATGCTGGAGTTCGTCCGTGCAGCAGTCTTCCTTGAGCAGGAGACGGTTGACGCTCTGGAGA
TTCGGACCAGGGATGGCCGAGCTGGTGTGCGAGTTCCAACCTTCGATGCCGTCCACCATCTGTGGTTGGTTGATGTAGCCTTCGGACCTGCCAGCCAACCGGCT
CGCGGCCAGCTCCAGGCGCTCCAGCATTGGCCGCAGAGCGGCTTCCGGGTCAACATCGTCCCAGAGAAGGACCAAGCTGATGATGGTGTACGGATAGTCCTTG
TCCAGATCCCAGGCCGAAGCGGTCAGACGGCCCAGGCCGATTTCATTACACATCACGGGAACGTCGTTGCTCCATGTGGACGGCTCCCAGTTCCGCTCACCAGG
ATTCCCGATTGTTACGCCTTCCAGGTTCCCCAGGAGGACGTGGAGTTTGCTGATGTATTCCGCCTCCAGCGCTTTCCGCTCTTCGTCGGTCTGGTTGTGGCGATA
GAAGGATGGAGGGCTGACTTTTGCATGGTAGAGTTTCATGGCGGTTCCTCGGTTTTTGAAGGCTTGAACGTTAGAAAATGGTGTCGCAGTATTTCTCGAAAGGA
CTCTGGCGCTTCTTCTCGCAGATCGCGCAGGTGACTTCCAGGTCGGGCAGCTCGCTGTAAGTCTTGCCGAGATACAGCCAGCGCTTGCACAGACTGCGGCCGTC
CGACGTGAAGAAGTGGACTTTGCGAGCATTGCCGGGTTGCGCCCAGCCGCCTTGATCGTTTTTGCGCTTGCTCATGGCGATATTTCCTTTGGATCTGGAATCCAT
GCCGTCCGTTCGCTCACCCAAACTCCGTCTACATAGATCAGGACTGACAGAGCAGTCGCGCCAAACCCGAAGCCTACATAGAATGAACCGGGATCGATTTCCAT
GGTGGCGCTATTGGTGGCGCTATTGAAATCGACTTCAAAGTCGAACATCGAATGGCCGCTCATACCATCACCATGTCGATTTCATTGATGAAGAAATGAACATC
GACACCATCGGCGCGACCGGTGTAACGCAGCCGAGTCGTCCCATCAATGTGGGCTTCCTCGACGCCGATGACTTCCAGGATGGTGTCGTTGCAGTAAAGCTTGA
CGAACATCTTGATGCCGGAGCCAATCGCCGCGAAGGCGATCTGCTTGTACAGGTCTTGCTTGATCATGCTTTGCGCTCCTGTTTGCTGGTGTAGATGGCTTCGAC
TTCGGCCTCAAGCTTCGCCCAAAGTTCGTTGTCCACCGGACCCCATGGTCCGGTCTGGGTGCCGTCAACCGGCGCGAACTTCCCACCGGCGCGACGATATTTGG
AACGGGTCTGGAGTTCGATGATTAGCCGTTCGTAGGCGTTGAATTGAGATGTCATTTCACAATCCTCTTTTGGACGTTCGCGTTTCGATGAGGTGACTATATCTA
AGTCGCCTCATCGAGTAAAGCACTTCTGCGAAATTATTTGATATTCTGTAAGGTCAGGAAGCCGGACGATTTGGTCAGTCGATGGAGCCGAGGCTCCACCCGTT
GCGGGCGAAGGCCGAGCGACCCGACAGCTTGCGGCACTGAATGGAGCTTCCATCGTCGAAAGTATAGGCTGTGGCCCAGTCAAGGCGCTCACGACGTACTGC
CGCATTGGCGATGTCTTCCAGACGGGCTTTAAGGAGTTGCTCGGCTTTAGTCATCTCACACCTCTTTGGTTTATTCACTCGATGAGGTGACTATACCTCAGACACC
TCATCGAGTAAAGCACTTTTGAGAGAATTATCTGAAATTTCTGGAAGCCAGGAACTGTCGCCAGAGCCAGTCAATGTGATCGTTCAGATAGCGCTCGCCATCGG
ATGACAGAGACAGGCAGCCGTCATTGATGCCGAGTTTGGAACTGGCAATCCGTTCGAATTCGAACTGGAGCGTTCCGGGCCGAGGGATATGGTGCAGGCAATA
TTTCTGCACGATCAGCAGTCCTCGAAAGGTTTGCGGTTCGCAATTTCCGCGATCCTTTGCATGCCGATGCGATAGAACTCGGCATCCTCGCGCGCCCGCGACAAT
GCTTCGCGCGCTTCGCAAGCCAACTTGTATTGATTGTTGGCATTGGCGATGCTTCCGTCCAGGCTTCTGTCAGACTCTTCCCGGAGCGCCTTTTGGGACTCCAGCT
CGGCCTCCAGCTCGCGGATTCGAAGGGCGAGCTGGCTATTCGTTTCGGCAGCTTTGTTTTCCAGATCGATGGCCGATTTCGCTGCTGTTTCGAGCCTGTCTTTGT
CGGCCATGAGGGTTTCCAGGCTCTTGTCGAGTGCTTCCAGAAGAGTCTTCTTGGACTCCAGCTCCAGCGAAAATTCGACGTTCTGCGCGGACAAGTTCTGCGAG
TGCTTCAGCAGTTCGTCGATTCTTCTTTGATGGCCCTTGATGGCCGAGTTCTTCGTTTCGACTTCGGCCTCCAAATCTCTGATTCTGAGTTGAAGCTGGCGATTCAC
CTCGGCCGTCTTGTCTTCGCGAGCGATGGAGTTTTGCAGGCATTCGTCCAGACGCGAGTTCTCCCGATCAAGCTCCATGGCCGTCAGGCTTTCGTCAGAAGTCAC
GCCTTCGGATTCGTCTTTCCGTCCCTGATCGGCCCGCAGATAATACTGTCCAGCGGCGAACGCCAGGAGGGCGCGGTTGGAAAACTCAGTAGCGCCCTGCAAGT
AAGAAGATTTGTATCGAGGAACGAACTCGG

Figure 8A

>NC_011810.1 Pseudomonas phage PB1, complete genome (SEQ ID NO: 1)

```
   1 ccttctcttc gtcccagcag aggctatctg ctatcggcca gaactttcga aactgggagg
  61 tgctgacgct tacatccact aggacgattt ctgcttcacc cacgacttcg agcttgaact
 121 tgacgtcacc gtcgatgctg ttgaaaggga ttggcttgga cacgacaatt ctcctgtgaa
 181 tggcgcgacc aaccggccgc gcctgatgat tactcttcgc cttcgtccgc gctcagccac
 241 tcttcgaagg cgaaattgac cttagactcg acccaatctt gaagctcatc ggcgaactcg
 301 tcactgtcga tgtccatcgg aatgcccaga gtctcttcgt tccacagttc ggcattcagt
 361 tcgaactgga tagccggttc gccatccaca ttcagcagga tgcggtctgc gacttcatag
 421 tcgtcgacat cgaagaggaa accgccgctg atgatgtgct ggatgaaagc ttcgtcgaag
 481 ttgctgacgc cgatattgat ctgcttagtc atttttctgg cccettattt ggcgagtttg
 541 tactgagctt tgagggtggt cagcttagct ttcagggcga tcatagcctg gccgcgcagg
 601 ccttccattt ctgcctcgct gatggcgatc ttggcggagc ggatttgatc gttgatctgg
 661 gatttggtca tttctgcgtt cctctgtttt ggagtgtttc gcgtttcgat gaagagatta
 721 tgacgctatt cagaatggaa gtaaagcaga attgtgaaat atttctcaaa gtggacgagc
 781 ggtctgttcg tcaggaatat ttcctcccat ggaaggcgtg tccgcatccg aagactgaca
 841 ggtatccgtt gacttcggat tgtctctttt cggagtcgat ttcgattctt agcatttcca
 901 gctcataccg ggccaggccg ccccactccc tttcgatgcg ttcatactcg gcttctaatc
 961 ggcgcagacg ttcaatcatg ggaatctcct ttggattgtt atagctagca tcattacgga
1021 caaacagtct ttcgtttcgc tgaagagatt atgccgttgg tcagaatgga agtaaagtgt
1081 attaacaata aaattatgtt caccgacgaa cggttgtgct cgaccgtctg ttgcggcgtc
1141 gatatactcg acctattgct gacaccggat tgattagaat gtacaaactc aaccctgcac
1201 tgcgagcggt ctggcgaact cgcgcccgtt acaaagtcat ttatggcggc cgggcgtctt
1261 cgaagtcaca cgacgcaggc ggtatcgccg tttacctcgc ggccaactat agactcaagt
1321 tcctctgtgc tcgccagttt cagaaccgca tcagcgaatc ggtctacacg ttgatcaagg
1381 acaagattga gaattctgag tacaacggcg agttcatttt cacgaagaac tcgatcaagc
1441 acaagaggac aggatcagaa ttcttattct atgggatcgc ccgtaacctg tcggaaatca
1501 agtccaccga aggcattgac attctctggc ttgaggaagc tcactacctt acccaggaac
1561 agtgggaagt cattgagccg accattcgga aagagaactc agaaatctgg atcatcttca
1621 acccgaacga agtaacagac ttcgtgtatc agaacttcgt ggtgaagcca cccaaagacg
1681 ccttcgtcaa gatgatcaac tggaacgaaa atccgtttct cagtgagacg atgctcaagg
1741 tcatccacga agcttatgag cgcgacaagg accaggccga gcacatatat ggagggattc
1801 cgaagacggg cggcgacaaa tccgtcatca acctcaagtt catccttgct gccattgatg
1861 cccacaaaaa actcggctgg gagccggccg ggtcgaagcg catcggcttc gacgttgcgg
1921 atgacggcga ggatgcgaac gccacgactc tcatgcacgg caacgtcatc atggaagtgg
1981 acgaatggga tggtctggaa gatgagttgc tcaagtcgtc cagtcgcgtt tacaatctgg
2041 caaagatgaa aggcgcctcg gtcacttatg actccatcgg cgtcggcgct cacgtcgggt
2101 ctaagttcgc cgaattgaat gactccagcc cagacttcaa actgacctat gatccattca
2161 acgcgggcgg cgctgtagat aagcctgatg atatttacat gaagctgccg cacactacga
2221 tcaagaacaa agatcacttt agcaacatca aggcgcaaaa gtgggaagaa gtcgcgacaa
2281 gattccggaa gacttacgag gcggttgtcc atggaaaggt ttatccattc gacgaattga
2341 tttcgatcaa ctctgaaaca attcacccgg acaaactaaa tcagctatgt atcgagcttt
2401 cctcgccgcg caaagacttg gatatgaacg gccgattcaa agtcgagtcc aagaaggata
2461 tgcgcgagaa gcgtaagatc aagtcgccga acatcgctga ttcggtgatc atgtcggcca
2521 ttctgccgat caggaagccc aaaggtttct tcgacttcta aacacagaaa agcccggagc
2581 gatccgggct tctggtctta ctcggtgcgg ttcctggcgc tgagtgtcga cgcaacggcc
2641 tcgccgactt ccagagcttt ctggcctgct gcgagcgctt cggtttccga ctcgacgatg
2701 aagtcatcgc cttgtccgtc gccgggcggc acctcgacca gcacggcttc ttcgccctcg
2761 aaacgcaggt cataagtctt ctcgacggac aggccgtaac gggcgttgag cgcatcccat
2821 agctgagctt cataggttcg aaggtcttgc agagatttct ggtgactgag catcgccatg
2881 tcgacggccc gttgcagggt ttcgtccagg acgttgagtc gcatgcgaag agaacgaatc
2941 cgctcgacga cttccgcatc cacaatgtgt ctttcgatca tcgcttttca cctttgctga
3001 atgttacgtt atagccgtta tcggccaaat aggtcagggc accttcgaat gaagttccga
3061 cgaggtgcct gagctgcatt tcgcgttgcg cagcgatcca aaatgcagtt ccggagaact
```

Figure 8B

```
3121 ctgcgcggcc ttccgacaga acctttccgt caggtccgtc gattcgaacg tgaacggaag
3181 atagcttcag agtcattagt gaatccctcc actggcttgc gacggcattc tttctgcgcg
3241 agcggatgcg cagtccgggc acgggcaggc ctggcggacg cgctccaact cgtcggcgtc
3301 catgacatag agcttcccat cggaagtgtc gtgcgccatg gcgatgttcg ggaagtcggt
3361 ggcactcagg ccggcgacag cgcggatttc gccccagagc gcttcattct cggcattcag
3421 acgagcggcg agcgcttcgt gctctttcgc tacacgcgcc atgaactcgt ccatccggaa
3481 tgcgaattcc gcatcgatgg cgcgggccga ggccatagag ctgaggtgaa tcggttcttt
3541 cttcatggta attctctttt ggctggggt ttgtggtcta cccaggccta ttcaaagcct
3601 ggtcgtcttg atgaagatga acaagaagac tgcaaacgcc aatagcgttc cagccaacat
3661 aaatactgca aatgccaata gcgttcctga gagcatgctc gcttgattct gcagctcagc
3721 gtactccttg gttgacagcc cttgctgcgc cgcctcggcc gcgaagcggg ttttcgcctc
3781 gataacttcc gggcgcagcg acaggacata ttctaaggcc tcttcccgcg ctttttcggc
3841 ctcgaccaac ctagggtcgc gggccgagac ttcgctgtgc cctggcctcg cgggatgggc
3901 ctgcagcgat ggaggaagtt cggcggccac gactccatag tcggagcagg cccaagcgat
3961 cccgatgagg atcgcgagga tggactggac gattcgcagc atcactttgt cgctaggaag
4021 actcatggtt aatcctccac cgaccgaacg atttccatat tgcgtccggc attggttccg
4081 gcagcgtagg cgcgccgacc gtcactgtct tccagacgca tgagtttggt aacattagac
4141 ttcttgtaac ccggatcgcc gaaatgttcg tggaccgcag cttccttaac caccaccaga
4201 gacgttccgg ccgaagaaac cagctccata cgtttccggg tgatggatct gaggcgatag
4261 ctgatttcct gggtcgcggc gagcttaaat tgcgcggcga ccttgacgtt gaaccgctcg
4321 aaaccttgag ccttctgata ttcccggcac agacggtcta ctgcctcgac cagggagttg
4381 aacatgttca ccgctagctc aacgtcagat ttgtagcctt taaagcggac ggcatggccc
4441 cagcgcttgg tggtgctgcc gtcgcgagcg ctcctggacg ccttcgccga tgctcggtga
4501 ttgttgatgc caccgacgaa atccatgatg caatcattgt acgtcgccac tgccacagag
4561 aagaacttca tccagttcgg gattgcggaa tagtagcgag tagcaatttg ctcgtcgaat
4621 tcttcgcgaa tctcgccggt cacttcgaag tcgtgaaggt catatttatc cttcagcttc
4681 ttcacgcgtt ctgccgcgat ggcagcttcg tgcggactgg aagagtcggc cgccatcgca
4741 gtcagcttgc gaatgcgatc tttcgccttc tcgatggctt caggagtgaa ttcgttctgg
4801 tcggtcatgg tcggttcctt ttgtctgaag gtttcgcgtt tcggatggagc tattctgcct
4861 tcatccagaa tggaagtaaa gcattttctt ccactatttc ggaagagcct ggaaatagct
4921 ccagatccaa tcgcctgcgg ccaggacaac gatgagaact gcgaagaaca cgactgcaga
4981 gaccaattgc gcgccaggct tcagcttggg atgactgagt ttgtgctcta ccggattcgc
5041 cggggcgctg gcgctgggcc cggcgtcttc tggaccaaag ccggcgccgc gctcgcgtgc
5101 ctggatagac gctatggatt tcaaatactc ggtctgcttt tgcgactctt cgtagatgcc
5161 ggcgacggcg aaccagagtg cgaacactac ggccgtgcag acgacccagg ctccggtcag
5221 aaggatggcc agcggaccga tgaggaagac ggaagccgcc aggatgatgg cgccgcccca
5281 gatgatgaag ccggccagac cattggtgat gtcgatacag aatttcttca tttttttggt
5341 tccttcggtc aagggatgga tgggatttgg aattcggcgc cgccgaggac atcaatgacg
5401 acctcccaga gcgtcggaac cgaccactga taacggtcga agtcggtttc aggatcgact
5461 cccagggtta cataggaagt ggccggccat ttgtgaacgg cgcctttttcg catgagagcg
5521 gccacgcgac cgtcaccgag cggattcgtc ctgtgaggaa cataagccga catcgaatat
5581 tgctgtccag caccaatgat gaattcttgc ctctggcgca gacatacaga gcctacaggc
5641 tcccaaccgc gaccgccgca ggcctggcga gccgaagaat gctcataccc ttcatgagtc
5701 aattcaccga gacgcgccga acggtccacg taataatttg tattctccag agacccaacc
5761 agaaccaagg actcgaaatc gaatcgatga tcgtggatgg aagagtgatg gaaacaaagc
5821 cggcgcggca gctccggatg ccacacatgg aggcgcccgg ccgggagctg gacctggatg
5881 aagcccaggc cgtgcagcgt gattctgtcc ttcatcggat cagggacggt gtccatggat
5941 aatcctcagt agcagaagtg gatggtaaag gttacgatgg ccaagccggt cgcccatagg
6001 agggcgaacc aggccatggc tttgattgta aggtggatca tccgaagaac tttccggcgc
6061 agatggggcc gatgcccatt tcgatggatg cgtgattggt caactcgcga ccgcagcagg
6121 agcattgacc agtcttccga ccgtaggcga ctgccgattc cattggcttt tcgaacatct
6181 tcaggatatc gccatactct gtgtcggtgc agtcgcggct cttgatgaat ttgccgttag
6241 tgatccggcc gaggtagatg tcgcccagga catacagact cccggcgttc cggctgttag
6301 cgctagcctc tttgaccaca acgatgagag gctcctcacc ttcgccagcc agacgcattt
6361 tcgggcgctt gatgccagag tctttcgcct tctcaaacgc cttctcgatt ccggaaatgt
6421 ccagagtcgg cgcagcagcc tcctgcgcgg ccactttctc gcgatgtttg gcgaggtttt
6481 cgatagctcg tttcgcagca gcgatctgat tttcggtcaa ggagccatat ctgtaaagag
```

Figure 8C

```
6541 aatccttaag gctctgggca aaactgaaag agttgtcggt ccaccactcg atgatgtccg
6601 ggtgagcggc ttcgaaagcc tgaattttaa ggccgcgata ttgctcggcc ttctggactt
6661 tctcgatgcg cttttctgca gccttagcac gactcttggc gcgttgctcc gggctgctct
6721 tgtactcttt atatccaacg ccgccgcagg caaagcaggc gcgaccataa gacgaaggac
6781 cacggtacag gccagtgcct gcgcatttgg ggcacttttc gcgatacagc ttcggttcct
6841 tccaggagtt cgggcgggca cccatggaca cctcttccag ggtcttcggc gcttcgttgt
6901 tgacctctac ggtagcgaag tcatcgccca ggtcttcgaa gccgttgaac agattctctg
6961 ctgcgttcat atcgattctc ctgtttggaa agttcgtttc gatgggttga ctatactcca
7021 taaatggaaa cgcggtagca cttcacgcta ccgttcgtcg ggttgctgac gatcaataaa
7081 tgtcgctgct gatcttaaac ccatgctcag cgccgtcgtt gtagtcatac tcagcatagc
7141 tgtcgcagta gtcattcaga tgctggatga ttccaagaac gtcgttagcg accctgtgac
7201 gcttcgccgc gatggtcttg gcaatgctgt cgccgacttc cagagtttcg gcggtccggc
7261 gatgaatcag caaacggctc caaagataga gtcggacccg gcgaatcatg tcatgatggc
7321 gcctcagtcg gctctgcaac ttttcaattt cgaattcgcg agacttgact actcgtcgaa
7381 gctgctgaac ttccaattcc aaatcggcct tagtagccat attcacctca gaaagggaaa
7441 tcgtctgagg ctccaggaag ctcgacaatt gttgttgagc ctgagcggtc gagtatgcac
7501 ccgaccgatc ctgccctatg ggataatgc ctgcacgaac cgtaacaagt aacttctttg
7561 acgattcgcc atgtcgatcc tccacaccac ctacatgctg gtgggcgctt cgacttcagt
7621 tttcgttcgt ccaggacggc tcgtctgtcg caggaaaggc agcgagcctt aaccgacgta
7681 accatgagtg tagtcgatca tgcgaatgag ttcgtcatcc accgattctc tcgacttcaa
7741 accgttcaac gaatccgact ggccgttgca atttccatta atatccatgg aagacagaaa
7801 gcctgccgac accactgtga tgtcaacttt atcgccagcc ttcttgaagc cttcgcattc
7861 ggcgtcgagg gccaccaacg cactcgcggc catgttgacg tgactgatta agtcggggaa
7921 gattacggga acttcacgag acattccccg gaccgtcatc ttcatcacta catatttcat
7981 actcactatc ctttttgtgt gtgaggaaag aatttgctgt tttccggatg gtggaaacgc
8041 tcggccgcag gcggtctttc ttccggacac tgaatcgtcg aaggcgggaa aaccgcgcta
8101 gagattatcg ccgcgagcag cgcagcggat gtcgacatcc acagggcagt ttccagactg
8161 acccgcactt ccggtcggcg cggcttcatt cgctccaacc ccttcccggc tcataagacg
8221 ggatgctgcc gccgcgaatc caactgtccc acatatggtt cagaccagtg ggcggctggg
8281 gcggcggact gtaaaagccg ggaacttctg tactgctgag gaaataaggc gtgcaaacgg
8341 cccgaacaac cagttgatgt cgctcccaca tcttatcaat cgctcttagc atgacgtctt
8401 cgcactgagc tttgctgtcg aaccgtctgc tggtatgatc cggcatctgg acacagccat
8461 cgccagtaca aaggaaagca gtggcgatcc atactgtgat gcttgccatt tcttcaccct
8521 ctttggtaga tgagcagatt ttattccatc tgctcttcag aagtaaagcg cttttcgtcg
8581 ggataaatgc cgatgatgtc tgcgtcgagc atccaaatgt ccacggacgg atcgtcgcta
8641 ttgatctgat acaggtggta caattctttc tcgtcacgcg ccgattcacc gcgaggttcg
8701 acagccaata tgcggccgtg cccttcgccg tgctcatcgc gatacatgac gtgatctccg
8761 acttcatagc actcttttct gacaaggcgc gagcgcgagc tgttcggcga ttccactacc
8821 caggaatcca caactgcgtc tttcacattg ctgtaccact tcgcagattt gtcgcagtcg
8881 aacacgccca gaacttcgcc gtccttcaac acgatatgta cgataggaag aagaggattc
8941 atgttaatct ccattggttg ataattagag tctaatctgc cgaaaagttc ccgtaaagaa
9001 ttattttctc ataactgatt agttgcgact gttaatgtga tgtatctgtt tgaatctctt
9061 ttgaacgttt gatgtttccc ctataataag tgcacacaac cagcaaccgc atggaattaa
9121 aatgtttaaa ctttcctgga tattcgggcg caaaaaggaa taatgttgcc tgttctgaat
9181 cggcgccgga gaaagtcgca cgaatccctc aacacgatcc gctcgaccct atgattaagc
9241 tggggaagat tcgcggctgg aatgtcgagc cggagaaagc cccggtcatc cgtagcgtga
9301 aggatttcct ggagccgggc ctatccgtcg caatggacag tgcgtatggt gacggaccca
9361 ccccagccgc gaaagctgcc gctggcggcc agaatcccta tgtagttccg accatgctgc
9421 aggactggta taactcccaa ggattcatcg gataccaagc ttgcgccatc atttctcaac
9481 actggttggt cgacaaagct tgctccatgt caggcgaaga cgccgcgcgg aacggatggg
9541 aactcaaatc ggatggccgg aagctgtctg atgaacaaag cgcgctgatc gctcggcgcg
9601 acatggagtt tcgcgtcaaa gacaacctcg tcgaattgaa ccgattcaaa aacgtcttcg
9661 gcgttcgaat cgctctgttc gtcgttgagt ctgacgatcc ggactactat gagaagccat
9721 tcaacccaga cggaatagcg cccggctcgt acaaggaat ttcccagata gatccatatt
9781 gggcaatgcc tcagctgacc gcagagtcca cggcagaccc gtctgccgaa cacttctatg
9841 agcccgattt ttggatcatc agcgggaaga agtatcatcg cagccatctg gtggtcgttc
9901 gtgggccgca gccgccagat atcctgaagc cgacatacat tttcggaggc atcccgctca
```

Figure 8D

```
 9961 cccagcgcat ttacgagcgc gtgtatgctg ccgagcgaac tgcgaacgaa gcgccgttgc
10021 tggcgatgtc gaagcgaacc agcaccattc acgttgacgt ggaaaaggcc atcgcgaatg
10081 aggatgcctt caacgcccgt ctggcgttct ggatcgccaa tcgagacaac catggcgtga
10141 aagttattgg tattgatgaa accatggagc agttcgatac gaacctgtcc gatttcgaca
10201 gcgtcatcat gaaccaatat cagctggttg cggccatcgc caagactcct gcgacgaagc
10261 tactcggcac ttctcccaaa ggattcaacg cgactggtga gcacgagacg atttcttatc
10321 acgaagagtt ggaatcgatt caagagcata tattcgaccc gctgcttgag cgtcattatt
10381 tgctgctggc aaaatcggaa gcaatcgatg tacagctgga aatcgtctgg aaccctgtgg
10441 attccacaac cagccagcaa caagccgagc tgaacaacaa gaaggctgct actgatgaaa
10501 tttatatcaa ttccggcgtc gtgtctccgg atgaagtccg cgagcgcctg cgtgatgatc
10561 cgcgctccgg ctataatcga ctcaccgacg atcaggccga aaccgagccg ggcatgtctc
10621 cggaaaacct ggccgaactc gaaaaggccg gtgcacagtc ggcgaaggcg aaaggcgagg
10681 ccgagcgagc cgaagcccaa gcgggcgccg tagaaggcgc aggcgaccca gttccggccg
10741 ctccacgcgg tactaagccc ctcgcgaaag cggccgagga aggggccggc gaggccgcta
10801 caccgccgtc gcggccgaac cccagggccg agcttcggaa cctgctgtcc gatctactgt
10861 cgaaactcga agccctggac gacgcgcagg ctccggacgg cgtggacata gagcaggatg
10921 acgcgccagg tctgaagaga acgtcaaagc cgagcgtatc gggtatggag ccttcggtgt
10981 tttcgtccaa ccgcatcgtc ggccctcgtg atcattctga actccagagg atcaaggtca
11041 atggaattac taccttgatc gaaaatccgc gcggaagtat ccggcaaggg aaggacggga
11101 gctggcgagt ccagatgaag caccactatg gattcatcaa aggtacgaag gggggctgatg
11161 gggatgaggt cgattgcttc gtaggcccga accttggttc gaaacgggtc ttcgtcgtca
11221 accaggtgaa caaagatggg caattcgacg agcacaagtg catgctcggt ttcaacaaca
11281 ttaacgacgc caagtctgga tatctgtctt gcttccgtcc gggctgggat ggactcggct
11341 ccatccatga agttgatctg cccgccttcc gtcgttggct ggcaaatggc gacacgacga
11401 agccatttgg aggcaagtga tggcgttcaa agcctccaag aaacgcgaac gccgggggcc
11461 tcttccagtc ggaagaggca agcccataat tccttctgct ggaatcgaag cctggtatcg
11521 aaagcaaatg aaggatatgg ccagactcat gatcgccgat tatcgaagtg aaatcgagaa
11581 ggccatatcc cagcctgcgg cagaacggtt tttcgcgaaa gacgaatcgg tgaacgtcct
11641 gttcaagatg actctgcgaa gccttcagca gcgatggaat cgcatctttg aaggtttcgc
11701 ggccaagatc gccccggagt tcgtcaatcg ggccgacgaa gccgcgaccg ctgcgactct
11761 acacagcctg tcggtggccg gcgtcgatca gccgcgagct tcatacaatg agagcgtcag
11821 gaacaccctg gaagccgcga ctacttacaa ccatacccto atcaccaaca ttcaagagga
11881 agtccacgag aaaatttaca catctgtaat gttgtctctg acttccccaa acccagagga
11941 acaaggaact tctggaataa caaatgcact tcgagaagtc ggaaagtttt ctgaaaaccg
12001 aatcgaactc atcgcaagag atcaaaccag taaactttac agttcgttga gtgatgagag
12061 aatggcagag aatggagtcg aagagttcga atggatgcac tcttcggcag ggaagacgcc
12121 tcgccatacc cacctggaaa aggacgggaa aagattcaaa ctgaatgacc ctagactttg
12181 ggaaggtcca aaggccgacc aaggaccgcc aggttgggcg attaactgcc ggtgcagaaa
12241 aatcccgatc atttagtcat cgataggagt gcgatatgcc gttagtccat ggaacttcca
12301 atgaagcccg ttctgaaaac atcaagcggg agattgaagc agggaaagac ccgaaacagg
12361 cagtcgccat agcctattcc gtccagcgca gcgagaaaga gaagaaggcg aaagattgtt
12421 cgcatgaact cgtcgctgat cttcgcgccc tggtagactc gctgtcgagg ctcgtgaaat
12481 gaaccgaaag acatgcatac gccgactcgc gaccgatgtg atcaaggcca atattaacgg
12541 cggattcttc agcctgaagt ttgccgcagt tgatctggcc atcatcggcg tctcaatcct
12601 gattgctttc ggcggatgat gccgcgagaa tccggattct gactaaaaat tctggtccgg
12661 atagccgcaa attaccgttt ctgggaaata gcggtaattt ggaaatccta ctgccgcaag
12721 gctttaacag gctaaattcc taatttccga tttcgccgca tgccgcaaaa gtatatagca
12781 tgggaaatta ggaataacgt tctaatagaa ttcatctata agtaacgtta taatataacg
12841 ttaatcgata tgctctatac gcattgaaat tcaattttta atcggtaaat tggtaatttg
12901 gattagttta aagattgaaa gtcttgcggc agtaggccta gacaaatccc gtcaaatttc
12961 cgaaaccaat ttaccagttt tcgcggctga ggaagtccgg taattaggtc acaatacaga
13021 ttctagtgta aattaacagt cgcggctaca tcgaattatt gttccgctta tttaccctta
13081 gatgtcctgc gtatataata cagccatagt ccacgactct tcgaattaac gatggcaaag
13141 tcgaaaagaa aaattgacga aaatggatat atgaccatcg agggctgtcc aatcagctct
13201 tatggcattt tccaatattc tgccggtcaa ctcggtcttc cgggcgatcc gatgcggatt
13261 gtcaacgtgt atcgtccgga gtctgccgtt agcgatcctg agtacatcga atctctgaag
13321 aatctcccgc tgatcgacga gcacgaaatg ctgtcgggat tcgacggcga tgacgatggc
```

Figure 8E

```
13381 gtggctcccg aagacaaagg cgtggaaggc atcatcacag ccaacgccta ctacgaagct
13441 ccatgggctc gcggcgatat ccgcatctat tcccgcaaca tgcagaatca gctggaaagg
13501 ggcaaggaag atctgtccct aggctatagt tgccgctaca ctgagcaacc cggcatctgg
13561 aatggaacgc cttatgaagt cgtccaggac aagatgcgcg gcaaccacat cgccctggta
13621 aaagagggtc gtgtgccggg ggccagagta ttggatggtc tgtgctttga ccatctcagt
13681 tttgatttca gaccatccga tgagggtaat gaaatgggtc tcaagaaagc caagcagaag
13741 actcctgtcc agcgcgcagg acaagctgct gattcggcgg tcgaagagtt gcgcgccctg
13801 tggccgaagc tctctgcatc tgtccagaag ttcctgggcg aagaggcgca ggagccggag
13861 catcaggaag gcgcaaccgc tccggccgaa ccgaccgaca gcgagcacat gaccgagcat
13921 ccgactctgg aaggcgctca ggaagacgac gaagagcacg aagaagcgcc gtccgttgtc
13981 gatccggccg tggtcgccgt cgagccggaa cagcaagaag gtgccgcatc cgaaatgtcc
14041 ggtgaaggcg aagtcgccga actgatctcc caggtcaagg ccattctggc tcgactggaa
14101 ggcacggtag ccgaagaggc ggacgaagaa catggcgaag gtcaagatgt cgtcgagggc
14161 ttggaagaac agagcatcct ctgcggcgcg caaaccgcca gcgacgatgg tggtgagggc
14221 aaggataaca gcgaggaact tcctgaaatg gcacaaaaga acgcgcaaga tgctgcaatt
14281 cgtggtctct atcgcgacat tgctgctaaa gatcgcctct acaagcgtct tagttccgtg
14341 gttggtgcgt tcgaccaccg agctatggac tcggctgaag tcgctgttta cggcgtgaag
14401 aagctggcga tcagctgtga gaagggccag gaagttctgg cgctcgacat gtacctgaaa
14461 ggcgtcgaag ctgctcgtgg cgcggccagc cgtcaatcga aagcccagga ttcggccagt
14521 tctgctccgc agtgcgccga gctggacagt tacctgaagg gggagtaacc catgttccag
14581 aaacaagtct atcgccagta cactcctggt tttcctggtg atctgatcga ggacggcccg
14641 aagcgtgcgc ggccgggtcg gatcatggcg ttggcatcgg tcactccggc cgcgactgcc
14701 accggcccca accgcatcag tcgcgcgttt ggttacgcag gtgatgtcgg ctccctcggt
14761 gaaggccagc cgaagaccgt tgccgcgcgc gcttctgaag tcgtggtcgg cggcgcgacc
14821 ttcttcggca tcctcggtca cccgaagcat tatgctctgt acgggtcggc cggcgattcc
14881 ctggctccca gttatgacct gcccgacggt tccgaaggcg agttcttcga catggccacc
14941 ggcctggtcg tcgaaatctt caacggcgca gaagccgctc tggatttgag ctacggcgat
15001 ccggtggcat atgtaccgaa caacctgcct accgccgaca acgccctggg cctgccggcc
15061 ggcgccctgg tcggtttcaa ggccggcgcc atgccaaccg gcctggttca aatccccaac
15121 gcgcgtatcg tcaatgccat cagcctgcct gcccagtcgg cgggaaatct ggtagctggc
15181 gttaccatcg tccagctcac gcagtaagga ggcgtcatga gccatatcag taagacccat
15241 tcgcgcctcg caggccgtca cgcaaaacca ttcgacctga agaacgtcac ccacgaagcc
15301 gtggccgccc tgagtcgcat cggcctggta ttcgatcacg ccgtcgtcca ggaccagatc
15361 aaggccttgg cgaaggccgg cgcattccgt tccggctcgg ccatggacag caacttcacc
15421 gccccggtga ccacgccgtc catcccgacc cccatccagt tccttcagac ctggttgcct
15481 gggttcgtga aggtcatgac cgccgcgcgg aaaatcgatg agatcatcgg catcgacacc
15541 gttggctcct gggaagacca ggaaatcgtt cagggtatcg ttgagccggc cggcactgcg
15601 gtggaatacg gtgaccacac caacatcccg ctgaccagct ggaacgccaa cttcgagcgc
15661 cgcaccatcg ttcgtggtga gctgggtctg ctcgtgggta ctctggaaga gggccgcgct
15721 tcggccattc gcctgaacag cgcagaggcc aagcgtcagc aggcggccat cggtctggaa
15781 atcttccgca acgccatcgg tttttacggc tggcagagcg gcctgggcaa ccgcacctat
15841 ggtttcctga atgaccccaa cctgccgcca ttccagactc cgccgagcca gggctgggcc
15901 actgccgact gggcaggcat catcggcgat atccgtgagg ccgtccgcca gctgcgcatc
15961 cagagccaag accagatcga cccgaaggcc gagaagatca ccatggccct ggccaccagc
16021 aaagtggact acctgtcggt gaccacgcct tacggcattt cggtttctga ctggatcgaa
16081 cagacctatc cgaagatgcg gatcgtgtcg gctccggagc tgtccggcgt ccagatgcag
16141 ggccaaacgc cggaagacgc cctggtcctc ttcgtcgaag aagtggacgc gtccgtcgat
16201 ggcagcaccg atggcggcag cgtgttcagc cagctggttc agagcaagtt catcaccctt
16261 ggcgtcgaaa agcgggcgaa gtcgtatgtg gaggatttct ccaacggcac cgccggtgct
16321 ctttgcaaac gcccttgggc tgtggtgcgc tacctcggca tctaaccgat gctgactcac
16381 caaaggccgg gcttccggcc tttgttcact ctgactctga ctcggttgta ggggccggtt
16441 agggcataat taataggact acgccaatga ctgtttacat cgtttccgca atgactcaat
16501 ccgtgtctta caatgcgtat gacacctctg atccgtccaa tcctcgcctc cagagaaagg
16561 tgctgattcg cggccgcgct ggtatcgcat ccgaaacctc cggcttcggc gacatgattt
16621 ccgacgcatc cgggcgcccg atctggacgc cgcagggcga ttgcacggcg gtgagcgatt
16681 ccgatttcga actgcttcag tccaacaaaa tcttcatgcg acacatggag aagggatatc
16741 tgcgagtcgt gaaaaccgac atcaccaatg accaccagcg gattgcgaaa gagactcgca
```

Figure 8F

```
16801 ccatggagcg cgatggcttc caacctctgg attctactcg cctgaagcag aagatcaaag
16861 tgactactgc cagcgcttcc caggaacaag agttccgggt ttaaccgagg gtttcggtat
16921 ggtaattttc gacgagcaaa agtttcgaac gctgtttccg gagtttactg atccggcttc
16981 ctatccggat gtgcgcctgc agctgtactt cgacattgcg tgcgaattca tttctgatcg
17041 ggattctcca taccgaattc tcaatggcaa agccttggag gcctgtctgt atctgctgac
17101 ggcccacctc ctttcgctgt cgacgatgca agttcagggc gcggccggtg gcggggtcac
17161 agcaggcggg actcaaggcg gtttcatcac tagcgctacg gtcggcgagg tcagcgttgc
17221 caagctcgcg ccccctgcca agaacggttg gcagtggtgg ctttccggga cgccttacgg
17281 tcaggaactg tgggcgctcc tgagtgtcaa ggcagttggc ggattctaca tcggcggcct
17341 tccagaacgt cgaggattcc gtaaggttgg agggacgttc tggtgatccc tggagcgaat
17401 ctgctgcgta tggcatttag cgtcatagga acgcagttcg ttcagtatcg caaattcgag
17461 cagaggacga agaatagcca ggcgcagtac gtttctgtgt ttggcgagcc attccaattg
17521 gccgcttcca tccaaagggt tcgtcgcgat cagtatgtcc agttcaatct ggagtttcaa
17581 cgaaattacg tcatgatctt tgccaacttt gagatggttg acttggatcg agatttggcc
17641 ggcgaccagt tcatctggac cggaagagtt tttcaactag agtctcaagg ctcttggttt
17701 tatcaggacg gctggggagt ctgcttagcc gtggatatcg gtacagccaa actagctgaa
17761 gacggaaccc tgactttcta ggtggcttat gttcgacggc gaactgatag aaaaattggt
17821 ggtcgagctt acttccgcca tgacgtcagc caaagaaact ttgcagtttc ctgattttga
17881 ggttgtgcag aaagcccagc cgacccaaca gggcacgtca accaagccta ccatcttctt
17941 ccagaagcta tttgacatcc ctcgcggctg gccggcaacc gattggtatc tggacaacgt
18001 cgccagaaaa tatgtagaaa ttactcgaca gcatgtcgag acgacttttc agataagttc
18061 ccttcattgg cagaatcctg agatggatca cgtagtcacg gcagccgata tcgccaatta
18121 cgtgagagct tatttccagg ctcggtccac cattcagcga gtcaaggaac tggacttcct
18181 tatccttcgc gtgtctcata tatccaacga ggcattcgaa aatgacaatc atcagttcga
18241 attccaccca agttttgaca tggttgtaac ttacaatcag tatattcgtc tgcacgaaaa
18301 cgcagcatat tcagccgatg ggcgctgat aggcatatga tcctgagacg cgattcagaa
18361 ctgatcgccg cgcacctgca gatgttaaga gccatgcgcg gcaggtccgt ttcggccgga
18421 tggtattcca ccgctcgata tcctgataag gcgggcggat cggtcggaat acaagtcgcg
18481 agaatcgcgc gcctcaatga gtacggcgga actatcgacc atccgggcgg gaccaggtat
18541 attagggacg ccattgttcg gggtcggttt gttggcgttc ggttcgtcag aaacgatttt
18601 ccgggagaaa ccgaggtaac aaaacctcac aggattacaa tcccggctcg accgtttatg
18661 cgatatgctt ggaacttatt ttccgcagat cgcgccgcaa tccagaatcg aatagccatg
18721 aggctggcca gaggacaaat cacgccggat caagcgcttg cccagatcgg cctggcgttg
18781 gaaggataca tagccagaag cataaggacc gggccatggg tggctaactc agcatctacg
18841 gtcaggagaa agggtttcaa cagaccgctg gtcgatacgg ctcacatgct ccagtcgatt
18901 agcagcagag taacataaac caggagatca tccagtgatc agtcagagcc gttatatccg
18961 gatcatttcc ggcgtaggcg caggcgctcc ggtcgcaggc cgaaagctga ttctgcgcgt
19021 catgaccacc aacaacgtca ttccgcctgg aatcgtcatc gagttcgaca atgccaacgc
19081 ggtgatgtct tacttcggcg cccagtctga agaatatcag cgcgctgcgg cctacttcaa
19141 gttcatcagc aagagcgtca attccccgtc cagcatcagc ttcgctcgct gggtcaacac
19201 cgccatcgcg ccgatggtag ttggcgacaa cctgccgaag accatcgccg atttcgccgg
19261 cttttccgca ggcgttctga ccatcatggt cggcgcgtct gagcagaaca tcacggccat
19321 cgatacgtcc gccgcgacct ccatggacaa cgtggcgtcg atcattcaga ccgaaatccg
19381 caagaatacc gatccgcagt tggcccaagc caccgtcacc tggaatccga ataccaacca
19441 gttcaccttg gtcggcgcta ccatcggcac cggcgttctg gccgtggcga aatcggccga
19501 tccgcaggac atgtccaccg ccctcggctg gtccacctcc aacgtcgtga acgtcgccgg
19561 tcaggctgcc gacctcccag acgcggccgt ggccaagagc accaatgtca gcaacaactt
19621 cggctcgttc ctgttcgccg ggcgaccct cgacaacgat cagatcaagg ccgtgtcggc
19681 ctggaacgcg gctcagaaca accagttcat ctatacggtt gcgacctctc tggcgaatct
19741 cggcgctctt ttcgacttgg tgaagggcaa ctccggaacc gcgctgaacg ttctgtctgc
19801 gactgcctcc aacgacttcg ttgagcagtg tcccagcgaa atcctggccg ccaccaacta
19861 tgacgagccg ggcgcttcgc agaactacat gtactatcag ttccctggcc gcaacatcac
19921 cgtgtccgac gataccgttg cgaacaccgt cgacaagagc cggggcaact acatcggcgt
19981 cacccaggcc aacggccaac agctcgcgtt ctaccagcgc ggcattctgt gcggcggtcc
20041 gaccgatgcg gtggacatga acgtctacgc caacgaaatc tggctgaagt ccgccatcgc
20101 ccaggccctt ctggatctgt tcttgaacgt gaacgccgtt ccggccagca tggtcggcga
20161 agcgatgact ctggccgtcc tccagccggt tctggacaag gcgacttcca acggcacttt
```

Figure 8G

```
20221 cacctatggc aaggacatca gcgccgtcca acagcagtac atcacccaaa tcaccggtga
20281 tcgtcgcgcc tggcgtcaag tccaaacctt gggttattgg atcaacatca ccttctccag
20341 ctataccaac agcaacaccg gcttgaccga gtggaaggcc aactacaccc tgatctattc
20401 gaagggcgac gcaatccgct tcgtcgaagg atcggatgta atgatctaac ggtttgcggc
20461 ggactcgacc gccgcaacct tccatgaatg gagtgaggaa taagcaatga tcaacatttc
20521 tgcgttcggc tcgattgccc aattcacggc aagcagaacc ttcccgaacg gattcacggt
20581 gaccgagttc gctgatgatg cggacccccat cgacagcccg ccgttcactg cggctgatac
20641 cggcgtcggc ctcaatggcg atatggtggt ttggaaccgg gccaacatcc tggaagtcgt
20701 cgtcaacgtc atcccgaaca ccgagggtga gcgcaacttg gccgtcctgc tggatgccaa
20761 ccgcaccgga aaagacaagt cgggtgctcg tgatgtcatc ggtctggtcg tggcgatgcc
20821 ggacggtagc aaaatcacct gtaccaacgg cactcccatc gacggcgttc tgatcaatgc
20881 ggtggcgagc gttggccgcc tgaagacgaa gccgtatcga ttccgtttcg agaaagtagt
20941 caaagccggt actagctgat gaagaagatt ccgctgacag cagtcccgaa tcaggcgatc
21001 tcatttaacg ccggcagcag ctattggaag attcgtctgt accagaatct ggatatgatg
21061 aatgccgata tcagccgcga cggcgtgatc gtttgtcatg ggtccgctg cttcggcgga
21121 attccgcttc tccagtatag ccaccagtat cgacccgact atggcaattt cgttttcgac
21181 cgtgacgccg attggacgtt gttcggcgac ggcataaacc tgttctatct ggacggtgtc
21241 gagttcgcag aatatcaggc gctggccacg aggaaagaat gagcacatca acgatcagaa
21301 ccggggtgaa caatgacatc cttttggacg acaatggaaa catggtcatt ctcagggatg
21361 tagaagcgtg cgcccaggac gttcgggcgg cgatgctcat gcgcaccggc gaaaacattt
21421 tcgatgtgga cgccggtgtg ggatattttg aatatatctt ctcgccgcag aagagctatg
21481 atgatgctcg caaatccatc gcggatgcaa ttttgtcatc gccggacgtg accggcatcg
21541 agcaacttga catcgacatc accggtgaag tcttcggcgt cgatgcgaaa gtcatcacca
21601 tccacgggcc tgtaactgca ggagtttgaa atgagtacca tccgcatcca atacgccaac
21661 ggcacccaac tattcttgga cggcaaaaac ccgccgctcc tggacccgct gccttctttc
21721 aacccgtcgg tcgaagacct ggaaggcctg gaccgcgaaa agaacactgg caagggcaac
21781 tcttcgtcgg ccggtattcc cgttcccccg gtgaacgtcg atccgaatgt cgacaacggc
21841 ggtgccatcc cagctccggc atcgaccggc acccctgcgg ccggatcgac cccggaaagc
21901 gcccaggaag cccctgcaga gggccaaggc gacgagaaag ggtccgagac gcccccgact
21961 actaccaagg aagaaaagac cgaggtagag gcctctgcag ccgctaaaga ggccaccgcc
22021 actaccaagc ccacggctcg caaaaccacc agcaagtaag gactcgacat gatcaacgtc
22081 agcggcttcg gcacgggaat tgtgatagtt tcaacctcgt cgttcccgat ggggttttcc
22141 ttgtcgaagt tcgctgatga tgagagtccg atatcatcca aagagctgga gccgttcggg
22201 tatgagatgc tttatgatgg cggtctgttt gccttcgata aggcggcccc tttggaagtg
22261 tccatatccg taatcgcagg gagcgaagat gatattaatc ttcgcatcct tctaaattcc
22321 aaaaagggat catttcgatt ccttccaggc gtcattccag acatgacgac tcttgttgca
22381 actcttcccg atggcggccg cactgttctg tccaacggaa ctatcatcaa gggtccggcc
22441 atagatacca tccagaacac cggacggcgc aaaggcaaca cgtatacttt tgttttcggc
22501 aactatctcg gcgcccagac tgcgcgtcaa gctatttcta acgttattca atcggttctg
22561 gaggtgatct gatgttaggg attttcacca gcctcctaag ctcgcggtct ttttcgattg
22621 tagatcagaa tacaaaccag ctagttgctg cggatttgag gataagccgg gttaacaccc
22681 ggttttcttc tgtagggcag cgccacatgc tggaagacgg tacgacaaag atggactcca
22741 gaacggtcca tcctatggag ataatcgttg aggtattctg cccttcaatt gatgtcgtag
22801 atcagattaa tcaactgctc ctggatcgtg atacgctgta caaagtcatc actcgcggca
22861 tggtattcga acggatgatg tgtaccagcg aagcgcttaa tcagacgcca gaaatgatat
22921 cggcaactcc tgcgcggctg acattttccc aagtgctcgt tcagaatccc aaaccaatca
22981 tgttcaggaa tgctggagac tcttccataa tcgaccgagg gttggccctg gccgaagacg
23041 ttgtgggctc ggccagtgac ctgttcgact acgcagtgaa cggcgtccag aacgccgcag
23101 acttgttctg aggtgccaat tgaactcttt cctcaaggcc attctcaaca cgcctactct
23161 caccatccgt gatgatttaa ccaaacttcc cgtttggaag agtctccaag tcaagaaagt
23221 ggaaatttac tcaccggctt ccgtagtgtc gaagcctttg gcgacgaaag accagacgga
23281 agctcaggtg tataccgaag cgctggacgt tgatgtgaag aacgggaaga tcattcagcc
23341 agtgcggctt cgcatcaatg ccatctgtcc agacttgtcc acagttgaaa gtatcatgaa
23401 tgcttttaat gacaatacct cgactttcgc catcacttcc aagtcgatat tggctgataa
23461 aatggccatc atgacgctcg atgtagatca atctcctgac atgctaaatg cggctgagat
23521 caacatggaa ttcgagcagg ttgagcctcc agtattgaat gaatttgatc cggctttccc
23581 tcaagatcgc ccaacttatg gcgtgcagat tcagtccctt tccgatgcaa atttgctaga
```

Figure 8H

```
23641 cttgggagcc accggcgatt cgatatcttc ggccgcaaaa tcgctatata atcgcgtgac
23701 cagttatttc tgaggatgta tcatgcttga aatcaacctt cccgatggcc gccaaactcg
23761 cgtacaaatc gaggcgtggt cggcattgga cggctgggaa ctccagcgcc gtttcgtcga
23821 gttcgcagtc agcaaggatg ccgacttccg ccgcgctttc accatggaaa tcctgagcta
23881 tgccaaagtc attctcggta acgatgattc cgaaattccg ttgactactg ctgcggtcat
23941 caacaaccac ctcggcaact ggaagaacgt tgaattcgtc ttcgattccg tcctcaagca
24001 caacggcatc gatccgacaa cgcacgccga ccgcccggac tattgggagc aagccggttc
24061 gcagatggca atcgcatttc tggccgaggc gtccaagctc attgggccag ctatgaaaat
24121 cgccgaagga ctcgccagca agccggagta attcatgtct agtgatttgg atgaattcat
24181 acttcggtat gaggccgaca cggccagagc cgaacgaaat ctggaacgtc tccagaatca
24241 gatcaggcgc gtaaacagcg catcgactag tggccttcaa gatttgcgcc acttcgcaga
24301 cggcgctgca accgaactcg gccgcgtggt tccgcaggtg gacgccgtaa cgagcgcgat
24361 tcgcgggatg aacgcccagc tcgcgatagg cgctactggc gtggccctgg tcgcggccgg
24421 cgtcaaggcg ttcatgaaca ccagggacca gtacaaccag cagcgcatcc aggcgatgga
24481 tatcggcatc gccccggcgc ggctggaaga gtaccagcgg aaactggccc gccagtctgg
24541 aggaacgatc agccgcgagc agggcgcgga aatgaccaaa aatctggccg acactttccg
24601 gcgagcttat cgcgatatcg gacgggtcgg cccagaggcg cggattctgc gcatggccgg
24661 cgtagatgtc ggaagcttcc agaaaggcat gaggccgctc aacgacatca tcactgagct
24721 ggccacgaag atggccaagt tgaaaccgga cgagatttcg gcatatgctg atgccctcgg
24781 cgtctcgcgg gactatctga gcaccctggc gaagatcggc ccggcaatgg gcaaagtcac
24841 tgagatgacg tcagaagagc ttcaggctag ggtcaggggc gagtcaaaca ttcagaagtt
24901 caatgatgct ttggcaaacc tcaaccaaac gttcacgact ctggaaaacc gcgttggcga
24961 aaaactcgcg cctgcattca ccaagttgat cgaaatcatc gacaaaattg tccaggccat
25021 tcccaatgaa gtggaagaat tcgccaagga cacgaaagcc cgctgggacg atggaatcac
25081 cggaaaggcc actgtgggcg gcgatatcct gtcccttctc agtcctggtg ctctgctagg
25141 tcgtctggcc tcctggggca ctcggcgcgg catggaagag gccggattaa tcgacaagtc
25201 aaaggtccca ggctcccaag gccaaaccag cgaagacctg gccaagaaac aggaagacca
25261 ggacaaagct acgaagtcca tgaaagagct ggagaaattg gccgaccaga ctacgaagtc
25321 aacgaatgat ttcgcggtgg cgatcaacat gttcagcgga gccgtgtcat cgttcgccaa
25381 tgccgttgac gagcgtcaag catgggcggc atgggcgggg gaaatcgggc gcgcagtggg
25441 catgggaagc accgcaccga cttcgcgagc aacaggggtt tatccgcacg cgatctacga
25501 tcagtcgaag agtggcgcgg ccggtcaagt attcggcgag cctattggcg cccagtctct
25561 gcgaaacagg atgttctcgc cgcagcgcaa ggccgagccg atcaacgtgc catcgtacat
25621 caatgacatc atcaaagatg catctaagat gtacaacatt cctgagatgg acatcaagaa
25681 gctcatatac actgaaagcc gattcaacgc tagggcgacc agcgaagccg gggcgaaagg
25741 cctcatgcag ctgatgccgg aaattgccaa ggcgtatgga atcaccgatg tgtatgaccc
25801 acgccaaaac atcctcggtg gaacgcgcct attgcgggaa aacctggacc gggccaaagg
25861 cgacatgcga ttggcgttga cctactacca tggcggcctc gacccgaaga actgggggcc
25921 aaggactcgc gcatatcctg gtttggtgat gagcgcacca attgaactga tggaggaagc
25981 ccagcgcaag cagaaggccg cggccatgac ggtcgccaac gagacgttcg cgccagaagg
26041 tggcgacatg gacattcgcc cctatgacgg cggaaggctg gaagctccgg accagggcag
26101 gaaggaggat gatcgccgcg aagctcgtcg atatgacgac agagttgtcc ggccggagat
26161 tcgcatcatc gaccgcatgc cagaccgcag tgacggcgaa attcttaaaa tgtctcagcg
26221 ccaagacgcc gaccgggcgg actctggatt ccggaaattc ccgaaccagg ttcgtggcga
26281 gacaaagcag aacatccagg cccaactcac tgccggagct attgcccaag tcatcggtgt
26341 taatcctaac caaattatgc gccgcgaaat cagccgttcc gacttgctgt tcggatacaa
26401 ccaggccatc ttgggcaaac agcaggaaat caaagccgct gcgacagagg ccaacaatgt
26461 attcctttct ccagccaagc tcgccgaagc tactgccaag gttaacgccg catcgcgaga
26521 aatggatatt ctcaggacgt atggggagaa gcttctgaag agcgctccag agcgcggcca
26581 ggaactgaca atcggtcgaa ttgatatgtt ggtaaacgtc accggcgcga attctccaga
26641 agaggctcgc gaaatcttca gcaggcaaac cgcagaacag ctgaccactg ccatccagga
26701 ctcccaaaac gattctgcaa ctaagatact ctactgatga aaaagagaat tctgcgagtc
26761 acattcaata tgccctatgg acccgaaatc atccgtgaag acctggatgt tcgggtccgg
26821 attatgaagg ctgcattgcg aattcaaaac cgagctaccc tggaaatctt tggactcacg
26881 acgcaattgc gcgagtctct tctgtcgcag ttcacagcgt ggaagcaccg gcagcgtcaa
26941 gtaggcatgg aagacgaact gatgatcaga gtatcggttg aggccggtta ttccgatcag
27001 ggccgcgaac aagtttccag agtatttgtc ggcgaagtgg caattgtcga tgtcatttcg
```

Figure 8I

```
27061 ccgccaccgg atattggaat tcgcatccaa tgctacacaa ggcaaatcga taggacgaag
27121 actattcgaa atatgccgcc agccaacacg acgtttgtaa agttcgtcga atggggcgca
27181 aatgaaatgg ggcttaactt catctgcgac accagctaca atgatcaagt tttgaagaat
27241 ccgggccggt cgatcactgt cgcgtcggca atcctggcat cgattcagga tatgtacatg
27301 ccggatgtgg ccgcgttcgt cgatgatgac attctggtcg tgaaggaccg ggataaggtc
27361 attcgtcctg atgaagttgc caacatcaac tcattcgtcg gcatcccttc atggtcggaa
27421 tggggcgtgg aatttcagtg tctgtttgaa ccgtcgattc gcgtggctgg cggtgtcgcg
27481 gtcgaatctc tcatgaatcc aagcgtcaac ggcaactatg tgatcaccgc tctagagtat
27541 gatttggcca gccgggatcg gccgttctat atcaaagtca tggggagccc agcagcgtaa
27601 tggccaggga aatcaaatca ttcaatatgt tcggcgtgca ctacaactcg cggcaattct
27661 ctgcggtcga tggactcagg atgatgtcgg gaatccatga tgttcctccg gaagaattgc
27721 tcaaagggac cgacgtgttg gcccatacgg aggaacaacc ggaaggcgtt tggcttccct
27781 tgaccgctgc gaacataaat ctttatgtaa ttgaccgggc gaacgtaata gctcccgtac
27841 aagtgcttgc gcttttgtct gaactggtca tagattggaa ctttggcttc ctcaaagatt
27901 ggacaggggt caaaattcca tcaagatttg tagaagatat caaaagcgtg aagacggccc
27961 attcgccttc cgtggtcgca agtttggtgg cgaatgggtc agcttctatg cgcgagctgg
28021 aagagtatta ttcgactcaa gatgccttta agatgattga catcatgact gcgaagagcg
28081 tgaatgaggc tctagcgtcc gaagcatcac agaacagaat caaaaaggga taattcctaa
28141 gcgagcctgg gaaggctata ctagaccggc caaatcagag gctttcccat gtccaatatt
28201 ccgctaacat ccgcaaaatc taccgacaga acgcgactga tcgccgctct tgacgctcgg
28261 tcgcggcggg atgcgctcga ctttgaagtc atgattcccg cccaggttgt tcaatatgat
28321 cgggcagaaa acatcgctac cattcaacct ctcatcacct gggttgatac ggaacacaat
28381 gccgtccagc ggcatcagct ggttgacatc ccggtgattt ccatgggcgc tggcggcttc
28441 cacataagtt tcccgatcca gcaggggggat atcggctgga tttacgcggc cgaccgcgat
28501 acttcccagt tcttggagtc gctatcgatg tcgaagccga acaccggccg catccacaaa
28561 tttgaacatg gtatgttcat accggacgta ttccgccgat acaccatcaa ttctgaagac
28621 tcggacgcga tggtcatcca atcgactagt ggagcgacca ggatatccat tcgcggagac
28681 aacatcaaga tcactgcgcc gtcgaatgta acagtggata ctccgcaggc gaatttcact
28741 ggagatgtga ctatcgccaa caccctggtt gtaaacggcg tcaacgtgaa caaccacggt
28801 cacctcgaaa acaatccgcc tgatacccgg actaaaggcg gcatgattgc ctaaggagaa
28861 tttcatggct agttttgatt tttctgattt aacagcgggg gggggttgta atggctaatt
28921 atgactacat agtagatact ggagtcatag tcgccgatac tgctgatatt ctgaaggacg
28981 ttgaagcgga attcagggca gccctcggcg ccaatatcaa cctggcggcc tcaacgcccc
29041 agggaactct ggtcgcggct gaaaccattg cgcgttctag cgtgatgagg aatgaagctc
29101 gcatcgccaa taccatcaac ccaaacgtgt ctttcggaac gttcctggac gccatctgtg
29161 cgctgatggg aatcgagcgc ggctctgatc tttcgacgtt cggctatggc gtccaggtga
29221 ccggccgcag ccagacccga atttccaccg ggtcgcgtgt gcagactccg gccggagcga
29281 ttttcacggt catgagtgac gttctgattc cggcaaccgg agtcgccacc atcgacgtaa
29341 aatcgcagga ctatggaaac atccctcttc ccgtaggaaa tctgatcatc atcgatggaa
29401 ccatcggttg ggccggggcg aaagtcatcg cttcaactcg cgtcgatcct ggcagccgcc
29461 aaatgaccga tgcagaattg aagaatgctc gcgtcaatcg tctggcgatc caaggccgca
29521 actcgacttt ggccattaaa gcgtatgtca gcgccgtgcc caacgttacc tcggtcaacg
29581 tcatcgaaaa caacaccggc acggttcaag ttgtcaacgg cgtatcattc acccttccgt
29641 atgcggtctg ggtctgcgtc gccggaaatc cggataagca ggctgtcgca gatgctctgt
29701 gggcggccca caacggcggg actccctggg actatggcgc ggccgacaac ggcgtccctg
29761 tggatgggcc tactggcgtt cctgttcgcg acccggcatc cggtcggaag tatgtggtga
29821 agtggactac tccgatcatg tatgacggat atgtaaacgt caccgttcag caaggctctt
29881 cctcggtcgc tccggaagca atccaaaacg cagttgtaaa ttacgcccag gggaaagtgg
29941 agggcgaaga gggattggtc gtcggcgcga gtctgtctgc ctttgaagtg gccggggcca
30001 tcgctcgcga gattcccgga atctacatta aactatgcca ggtggcttgc gtcccggctg
30061 gatcgccggc cccggccccc ggcgacttct cgcctgagta cgtcatgagc gcattcggtc
30121 aggctaccat ttcggttggc aacgttaggg tgactttcgt atgactctgc ccgcgtacaa
30181 ttctgatatt caacaggcgc tgaagtggct ccataaccag gcccctggga tcaccggctt
30241 ggttcagcga aaagctcaat ggtatgaccg tttcagtcgt cagttttggg ttaactggga
30301 gcgcgacgtt ttcaacctga agaccgccaa cccgttcggc ctcatggtgt ggtgcatcat
30361 cctcggcacg ccgtcgaaag gattcggcct atatccaaaa aacagttctt gggcattcgg
30421 tcggctacgc cagaacttca tctatagcgg tacacaagtt ccgccaccgg cagacgcatc
```

Figure 8J

```
30481 gccgggcggc aacttctacg gtggcggcaa tgccgaaatt ctcaacttgg acgaaatcag
30541 gaaagtgctt cagctaagat atgtagcgct gatttcgaac ggctcgattg catatatcaa
30601 tcgcatgctt cgctacatat tcaatgatga tgagccgtgg gacgaggcga ccggtctgta
30661 cttctatctc atggactcaa ccggcgagga tggccctgtg gagaacttgg ccatatatcg
30721 gaaagattgg gaaggtatgg tgctgttgtc cagttcgccc agaacgaacc atgtgctgac
30781 atcgacccct gccagcgacg ccgattggcc gggagtcgat ccggccgcga gcggtcttcc
30841 ggtaacggtc gaaacggcgt ccgctacggc cccggacggc tccgctacgg tgtgcaagct
30901 tactaagccg gccgggagta ccgcttacgt ctccgcgccg atagatgggc cgctggggtc
30961 cggtagcact gtaacgttct cgttcttcgc gaaagccggc tccacccgtt tcattgcaat
31021 tcagtcggct gccgatttcc ccagtcgagc cgatgccgtt ttcgacctgg attccgggca
31081 cgtgatcagc gatcagatgt tggacagcag cgtggtaagc gcccgaatga ttcgtctgga
31141 gaatggctgg tggcgttgcg ttctcacgac caagaccgtc agctcttcgt tccgcgcggc
31201 ttacatcgct ccggcagaaa ccaacttcag ctggattgat tcgaattcca gcgcggcgat
31261 tgatgtgctt atctggggcg ctcagatcga actgggtgat actccaaccg gatacttgga
31321 gactaccgga acgcccgtaa ccatcaccga ttacgttctg cagagcgccc agaccggaac
31381 ggtcaagttc acacagcctc ttccgaccgg agtagaagcg tattggactg gagactggaa
31441 aggtgggtct gcgaccgagc cggccagatt cgcagtaggg gatgggactc aagatacatt
31501 caatctgtcc agccctgcat acatcggcct acccactagt ggggcgttca agctagaata
31561 cagagttggt ccggcgctta atttgtcgcc gcaattgatc aacctcatga atgaccgggc
31621 ggtcggtatc atgccgactt gcgccggttg cgatgtaaaa gtcattcagg agtaatgacg
31681 tgatcacacc cgaactgata cccagtccgt ttgctgcgca gggcgacaaa gacccgatcc
31741 cgcagacctc ttccactggc tttgccaacc ttcgcgacgg ctacacgccg gactacgaaa
31801 tcagtctggc gtcgaacaac ccgcaggcca aagcggtcga gcggaaaatt caaaaccaac
31861 tcttcttcat cgcgacccag aacgcacagg cttggcagcg gcaaatggcg ccgccgtggt
31921 ttcagggcat gcctggcggc tacgaacaga atgcagaagt cgtgcgagtc ggcaatgacg
31981 gcataatgcg gcgttatcgt tccatggtga atgccaatgc gagcgacccct ctcagcagca
32041 cgacttggga agaacaaccc gcatggtcgg tgatgcgctc caacataccg atgccagctg
32101 gaggcccagg cctatcttct ggcggagaag tcatcacgac cggccgcaac ttcaatgacc
32161 tgttgaatgg gacgtgggag ttcttctctg attcagtggt cgtcgcttct cagaacgccc
32221 ccgtatatcc cgcttcggct ggtgcagcag ctggaatgtt ggaggcgaaa tcctggatat
32281 ccgggtccaa tacattctgc gttcaacgct acactgaccg cgtcgggaac gtcgctgtgc
32341 gcgggcttaa tgccggggcc tggaccaact ggatgtacgc agtaaatgtc atggccctcc
32401 aacaaggccg tgtgacctat ggggtcgcgg ctggctcggc gaacgcttac acgttgacgc
32461 tcgttccgca gctccaaggc ggcctggtgg acggcatgat ccttcgggtc aagttcaaca
32521 ccgttaacac cggcgcctcc accatcaacg tctccggatt tggcgccaag gccatcgtcg
32581 gcgcggcaaa cttcccgttg actggtggag aactcggtca aggactcatt gctgagcttg
32641 tattcgacgc caccggcgac cgttggagga ttctcgcagg cgcgccgcgc atccaagtag
32701 gcaacgccga tcaagattat caggctccca gctggaaaca ggttaaggac tatgtcgcgt
32761 cccaaaagtt gactgaagtg gactgggctg acgtcgtcaa caagccgaac gtcgccatcc
32821 aagacaccac accgtggttc gccaatctgg agttgtctga cgctcgtcct ttcatcgatt
32881 tccacttcaa caacaaccgc gccaaagact tcgactatcg ctttatctct gaagctgatg
32941 ggtcgatggc gttctattct cgccaggggt ccgctggtcc tacccaggat atcctgttca
33001 gcaggtcgaa tgttacattc ctccagccgc gactggatgt tgcgaaaaac ctcgcgtaca
33061 tcgcgaactc tggccccctt tggcagaaca caactgccga tcagcccggt tggaaattca
33121 ccttcgcaca aggtgtggac gccaacaaca acgcggttat cgcagtcaat accaccaacc
33181 cggacggctc ttatcgctcg caggtcatgc gatgggactg ggcgtccacg aacgtcatat
33241 tcaacaatcg ccctctgttt gctggacaat atgttccgtg ggactccgga aactttgatc
33301 cggccaccaa gctcactgtc ggtactacca acaatatttc ggggccgacc ggaattcgta
33361 ataccaccag caataccgga aatatgaaca cctggggctc cagctccaca actgcatcgt
33421 atggaaacgc agctcttcaa atcttcggta gagggggtgg cgagcctgcg gccatctact
33481 tcgacaactc ccaaaccggc tggtatttgg gaatggacaa ggacggccaa ttgaagcgag
33541 caggctggtc gctcggcaat aactcctatg tggtcactga cgagtcgaat attcggaatc
33601 acgtcaatgg aatgtctggc gctcctgttt ggggaggtca atggttctgg ggtgaatgga
33661 acttcaaccc gaacacaaag ctaaccatca aagccggcac gcaggagact agcagcactg
33721 cgatattcag cggaaccctg ccgtttgcac caatcgcgtc tctgtccgac tattcccagg
33781 cgcccctgac gatttataac tcgccgactg ggccatctgc taagcctgct gtgatcgcgt
33841 ttattcgccc tgggaactgg ggcgcgttct tcggcatcga taccgacaac aagctgaaat
```

Figure 8K

```
33901 ggggcggcgg atcgctcggc aacaactcca gggaaatcgc cgattccagc aacatcatga
33961 atctttgggc gtccaacccg accgcgccgt cctggaacgg ccaaaccgtc tggcgatccg
34021 gaaactttga tccggcgacg aaagtggatt tgaacgccgc gaacgccacc aacggcaaca
34081 tgatcttcaa ccgcatttcg ggtactggta gcggcatcgc ttcgtccggt cgagttggtg
34141 ccatcaacct acagaatggc gcgcattcag ggcaagcggc cgcagtcact ttcgagcgtg
34201 gtggaagtat cttcgtcaac ttcggcttgg ataccgacaa cgttctcaaa gtaggtggtg
34261 gaaacctggg ggcaaacgcc tacccagtca tccacgccgg gaactacaac aactacatca
34321 accaggcgtt ggttcaggtc ggtctgggcg gagtcggttc ctatggcatt ttcgcggttc
34381 tggataatgc cgctccaatc gcaaccgttc aaccccggagt ggtagtggac ggttccattc
34441 tcatctactc gtcttgcgcc gcaaactaca atagcggtca aaaacctgcc ggaacttggc
34501 gctgcatggg atatgtagtc aacagagacg ccaacacccc tgactccgcg accctttttcc
34561 agcgagtgac gtaaaatgag atggacgcgg atcagaaacc cacgttggct ggacgcagta
34621 aacatccacg ccatggtgac tttcgaggga atcggtgaag tgccgttcac cgccaatccg
34681 caagacgtgg aggcccacgg aagggccata tacgctgcga ttctatctgg ggagcacggg
34741 cctatcgccc cggtcgattc gaagcgggag aaggccttgc aggacgctat acgagccagg
34801 gaaaagcggg ctatccttcg ggatacccgc tggcccatag atcgtcacga cgagcagaga
34861 cggctgggta tcgaaaccac ggacggccct gggctgatcg cagccctcgt tcactggagg
34921 cagcagattc gcgactggaa tagcggggat cggccgcgac ttcccatggc tctgaaaaca
34981 atgttcaaaa atcaggagta ctgatgaaaa taacgaagga tattttgatc accggaaccg
35041 ggtgtaccac ggatcgggcg atcaagtggc tggatgacat ccaggcggcc atggataaat
35101 tccagatcga gtcgccgcga gccatcgcgg cttacctcgc caacatcggt gtcgaatccg
35161 gtggactggt gagtctggtg gagaatctca actacagcgc tcaaggactg gccaacactt
35221 ggccgcgccg atatgccgtg gacccgcgtg tccgtccgta tgtaccgaac gctctggcga
35281 accgcctggc tcgcaatccg gtcgccatcg ccaacaacgt gtacgctgac cgcatgggta
35341 atggatgcga gcaggacggg gacggctgga agtatcgcgg tcgcggactg attcagctga
35401 ccgggaaatc gaactatgcc ctgtttgccg aagactccgg catggacgtt ctggagaagc
35461 cggagctgct ggaaactcct gccggcgcgt cgatgtcttc ggcatggttc ttctggcgca
35521 atcgctgcat acccatggcg gaatccaaca acttctctat ggtcgtgaag accatcaacg
35581 gcgctgcgcc gaacgatgcg aaccacggtc agctccggat aaaccgatat gtgaagaccg
35641 tcgccgcgat caatcaaggc tcctgatctt ctccgaaaag aaaggccgct tattcagcgg
35701 ccttttttgct ttccggcttt gcctcttcaa tctttctgac ttcagtaggc gcgacggact
35761 cttcctgggt aactgagtcc acatagttcc ctagcgaact caaaacgccg attaacagcg
35821 ctcttaccac tttatcctta actgtctcgc ctatgatctt tgtcagaacg gatatcaact
35881 cttccccggag ccttgggctt attcttggcc gaaagcgctt gcgatgctct ttgcgtttca
35941 tgtttagtcc tctgtttgcg gtcttctcct caccccgata atggcttggg gatgcgctgt
36001 gttaatcgga agggtcgggc gctattataa ctcgacgaaa atgctcgcgc ttaactgttt
36061 aacgatacgc accgcgatat taaatcgcct tctttctggc caaggaactc tggcggccga
36121 gtccggtcta aggcttaatt tgtcgacatt aaaacgagaa aacccggatc gcctttaggg
36181 taaggagtcc gggtttttctt cgctctagtg tacgctagaa tcagtggctg gcaccccatc
36241 cgtccagcca gcagtcgaag acagcgtgtc gtggcttatc cttggcgcca tgggagaagt
36301 gcttaaatcg gatgacctgg cgcttgagat gttccctgtc attccagagc cgtttttttct
36361 cgtcgtgggt caggctggac gccgacacat tgaaggtaac tccaggccac aaaacctcgt
36421 tgcggcagac gaatgctcca accatgcctg atggggccag attttccgca tggctggagc
36481 gggccgtgcg acctagctca tccgtgaatg cttcgttgtt gttgtgcatc agctcttcga
36541 cgtcaacaat ctctgcttca tcatagtcat agcgcttaac cttgacacag taaccttcct
36601 tggcagtaga gcgcccgaac ttgtatgcgc catcagcgcg cttgcccatg gagccttcga
36661 atccaagtcc tgtgtggcga cgttcgactt cgctgaactg ttcgatggag gtgaccagtt
36721 cctgctcgac taggtgaatc ctctcatagc cgatgcagtt cttcagaaag ctgacgcgct
36781 cggcagctct ggccagtcgc tcttcggtcg gcgcgcgcgg atcggtgaaa tcgtcaaaca
36841 cgtggaaaga ccaatccggt tcaccgtcgc gacggcgaag gtcgccggac gacttctgga
36901 atactttcgg gtctctgatg tcgccgcaga ccagttcgcc atccaggcca tcgaacattg
36961 catcgctgag atattcacgg atggactggt tggtctgcgg ctttaggctt cgcgtcaagg
37021 cttcgccttc aaatatgaaa cagcgaaaac catcgatctt cggagaaaag tacatcggca
37081 actggccgtc cagaagttcc gggtcatagt tcgatgcgag catgggtttc atacagtact
37141 ccagaaagaa gcccggcgaa ccgggctgaa tggcggtaag ccggatcaga tggtttcgtt
37201 ggcgtgattc agctcggcca tgatcgatgc atagcgctca tccgactcct tgatgaacac
37261 gccgttgtac attacgccct tgcgatcctt gatggtgtcg taggccgcct ggtagcattc
```

Figure 8L

```
37321 gagcatgctg gtgtcgtgct cttctgccgc gtcgaacagg gatgcgactg ccatgaccaa
37381 gctcttgatg gcaagccact gatttccgcg agccagcgag ccggccaggt cgccgagtaa
37441 tttcagatct tcgccgtagg acgggcggcg ctcgaccgcc aagacgaagg ctgacatatg
37501 gtcgagcaga ttttcgccga gctgcgcggc catgatggtg gccacgacca tgacatcgcc
37561 gatgccgtct ttcacttcgg cggtgtcatt ctggatgtag gcttcgcaaa cttctgcgaa
37621 ttcttctacc agcttgagaa actgatcttt ggccgaagag cctttgatca ggttacggtc
37681 ggcacccccat tttaccacca ggtcatggag ttcgctattc atgattcgtt cgatgatcat
37741 tctttcgatt ccttctgtat ttgggatttg actgcgttga tgatggacgc cgtgctctgg
37801 cgcgatccgt ccttagtggt gccgaagtaa aaggccataa cagacttcag ttcggcaaac
37861 caatagccga tgatagtgcc gatggcgaca gaggaagtcg ggtccatcag cgcctcgcgg
37921 ccgaatgtga aaattgcgat gatgatgaga atggaaccgg tcagaagagc gaaggttatc
37981 gccgggcgaa cgaagtcatt ttgttgcgcg gcaagccttc tcgccgaatc tctgtctgcc
38041 gcctcggcgg cgaactggct gagttcggcc tggagctggt tctgctcaga ctgaagacgg
38101 ttttgttcgg cctggatggc cagttcctgg agacgaacac gctcggcgct ctggagttct
38161 gcgaggcgcg ctagagcctc cggattcgcg tctagagcgc tcgcgaccga tgctgggtcg
38221 gccttcgacc ctagagccgt cgcgacgata gcgccaacgg cggcgcctgc aggcccaccc
38281 aggagcgacc ccagggccgg ggcagcagcg ccgatcttac tacctatgtc cttccagtcc
38341 attttcgatt cctcaaaaga aaggcgccat tacagcgcct ttctctggcc gttgacgtta
38401 gaactcttcg gcttcggtag cgccgccaac gccgccggtg tcgccgcgag gctgttcctg
38461 cttgctgtag tccaccttca cttcgccgcc gacgaacgac ttgtacagat cggccgcagc
38521 cttgaagtga tccgggtttt tcaccaggcc ttccagttcg aactggacgc cggaccagct
38581 gcccttgtcg ttcgacagac cgacggtggt catgcggacc aggttggcga aagtcggcgg
38641 ggtgcgcagg ccctgcggag tctggacttt cttctgggac agcgcggtca tgagcttctt
38701 cgaggccttg atctgcgaag acgacaggga gatcagggcc tggccgaaat cgccggtttc
38761 cggatcgatg acgatgacgt aatggccacg ggtgtcggcg aagtaatcag atttcttgtc
38821 gcttaccgaa ccgtcttcgt tcggcgcgta cagtcgccct tctacttcct tcaccttggt
38881 cgggtctttc atcatttcct tgaagtcttc gacgctgatg gacccttttga aaccgccttc
38941 ggcatcgcgg ccggcccagc gaatgaactc gcgacgatac gcggccggga tgatcagcag
39001 accggttttg ccgtcgtaaa tcttgccggt gacggtattc aggaacatgc cggccttcgc
39061 gccctcgatg tatttcgggt cgtcttcatc gacctgcggc gacatctttt gcagcacttg
39121 gatgaaggga atggcatagg aatctgcgtc agccccttcg aaaccagcgc cgtcatacgc
39181 gcccaggtcc atgaagtcgg gaacgtcagt agtcgcgacg gcgccgccgt tggccactgc
39241 aacggccttg gtttcttcgg ttgcttcgga agtctcggtt ttcttgccag ccatgttagg
39301 ctccttgttt gtcgaatttc agttatcgct aactgtgggt ttataataac ggaagttgca
39361 gcgaagtaaa gcaaattaca tgttaagatt tgctcttttt caccttcggc ttcgtgatct
39421 tggcctcttt atattcgtgg acgccgatga aatctggcaa ctcttcgccc ttctccaggt
39481 actcgcgacc gaacgcctgg agggtctggt agtgaacatc gcggttgatg gtggcgtcat
39541 agccggcttc gatgatcgct tcggccgcct tcttcgcatc ttccatttct ccgcgaccga
39601 attctgccag aactttggtc ttgatgatgc cgtcgttgtc tgtgtcttcc agccacttcc
39661 agaacttcga cttgttctct tccttgacgg aaatgatggc tttcggctcg acttttaccg
39721 tgcggccatc agccagagtc gtggtcttct ggccgagttc ctccagaagt tcaggaatgg
39781 tattgcgctt gagggtcttc agctcttctt ctttttcggc cagcgccttt tgcaattcga
39841 ggatttcgcc gtccagctgc gaagccttgt ccaccaagtt cagcagtcga tggccgatgt
39901 cggtagcttc gactgccatt tcatccatga cgccgaaata gtcaatttcg cccggcgcat
39961 tgtccttcag atactccgga acttccaatt cttgctcgct catgtcagcc tccaacttag
40021 tgatgttccc ttacttgaac taagtattga gtagatatta tgccgcatct tccttgatac
40081 ggctactgat ttacatatta aatttcgtcg cgagtgctaa cgtcagcctc gaacactcca
40141 tcgacgacat aactcgcaag attgcgcttc cactccaagc taacctggat tttctcgtcg
40201 atggagtcca gacagatgag gtcgaagtac aggacagagt tgatggtccc gatgcgatgg
40261 tttctgtctt cggactgcat ccgcaactcg ttgtcttcgt cggtcgtgta gtaaattgcc
40321 acgtctgcgg cagtgagcgt gattccgatc ccagcagcgg ccgggtttcc caggaagact
40381 tggacgcgct ttgcctgaaa atcatcgatc agtttttctc gttctgcctc tttggtctcg
40441 ccataatagg ctccaaacga aattccttgg gcctcaagat acgcagcgat ctggccgatt
40501 tcgtgaatcc gcatggccca gatgatgata gaccgttccg ggtcttcctc caacagaccc
40561 tccagaaggt cggtgaatac cgcgaatcgc gggttgtctt cgggcggcag gatcaccggt
40621 tccccataga cgttgatata gccggacgcc acttgcttga gtttcgaacg cgctgctgct
40681 gcatcgaacg atacatccag catgaaatct tcgttcttga gcacgaaatg gtagtcctct
```

Figure 8M

```
40741 tcaacgcgct gataaatctt cctttgctcc ggcgacattt cgaaatatat gcgcttgtaa
40801 accttttctg gcaggaatgg caatgcctct ttcttcgtga cccggaagct gtgcggctcg
40861 atcagggacc gcagtttgtc aagatttcgg aatactggtc gcccaaaatc gtctttttcg
40921 acgagctgag gtggaacagt gctcttccca tccaatttgc gcatgatggc gaccattcgc
40981 gggtcgtcac ttggaaccag aacggaaaat tcagccacga acgcgcgata ggatttcgtc
41041 cccagaattc catcacgcag gaattgaaac tgcataaaca aatccgtagg cgctcgcgtc
41101 agaggcgtac cagagagtat gcggcgcgcc acggccttct cgcccagctt tacgatcttt
41161 ttcgctcgtt tggcctgtgg gttcttgatc ctcgttgatt catccacaat tgcgcagact
41221 ttgaacgtct taaggaatcg ctccacttcg tcatagccag actgatggtt gatggcatcg
41281 acgtttatgg caaagacccg aagaactttt tcatcagcga atgtctcggc atacagacga
41341 tccagacgcg ccctggcctt tttggaagtc ggtcggccgc gccaatccac gcacagagtc
41401 ttgatagcaa cgtgggtggg aatctcgcgc agaatccagt tcgtgtgtac gcccttgggg
41461 gcgacgatga gcagcgcgtc aacccttcct tgcaggaaga gcctaactga gtctgccaaa
41521 gtagtccagg tcttcccggt gccttgctcc atcaggtatg cgaaattcct tttgttaagg
41581 gaagcctcca gggcattgaa ctggtgttgc atcgcctcgg tcttcatgcc cttgactgga
41641 aaggttttgg ctttcatttg ttctccagat cggcgagaaa ttgaatgatg ttgtccagtc
41701 cttctgcatg actcgcgact tccaccaggt cgcggctgtt aagatcgaac agatcgagca
41761 ttggattcag gagcagccaa tcggttccga ttttcaccag aacgaagccg cgaccacccc
41821 agccgatccg ctcccgaagg aaagggattt gcccaggctc gaaacagcgc gccattgggc
41881 aggtagaggt gcgctttggc caagcttcca gagccttgaa ctcgacccaa aactggacac
41941 cgtgacgatt caggcatatc gaatcggaca tgccggaccg gcgcgtctcc aggaaatcga
42001 ccaggattct gcctagcgag cgttgcttaa acgcattcgc ggctttcgtt tcgcgatcat
42061 tcatcgccat tcccctcttc ggaatctttc tctgcttgcg ctgccaactt tgctttctcg
42121 cgttcggtca atatccgctt gacggccttc acgatgaaca tatcgattcc gctgagcttc
42181 catcctttga tgaggaacca agagccggta ggcgtacctt cggcgatatt cttaccgtac
42241 tgaagatatt tttcagggcg aatcctgaaa cgaatcggtt ggtcaaccga gtcatccacg
42301 cacatcaaat cgaggaactg cgactggcct ttgtacaccg gattctttcc ttggtcagcc
42361 ctcttcttct ggcggatcgg ttcattctca tccgacagaa ctttctttac cagcttgacg
42421 ataactaggc catcgtcgcc atcgcggata tcacgaatgt tctgaatggg atttccggaa
42481 gtcaccccaa ccaactcagg attgtcatag gcatgacccc agagcgtatg agattcattc
42541 aaatccgcga attgaacctc agaattcgac aaactcgcgg caactttctc ccaatcctga
42601 agcgttttaa gatgggagcc ggccagctct ttatattgcg ccttcaactc cttcagttca
42661 gctttcaact ccttgagatc agctttgagt agcttctcca gttctttgtc tctgcttact
42721 ttcgccgaaa gaatctgggc ttccagcgcg gcaacgtcat cggccttatc ctctacatcc
42781 tgcgccgaaa tcgggcaatt ggccagggcg atcctcgcgg ccttgacttc ctcgcgaaga
42841 cgcaagaatc gctcggcctt agccgggccg aagcctttgg cgttcatgat gccgccgatc
42901 aggcgtccgt ccgctacaac ccagttgagt tcggaatgct ccgggtccag ggccgtatat
42961 tctacgcctt ctttggccaa ttcgcgaagg atagacacag tttgctggtc gtccttcgcc
43021 gcccgaaggc acgcggccgc gtattccagg cgatgatacc gcttcatgta gcaagtccag
43081 tacgtcacca cggcatagct tacagagtgg gagcggttga atccccaggc gccgaatgtc
43141 accatttcct gccaaactcg gtgagcgtct tccggggcga cgcctatggt cttggcgccc
43201 tcgatgaaca attctcggcg cttgttgaag aactcttcgc ccttccgcgc cgacatcgct
43261 ttccggatcg ccgacgtttg ttcccagtcg aactgaccaa tgtccttaac aattgacatg
43321 atctgttctt ggtacaggaa cacgccatac gtccccgaca aatactgctc gacctgcgga
43381 atggtatagg tcacaggctc gcgaccggct acgcgctcga tgtatttcgt ggccatgccc
43441 gaagacaacg gacccggacg agcgagcgcc gtgatgtggt cgatgttttc gaacgcggtg
43501 atgtttatcg cattggcgac cgagcggacg gcctggcctt cgaactggaa gatgcctgac
43561 atcttgtctt cgttgagaac atccaaaacc gccttgtcgt tcagcggcaa gtcgtacaac
43621 tcttgcgccg tcacgcaatt cgcatcttga attacgccca gcgttcgaag acctagcgcg
43681 tcaatcttga gaagattcaa atattccgaa tcaggcttgt cgagctgcgc gacgccttca
43741 gaagtaaccg tacagaaatc gattacttca tcgttgcaga ccaggatgcc tgccgcgtgg
43801 acgccggagt gggatgggtg aatttcgagg tcgcccatgc aggcggacgc aatctcatac
43861 ttttcgcgga agtcgcggcc gggttgagtc ttttcgaaag tgtcctccaa tccttttcca
43921 tatcgttcgt ccgccgaagt atattcgatg atcgagtttt tgatgttgtc ggtgtcatgg
43981 aatggaatgc cgaagcgctt tccgacgtga gcgataaccg acgcggcctt tagtgtgttg
44041 atgttcccaa gctttaccac gttccaagtg ccgtatttct gctggagata ttcgaacact
44101 agatagcgat gggtatcggc gaagtcgata tctatatcgg gaagatcgga acgggaaatg
```

Figure 8N

```
44161 tcgataaagc gctggaagag aaggcgatgc gggagcggat cgacctcggt aattcccagc
44221 aggtagcaga ccaaagagcc ggccgaagag ccgcgagccg gaccgaccag catatgcttc
44281 ttggcgaagg caaccagatc ggccacaacc agaaagtagc tgtcgaagtc tttcagctga
44341 atctgcttga tttcttcctg gaaccgatct tcgtaaactt gggtccattc cttgatgtgg
44401 ccgcgactga gacggtaggc ttggccctcg cgagccaggg cgacgatatc accatccagg
44461 tggatcatcg gcgctttcgc cagctttacg tcgaccagct gctcgaccac cgcatgcgta
44521 ttggcaacgg ctttgtcgaa ctcttcgcgg gtcatgatat ggcgaagacg ggcccacaac
44581 tcttcctcag tcgcgatgtg gcgaaggccg accgattccc gaaccttcca ggccgaagca
44641 aaatctgcat ggtcgatgga cggcatgtcg ttgtaggagg taatcaccac aggcttgccg
44701 aacgccctgg ccgtctccat agcgccgtgt gcggctacca tcgacgcagg attgatgtca
44761 atgtaatcga ttccggccaa gtccaagtag gcataggcct cgccggcgaa cttgatgacg
44821 ccgtcagcat cctggaattc ttggggagac aatccttgat tctggacagt tttggacgtc
44881 aggcgataga actttctggt atctttggct agcgcccagg ctttcagttt cagctctttg
44941 tcaccatcat cggcgcattt gatcgggatt tccatgccga atccgcgagg aagttctgcc
45001 ttggtggcag cctgctccca gcggacgtgg ccccatgtcc catcatcgac gatggcgaca
45061 aagggcgatt cgatttcttt ggcgcgctca atgatttccg gaaacctgcc atatgcggcg
45121 ccgtatgagt agccggagcg aacgcggagt tgagggaaag acattatgcg gcctccattg
45181 cttgatatgc tcgatatact cccatgcgct tgcaaacttc gtggagcagc cgcacgtcgt
45241 ccaatgcccg gtgcttctga acataagggc cgcagtagtg ctcatacaga tgctgcagcc
45301 gcatgcggtg gccgaacaat ggcgccgact cttctacagt acagatatcg agcgatggga
45361 agttgacttc ttccaggccg agctttccgc gagccaaatc gcaggtaagc atgaatttat
45421 cgaatggaag gttgtgggca atatttgcgt cggccttcga aaagaaatcg cgaactttct
45481 ggcgttgatc gaggaacgat gggtgtttga ttaagtcttc attcttcagg cctgtgatct
45541 ttgtaatgat ttcttctatc acaatcccag ggttgcaaat gaactcgact tcatccaaaa
45601 tcgtctcgcc atcggtgatc actccggcga attcaatgat cctcggttgc tttctcagac
45661 ttaccctctg gtggaacggg agtcctgtgg tctcagtatc ccatacggcg aatctcatgt
45721 ctgttccctc ttatgtcgaa aggccggctg ctttcgcgac cggcctgaag agtataccgc
45781 aacggcgcag ggtttatgcc ttctgtccgt ctttcggcgt gatgcggccg gagtgcatgg
45841 tggcgtggac gaacgctgaa tagttgatca agtcaaatac cgaatcgtca tcctcaaacc
45901 cactattcgc caggcgagtg agtttgccaa ctgtatgcat cacgaacagg gcgagccgat
45961 gatcatctgc ggtcttcgcc accatgccat tcgggaagag gatttccatg atcttgccat
46021 acatcagatc atttcgacca taagcgctct ggcggtcgcg gaaaatttct gcggctgagg
46081 acaggttgtt gagaacatcc tccacgaaat catcgggatc ggcatcaccg tcaccaggcc
46141 aggcggattc catggcgaac ggcgctgctg cgtcttcggt cggctcttcg gccggctctt
46201 cggctggctc ttcggccggt gcttcgtaga gcggagacgg ggcctgcgca aacgcctcgt
46261 cgagggtagg ggcggagtcc ggggcgaccg ggaacggctc gcctgctatg tcgttgggcg
46321 cgctaccggg atcgctatcg gccgcgacgg cgaagaacgg cgcatcgcag ccttccaggt
46381 ccaggatata ggcgtcgatg cccaggccct tgtaggcgtc gatgatatcc tggcggtcat
46441 cgaatgccgc gacgatcttt gtcaggccgt cgatcttctt caaaatatct agcgcgactg
46501 agcgcttgaa ctccggcgcc ggctgggtgc ttccatactc ccgcatgatg agctcatatt
46561 cgcgatgttc ggcgataccc aggtcgcgat ggattttcgc cctggtctgg aaatagttgt
46621 tgtcggttcg gccggtgatg aagaaaatca tcaggtcggc gtcgatggcg ttacggattc
46681 gtgctactgc atgcggattg agcttgtcct tgtcgaggcg ggaatggtac tcgtcccatt
46741 gcttttccag ggcgaagctt ttacggtggc tatcgtcgaa gacgcatccg tccagatcga
46801 agatcatgat gccattcttg ggttttcgtg ccatattcag atttcctcgc tttctgcttt
46861 ctgggtgatg gttttctcga tgaaagcgcc atcggaagtt agacggaaca gctcaccgtt
46921 ctggaccaga tcgaacgatt tcacgttcat ggtgacgcga attgattcgc cgccgttggt
46981 cacttcgact tgtgcgacat caccaacctt ctcgatgatg atcttcatgc tacattgact
47041 tcccattgac cgctacagga ttggcctctt gtttctccga tccccagaac tcgcggcgca
47101 gctcttcctg ctcggccgag cgatccatcc atggacgata gaacttgcac tgatagatcg
47161 gtttcaccgg caactcaaca acaggaatct ggccgggctt cgtctccaga gcggacatga
47221 agcggtcaca ggattgctca tgaatctcat cttcattcag aaccttcgat ccatagcgcg
47281 ggaaggcaca ggagccagtg gcgacgcagt gcggctggag cagactatcg aacataggat
47341 agacttccag aaccagtcgg cgcatttcgc ggaaggcttc ctgatactca ccttgcgtac
47401 gaacacacag gcgaactttc gccatgtcgc tcagagtgcg cagattgaat ttggccgcga
47461 tcttcgtttc catgttggaa gggatgatgg cacgagcatc ctgaagcgat gcgccggcct
47521 ccaagagctt ctggtaactg gtctgcgcgt cggcgattgc atcatgccac aggcggttca
```

Figure 8O 47581 gctcttcacg agcgtgatag gtcgggtccg gctcaccatt ggccgtagcc ttctcatcga
47641 aatcccagcg gaacgcttcc ggctgaacaa cggcgctaac ctccagagcg cgactggttt
47701 cctgctggta agccccggtc cgagtccgaa cgagttgatg agtgaaattc ttgctgacgc
47761 cctcgatctg gaagatgaag tccacgaatt cgaatggcga gcgaatggtg tccagcatgt
47821 acttccagtg gtcgagcttt tcggcttcgg tcatggtcgc cgggtcttgg ccgcgcatgc
47881 gggtggattt tgtgcccagg agaagttccc aggcgttctg agtataactg atcagagaaa
47941 ttttcatcag aaatcttccg gaattggcgt gaaagtgaat ttctccgtca gcgcaatggc
48001 caacgcttgt gcatcttcct tgtgtagacc gtatctgtcg atctcttcgg ccagcaattt
48061 gcacgcctcc agacggtctt catactcttc ggcgtggcac atggacgaga agatagtgcc
48121 atcagaggtc cggtacacca gttcaatgga cattactgta atcctcagta gcagcggatg
48181 atttcggcgc gaatatcgcg acggtccagg taatgctcaa taatcttgtc gcgggcgcgc
48241 tcggcctctt cgcgactgcc gaacgacagg ttgaacgaag tgaaaggctt atcgtccagg
48301 cgtccatcgc caatcaggta caggatgcct accagcacga aagacggcgc tgtctgtcgc
48361 gtttgcggcg ggtcgatttg catttcgagg aaagacatag gaacctcttc aggatggtct
48421 ggtgcgtaca ttaatagcgc tcctgctgag cagccaccgt ctccggttcg tagatgatca
48481 tatccacgat ttccgggcac tggcttttca cccagtcgat ggccgcaacc aacgttgtag
48541 cggcgccgaa ggtgaaagtg cggtaagact catggatgta cggcgcaccc atggagtcgc
48601 gctcggtcgt gcgagaaatg actactttga tgttaacgat ccggcccatc ttcggcctcc
48661 actttagcga tgatatcgga caggctcagc ttctcgccat tcaggaaata actggcgcga
48721 agcttcctgt cgccttctgg cccgacgatc cgggccgtta ttgtgagact cccgccgcca
48781 agggcatctg tggccctgaa gaaagccagc agcgcccgct tgagcgctgc ctcgcgagga
48841 tcgactgcca ttaacctatc acattccagc cgtgctgggc gcaccacacc gcgccagctc
48901 ccgcaggaag gctgttaaga aggaacactg gggtcaggcg gccatcctcg gtcatgtgga
48961 tgaagtagcg tgcactttca ccgagccatt cggccttggc gatggcgcgt tcgagattgg
49021 ccttggtggc gtaggtcttg gtggtgtttt tgtcggtgga gaaggttact tcgcgggcca
49081 ttttgtcgat tccttttggt tgaagggttt cgcgtttcga tgagggaata ctactctcac
49141 ctggctcaga agtaaagcac tttgtgtaaa ttatttcacg aacatcttct tggccttctg
49201 ataagacgaa gaagtcatca ggcgctcgat gacgtccatg tccgaaacca gatcgtccag
49261 aaggacgttt cgccaggtcg cgaaccgacc gagcgagaag atgccggctt catgggtgag
49321 attccagatc atggattcgc gctcgtcgcg gccgagcgga atgattttac ccttggtctg
49381 gacggtcggc tcgccgtccg gaatgagatt cttcttcctg atgccgaagg ccgagcaaac
49441 ttcatccagg tcccagttgc tgtcccattc gatggtttcg atttcaccag ccgcagtctc
49501 cacgatgccc ttagtaacgg attcgacgat aagggtgtcg ccggtgatgg acgctcgaaa
49561 cgttcccact tcgggaccag ggaaatacac cgtctggaag acatcacaag gaatggaaag
49621 cttgtaccga ctcacgacga tggaggttcc ttcgccgaat gacgggtcga tccccaggtc
49681 cagccctgcc gcagccagat tggcgcggaa tggtgctgtg ctgatgatat taacgtgatc
49741 atcttgccgg cgaaggaact ggaagaaaga ggcgtcgaaa ggcctgcccc agctgatgcg
49801 attcgctagc ttagcgacca gctgctcata gtagtctgcc ggcgcgatcc aacgcttttc
49861 ggtcgccata ttccagatgg accgatccga caggccgccc gttactttcc tggagtacat
49921 gttgcagtag tcgatgcgcg gctgggaaac gaactcgccg tcaatgtaga tggccttgtg
49981 tacggtgact tcgcggaacg ggatgccggt gagttggccg atgactggtg agcggaaccg
50041 caagagcgcg ttgtggcgtt ccttgctcgt cggcgtcgcc gcgtcgatga tttgggcttg
50101 agggaaacga tgcgcggcga tcaggccggc gagtccggct ccccacgatga taactttgtg
50161 atcaggaatc atgagatgtt ccttatgagt gtacagaact tgggaggata aaaaagggac
50221 ccattttcat gagtcccttg aagagctaga cgattcggtc tcagaagagc ggcggcttac
50281 tcttcttcac catcggaacc gtcggcgccc tgaccttcac cgtcgtgctc ctggccttca
50341 tcggccttct cgtcatcgcc ctggccagct tcgtcttcct tcgaagcgat ggcaaccaga
50401 tcgacccagc ccatgatttc cagcttgctc aggtagctgc gaaccgaggt gccgtacagc
50461 aagtgggcca ccttctcgcc gaaggattcg atttcgaccg gctcaccaac ggtgcagtgc
50521 tcgttgatgt aagcgaacac cttgccgcga gtcgagaagg cctgcggggt tccatgaccg
50581 tcgccggtcg ggatgaagtg ggtggcacgc ggacggcgcg aaccattgga cttcaggtct
50641 tcgcgacggg cttctgcctt cgcgcggcgc tcttcctgct cttccttgcg acgcttcttc
50701 tcggcttcgc gctctgcctt cttctcttcg gccaggcgct tgcgctcttc ttcgcgggct
50761 gctttctggg cttcctgcgc ggctttcttc tcttcggcct tcctggcgcg ctcggcttcc
50821 ttctcggcct tcttctgctc gcgctcggct tccttcgcct tggccttctc ggcctgctca
50881 gcttccttgg ccttggcctt ttcagcacgc tcggcttcct tggcggcggc cttttccttc
50941 gccttctcgg cgcgctcggc ttccttcttc tcgcgctcgg ccttgcgctt ctcttcgcgc

Figure 8P

```
51001 tcggctttct tctgctcggc ttccttggcc ttggcctcgg ccttctcggc gcgctcgcgc
51061 tctttacgtt ggcgctcagc ggccttctcg gccttgcgca gggtagctgc ttgttccttg
51121 gtcagctctt cgccttgggt ctgttcgttc tggtccttct gttccatgtt cttactccgg
51181 gaatgttcaa agggatggct tattggcctg tgcggggatt atctctaaac taattgaaga
51241 agggaatacc cttagcctga actttcctaa atattttctt tcgggaaagt ccaaactcta
51301 gggaacttat ttatgttcga gaagttccta gcttttacgc aagaacagta agtattcgat
51361 tgcgcgagtt atcccagtat acatcaactg actataaggg atggacggca agtttcttc
51421 taacatggcg acccgtttcc attctgatcc ctgcgacttg tggaacgtca tcgcccatcc
51481 gaagtcgaat ccgccaatgg ccttctgcgc ctccagccgc acgtcttcct cgaccgaaaa
51541 actcagagga ttgaacttaa cccagcgttc aaagttcgta ccgataatgc gaactttggc
51601 gaacaacatt tcatcaggct cgtcatcatc ttcttgccct tcaggaaccg gcttgaagtc
51661 cagcagaatg gcttgttcgc cgttcatgat tccatattcg tgctggttcc cagtgcatac
51721 cagcttctcg ccgattcccg gctgcgcacc tttgtagccg aggattcggc gagcgcgtgc
51781 gttcaagcga cggcgagtat tgttgtaagc acaaagaatc acgccatcat cgtccaggaa
51841 cgtccgcatt tcatcatccg acatatcgaa gccggcccgg accaatatgt cgtcatactc
51901 gcggcagggc aggcgctttc cctggcggac gaacatcgac gcccgaacga tattgccagc
51961 gttgcgctcg atttcggtca tgatggtgtc acagctgttc tcgtggaaaa tctggacgcc
52021 gcgtacagga ggaacttggc caaagtcgcc aatctccaga accggaattc ggtgcgacaa
52081 caggcgctct tcatcccact cgccgatcat ggacgactcg tcgagaacta ccaacttcgg
52141 tttctcgtcg agcgagtctt tgttggcaaa catgatttcg ccgtcttcat cttcaccaat
52201 cggtcgatag ataaagctgt gaagagtccg ggcattgacg caacctttct cacgaagccg
52261 cgcggcggcc tttccggtcg gcgcgatgaa gactgtccag tccatcgagc agcaaagttc
52321 ggcgatgatc ttcgcaatag aagtcttacc agttcctgca aaaccggcga gtcgatagac
52381 ctgacggcgg tgcgctcgat cacaccaacc gcgataccag ttaacgacgg aatttatcgc
52441 gtcgatctgc tggctattag gtcggaagcc gaatcgctct tcgatctgat cgacggtgaa
52501 gttagatgct gacatatttg cgttctccaa cgctaggttt aattgaattg agactcagtt
52561 taagcagacc gtccacagac cacccagtat cacgacgata tttgcggccg tgcggatcga
52621 catagaagtt tttcgtgcgc cgcaacagga catagtgcca agcagcaccg agcgcatgga
52681 cccttccttt ataagggaag gccttaagtt gctctgcggc cttcttcgcc ccagggagcc
52741 agcggacggt cgaaaggacc aagaccgcac ccttgacagc ctgggaagcg gcgcggccgt
52801 cctgtgggct atagcgatgt ctatcggggt ctacccagtg gtggttgcca cgccggagct
52861 tcaccgtccg ggaccggccc tcaaacacca cagtaccttc gtgagtaaaa atatgttccg
52921 ccatggaatg ttccttataa cgtacagttc tgctttacct ctgcgcaaga agagtatact
52981 atcagctgac tcgtcaaagc gagctaattt aatccgactt tacttcggca ggaaagtggc
53041 cgatactagc gccgccgcct gtactgccct ccaaaacaga ggatacatta aatgcaagaa
53101 tgcaagattt cccgcgacca actcccggtc ggcaatccga atcccaatgt cgacaagact
53161 cgcgacccga acctaaagcc cggctacctg cgtcgcagtc gcgagctgga cccggctctg
53221 gccgttcgca tccgtcgcga gctgatccat gcggaagcct ccgacttggc catggccggg
53281 tgggtcaatt cccagtccag cctctatgga tcgaaagcgt tcccgcgcca ttccgtcgtt
53341 cgcgtgactg ggatggcgga atctgaaacg aacgtcggaa tgctcatcgg attcatcgag
53401 caccgcaagc acggtgaatg ggcagttctg gaaactggga cgaaagaagg cggcgcgatc
53461 accatcccag tcgagagcat catgcgtgcg tcattcgcag aggccgaaga attcgccgag
53521 aaatggaagc gtaacctggg gtggcgcctc ctgcgtcagc ttcgtgaatg cggcgccctg
53581 gccgggactg aagacgaatt cctgcggcgg ataatcaatc gatatgttcg cgatctcacg
53641 atactcgccc accacaaagc cggcgcagac aaaagctata ccgatgcagt gctcaaaagt
53701 atcggcgaag catggccgca gattcctgcc ggaacattcg tcggccaccg agtcgcgcaa
53761 ctcctgatca atcacaaact aggccgagct ggcaccatct tgaatgacct ggtggacttc
53821 ctggagaggt tcgcggccgg tcgtgataaa gtgctcaata tcgccatttg taattgaggt
53881 tagtgatatg ccagatttga tgaagctgag tcataggcaa gttgaagctc tgctagggct
53941 gtctaggaat tcttacaatt ggattcacgg tccttcgact gattcaacct tgaaggctct
54001 gagacgaatg ggactcgtaa atttgtcctg ggatgattct gtagctggat acatgttcgg
54061 cagtcagcct tgttggagca taactgacgc cgggaaaaaa cgaatcctgg caatgcagga
54121 aactctgaca gaagagcctg aacagcaatt taatcccagc ccatgccgcc atgagccagg
54181 taagtccgat tctgatcgac ttgctaagca actagaaacc atcgctcgtc tggaaaagga
54241 acttgaagca tcggaaaagc gcgggagcga actggcagca agctattgcg acggcgtggt
54301 cggtgatgaa tacggccaca cttattgccg ttataaggcg gaacgcgata cagctctggc
54361 cagggtcgct gagctggaag gaaagttgac tgattgggta cacgaaggat tccggctcaa
```

Figure 8Q

```
54421 cgaagcactg gcagcggcac agaccgccca cgaatgtacc atgggcgtag gcgacggcga
54481 cggcaagttg ctagttcatg gtgaccacgc cagcatcaaa gctgcccaga agatcgtcat
54541 agagcgcgac gccgcgttgg tcaggatagc ggagcttgaa tctaagcttg cggagacgca
54601 accctacaaa caacacccgc aaatcatagg gtacgcccgc aaaaaggaac ttgcgccatt
54661 gctcgatcca agccaacccg gtggaagcta catctatatt ggactggacc atccggcctg
54721 ctgggcggaa gagccacctt acgaattctt gacccctttg tataccggtc ctgtggcgag
54781 tcacagcgtg ccggatggtt acgccctaat tccggttaag gagactgagg cgatgcacga
54841 tgccgtaatg gcgctgttgt acaacggcat agcccgcacc gatacacaaa agctgctgga
54901 tgcgtacatc aacgccgcga ctaacaagga gtccgtgtaa tggaaccgaa gaaaccttca
54961 ccagtagatg gagtcatcat gaccagcctc gacgttctca ggaaggcaaa gcctgaagcg
55021 caggacgagt atgctctgtc catgttcgca acggcgatcc gccagaagtt gcagcgctcc
55081 cgcgacaagg gccgaggcgg atggatcgat tgcgacgaaa atgttctgct ggatggattc
55141 gccgaacatg cgctgaaggg caatgagaac aatctcctgg acctggcgac gttcctgatg
55201 ttcatgtggg ttcgcggcat cgatgatgcg aagattcccc cggcgctaga aaaggcgcgg
55261 cagcacaagg tcactgaagc ttgggaccag atcaacgaag gaaggacaag ctatgccggt
55321 aaggccggcg gcaagcgaca attcgtggaa gtgcctcgac gcaaagggcg cccggagcgg
55381 ctcgcatgaa gcctcacgaa ataagattgg cccaggccga agaattcctg agagaactcg
55441 gccgagggat tccggaagac gaacgggtga tggtcggcta cgctgaagag gccacagtcc
55501 agaccgacga aaacggccgc aagctcaacg caggctggtg gcccgtgccc tggaaggaag
55561 gcaagtacat caattccaga tccaacgctt atgcctgtat atcgtcatcc atcaagacgc
55621 ccaacccgaa gactggccag atgcgatact ggcgcggcga ggcctctttc ggccacggac
55681 tggcgttaat ggtcgatgac atcggctccg gcaaagggtc caagggcgac ttcaaccgcg
55741 acgagttccg cgagcgcctg gagccgaccg cgattgtgga gacttcgccg aacaactacc
55801 agttctggta tttcttcaaa gagccgatgt cccacatgct ccagtttaag gcattgctct
55861 attcgttcgt ggaccaggtg ctaaagaaag gcggcgacaa caccgtcaaa gacgtaagcc
55921 gttatggtcg catgccattc ggcttcaaca ataagcgcgg ggaagacggc aacttcaagt
55981 atgccgacga aaacggcaag cccgaactcg tgcgtttgta tcacgcagac tattccaagc
56041 gctactcgcc agaggaaatc gcccaggcct tcggcgtccg catcatcatg ccacagatga
56101 agaaggtgga gataaaccgc gacgattggg tttatgacca ggtgtggcta aagtatgccg
56161 agcacatctg cacgaaatac aaaatgggcg aggcagcggg cggccaagtc caacagaata
56221 tgtccggtaa atatcgcatc cgctgcccat ggggagacga gcatacaaat ggcgatccat
56281 ttggcgccta ctttcgcgga ccgatccctg gagccgagca cgaatatgtg ttcggttgcg
56341 gccacgatac ctgccgcaaa gagcatcgcc ggacgtgggc ggccttcacg gatgaagtcg
56401 tgctacccta tatcgtcgaa caattggaaa gaatcaaccg ccgtcacatc ggtgaggagt
56461 agacaatatg caaaacgatc ctggaatcct gatcacagcc attggcttgc tgttcctcgg
56521 ccttatcatc ttcttcgaag gcctaaaggg atggaaaata caagtcgcaa acttcctcgc
56581 gtcgcttctg tgcttcttct tcggcctttc tgctttgacg ttctggttcg tcgtggcgtt
56641 tgacgtattt taatcgacga acggtacaga aattttcgga tggggacgga acttattagc
56701 tatgccggtt taggtaggag ataatagccg tccctttcgc ctcaatatgt agaggcaatg
56761 ttgaatccga tcatgtaaag cagaaggcgg caaacctaac atgattatcg acgaagataa
56821 tatttttgat gatgacgaat cagggtccag tgagttcgat ctcacacaga tagaagatgc
56881 tggaatggac cctttgatga ccgccgcgag caaggcggcc gatgatgcga ttgcgaggaa
56941 cgaaacgcac cgcgcacaaa aggcggcaag atacgccgag gcgtatgcgg aaccagactt
57001 gagaaagcga gcgcgattgt tgatgctcga ccaggcgttc gatcttccgg tcagccgggt
57061 ggtgaaaggg ccgttcgatg acttcatcac taaatacagc tcgacttccg acagcaacta
57121 tctcgcggtg tacgatactt tgttctgcaa gggtgatgga accgtcccgc atccgcactt
57181 cgacgagttt cgcggacggc tggtggacca tcgcggcgtg gcgttcaaca acaagaccct
57241 cgacccgatt gacctgatgg gcgccctcgc ggctgcggcc ttggacgatc cctcgattaa
57301 gaagacgatt gagacttgct gcgtttgggc gcgtcgatac cgccgcaact cgctgataga
57361 gacgttcgag aagaagatac cggagtggga cggcgaagag cgaattagca cgttgctgat
57421 cgatcttttt aagccattcg acaccgaatt gaaccggatg gtgagcaagt atttctggct
57481 gagcctgtac tgccgcatca actatcctgg aatctcggcg ccgatctcgc tggcgttgat
57541 tggtgggcag gatgcgggga aatcctattt cggcctgctg atctgcaagg aactgtcggg
57601 cggtcgcgat ctggctcccg tccagctcga cctgagccga cacgaccaga caccattcct
57661 gcgcaacatc accggcaact cggtcattgc gaacgtcggg gaaatgtccg gcttcaaaaa
57721 gggcgacatg gaacgcatca aggagttctt ggtgcggtct tctgatacat tcgaccagaa
57781 gtttgagccg ggcgaaacga tcaagcgaca atggatcacc atcatggacg gcaacggcta
```

Figure 8R

```
57841 cgatggactc cagcgggacg actctggtaa ccgacgtttc tatcctatgt ttgttgcgca
57901 actgccccgat gaggatggaa agccgaactg ggttaagccg ggcgatggca atgaaccgtt
57961 caaggtggac ttcaccgact tcggccgcaa attctggcaa gcgatggctg aatgccgcgc
58021 atggatcgaa gagcacggcg tcgatggcta cctgaatatg gtgtcggaag caaaccgcga
58081 agtccagaac ttctctattt cggaaatgga gaatgcgcgc ggcgtggttc gcgacgatac
58141 gattgatatg tatctgatca atgtcctgat cagttgtgag ttcgaagagg ttaagcctgg
58201 tgggaattcc aagactcctg ggtggagggc agacaccgtt tccattctga agtggttcga
58261 tattctcgcc aggaagaagc cgatttctcg ccatttaact ccacacctga aagcgctggg
58321 attcattccg aataagaacg gcctgaatgg atggtgcctg cctgtggata aggtcgcgcc
58381 tgactggtcg aagaatatgc agacgacgct gccgccattc aatgatgcgc tggtgtatct
58441 gttgagaaag ggcgatccgg atatgaccga tgaggctgcc atggcaaaaa ttcgagcagt
58501 acgggcagag cgagccaaga tattgggcga ggatttctga taggtcgatt gagttggagt
58561 ggattaggcc gccttcgggc ggtcttttct ttgtcgcgga gaacattaat ttagcttgtg
58621 aacgggtgag gcttgaaagc tatgtgggaa ttaggttggc gtggcgatgg cgtattatgg
58681 gaagttaata gatttcggta ttggtctgga gtgtatgatg gttggatttt gcgtgaaatg
58741 ttgagaaatt gtgggtttga ggtggatttt tgtgtggaaa tagccgcaaa ttcctggatt
58801 gctattctga ctgggaagat gggaggccta ctgccgcgcg ggtttgcggc catattccct
58861 aattcccggg tttttcgagc atggtttaaa actattctac agcgaaaatc gattgcacaa
58921 tcctaataga aaaaatctat cacggacgtt acctatcttt aaaattaata aaattaatgg
58981 taatttggta atttggaata gtttagtctt tgaaagcctc gcggcactaa gccggtacac
59041 tacccgtcga gtttccgatt ccactcaact cgcggcaggg tcgccggaaa cttccgtcct
59101 tccaaaccat gggcagcggc aacaccacgg cggactaagc ggcaggggcc aaaactcgac
59161 gagcggaacc ggaaatttgg tcacagggca gaatcgctca cctggacata ttcctaacat
59221 ccgatttaac attcaatcca aacactcacc gccaccatcg cccgccaccc accaatccga
59281 ccctcacccg ccagcagacc gcccatataa catcctataa caccacctaa cactcattca
59341 ccatcaaacc cacccagacc tacaggccac ccacaagcag cccatagacg cgctccctgg
59401 ccccatagta caatcgcgcc atactcagtg tcgcggcaag caccaggtcc cagccaccta
59461 cccagccacc gcgacggtcc aagaatcgaa ctccagggac gcagcaacaa atgaccgcca
59521 aatattacag ccccgacgat ttagtcacgc cacaggaatt cgctgatccg cagttcgcgg
59581 cgatcaacca gaagcgtttc gatctgtaca tcgacctgcg cgttcaaggc tatagctcct
59641 ggcgggtctt cagagcgatc tggggcgaag agcacatgga tggcccggcc caggcccgca
59701 tcttcgcgat ggagtccaac ccgtactatc gcaagcaatt caaagccaag ctgaatgcga
59761 ccagaacgtc cgatctatgg aatccaaaga cggcgcttca cgaacttctc cagatggttc
59821 gtgatcccac cgtcaaggac tccagccgtc tgtcggccat caaggaattg aacgttctgg
59881 ccgaaatcac gttcgttgac gagtctggta agaccagggt aggtcgcgga ttggccgact
59941 tctacgcatc agaagccgag gctcagaccg ccaccgtcgc tgctgcggcc gaagccaatg
60001 gctatgtgca ggacggcgaa gagggcgatt tcccgtcccc gacgccggag ccgaccgagg
60061 aagaccgcgc caaccccatt cagacataaa ataacatcgt tctaggcccg aatcggaccg
60121 aactaaggcg acggtagcgg gttgggacga aaaacgattc tagggctgtt ctaggaagcc
60181 gaccaataac aatcagaaac gacaaagccc cggactctag ttcagaatcc ggggctttct
60241 ttttgggttt cttattctcc agcttcgatg atttcgaagt tgtatttgac gccttcgtgc
60301 tcgaaagtca acttgccggc ttccttcagc tgcatgcgga agcggatgtg cttcgaagag
60361 ggcaggccga actcgatgaa tgctgcgttg gtggaccgga actcaccgcg cttgcctttg
60421 acggtaacgg caactccatg acgctgagtg cgctttctgg agacttccgg gtctttccag
60481 gagttggcga tggctgccga caggtctttg gcctctttgg ccttctctgg agcgttcttc
60541 gcctcttcgc gcatcttcct gatttcttcc agcgcttcct cttcggtgat ttcctcttcc
60601 ggcttcaggc tctcttcctc ggccttctct tcttccttct tcttggaagt gcgggttttg
60661 taaaccttgg ccggggcttc ctcttcctgg aaggcttctt cctcggccgg cagagcgttc
60721 aggatggcga ggcagcgacg ctcggcggtc ttgcggtcgg agaagcgctt tacagtcgca
60781 tcggcgttgt gagagttgta gaaggcgacc agttctttca tttctgcgtt ctggatgtcg
60841 ccgaaggttt tgatggagtt ggtcatttct gcgatcctct gttttggaag atttctttcg
60901 ggcttcggtt tgtcgccccg ttgaaagaga ttatgcctag atcgatgctg cgtgtctaca
60961 tttattttag cagaatgatg atgaacccga cgaacggttg tcggatgtga aaacaccgca
61021 ggacaggctg cggtgttttc tggacgatgg tgcgacggtc agaaagtcgg gaccgtgatc
61081 ggctcgattg gtaggtcgcc gggcttgtcg ttgtccgacg cgggtgacga acttgacggt
61141 atggctccgg accgaagacc cagcggttca ggccgcctgc ttacctgcgg aggtggcgga
61201 gcttttggcg ctttcggaac tggaggtact ggaggcgccg gcggagacat cggcccttct
```

Figure 8S

```
61261 ggaagatcgg gaaggctcgg cgctttcggt tcgtggtaaa ccgtcgtgtc gttgcctggt
61321 tctgcgggat cgacgcccat gaatggagtg gtgacgcagc gcatgttcgg atagttcggc
61381 agcgttttca aagcgatgga gtctgcccag acatacggat tcttgtgatt accagggccg
61441 tggctgatga tctcggcagg catgtggccg ttgaggttca gccactccgc cgccccttgc
61501 cgagacagcg ggcttaccac gatctggcca gtggcctctt cggcaacagc gaacagatcg
61561 ccgagtttga atccgatgat caaatagttg gacctggcct cgccgacgaa tgcgacagtt
61621 tcagtgccgt gatggatatc ttgatcttcc catatgtata gcatgatgcg ccctcagtaa
61681 ggttgcttga tgtgatcgac cagggacatt ccggccggaa ttttgaagcg tatgtactcg
61741 atcataatcg cagttcggcg acgattcgtt cctgcctcgt cattcacgaa gagttcgcac
61801 tggttcggaa tgactcgcgt caccagagct tcgcctttcg agccgtagaa cttgatgtag
61861 gctgcgacgc ctcgcgtcat gttcagttgg atcgtttcgc agagtcgctg cgcggccgac
61921 gcgctggaca gatctgtcgg actgaccgtc acccagtaat gagcatttgc tgtttgttct
61981 ttgtcagaca tcaatggtct ccagtgagaa agccctgccg agtcgcagag gctggttgct
62041 gttagtcgcg cttcaacaga acgactttgt catatgcgcg atatttaccg cgccagtctt
62101 cccagtagtc gccggccggg caggtgagct ccagggtgat ttcgtcgcgc cagcattcga
62161 cagaaagtac aatagccttg ttccttgctg cggcatctgc tctgagctta atcagaattt
62221 cgtcgccagt tttcagctca tcaactctca caactttggc catgacacac tcctgtttga
62281 agaggcgcga ccggaaccaa cccagccgcg ccgatggatt aacgtttgtg aaggatggac
62341 acggcgtcca cgtcgaggat gctgatggta cggcgacggc gcggattgct gcgttcatgg
62401 atgcgaatca ggtcagcaga tgtagcttcg tgcaccaccc atacatcttc tggcttctgc
62461 gtccggagca ggatcgttac ctctgtgttc tgggcgaggc cgttgcagat gaacgtgaac
62521 ttggacgagg gagttctgta catttctaga ttccttttttg gactttgggt ccgacttctc
62581 agccggtgaa gagattatgc ccttattttg gccgccgagt aaagcatttg tgtatcaatt
62641 ctcccgtcag gtggaaccaa agtgcggtat cgcttatggc tacgctaccg cgccatggcc
62701 cttcttgctc gcacactgcg aaccacaggc tgatttccat ccttgccagg actcggccga
62761 aagattcgaa cctgcgccga ctggacagga tgtcgacatt cactcgtcga ttgacctcgt
62821 accggcgacc gttgatgacg aagaccagcc gcagggtttg tccgtcaaga cactcccagt
62881 atctggtttc atatcggagc caatagcgct tgcctgtcgg ccctaccata gtcatccttc
62941 tatgctcctg gccgctccac ggggaccggg cggtggagtc ggatcgaatc gacccaggat
63001 gtaatcgggc cgacgcgctt cctgcggaca aacggcgaga aggcgccatc ctgcgtccag
63061 ggcatgctgg agttcgtccg tgcagcagtc ttccttgagc aggagacggt tgacgctctg
63121 gagattcgga ccagggatgg ccgagctggt gtgcgagttc caaccttcga tgccgtccac
63181 catctgtggt tggttgatgt agccttcgga cctgccagcc aaccggctcg cggccagctc
63241 caggcgctcc agcattggcc gcagagcggc ttccgggtca acatcgtccc agagaaggac
63301 caagctgatg atggtgtacg gatagtcctt gtccagatcc caggccgaag cggtcagacg
63361 gcccaggccg atttcattac acatcacggg aacgtcgttg ctccatgtgg acggctccca
63421 gttccgctca ccaggattcc cgattgttac gccttccagg ttccccagga ggacgtggag
63481 tttgctgatg tattccgcct ccagcgcttt ccgctcttcg tcggtctggt tgtggcgata
63541 gaaggatgga gggctgactt ttgcatggta gagtttcatg gcggttcctc ggtttttgaa
63601 ggcttgaacg ttagaaaatg gtgtcgcagt atttctcgaa aggactctgg cgcttcttct
63661 cgcagatcgc gcaggtgact tccaggtcgg gcagctcgct gtaagtcttg ccgagataca
63721 gccagcgctt gcacagactg cggccgtccg acgtgaagaa gtggactttg cgagcattgc
63781 cgggttgcgc ccagccgcct tgatcgtttt tgcgcttgct catggcgata tttcctttgg
63841 atctggaatc catgccgtcc gttcgctcac ccaaactccg tctacataga tcaggactga
63901 cagagcagtc gcgccaaacc cgaagcctac atagaatgaa ccgggatcga tttccatggt
63961 ggcgctattg gtggcgctat tgaaatcgac ttcaaagtcg aacatcgaat ggccgctcat
64021 accatcacca tgtcgatttc attgatgaag aaatgaacat cgacaccatc ggcgcgaccg
64081 gtgtaacgca gccgagtcgt cccatcaatg tgggcttcct cgacgccgat gacttccagg
64141 atggtgtcgt tgcagtaaag cttgacgaac atcttgatgc cggagccaat cgccgcgaag
64201 gcgatctgct tgtacaggtc ttgcttgatc atgctttgcg ctcctgtttg ctggtgtaga
64261 tggcttcgac ttcggcctca agcttcgccc aaagttcgtt gtccaccgga ccccatggtc
64321 cggtctgggt gccgtcaacc ggcgcgaact tcccaccggc gcgacgatat ttggaacggg
64381 tctggagttc gatgattagc cgttcgtagg cgttgaattg agatgtcatt tcacaatcct
64441 cttttggacg ttcgcgtttc gatgaggtga ctatatctaa gtcgcctcat cgagtaaagc
64501 acttctgcga aattatttga tattctgtaa ggtcaggaag ccggacgatt tggtcagtcg
64561 atggagccga ggctccaccc gttgcgggcg aaggccgagc gacccgacag cttgcggcac
64621 tgaatggagc ttccatcgtc gaaagtatag gctgtggccc agtcaaggcg ctcacgacgt
```

Figure 8T

```
64681 actgccgcat tggcgatgtc ttccagacgg gctttaagga gttgctcggc tttagtcatc
64741 tcacacctct ttggtttatt cactcgatga ggtgactata cctcagacac ctcatcgagt
64801 aaagcacttt tgagagaatt atctgaaatt tctggaagcc aggaactgtc gccagagcca
64861 gtcaatgtga tcgttcagat agcgctcgcc atcggatgac agagacaggc agccgtcatt
64921 gatgccgagt ttggaactgg caatccgttc gaattcgaac tggagcgttc cgggccgagg
64981 gatatggtgc aggcaatatt tctgcacgat cagcagtcct cgaaaggttt gcggttcgca
65041 atttccgcga tcctttgcat gccgatgcga tagaactcgg catcctcgcg cgcccgcgac
65101 aatgcttcgc gcgcttcgca agccaacttg tattgattgt tggcattggc gatgcttccg
65161 tccaggcttc tgtcagactc ttcccggagc gccttttggg actccagctc ggcctccagc
65221 tcgcggattc gaagggcgag ctggctattc gtttcggcag ctttgttttc cagatcgatg
65281 gccgatttcg ctgctgtttc gagcctgtct ttgtcggcca tgagggtttc caggctcttg
65341 tcgagtgctt ccagaagagt cttcttggac tccagctcca gcgaaaattc gacgttctgc
65401 gcggacaagt tctgcgagtg cttcagcagt tcgtcgattc ttctttgatg gcccttgatg
65461 gccgagttct tcgtttcgac ttcggcctcc aaatctctga ttctgagttg aagctggcga
65521 ttcacctcgg ccgtcttgtc ttcgcgagcg atggagtttt gcaggcattc gtccagacgc
65581 gagttctccc gatcaagctc catggccgtc aggctttcgt cagaagtcac gccttcggat
65641 tcgtctttcc gtccctgatc ggcccgcaga taatactgtc cagcggcgaa cgccaggagg
65701 gcgcggttgg aaaactcagt agcgccctgc aagtaagaag atttgtatcg aggaacgaac
65761 tcgg
```

RECOMBINANT PB1 BACTERIOPHAGES AND USES THEREOF

SEQUENCE LISTING

The instant application contains a Sequence Listing which has been submitted electronically in ASCII format and is hereby incorporated by reference in its entirety. Said ASCII copy, created on Feb. 26, 2018, is named 102590-0607_SL.txt and is 176,819 bytes in size.

TECHNICAL FIELD

The present technology relates generally to compositions including recombinant PB1 bacteriophages, methods for making the same, and uses thereof. The recombinant PB1 bacteriophages disclosed herein are useful for the identification and/or antibiotic susceptibility profiling of specific bacterial strains/species present in a sample.

BACKGROUND

The following description of the background of the present technology is provided simply as an aid in understanding the present technology and is not admitted to describe or constitute prior art to the present technology.

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days. Additionally, some bacterial strains are not amenable to culturing and in vitro analysis in light of their fastidious nature. In other situations, the observable behavior of some bacterial strains is not readily distinguishable from others. Moreover, individual strains of a particular bacterial species may exhibit resistance to otherwise effective antibiotics.

Early and accurate identification of the bacterial strain(s) responsible for a patient's illness and determining its susceptibility to various antibiotics is an important aspect of the treatment selection decision process.

SUMMARY OF THE PRESENT TECHNOLOGY

In one aspect, the present disclosure provides a recombinant PB1 bacteriophage nucleic acid sequence, wherein the nucleic acid sequence between position 28,851 and 28,852 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In certain embodiments, the open reading frame of the heterologous nucleic acid sequence is operably linked to an expression control sequence that is capable of directing expression of the reporter protein. The expression control sequence may be an inducible promoter or a constitutive promoter. Additionally or alternatively, in some embodiments, the recombinant PB1 bacteriophage nucleic acid sequence comprises a sequence selected from the group consisting of SEQ ID NO: 2, SEQ ID NO: 3, SEQ ID NO: 4, and SEQ ID NO: 5.

Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherryl, PATagRFP, Kaede (green), Kaede (red), KikGR1 (green), KikGR1 (red), PS-CFP2, PS-CFP2, mEos2 (green), mEos2 (red), PSmOrange, or Dronpa. Examples of chemiluminescent protein include, but are not limited to, β-galactosidase, horseradish peroxidase (HRP), or alkaline phosphatase. Examples of bioluminescent protein include, but are not limited to, Aequorin, firefly luciferase, *Renilla* luciferase, red luciferase, luxAB, or nanoluciferase. In some embodiments, the bioluminescent protein is nanoluciferase.

In one aspect, the present disclosure provides a vector comprising any of the recombinant PB1 bacteriophage nucleic acid sequences disclosed herein, as well as bacterial host cells comprising the vectors of the present technology. The bacterial host cell may be a natural or non-natural host for PB1 bacteriophage.

In another aspect, the present disclosure provides a recombinant PB1 bacteriophage comprising any of the recombinant PB1 bacteriophage nucleic acid sequences of the present technology. Also provided herein are recombinant PB1 bacteriophages comprising a nucleic acid sequence selected from the group consisting of SEQ ID NO: 2, SEQ ID NO: 3, SEQ ID NO: 4, and SEQ ID NO: 5.

In one aspect, the present disclosure provides a bacterial host cell comprising a recombinant PB1 bacteriophage disclosed herein. The bacterial host cell may be a natural or non-natural host for PB1 bacteriophage.

In one aspect, the present disclosure provides a method for identifying at least one bacterial strain or species in a test sample obtained from a subject comprising (a) contacting the test sample comprising bacterial cells with a recombinant PB1 bacteriophage of the present technology; and (b) detecting the expression of the reporter protein of the recombinant PB1 bacteriophage, wherein detection of the reporter protein indicates the presence of at least one bacterial strain or species in the test sample. In some embodiments of the method, the expression of the reporter protein is measured in about 5, 10, 15, 20, 25, 30, 35, 40, 45, 50, 55, 60, 65, 70, 75, 80, 85, 90, or 120 minutes after contacting the test sample comprising bacterial cells with the recombinant PB1 bacteriophage.

In another aspect, the present disclosure provides a method for determining the antibiotic susceptibility of a bacterial strain or species in a test sample obtained from a subject comprising (a) infecting a plurality of test samples comprising bacterial cells with a recombinant PB1 bacteriophage of the present technology and an antibiotic, wherein the plurality of test samples is derived from the subject; (b) detecting the expression of the reporter protein of the recombinant PB1 bacteriophage in the plurality of test samples; and (c) determining that the antibiotic is effective in inhibiting the bacterial strain or species in a test sample when the reporter protein expression levels of the recombinant PB1 phage infected bacterial cells in the test sample are reduced relative to that observed in an untreated control sample comprising bacterial cells, wherein the untreated control sample is derived from the subject and is infected with the recombinant PB1 bacteriophage of the present technology. The expression of the reporter protein may be measured in about 5, 10, 15, 20, 25, 30, 35, 40, 45, 50, 55, 60, 65, 70, 75, 80, 85, 90, or 120 minutes after infecting the plurality of test samples comprising bacterial cells with the recombinant PB1 bacteriophage.

Additionally or alternatively, in some embodiments of the methods disclosed herein, the test sample is blood, sputum, mucus, lavage, saliva, or a swab obtained from the subject. In some embodiments, the subject is human.

In certain embodiments of the method, the antibiotic is selected from the group consisting of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In one aspect, the present disclosure provides methods for making a recombinant PB1 bacteriophage comprising (a) contacting a first PB1 bacteriophage genome comprising a single first recognition site with a first restriction enzyme in vitro under conditions where the first restriction enzyme cleaves the first recognition site to produce a cleaved first PB1 bacteriophage genome; and (b) recombining in vitro the cleaved first PB1 bacteriophage genome with a heterologous nucleic acid in the presence of a recombination system under conditions to produce a recombinant PB1 bacteriophage genome, wherein the heterologous nucleic acid sequence comprises an open reading frame that encodes a bioluminescent protein, a fluorescent protein, a chemiluminescent protein, or any combination thereof. The first PB1 bacteriophage genome may be recombinant or non-recombinant. The cleaved first PB1 bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment. In some embodiments, the first restriction enzyme is Bsu36I.

Additionally or alternatively, in some embodiments of the methods of the present technology, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the recombination system comprises a 3'-5' exonuclease, a DNA polymerase, and a DNA ligase.

Additionally or alternatively, in some embodiments, the method further comprises propagating the recombinant PB1 bacteriophage genome in a bacterial host. For example, the bacterial host may be transformed with the recombinant PB1 bacteriophage genome via electroporation. The bacterial host may be a non-natural bacterial host cell or a natural bacterial host cell for PB1 bacteriophage.

Also disclosed herein are kits comprising one or more coded/labeled vials that contain the recombinant PB1 bacteriophage of the present technology, instructions for use, and optionally at least one antibiotic.

BRIEF DESCRIPTION OF THE DRAWINGS

FIG. 2B also discloses SEQ ID NOS 11, 11, 11, 11, and 11-13, respectively, in order of appearance.

FIG. 2C also discloses SEQ ID NOS 14, 14, 14, and 14, respectively, in order of appearance.

FIG. 6 shows the heterologous nucleic acid sequence that was inserted into PB1 phage genomic DNA that was cleaved between position 28,851 and 28,852 of SEQ ID NO: 1 (SEQ ID NO: 2). The underlined sequences represent the homologous 5' and 3' flanking regions of the heterologous nucleic acid sequence.

FIGS. 7A-7K show the genome sequence of the recombinant NanoLuc® PB1 phage disclosed herein (SEQ ID NO: 3).

FIGS. 8A-8T show the genome sequence of the non-recombinant PB1 phage (SEQ ID NO: 1).

DETAILED DESCRIPTION

Figure 1:
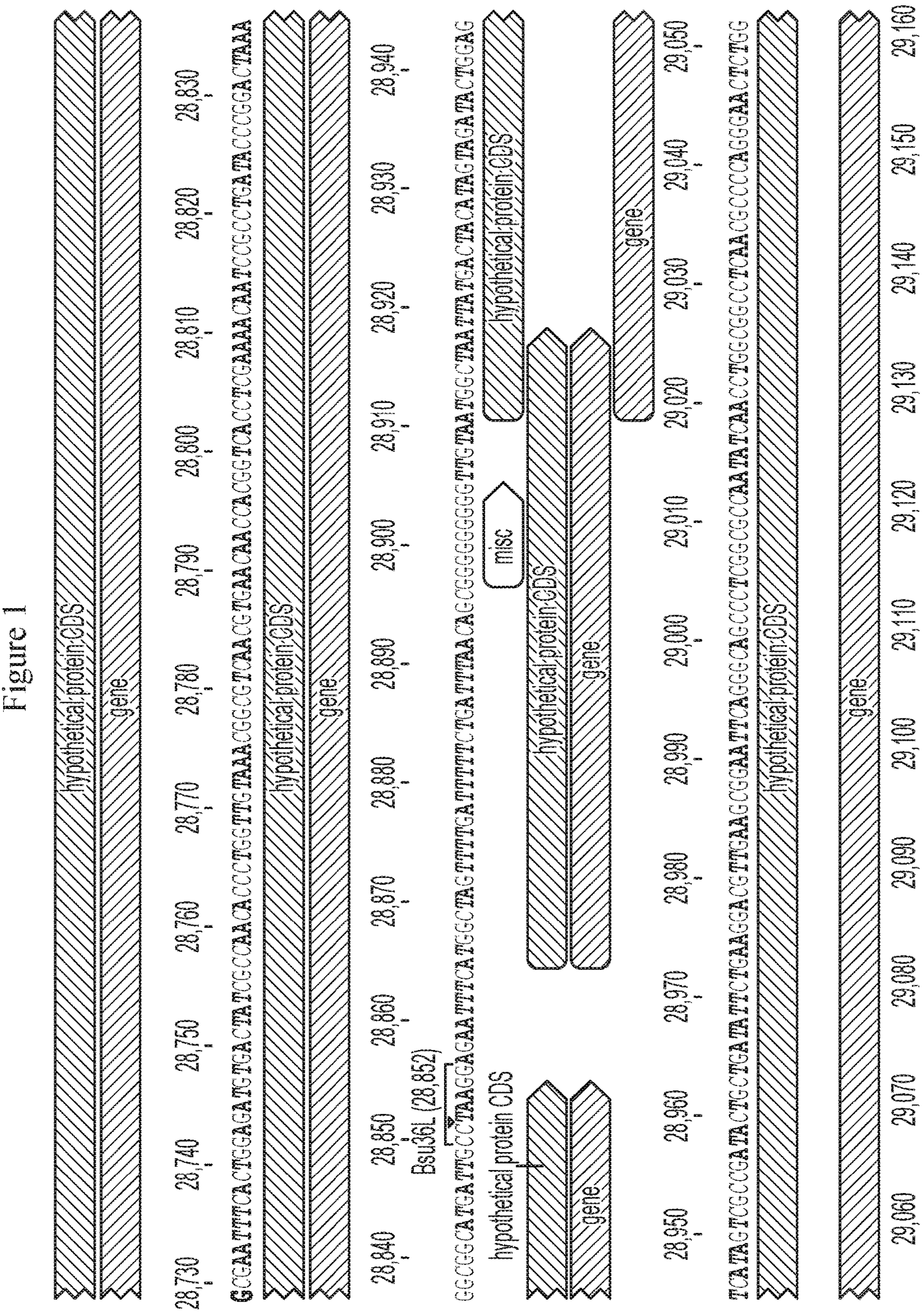
FIG. 1 shows the location of the Bsu36I recognition site within the PB1 bacteriophage genome (SEQ ID NO: 10).

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both).

As used herein, a "cleaved first PB1 bacteriophage genome" refers to the PB1 bacteriophage genome fragments that are formed after a first PB1 bacteriophage genome has undergone enzymatic cleavage with a restriction enzyme. Restriction enzymes refer to bacterial enzymes each of which cleave double-stranded DNA at or near a specific nucleotide sequence known as a "restriction site", "recognition site", or "double-stranded recognition site."

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, a "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to a nucleic acid of interest to initiate, regulate or otherwise control transcription of the nucleic acid of interest.

As used herein, a "phage genome" or "bacteriophage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion or an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, a "recombinant PB1 bacteriophage" or "recombinant PB1 phage" means a PB1 bacteriophage whose genomic DNA comprises a heterologous nucleic acid sequence that encodes a bioluminescent protein, a fluorescent protein, a chromogenic protein, or any combination thereof.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, "a sub-sample" refers to one or more samples containing bacterial cells that are derived from a test sample obtained from a subject. In some embodiments, the sub-sample is void of non-bacterial cells (e.g., human cells). In some embodiments, the sub-sample contains lysed human cells.

As used herein, "test sample" refers to a sample taken from a subject that is to be assayed for the presence of bacteria and/or for the antibiotic susceptibility of bacteria present in the sample. In some embodiments, the test sample is blood, sputum, mucus, lavage, or saliva. In certain embodiments, the test sample is a swab from a subject.

As used herein, the terms "subject," "individual," or "patient" are used interchangeably and refer to an individual organism, a vertebrate, a mammal, or a human. In certain embodiments, the individual, patient or subject is a human.

As used herein, a "vector" refers to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances no more than 500,000 bp. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

Recombinant PB1 Phage Compositions of the Present Technology

PB1 bacteriophage has a genome size of 65,764 bp (NCBI Reference Sequence: NC_011810.1). In one aspect, the present disclosure provides a recombinant PB1 bacteriophage nucleic acid sequence, wherein the nucleic acid sequence between position 28,851 and 28,852 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In some embodiments, the heterologous nucleic acid sequence further comprises at least one segment that corresponds to at least part of the excised endogenous phage genome sequence between position 28,851 and 28,852 of SEQ ID NO: 1.

Also disclosed herein are recombinant PB1 bacteriophages that comprise any recombinant PB1 bacteriophage nucleic acid sequence disclosed herein. In some embodiments, the reporter protein(s) encoded by the heterologous nucleic acid sequence produces a detectable signal upon exposure to the appropriate stimuli, and the resulting signal permits detection of bacterial host cells infected by a recombinant PB1 phage of the present technology.

In certain embodiments, the open reading frame encodes a reporter protein that serves as a marker that can be identified by screening bacterial host cells infected by a recombinant PB1 phage of the present technology. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the PB1 phage genome with no loss of endogenous PB1 phage genomic sequence. In some embodiments, the heterologous nucleic acid sequence replaces an endogenous PB1 phage genomic sequence. In some embodiments, the heterologous nucleic acid sequence includes an endogenous PB1 phage genomic sequence that was previously excised from the phage genome.

In certain embodiments, the heterologous nucleic acid sequence replaces an endogenous PB1 phage genomic sequence that is less than the length of the heterologous nucleic acid sequence. Accordingly, in some embodiments, the length of the recombinant PB1 phage genome is longer than the length of the wild-type PB1 phage genome. In some embodiments, the heterologous nucleic acid sequence replaces an endogenous PB1 phage genomic sequence that is greater than the length of the heterologous nucleic acid sequence. Thus, in some embodiments, the length of the recombinant PB1 phage genome is shorter than the length of the wild-type PB1 phage genome. In certain embodiments, the heterologous nucleic acid sequence replaces an endogenous PB1 phage genomic sequence that is equal to the length of the heterologous nucleic acid sequence.

In certain embodiments, the open reading frame of the heterologous nucleic acid sequence encodes a reporter protein that confers a phenotype of interest on a host cell infected by a recombinant PB1 phage of the present technology. In some embodiments, the phenotype of interest is the expression of the gene product encoded by the open reading frame of the heterologous nucleic acid sequence.

In certain embodiments, the open reading frame of the heterologous nucleic acid sequence is operably linked to an expression control sequence that is capable of directing expression of the open reading frame, wherein the open reading frame encodes a reporter protein (e.g., a bioluminescent protein, a fluorescent protein, a chemiluminescent protein, or any combination thereof). In some embodiments, the expression control sequence is located within the heterologous nucleic acid sequence. In other embodiments, the expression control sequence is located in the endogenous PB1 phage genome sequence. For example, the open reading frame may be inserted into the PB1 phage genome downstream of or in the place of an endogenous PB1 phage open reading frame sequence. In some embodiments, the expression control sequence is an inducible promoter or a constitutive promoter (e.g., sarA promoter or 1pp promoter). See e.g., Djordjevic & Klaenhammer, *Methods in Cell Science* 20(1):119-126 (1998). The inducible promoter or constitutive promoter may be an endogenous PB1 phage promoter sequence, a phage promoter sequence that is non-endogenous to PB1 phage, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include, but are not limited to, blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOK, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherryl, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid sequence comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type PB1 bacteriophage and the bacterial host cell. Accordingly, detection of the epitope in a sample demonstrates the presence of a bacterial host cell infected by a recombinant PB1 phage comprising a heterologous nucleic acid sequence, wherein the open reading frame of the heterologous nucleic acid sequence comprises the epitope. In other embodiments, the open reading frame of the heterologous nucleic acid sequence comprises a polypeptide tag sequence, such that the expression product of the open reading frame comprises the tag fused to a polypeptide or protein encoded by the open reading frame (e.g., poly-histidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, an antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Also disclosed herein are recombinant PB1 bacteriophages comprising any of the recombinant PB1 bacteriophage nucleic acid sequences disclosed herein. In some embodiments, the recombinant PB1 bacteriophages comprise a nucleic acid sequence selected from the group consisting of SEQ ID NO: 2, SEQ ID NO: 3, SEQ ID NO: 4, and SEQ ID NO: 5.

In another aspect, the present disclosure provides a vector comprising any of the recombinant PB1 bacteriophage nucleic acid sequences disclosed herein, as well as bacterial host cells comprising the vectors of the present technology. The bacterial host cell may be a natural or non-natural host for PB1 bacteriophage.

The present disclosure also provides a bacterial host cell comprising a recombinant PB1 bacteriophage disclosed herein. The bacterial host cell may be a natural or non-natural host for PB1 bacteriophage.

Methods of Making Recombinant PB1 Bacteriophage of the Present Technology

In one aspect, the present disclosure provides methods for making a recombinant PB1 bacteriophage comprising (a) contacting a first PB1 bacteriophage genome comprising a single first recognition site with a first restriction enzyme in vitro under conditions where the first restriction enzyme cleaves the first recognition site to produce a cleaved first PB1 bacteriophage genome; and (b) recombining in vitro the cleaved first PB1 bacteriophage genome with a heterologous nucleic acid in the presence of a recombination system under conditions to produce a recombinant PB1 bacteriophage genome, wherein the heterologous nucleic acid sequence comprises an open reading frame that encodes a bioluminescent protein, a fluorescent protein, a chemiluminescent protein, or any combination thereof. The first PB1 bacteriophage genome may be recombinant or non-recombinant. The cleaved first PB1 bacteriophage genome comprises a first cleaved bacteriophage genomic fragment and a second cleaved bacteriophage genomic fragment. In some embodiments, the heterologous nucleic acid comprises a 5' flanking region that is homologous to the 3' end of the first cleaved bacteriophage genomic fragment, and a 3' flanking region that is homologous to the 5' end of the second cleaved bacteriophage genomic fragment. In some embodiments, the first restriction enzyme is Bsu36I.

Additionally or alternatively, in some embodiments of the methods of the present technology, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the recombination system comprises a 3'-5' exonuclease, a DNA polymerase, and a DNA ligase.

Additionally or alternatively, in some embodiments, the method further comprises propagating the recombinant PB1 bacteriophage genome in a bacterial host. For example, the bacterial host may be transformed with the recombinant PB1 bacteriophage genome via electroporation. The bacterial host may be a non-natural bacterial host cell or a natural bacterial host cell for PB1 bacteriophage.

In some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Bacterial Identification and Antibiotic Susceptibility Profiling Methods of the Present Technology Accurate identification of bacterial species within a biological sample informs the selection of suitable therapies for treating bacterial infections. The recombinant PB1 bacteriophages disclosed herein may be used to identify bacteria present within a biological sample (e.g., whole blood, plasma, serum). Such methods entail contacting the biological sample with a recombinant PB1 bacteriophage disclosed herein, and detecting the presence of bacterial host cells infected by the recombinant PB1 phage, wherein the recombinant PB1 phage comprises a heterologous nucleic acid sequence that encodes a detectable gene product, thereby leading to the identification of bacteria present within the biological sample.

Additionally or alternatively, the recombinant PB1 bacteriophages disclosed herein, may be used in methods for profiling antibiotic susceptibility of bacteria present within a biological sample (e.g., whole blood, plasma, serum). These methods include (a) infecting the biological sample with an antibiotic and a recombinant PB1 bacteriophage disclosed herein, (b) detecting the presence of bacterial host cells infected by the recombinant PB1 phage, wherein the recombinant PB1 phage comprises a heterologous nucleic acid sequence that encodes a detectable gene product, and (c) determining that the antibiotic is effective in inhibiting the bacteria present in the biological sample when the levels of recombinant PB1 phage infected bacterial host cells is reduced relative to that observed in an untreated control sample.

In one aspect, the present disclosure provides a method for identifying at least one bacterial strain or species in a test sample obtained from a subject comprising (a) separating bacterial cells isolated from the test sample into one or more sub-samples, (b) infecting each sub-sample with at least one recombinant PB1 bacteriophage disclosed herein, wherein each recombinant PB1 bacteriophage comprises a heterologous nucleic acid sequence encoding one or more reporter genes, and (c) identifying at least one bacterial strain or species in the test sample by detecting the expression of the one or more reporter genes of the at least one recombinant PB1 bacteriophage. In certain embodiments, the at least one PB1 bacteriophage comprises a nucleic acid sequence selected from the group consisting of SEQ ID NO: 2, SEQ ID NO: 3, SEQ ID NO: 4, and SEQ ID NO: 5. In certain embodiments, the method for identifying at least one bacterial strain or species in a test sample does not require the culturing of bacterial cells from the test sample or a sub-sample.

In some embodiments, identification of at least one bacterial strain or species includes detecting the expression of the one or more reporter genes of the at least one recombinant PB1 bacteriophage, e.g., detectable expression of green fluorescence indicates the presence of bacterial species A in a test sample or sub-sample. In some embodiments, the absence of at least one bacterial strain or species is identified by the lack of detectable expression of the one or more reporter genes of the at least one recombinant PB1 bacteriophage, e.g., undetectable expression of green fluorescence indicates the lack of bacterial species A in a test sample or sub-sample.

In some embodiments, the at least one recombinant PB1 bacteriophage infects a single species of bacteria. In certain embodiments, the at least one recombinant PB1 bacteriophage infects two or more species of bacteria.

In some embodiments, detection of the expression of the reporter gene is detection of the gene product itself, e.g., a fluorescent protein. In some embodiments, detection of the expression of the reporter gene is detection of an enzymatic reaction requiring the expression of the reporter gene, e.g., expression of luciferase to catalyze luciferin to produce light.

In some embodiments, the expression of the one or more reporter genes is detected in about 5, 10, 15, 20, 25, 30, 35, 40, 45, 50, 55, 60, 65, 70, 75, 80, 85, 90, 120 minutes or any time between any two of the preceding values after infecting a sub-sample with the at least one recombinant PB1 bacteriophage disclosed herein.

The present disclosure also provides a method for identifying at least one bacterial strain or species in a test sample obtained from a subject comprising (a) infecting the test sample comprising bacterial cells with a recombinant PB1 bacteriophage of the present technology; and (b) detecting the expression of the reporter protein of the recombinant PB1 bacteriophage, wherein detection of the reporter protein indicates the presence of at least one bacterial strain or species in the test sample. In some embodiments of the method, the expression of the reporter protein is measured in about 5, 10, 15, 20, 25, 30, 35, 40, 45, 50, 55, 60, 65, 70, 75, 80, 85, 90, or 120 minutes after infecting the test sample comprising bacterial cells with the recombinant PB1 bacteriophage.

Additionally or alternatively, in some embodiments of the methods disclosed herein, the test sample is blood, sputum, mucus, lavage, saliva, or a swab obtained from the subject. In some embodiments, the subject is human.

In another aspect, the present disclosure provides a method for determining the antibiotic susceptibility of a bacterial strain or species in a test sample obtained from a subject comprising (a) separating bacterial cells isolated from the test sample into a plurality of sub-samples, (b) infecting the plurality of sub-samples with a recombinant PB1 bacteriophage disclosed herein and at least one antibiotic, wherein the recombinant PB1 bacteriophage comprises a heterologous nucleic acid sequence encoding a reporter gene, and (c) detecting the expression of the reporter gene of the recombinant PB1 bacteriophage in the presence of each antibiotic. In some embodiments, the method further comprises determining that the bacterial strain or species in the test sample is susceptible to an antibiotic if the reporter gene expression of the recombinant PB1 bacteriophage in the antibiotic treated sub-sample is decreased relative to that observed in a control sub-sample that is not treated with the antibiotic. In other embodiments, the method further comprises determining that the bacterial strain or species in the test sample is resistant to an antibiotic if the reporter gene expression of the recombinant PB1 bacteriophage in the antibiotic treated sub-sample is comparable to that observed in a control sub-sample that is not treated with the antibiotic. In certain embodiments, the method for determining the antibiotic susceptibility of a bacterial strain or species in a test sample does not require the culturing of bacterial cells from a test sample or a sub-sample.

Additionally or alternatively, in some embodiments of the recombinant PB1 bacteriophages of the present technology, the reporter gene is nanoluciferase. In certain embodiments, recombinant PB1 bacteriophage comprises a nucleic acid sequence selected from the group consisting of SEQ ID NO: 2, SEQ ID NO: 3, SEQ ID NO: 4, and SEQ ID NO: 5.

Examples of antibiotics include one or more of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In some embodiments of the method, the differences in the reporter gene expression of the recombinant PB1 bacteriophage observed in the antibiotic treated sub-sample and the untreated control sub-sample is defined as μ.

Additionally or alternatively, in some embodiments of the method, the expression of the reporter gene is detected in about 5, 10, 15, 20, 25, 30, 35, 40, 45, 50, 55, 60, 65, 70, 75, 80, 85, 90, 120 minutes or any time between any two of the preceding values after infecting a sub-sample with a recombinant PB1 bacteriophage disclosed herein.

In some embodiments, two or more sub-samples are tested for antibiotic susceptibility in series. In some embodiments, two or more sub-samples are tested for antibiotic susceptibility in parallel. In some embodiments, one or more sub-samples are tested for antibiotic susceptibility in a running assay (where resistance or sensitivity to one antibiotic is determined and the resistance or sensitivity to a second, third, fourth, fifth, etc., antibiotic is being assayed).

In some embodiments of the methods disclosed herein, isolating bacterial cells from a test sample includes incubating the test sample with distilled water to form a mixture, centrifuging the mixture to form a pellet that includes bacterial cells, and re-suspending the pellet to form a bacterial suspension comprising isolated bacterial cells after discarding the supernatant. The pellet may be re-suspended in a phosphate buffer. In some embodiments, the bacterial suspension is divided into one or more sub-samples.

In certain embodiments of the methods disclosed herein, mixing the test sample with distilled water will lead to the lysis of cells that lack cell walls (e.g., mammalian cells and red blood cells) while leaving cells with cell walls (e.g., bacteria) intact. Without wishing to be bound by theory, in some embodiments, the removal of cells that lack cell walls enhances the detection of reporter gene expression in bacterial cells infected with a recombinant PB1 bacteriophage, as intact non-bacterial cells (e.g., red blood cells) may quench reporter gene expression. In some embodiments of the methods of the present technology, the mixture is about 90% distilled water and 10% test sample, about 80% distilled water and 20% test sample, about 70% distilled water and 30% test sample, about 60% distilled water and 40% test sample, about 50% distilled water and 50% test sample, about 40% distilled water and 60% test sample, about 30% distilled water and 70% test sample, about 20% distilled water and 80% sample, or about 10% distilled water and 90% test sample. In some embodiments of the methods disclosed herein, the mixture is incubated for 1, 2, 3, 4, 5, 6, 7, 8, 9, 10, 11, 12, 13, 14, or 15 minutes, or any time between two of the previously listed time points. Additionally or alternatively, in certain embodiments of the methods disclosed herein, the mixture is centrifuged for 1, 2, 3, 4, 5, 6, 7, 8, 9, 10, 11, 12, 13, 14, or 15 minutes, or any time between two of the previously listed time points.

Additionally or alternatively, in certain embodiments of the methods disclosed herein, each of the one or more sub-samples comprise between about 5 to 500, about 10 to 400, about 20 to 300, about 30 to 300, about 40 to 200 or about 50 to 100 bacterial cells. In some embodiments of the methods disclosed herein, each of the one or more sub-samples comprises between about 100 to 10,000, about 200 to 9,000, about 300 to 8,000, about 400 to 7,000, about 500 to 6,000, about 600 to 5,000, about 700 to 4,000, about 800 to 3,000, about 900 to 2,000, or about 1,000 to 1,500 bacterial cells.

In another aspect, the present disclosure provides a method for determining the antibiotic susceptibility of a bacterial strain or species in a test sample obtained from a subject comprising (a) infecting a plurality of test samples comprising bacterial cells with a recombinant PB1 bacteriophage of the present technology and an antibiotic, wherein the plurality of test samples is derived from the subject; (b) detecting the expression of the reporter protein of the recombinant PB1 bacteriophage in the plurality of test samples; and (c) determining that the antibiotic is effective in inhibiting the bacterial strain or species in a test sample when the reporter protein expression levels of the recombinant PB1 phage infected bacterial cells in the test sample are reduced relative to that observed in an untreated control sample comprising recombinant PB1 phage infected bacterial cells, wherein the untreated control sample is derived from the subject and is infected with the recombinant PB1 bacteriophage of the present technology. The expression of the reporter protein may be measured in about 5, 10, 15, 20, 25, 30, 35, 40, 45, 50, 55, 60, 65, 70, 75, 80, 85, 90 or 120 minutes after infecting the plurality of test samples comprising bacterial cells with the recombinant PB1 bacteriophage. In other embodiments, the method further comprises determining that the bacterial strain or species in the test sample is resistant to the antibiotic when the reporter protein expression levels of the recombinant PB1 bacteriophage infected bacterial cells in the test sample are comparable to that observed in an untreated control sample comprising recombinant PB1 phage infected bacterial cells, wherein the untreated control sample is derived from the subject and is infected with the recombinant PB1 bacteriophage of the present technology.

In any of the above embodiments of the methods of the present technology, the test sample is blood, sputum, mucus, lavage, saliva, or a swab obtained from the subject. In some embodiments of the methods disclosed herein, the test sample is obtained from a mammalian subject, including, for example, farm animals, such as sheep, pigs, cows, and horses; pet animals, such as dogs and cats; and laboratory animals, such as rats, mice and rabbits. In one embodiment, the mammal subject is a human.

Kits

The present technology provides kits including the recombinant PB1 bacteriophages disclosed herein for bacteria identification and antibiotic susceptibility profiling.

In one aspect, the kits of the present technology comprise one or more coded/labeled vials that contain a plurality of the recombinant PB1 bacteriophages disclosed herein, and instructions for use. In some embodiments, each coded/labeled vial corresponds to a different recombinant PB1 bacteriophage. In other embodiments, each coded/labeled vial corresponds to the same recombinant PB1 bacteriophage. In some embodiments, the kits of the present technology comprise one or more coded/labeled vials that contain at least one recombinant PB1 bacteriophage comprising a nucleic acid sequence selected from the group consisting of SEQ ID NO: 2, SEQ ID NO: 3, SEQ ID NO: 4, and SEQ ID NO: 5.

In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage genomes for extended periods, such as under bacteriophage-specific, controlled temperature, moisture, and pH conditions.

Additionally or alternatively, in some embodiments, the kits further comprise vials containing natural or non-natural bacterial host cells. In some embodiments, the bacterial host cells are *Pseudomonas aeruginosa*. In certain embodiments, the bacterial host cells are *Pseudomonas aeruginosa* strain PAO1.

The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids of the recombinant PB1 bacteriophages disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics. In some embodiments, the plurality of antibiotics comprises one or more of rifampicin, tetracycline, levofloxacin, and ampicillin. Other examples of antibiotics include penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

EXAMPLES

Example 1: Design and Methods for Generating the Recombinant PB1 Bacteriophages of the Present Technology This Example demonstrates that the methods of the present technology are useful for making the recombinant PB1 bacteriophages disclosed herein in a bacterial host cell.

The sequence of the initial PB1 (ATCC 15692-B3, Manassas Va.) genome is shown in FIGS. 8A-8T and is represented by SEQ ID NO: 1. FIG. 1 shows the location of the Bsu36I recognition site within the PB1 bacteriophage genome. FIG. 6 shows the donor template nucleic acid sequence that was inserted into PB1 phage genomic DNA that was cleaved between position 28,851 and 28,852 of SEQ ID NO: 1 (SEQ ID NO: 2).

PB1 bacteriophage DNA was digested with the restriction enzyme Bsu36I, which cuts directly upstream of the stop codon of gene 42. Using the NEBuilder HiFi DNA Assembly® (New England Biolabs, Inc., Ipswich, Mass.) protocol, the donor template (containing the Nanoluc® gene (Promega, Madison, Wis.), 24 base pairs of homologous PB1 phage sequence that is located 5' to the Bsu36I site, and 24 base pairs of homologous PB1 phage sequence that is located 3' region of the Bsu36I site) was inserted into the PB1 phage genome via PCR using primers SJG146 5' CGGACTAAAGGCGGCATGATTGCCTAAAAGGAGATTCAACATGGTCTTCAC 3' (SEQ ID NO: 6) and SJG147 5' ACTAGCCATGAAATTCTCCTTATTACGCCAGAATGCGTTCGC 3' (SEQ ID NO: 7).

The PCR product was generated after amplifying the synthetic nanoluciferase template gBlocks® (IDT, Coralville, Iowa). The stop codon for gene 42 was re-introduced with the insertion of the nanoluciferase target substrate to repair the gene.

Primers flanking the Bsu36I cut site were designed using Geneious Software (Biomatters Ltd., Auckland, New Zealand) and the NEB hotstart PCR® (New England Biolabs, Inc., Ipswich Mass.) was performed to assess proper insertion of the nanoluciferase gene within the Bsu36I locus. The primer set used for the screening PCR was: SJG148 5' TCATACCGGACGTATTCCGC 3' (SEQ ID NO: 8) and SJG149 5' GGCGATGCGAGCTTCATTC 3' (SEQ ID NO: 9).

Results.

Figure 2A:
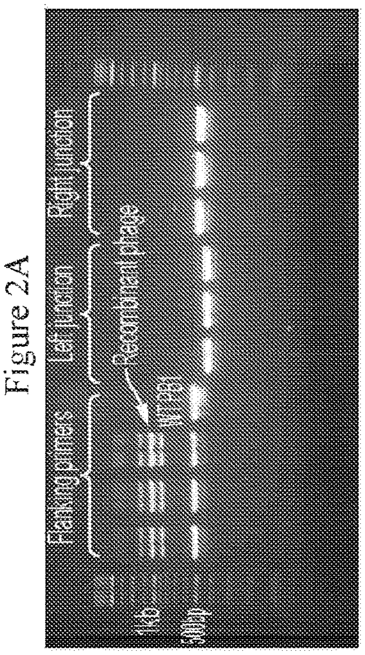
FIG. 2A shows the junctional and flanking PCR assays that tested for the presence of recombinant PB1 bacteriophage.
Figure 2B:
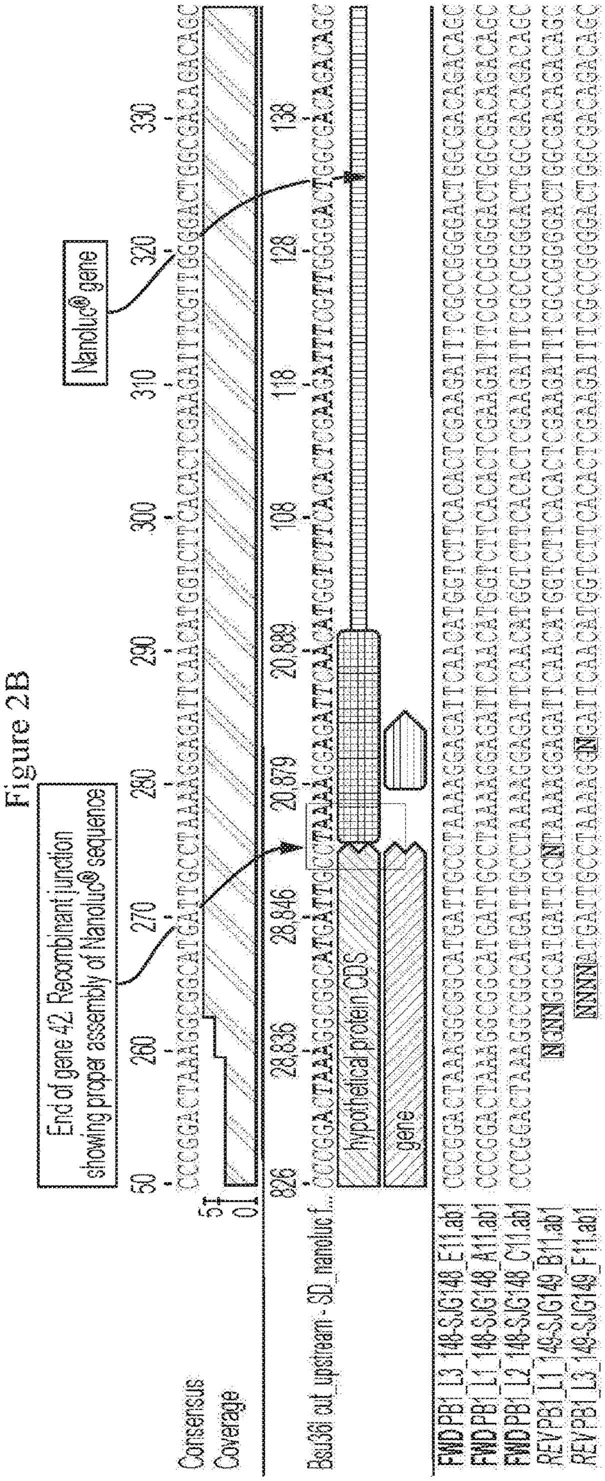
FIG. 2B shows the upstream junction sequence of the nanoluciferase insertion in the recombinant PB1 phage genome: 5' CGGACTAAAGGCGGCATGATTGCCTAAAAGGAGATTCAACATGGTCTTCACACT CGAAGATTTCGTTGGGGACTGGCGACAGACAGC 3' (SEQ ID NO: 4).
Figure 2C:
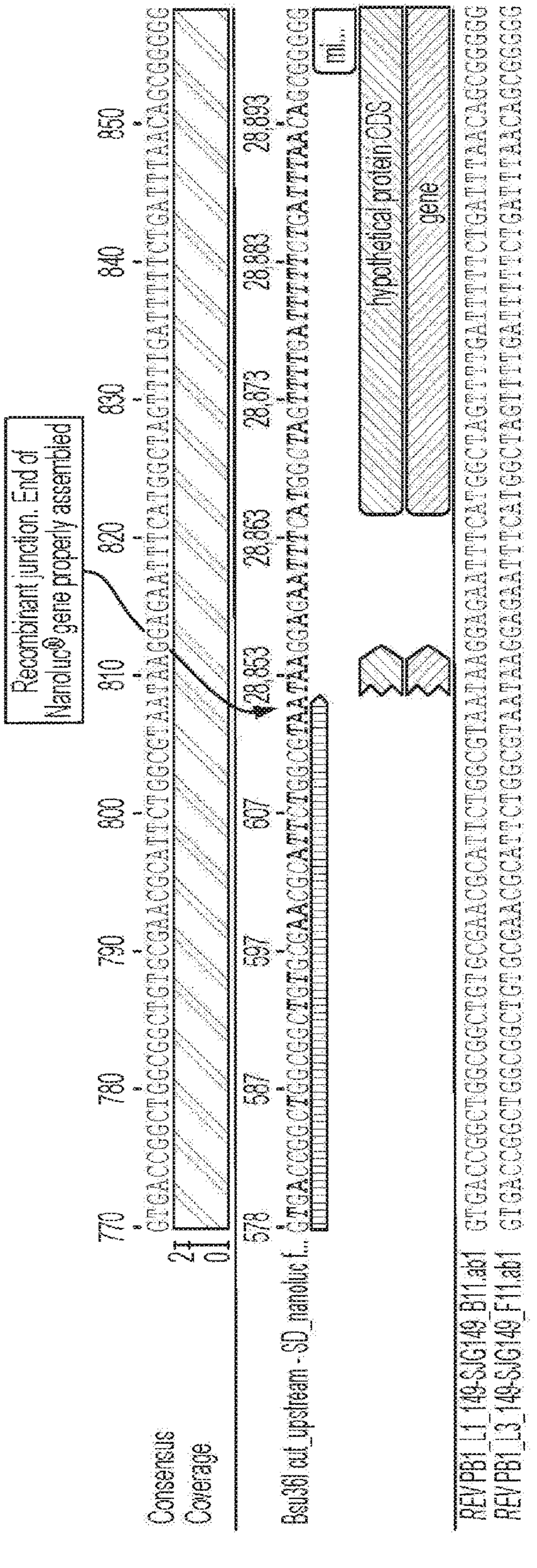
FIG. 2C shows the downstream junction sequence of the nanoluciferase insertion in the recombinant PB1 phage genome: 5' TGACCGGCTGGCGGCTGTGCGAACGCATTCTGGCGTAA 3' (SEQ ID NO: 5).

As shown in FIG. 2A, recombinant NanoLuc® PB1 phage yielded a 1000 base pairs (bp) amplicon, whereas wild-type PB1 phage yielded a 500 bp amplicon. PCR products were subjected to Sanger sequencing in both forward and reverse directions to confirm the sequence of the nanoluciferase insertion at the Bsu36I locus. FIGS. 2B-2C show the upstream and downstream junction sequences of the nanoluciferase insertion at the Bsu36I locus within the recombinant PB1 phage. FIGS. 7A-7K show the complete genome sequence of the recombinant NanoLuc® PB1 phage (SEQ ID NO: 3).

These results demonstrate that the methods of the present technology are useful for making the recombinant PB1 bacteriophages disclosed herein in a bacterial host cell. Accordingly, the methods disclosed herein are useful for generating recombinant PB1 bacteriophages that can be used in the identification and/or antibiotic susceptibility profiling of specific *Pseudomonas aeruginosa* strains present in a sample.

Example 2: Functional Activity of the Recombinant PB1 Bacteriophages of the Present Technology This Example demonstrates that the recombinant PB1 bacteriophages of the present technology are useful for the identification and/or antibiotic susceptibility profiling of specific *Pseudomonas aeruginosa* strains present in a sample.

Phenotypic Verification.

Products of the NEBuilder recombination reaction described in Example 1 were directly electroporated into electrocompetent *Pseudomonas aeruginosa* PAO1 cells. Briefly, PAO1 cells were grown in 25 mL LB broth at 37° C. while shaking until an OD600 value of 0.8 was reached. At room temperature, alginate lyase (Sigma-Aldrich, St Louis, Mo.) was added to cells to a final concentration of 2 units/mL and incubated for two hours. The cell suspension was centrifuged at 8500×g for 5 minutes. The supernatant was removed and the cells were resuspended in 25 mL 300 mM sucrose. Cells were centrifuged again at 8500 xg for 5 minutes and resuspended in 10 mL of 300 mM sucrose. Cells were then centrifuged at 8500×g for 5 minutes and resuspended in 4000 of 300 mM sucrose. 2 μl of the NEBuilder recombination reaction was added to 100 μl electrocompetent cells in a 2 mm electroporation cuvette and electroporated at 2.4 kV, 400 ohms, and 25 uF. To recover cells, 450 μl of pre-warmed LB was added to the cuvette, and the cells were incubated at 37° C. for 1 hour, and then plated for plaque forming units. Plaques were screened via PCR and sequenced to confirm proper assembly. PAO1 cells were infected with recombinant and wild-type plaques, and were then assayed for luciferase production with the Nano-Glo Luciferase Assay System (Promega Inc, Madison, Wis.). After 1 hour of infection, the measurement of luminescence of the recombinant luciferase PB1 phage yielded 2.15E9 relative luminescence units (RLUs) compared to that observed in wild-type PB1 phage (1289 RLUs).

NanoLuc® Signal Production and Sensitivity Assays.

Figure 3:
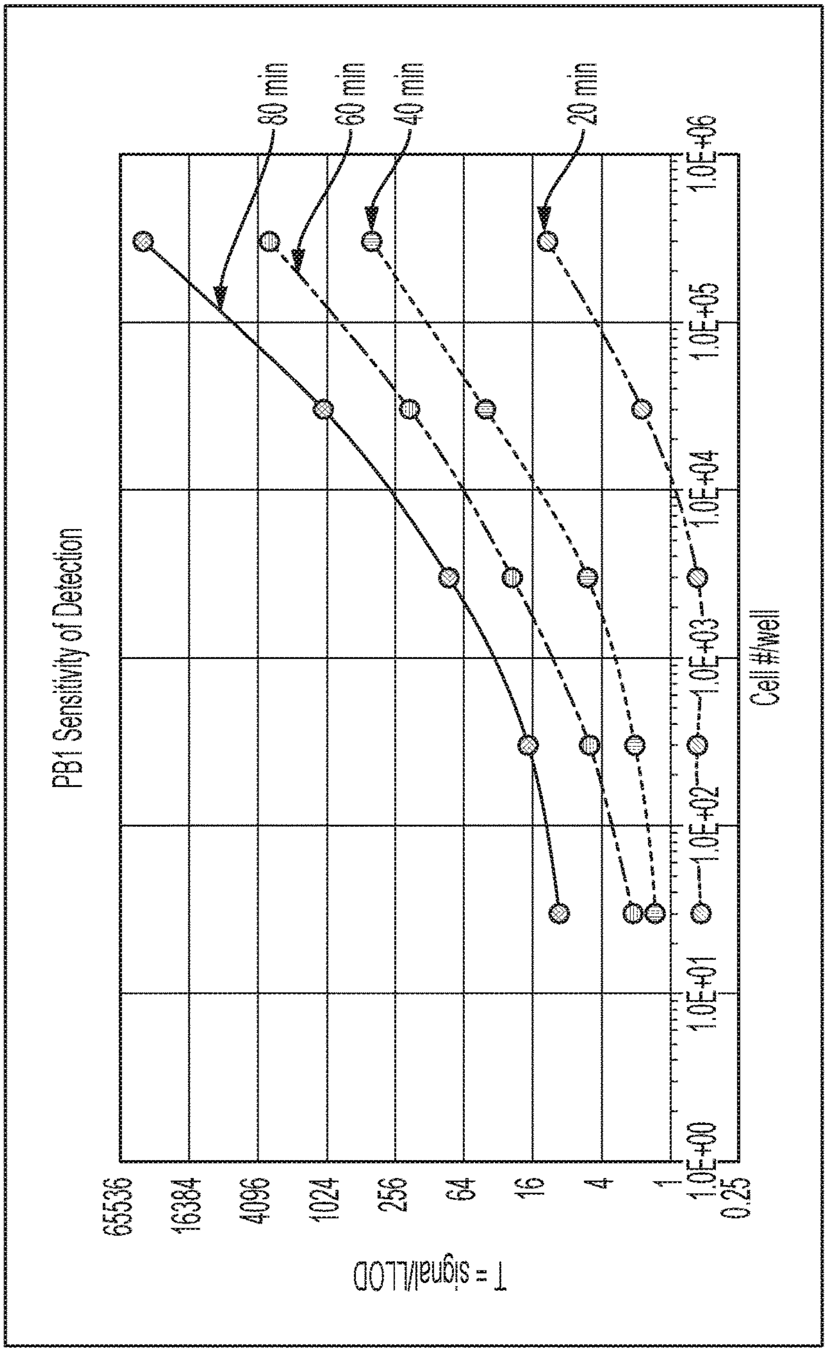
FIG. 3 shows the luminescence activity profile of the recombinant PB1 phages of the present technology at different concentrations and time intervals. Different concentrations of *P. aeruginosa* strain PAO1 cells were infected with the recombinant PB1 phages of the present technology. Detection was performed with a standard luminometer yielding Relative Luminescence Units (RLU). Tau(T) was calculated by dividing RLU from recombinant PB1 phage infections by background (defined by 3× the standard deviation of the recombinant PB1 phage only signal without cells (negative control) added back to the average signal for the negative control). Time points for luminescence signal were taken at 20, 40, 60, and 80 minutes.

NanoLuc® signal production and sensitivity were evaluated by infecting *Pseudomonas aeruginosa* PAO1 cells with the purified recombinant Nanoluc® PB1 phage and measuring luminescence at 20, 40, 60, 80 minutes post infection. Briefly, bacterial cells were grown to mid log-phase growth in TSB medium and serially diluted in log steps in a microtiter plate to obtain concentrations of $10^5$ bacteria/100 μl down to 1 bacterial cell/100 μl. Cells were plated for colony forming units. Recombinant Nanoluc® PB1 phage was added to each well at a constant concentration of $10^6$ phage/well. For each time point, luminescence was measured using the Nano-Glo® Luciferase Assay System (Promega Inc, Madison Inc). FIG. 3 demonstrates that the intensity of the NanoLuc® signal produced by a recombinant PB1 phage strain containing the NanoLuc® insertion was dependent on bacterial cell concentration and time.

Figure 4A:
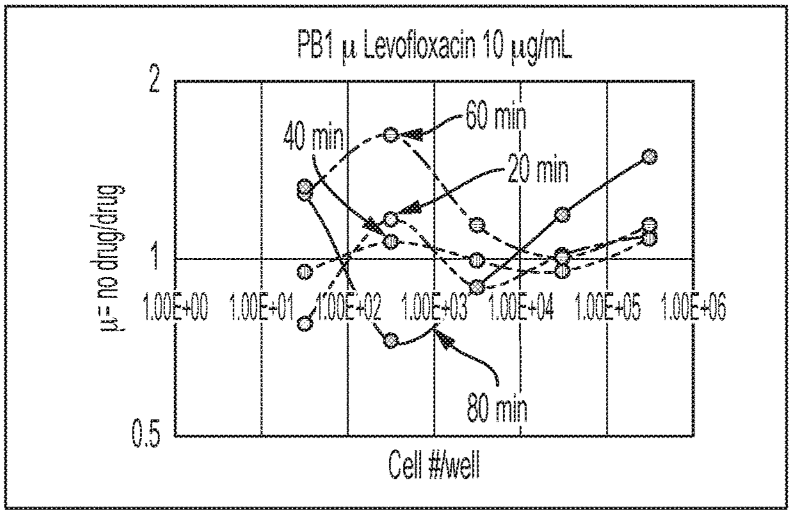
FIG. 4A shows antibiotic susceptibility profiling results using recombinant PB1 phages to evaluate the response of a drug resistant strain to levofloxacin.
Figure 4B:
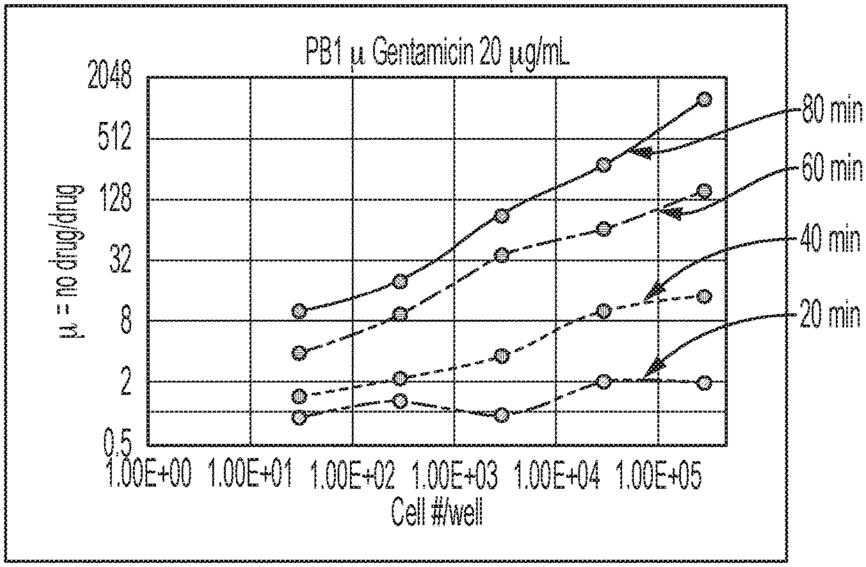
FIG. 4B shows antibiotic susceptibility profiling results using recombinant PB1 phages to evaluate the response of a drug sensitive strain to gentamicin.

FIG. 4A shows antibiotic susceptibility profiling results using recombinant PB1 phages to evaluate the response of a drug resistant strain to levofloxacin. FIG. 4B shows antibiotic susceptibility profiling results using recombinant PB1 phages to evaluate the response of a drug sensitive strain to gentamicin. As shown in FIG. 4B, there was a steady increase in μ value over time because the 'no drug' sample continued to generate a luminescent signal, whereas the gentamicin treated sample showed a decline in luciferase activity. In contrast, no such correlation was observed in the drug resistant strain in response to levofloxacin. See FIG. 4A.

Figure 5:
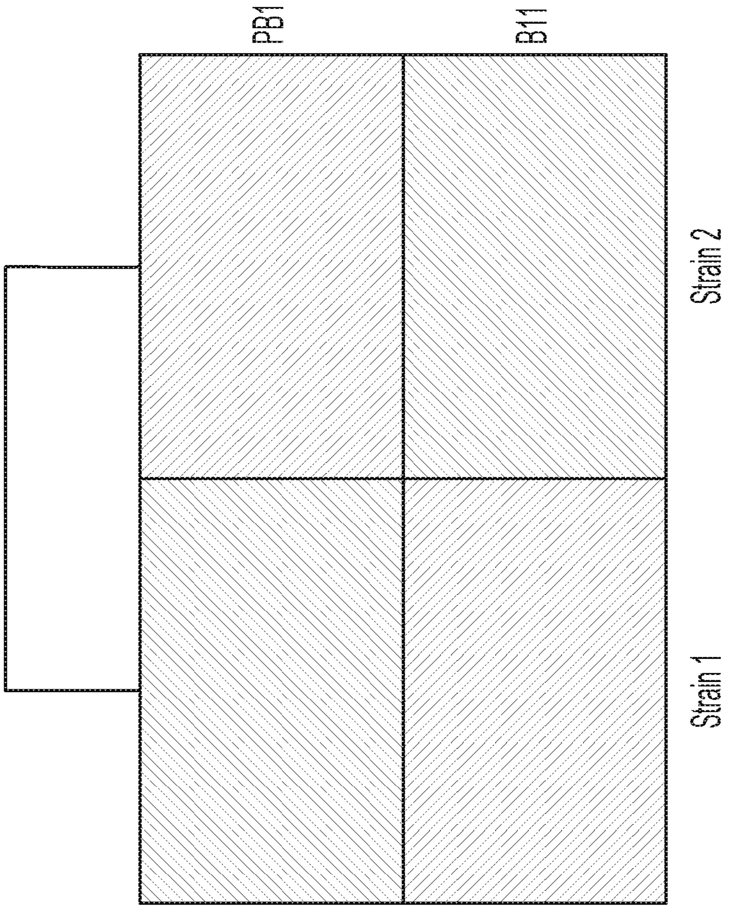
FIG. 5 shows a comparison of the host ranges of recombinant NanoLuc® B11 phage, and recombinant NanoLuc® PB1 phage. Light grey indicates strain detection whereas dark grey represents the lack of recognition. This graph represents complementarity in host range.

*P. aeruginosa* clinical isolates (designated as strains 1-2) were infected with the recombinant NanoLuc® PB1 phages disclosed herein and a recombinant NanoLuc® B11 phage for 1 hour. FIG. 5 shows that the recombinant NanoLuc® PB1 phages of the present technology successfully infected a *P. aeruginosa* clinical isolate (strain 2) that was incapable of being infected with a recombinant nanoluciferase expressing B11 phage.

These results demonstrate that the recombinant PB1 bacteriophages of the present technology are useful for detecting and/or profiling the antibiotic susceptibility of target bacterial strains/species present in a sample. Accordingly, the recombinant PB1 bacteriophages disclosed herein are useful for the identification and/or antibiotic susceptibility profiling of specific bacterial strains/species (e.g., *Pseudomonas aeruginosa* strains) present in a sample.

Example 3: Antibiotic Susceptibility Profiling Using the Recombinant PB1 Bacteriophages of the Present Technology Antibiotics were prepared by performing eleven 2-fold serial dilutions in Mueller Hinton Broth (Sigma, St. Louis, Mo.) in 96 well microtiter plates at a final volume of 100 μl. One column contained broth only and served as a no drug control.

Cells from an overnight growth blood culture in 25% human blood and 75% Tryptic Soy Broth TSB were diluted 1:10 in Mueller Hinton Broth. From this dilution, 5 μl of cells was added to each well of the antibiotic plate. Cells were pretreated with antibiotics (meropenem) for 120 minutes at 37° C. After the 120 minute pretreatment, 10 μl of phage suspension comprising the recombinant PB1 phage of the present technology (1E6 pfu/reaction well) was added to each well and incubated at 37° C. for 45 minutes. After infection with the phage, 50 μl of the reaction was added to 50 μl Nano Glo Luciferase Substrate (Promega, Madison, Wis.) in a luminescent plate and read in a luminometer. The minimal inhibitory concentration (MIC) of each sample was determined using the ETEST® method (Biomerieux, St. Louis, Mo.) according to the manufacturer's instructions. The differences in the reporter gene expression of the recombinant PB1 bacteriophage observed in the antibiotic treated samples and the untreated control samples is defined as μ.

Figure 9:
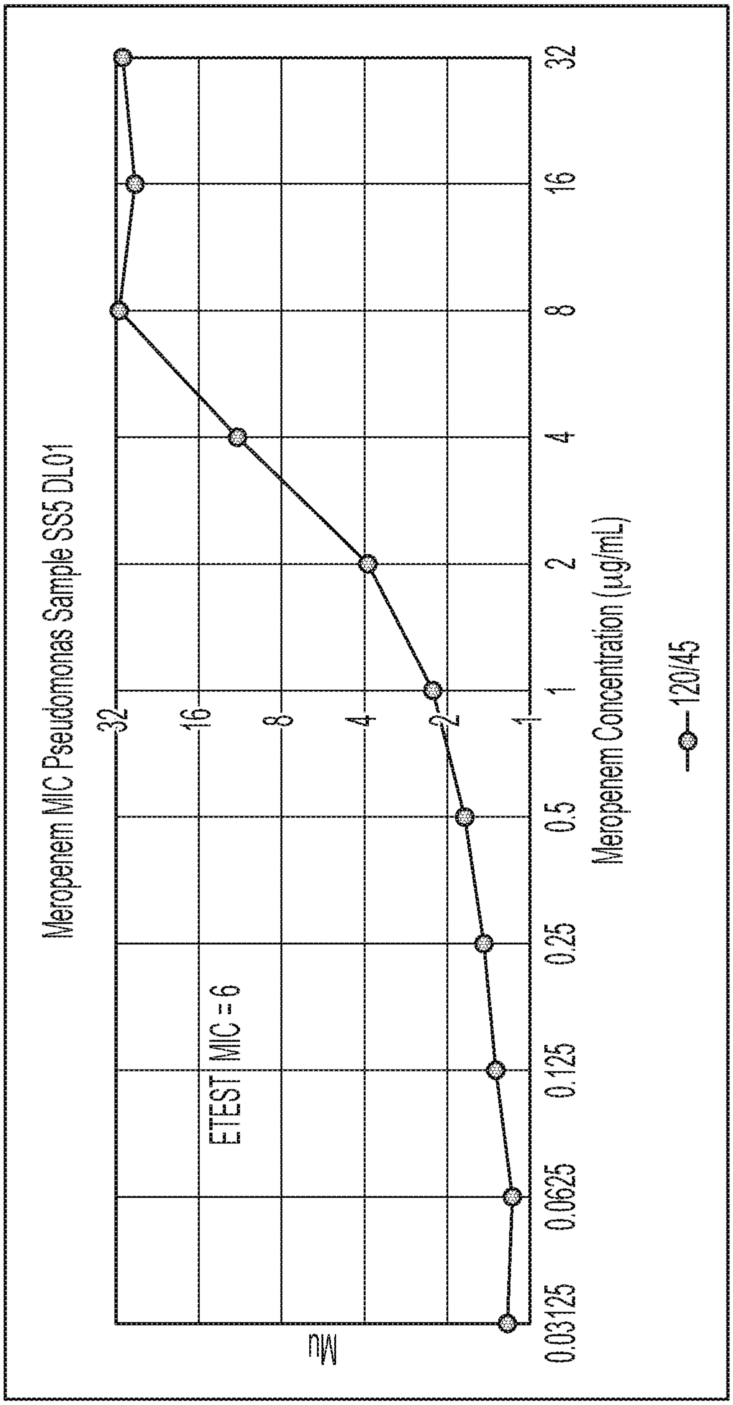
FIG. 9 shows the antibiotic susceptibility profile of a *P. aeruginosa* strain to meropenem using the recombinant PB1 phages of the present technology.

FIG. 9 demonstrates that the recombinant PB1 bacteriophages of the present technology were effective in determining the antibiotic susceptibility profile of *P. aeruginosa* strain SS5 DL01.

These results demonstrate that the recombinant PB1 bacteriophages of the present technology are useful for determining the antibiotic susceptibility of a bacterial strain or species in a test sample. Accordingly, the recombinant PB1 bacteriophages disclosed herein are useful for the identification and/or antibiotic susceptibility profiling of specific *P. aeruginosa* strains present in a sample.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A recombinant PB1 bacteriophage nucleic acid sequence, wherein the nucleic acid sequence is inserted between position 28,851 and 28,852 of SEQ ID NO: 1 with a heterologous nucleic acid sequence comprising an open reading frame that encodes a reporter protein, wherein the reporter protein is a bioluminescent protein, a fluorescent protein, a chemiluminescent protein, or any combination thereof.

2. The recombinant PB1 bacteriophage nucleic acid sequence of claim 1, wherein the open reading frame of the heterologous nucleic acid sequence is operably linked to an expression control sequence that is capable of directing expression of the reporter protein.

3. The recombinant PB1 bacteriophage nucleic acid sequence of claim 2, wherein the expression control sequence is an inducible promoter or a constitutive promoter.

4. The recombinant PB1 bacteriophage nucleic acid sequence of claim 1, wherein the fluorescent protein is selected from the group consisting of TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherryl, PATagRFP, Kaede (green), Kaede (red), KikGR1 (green), KikGR1 (red), PS-CFP2, PS-CFP2, mEos2 (green), mEos2 (red), PSmOrange, and Dronpa.

5. The recombinant PB1 bacteriophage nucleic acid sequence of claim 1, wherein the chemiluminescent protein is β-galactosidase, horseradish peroxidase (HRP), or alkaline phosphatase.

6. The recombinant PB1 bacteriophage nucleic acid sequence of claim 1, wherein the bioluminescent protein is Aequorin, firefly luciferase, *Renilla* luciferase, red luciferase, luxAB, or nanoluciferase.

7. The recombinant PB1 bacteriophage nucleic acid sequence of claim 6, wherein the bioluminescent protein is nanoluciferase.

8. A recombinant PB1 bacteriophage comprising the recombinant PB1 bacteriophage nucleic acid sequence of claim 1.

9. A recombinant PB1 bacteriophage comprising a nucleic acid sequence selected from the group consisting of SEQ ID NO: 2, SEQ ID NO: 3, SEQ ID NO: 4, and SEQ ID NO: 5.

10. A bacterial host cell comprising the recombinant PB1 bacteriophage of claim 8.

11. A vector comprising the recombinant PB1 bacteriophage nucleic acid sequence of claim 1.

12. A bacterial host cell comprising the vector of claim 11.

13. The bacterial host cell of claim 10, wherein the host cell is a natural or non-natural host for PB1 bacteriophage.

14. The bacterial host cell of claim 12, wherein the host cell is a natural or non-natural host for PB1 bacteriophage.

15. A kit comprising one or more coded/labeled vials that contain the recombinant PB1 bacteriophage of claim 8, instructions for use, and optionally at least one antibiotic.

16. A method for identifying at least one bacterial strain or species in a test sample obtained from a subject comprising (a) contacting the test sample comprising bacterial cells with the recombinant PB1 bacteriophage of claim 8; and (b) detecting the expression of the reporter protein of the recombinant PB1 bacteriophage, wherein detection of the reporter protein indicates the presence of at least one bacterial strain or species in the test sample.

17. The method of claim 16, wherein the expression of the reporter protein is measured in about 5, 10, 15, 20, 25, 30, 35, 40, 45, 50, 55, 60, 65, 70, 75, 80, 85, 90 or 120 minutes after contacting the test sample comprising bacterial cells with the recombinant PB1 bacteriophage.

18. A method for determining the antibiotic susceptibility of a bacterial strain or species in a test sample obtained from a subject comprising (a) infecting a plurality of test samples comprising bacterial cells with the recombinant PB1 bacteriophage of claim 8 and an antibiotic, wherein the plurality of test samples is derived from the subject;

(b) detecting the expression of the reporter protein of the recombinant PB1 bacteriophage in the plurality of test samples; and (c) determining that the antibiotic is effective in inhibiting the bacterial strain or species in a test sample when the reporter protein expression levels of the recombinant PB1 phage infected bacterial cells in the test sample are reduced relative to that observed in an untreated control sample comprising bacterial cells, wherein the untreated control sample is derived from the subject and is infected with the recombinant PB1 bacteriophage.

19. The method of claim 18, wherein the antibiotic is selected from the group consisting of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

20. The method of claim 18, wherein the expression of the reporter protein is measured in about 5, 10, 15, 20, 25, 30, 35, 40, 45, 50, 55, 60, 65, 70, 75, 80, 85, 90, or 120 minutes after infecting the plurality of test samples comprising bacterial cells with the recombinant PB1 bacteriophage.

21. The method of claim 18, wherein the test sample is blood, sputum, mucus, lavage, saliva, or a swab obtained from the subject.

22. The method of claim 21, wherein the subject is human.

23. A method for making the recombinant PB1 bacteriophage of claim 1 comprising (a) contacting a first PB1 bacteriophage genome comprising a single first recognition site with a first restriction enzyme in vitro under conditions where the first restriction enzyme cleaves the first recognition site to produce a cleaved first PB1 bacteriophage genome; and (b) recombining in vitro the cleaved first PB1 bacteriophage genome with the heterologous nucleic acid in the presence of a recombination system under conditions to produce a recombinant PB1 bacteriophage genome, wherein the heterologous nucleic acid sequence comprises an open reading frame that encodes a bioluminescent protein, a fluorescent protein, a chemiluminescent protein, or any combination thereof.

24. The method of claim 23, wherein the first restriction enzyme is Bsu36I.

* * * * *

SEQUENCE LISTING

<160> NUMBER OF SEQ ID NOS: 14

<210> SEQ ID NO 1
<211> LENGTH: 65764
<212> TYPE: DNA
<213> ORGANISM: Pseudomonas phage PB1

<400> SEQUENCE: 1

```
ccttctcttc gtcccagcag aggctatctg ctatcggcca gaactttcga aactgggagg     60
tgctgacgct tacatccact aggacgattt ctgcttcacc cacgacttcg agcttgaact    120
tgacgtcacc gtcgatgctg ttgaaaggga ttggcttgga cacgacaatt ctcctgtgaa    180
tggcgcgacc aaccggccgc gcctgatgat tactcttcgc cttcgtccgc gctcagccac    240
tcttcgaagg cgaaattgac cttagactcg acccaatctt gaagctcatc ggcgaactcg    300
tcactgtcga tgtccatcgg aatgcccaga gtctcttcgt tccacagttc ggcattcagt    360
tcgaactgga tagccggttc gccatccaca ttcagcagga tgcggtctgc gacttcatag    420
tcgtcgacat cgaagaggaa accgccgctg atgatgtgct ggatgaaagc ttcgtcgaag    480
ttgctgacgc cgatattgat ctgcttagtc atttttctgg ccccttattt ggcgagtttg    540
tactgagctt tgagggtggt cagcttagct ttcagggcga tcatagcctg gccgcgcagg    600
ccttccattt ctgcctcgct gatggcgatc ttggcggagc ggatttgatc gttgatctgg    660
gatttggtca tttctgcgtt cctctgtttt ggagtgtttc gcgtttcgat gaagagatta    720
tgacgctatt cagaatggaa gtaaagcaga attgtgaaat atttctcaaa gtggacgagc    780
ggtctgttcg tcaggaatat ttcctcccat ggaaggcgtg tccgcatccg aagactgaca    840
ggtatccgtt gacttcggat tgtctctttt cggagtcgat ttcgattctt agcatttcca    900
gctcataccg ggccaggccg ccccactccc tttcgatgcg ttcatactcg gcttctaatc    960
ggcgcagacg ttcaatcatg ggaatctcct ttggattgtt atagctagca tcattacgga   1020
caaacagtct ttcgtttcgc tgaagagatt atgccgttgg tcagaatgga agtaaagtgt   1080
attaacaata aaattatgtt caccgacgaa cggttgtgct cgaccgtctg ttgcggcgtc   1140
gatatactcg acctattgct gacaccggat tgattagaat gtacaaactc aaccctgcac   1200
tgcgagcggt ctggcgaact cgcgcccgtt acaaagtcat ttatggcggc cgggcgtctt   1260
cgaagtcaca cgacgcaggc ggtatcgccg tttacctcgc ggccaactat agactcaagt   1320
tcctctgtgc tcgccagttt cagaaccgca tcagcgaatc ggtctacacg ttgatcaagg   1380
acaagattga gaattctgag tacaacggcg agttcatttt cacgaagaac tcgatcaagc   1440
acaagaggac aggatcagaa ttcttattct atgggatcgc ccgtaacctg tcggaaatca   1500
agtccaccga aggcattgac attctctggc ttgaggaagc tcactacctt acccaggaac   1560
agtgggaagt cattgagccg accattcgga aagagaactc agaaatctgg atcatcttca   1620
acccgaacga agtaacagac ttcgtgtatc agaacttcgt ggtgaagcca cccaaagacg   1680
ccttcgtcaa gatgatcaac tggaacgaaa atccgtttct cagtgagacg atgctcaagg   1740
tcatccacga agcttatgag cgcgacaagg accaggccga gcacatatat ggagggattc   1800
cgaagacggg cggcgacaaa tccgtcatca acctcaagtt catccttgct gccattgatg   1860
cccacaaaaa actcggctgg gagccggccg ggtcgaagcg catcggcttc gacgttgcgg   1920
atgacggcga ggatgcgaac gccacgactc tcatgcacgg caacgtcatc atggaagtgg   1980
acgaatggga tggtctggaa gatgagttgc tcaagtcgtc cagtcgcgtt tacaatctgg   2040
caaagatgaa aggcgcctcg gtcacttatg actccatcgg cgtcggcgct cacgtcgggt   2100
```

-continued

```
ctaagttcgc cgaattgaat gactccagcc cagacttcaa actgacctat gatccattca   2160
acgcgggcgg cgctgtagat aagcctgatg atatttacat gaagctgccg cacactacga   2220
tcaagaacaa agatcacttt agcaacatca aggcgcaaaa gtgggaagaa gtcgcgacaa   2280
gattccggaa gacttacgag gcggttgtcc atggaaaggt ttatccattc gacgaattga   2340
tttcgatcaa ctctgaaaca attcacccgg acaaactaaa tcagctatgt atcgagcttt   2400
cctcgccgcg caaagacttg gatatgaacg gccgattcaa agtcgagtcc aagaaggata   2460
tgcgcgagaa gcgtaagatc aagtcgccga acatcgctga ttcggtgatc atgtcggcca   2520
ttctgccgat caggaagccc aaaggtttct tcgacttcta aacacagaaa agcccggagc   2580
gatccgggct tctggtctta ctcggtgcgg ttcctggcgc tgagtgtcga cgcaacggcc   2640
tcgccgactt ccagagcttt ctggcctgct gcgagcgctt cggtttccga ctcgacgatg   2700
aagtcatcgc cttgtccgtc gccgggcggc acctcgacca gcacggcttc ttcgccctcg   2760
aaacgcaggt cataagtctt ctcgacggac aggccgtaac gggcgttgag cgcatcccat   2820
agctgagctt cataggttcg aaggtcttgc agagatttct ggtgactgag catcgccatg   2880
tcgacggccc gttgcagggt ttcgtccagg acgttgagtc gcatgcgaag agaacgaatc   2940
cgctcgacga cttccgcatc cacaatgtgt ctttcgatca tcgcttttca cctttgctga   3000
atgttacgtt atagccgtta tcggccaaat aggtcagggc accttcgaat gaagttccga   3060
cgaggtgcct gagctgcatt tcgcgttgcg cagcgatcca aaatgcagtt ccggagaact   3120
ctgcgcggcc ttccgacaga acctttccgt caggtccgtc gattcgaacg tgaacggaag   3180
atagcttcag agtcattagt gaatccctcc actggcttgc gacggcattc tttctgcgcg   3240
agcggatgcg cagtccgggc acgggcaggc ctggcggacg cgctccaact cgtcggcgtc   3300
catgacatag agcttcccat cggaagtgtc gtgcgccatg gcgatgttcg ggaagtcggt   3360
ggcactcagg ccggcgacag cgcggatttc gccccagagc gcttcattct cggcattcag   3420
acgagcggcg agcgcttcgt gctctttcgc tacacgcgcc atgaactcgt ccatccggaa   3480
tgcgaattcc gcatcgatgg cgcgggccga ggccatagag ctgaggtgaa tcggttcttt   3540
cttcatggta attctctttt ggctgggggt ttgtggtcta cccaggccta ttcaaagcct   3600
ggtcgtcttg atgaagatga acaagaagac tgcaaacgcc aatagcgttc cagccaacat   3660
aaatactgca aatgccaata gcgttcctga gagcatgctc gcttgattct gcagctcagc   3720
gtactccttg gttgacagcc cttgctgcgc cgcctcggcc gcgaagcggg ttttcgcctc   3780
gataacttcc gggcgcagcg acaggacata ttctaaggcc tcttcccgcg ctttttcggc   3840
ctcgaccaac ctagggtcgc gggccgagac ttcgctgtgc cctggcctcg cgggatgggc   3900
ctgcagcgat ggaggaagtt cggcggccac gactccatag tcggagcagg cccaagcgat   3960
cccgatgagg atcgcgagga tggactggac gattcgcagc atcactttgt cgctaggaag   4020
actcatggtt aatcctccac cgaccgaacg atttccatat tgcgtccggc attggttccg   4080
gcagcgtagg cgcgccgacc gtcactgtct tccagacgca tgagtttggt aacattagac   4140
ttcttgtaac ccggatcgcc gaaatgttcg tggaccgcag cttccttaac caccaccaga   4200
gacgttccgg ccgaagaaac cagctccata cgtttccggg tgatggatct gaggcgatag   4260
ctgatttcct gggtcgcggc gagcttaaat tgcgcggcga ccttgacgtt gaaccgctcg   4320
aaaccttgag ccttctgata ttcccggcac agacggtcta ctgcctcgac cagggagttg   4380
aacatgttca ccgctagctc aacgtcagat ttgtagcctt taaagcggac ggcatggccc   4440
```

-continued

```
cagcgcttgg tggtgctgcc gtcgcgagcg ctcctggacg ccttcgccga tgctcggtga   4500
ttgttgatgc caccgacgaa atccatgatg caatcattgt acgtcgccac tgccacagag   4560
aagaacttca tccagttcgg gattgcggaa tagtagcgag tagcaatttg ctcgtcgaat   4620
tcttcgcgaa tctcgccggt cacttcgaag tcgtgaaggt catatttatc cttcagcttc   4680
ttcacgcgtt ctgccgcgat ggcagcttcg tgcggactgg aagagtcggc cgccatcgca   4740
gtcagcttgc gaatgcgatc tttcgccttc tcgatggctt caggagtgaa ttcgttctgg   4800
tcggtcatgg tcggttcctt ttgtctgaag gtttcgcgtt tcgatggagc tattctgcct   4860
tcatccagaa tggaagtaaa gcattttctt ccactatttc ggaagagcct ggaaatagct   4920
ccagatccaa tcgcctgcgg ccaggacaac gatgagaact gcgaagaaca cgactgcaga   4980
gaccaattgc gcgccaggct tcagcttggg atgactgagt ttgtgctcta ccggattcgc   5040
cggggcgctg gcgctgggcc cggcgtcttc tggaccaaag ccggcgccgc gctcgcgtgc   5100
ctggatagac gctatggatt tcaaatactc ggtctgcttt tgcgactctt cgtagatgcc   5160
ggcgacggcg aaccagagtg cgaacactac ggccgtgcag acgacccagg ctccggtcag   5220
aaggatggcc agcggaccga tgaggaagac ggaagccgcc aggatgatgg cgccgcccca   5280
gatgatgaag ccggccagac cattggtgat gtcgatacag aatttcttca ttttttttggt  5340
tccttcggtc aagggatgga tgggatttgg aattcggcgc cgccgaggac atcaatgacg   5400
acctcccaga gcgtcggaac cgaccactga taacggtcga agtcggtttc aggatcgact   5460
cccagggtta cataggaagt ggccggccat ttgtgaacgg cgccttttcg catgagagcg   5520
gccacgcgac cgtcaccgag cggattcgtc ctgtgaggaa cataagccga catcgaatat   5580
tgctgtccag caccaatgat gaattcttgc ctctggcgca gacatacaga gcctacaggc   5640
tcccaaccgc gaccgccgca ggcctggcga gccgaagaat gctcataccc ttcatgagtc   5700
aattcaccga gacgcgccga acggtccacg taataatttg tattctccag agacccaacc   5760
agaaccaagg actcgaaatc gaatcgatga tcgtggatgg aagagtgatg gaaacaaagc   5820
cggcgcggca gctccggatg ccacacatgg aggcgcccgg ccgggagctg gacctggatg   5880
aagcccaggc cgtgcagcgt gattctgtcc ttcatcggat cagggacggt gtccatggat   5940
aatcctcagt agcagaagtg gatggtaaag gttacgatgg ccaagccggt cgcccatagg   6000
agggcgaacc aggccatggc tttgattgta aggtggatca tccgaagaac tttccggcgc   6060
agatggggcc gatgcccatt tcgatggatg cgtgattggt caactcgcga ccgcagcagg   6120
agcattgacc agtcttccga ccgtaggcga ctgccgattc cattggcttt tcgaacatct   6180
tcaggatatc gccatactct gtgtcggtgc agtcgcggct cttgatgaat ttgccgttag   6240
tgatccggcc gaggtagatg tcgcccagga catacagact cccggcgttc cggctgttag   6300
cgctagcctc tttgaccaca acgatgagag gctcctcacc ttcgccagcc agacgcattt   6360
tcgggcgctt gatgccagag tctttcgcct tctcaaacgc cttctcgatt ccggaaatgt   6420
ccagagtcgg cgcagcagcc tcctgcgcgg ccactttctc gcgatgtttg gcgaggtttt   6480
cgatagctcg tttcgcagca gcgatctgat tttcggtcaa ggagccatat ctgtaaagag   6540
aatccttaag gctctgggca aaactgaaag agttgtcggt ccaccactcg atgatgtccg   6600
ggtgagcggc ttcgaaagcc tgaattttaa ggccgcgata ttgctcggcc ttctggactt   6660
tctcgatgcg cttttctgca gccttagcac gactcttggc gcgttgctcc gggctgctct   6720
tgtactcttt atatccaacg ccgccgcagg caaagcaggc gcgaccataa gacgaaggac   6780
cacggtacag gccagtgcct gcgcatttgg ggcacttttc gcgatacagc ttcggttcct   6840
```

-continued

```
tccaggagtt cgggcgggca cccatggaca cctcttccag ggtcttcggc gcttcgttgt   6900
tgacctctac ggtagcgaag tcatcgccca ggtcttcgaa gccgttgaac agattctctg   6960
ctgcgttcat atcgattctc ctgtttggaa agttcgtttc gatgggttga ctatactcca   7020
taaatggaaa cgcggtagca cttcacgcta ccgttcgtcg ggttgctgac gatcaataaa   7080
tgtcgctgct gatcttaaac ccatgctcag cgccgtcgtt gtagtcatac tcagcatagc   7140
tgtcgcagta gtcattcaga tgctggatga ttccaagaac gtcgttagcg accctgtgac   7200
gcttcgccgc gatggtcttg gcaatgctgt cgccgacttc cagagtttcg gcggtccggc   7260
gatgaatcag caaacggctc caaagataga gtcggacccg gcgaatcatg tcatgatggc   7320
gcctcagtcg gctctgcaac ttttcaattt cgaattcgcg agacttgact actcgtcgaa   7380
gctgctgaac ttccaattcc aaatcggcct tagtagccat attcacctca gaaagggaaa   7440
tcgtctgagg ctccaggaag ctcgacaatt gttgttgagc ctgagcggtc gagtatgcac   7500
ccgaccgatc ctgccctatg ggataatgc ctgcacgaac cgtaacaagt aacttctttg    7560
acgattcgcc atgtcgatcc tccacaccac ctacatgctg gtgggcgctt cgacttcagt   7620
tttcgttcgt ccaggacggc tcgtctgtcg caggaaaggc agcgagcctt aaccgacgta   7680
accatgagtg tagtcgatca tgcgaatgag ttcgtcatcc accgattctc tcgacttcaa   7740
accgttcaac gaatccgact ggccgttgca atttccatta atatccatgg aagacagaaa   7800
gcctgccgac accactgtga tgtcaacttt atcgccagcc ttcttgaagc cttcgcattc   7860
ggcgtcgagg gccaccaacg cactcgcggc catgttgacg tgactgatta agtcggggaa   7920
gattacggga acttcacgag acattccccg gaccgtcatc ttcatcacta catatttcat   7980
actcactatc ctttttgtgt gtgaggaaag aatttgctgt tttccggatg gtggaaacgc   8040
tcggccgcag gcggtctttc ttccggacac tgaatcgtcg aaggcgggaa aaccgcgcta   8100
gagattatcg ccgcgagcag cgcagcggat gtcgacatcc acagggcagt ttccagactg   8160
acccgcactt ccggtcggcg cggcttcatt cgctccaacc ccttcccggc tcataagacg   8220
ggatgctgcc gccgcgaatc caactgtccc acatatggtt cagaccagtg ggcggctggg   8280
gcggcggact gtaaaagccg ggaacttctg tactgctgag gaaataaggc gtgcaaacgg   8340
cccgaacaac cagttgatgt cgctcccaca tcttatcaat cgctcttagc atgacgtctt   8400
cgcactgagc tttgctgtcg aaccgtctgc tggtatgatc cggcatctgg acacagccat   8460
cgccagtaca aaggaaagca gtggcgatcc atactgtgat gcttgccatt tcttcaccct   8520
ctttggtaga tgagcagatt ttattccatc tgctcttcag aagtaaagcg cttttcgtcg   8580
ggataaatgc cgatgatgtc tgcgtcgagc atccaaatgt ccacggacgg atcgtcgcta   8640
ttgatctgat acaggtggta caattctttc tcgtcacgcg ccgattcacc gcgaggttcg   8700
acagccaata tgcggccgtg cccttcgccg tgctcatcgc gatacatgac gtgatctccg   8760
acttcatagc actcttttct gacaaggcgc gagcgcgagc tgttcggcga ttccactacc   8820
caggaatcca caactgcgtc tttcacattg ctgtaccact tcgcagattt gtcgcagtcg   8880
aacacgccca gaacttcgcc gtccttcaac acgatatgta cgataggaag aagaggattc   8940
atgttaatct ccattggttg ataattagag tctaatctgc cgaaaagttc ccgtaaagaa   9000
ttattttctc ataactgatt agttgcgact gttaatgtga tgtatctgtt tgaatctctt   9060
ttgaacgttt gatgtttccc ctataataag tgcacacaac cagcaaccgc atggaattaa   9120
aatgtttaaa ctttcctgga tattcgggcg caaaaaggaa taatgttgcc tgttctgaat   9180
```

-continued

```
cggcgccgga gaaagtcgca cgaatccctc aacacgatcc gctcgaccct atgattaagc   9240
tggggaagat tcgcggctgg aatgtcgagc cggagaaagc cccggtcatc cgtagcgtga   9300
aggatttcct ggagccgggc ctatccgtcg caatggacag tgcgtatggt gacggaccca   9360
ccccagccgc gaaagctgcc gctggcggcc agaatcccta tgtagttccg accatgctgc   9420
aggactggta taactcccaa ggattcatcg gataccaagc ttgcgccatc atttctcaac   9480
actggttggt cgacaaagct tgctccatgt caggcgaaga cgccgcgcgg aacggatggg   9540
aactcaaatc ggatggccgg aagctgtctg atgaacaaag cgcgctgatc gctcggcgcg   9600
acatggagtt tcgcgtcaaa gacaacctcg tcgaattgaa ccgattcaaa aacgtcttcg   9660
gcgttcgaat cgctctgttc gtcgttgagt ctgacgatcc ggactactat gagaagccat   9720
tcaacccaga cggaatagcg cccggctcgt acaagggaat ttcccagata gatccatatt   9780
gggcaatgcc tcagctgacc gcagagtcca cggcagaccc gtctgccgaa cacttctatg   9840
agcccgattt ttggatcatc agcgggaaga agtatcatcg cagccatctg gtggtcgttc   9900
gtgggccgca gccgccagat atcctgaagc cgacatacat tttcggaggc atcccgctca   9960
cccagcgcat ttacgagcgc gtgtatgctg ccgagcgaac tgcgaacgaa gcgccgttgc  10020
tggcgatgtc gaagcgaacc agcaccattc acgttgacgt ggaaaaggcc atcgcgaatg  10080
aggatgcctt caacgcccgt ctggcgttct ggatcgccaa tcgagacaac catggcgtga  10140
aagttattgg tattgatgaa accatggagc agttcgatac gaacctgtcc gatttcgaca  10200
gcgtcatcat gaaccaatat cagctggttg cggccatcgc caagactcct gcgacgaagc  10260
tactcggcac ttctcccaaa ggattcaacg cgactggtga gcacgagacg atttcttatc  10320
acgaagagtt ggaatcgatt caagagcata tattcgaccc gctgcttgag cgtcattatt  10380
tgctgctggc aaaatcggaa gcaatcgatg tacagctgga aatcgtctgg aaccctgtgg  10440
attccacaac cagccagcaa caagccgagc tgaacaacaa gaaggctgct actgatgaaa  10500
tttatatcaa ttccggcgtc gtgtctccgg atgaagtccg cgagcgcctg cgtgatgatc  10560
cgcgctccgg ctataatcga ctcaccgacg atcaggccga aaccgagccg ggcatgtctc  10620
cggaaaacct ggccgaactc gaaaaggccg gtgcacagtc ggcgaaggcg aaaggcgagg  10680
ccgagcgagc cgaagcccaa gcgggcgccg tagaaggcgc aggcgaccca gttccggccg  10740
ctccacgcgg tactaagccc ctcgcgaaag cggccgagga aggggccggc gaggccgcta  10800
caccgccgtc gcggccgaac cccagggccg agcttcggaa cctgctgtcc gatctactgt  10860
cgaaactcga agccctggac gacgcgcagg ctccggacgg cgtggacata gagcaggatg  10920
acgcgccagg tctgaagaga acgtcaaagc cgagcgtatc gggtatggag ccttcggtgt  10980
tttcgtccaa ccgcatcgtc ggccctcgtg atcattctga actccagagg atcaaggtca  11040
atggaattac taccttgatc gaaaatccgc gcggaagtat ccggcaaggg aaggacggga  11100
gctggcgagt ccagatgaag caccactatg gattcatcaa aggtacgaag ggggctgatg  11160
gggatgaggt cgattgcttc gtaggcccga accttggttc gaaacgggtc ttcgtcgtca  11220
accaggtgaa caaagatggg caattcgacg agcacaagtg catgctcggt ttcaacaaca  11280
ttaacgacgc caagtctgga tatctgtctt gcttccgtcc gggctgggat ggactcggct  11340
ccatccatga agttgatctg cccgccttcc gtcgttggct ggcaaatggc gacacgacga  11400
agccatttgg aggcaagtga tggcgttcaa agcctccaag aaacgcgaac gccgggggcc  11460
tcttccagtc ggaagaggca agcccataat tccttctgct ggaatcgaag cctggtatcg  11520
aaagcaaatg aaggatatgg ccagactcat gatcgccgat tatcgaagtg aaatcgagaa  11580
```

-continued

```
ggccatatcc cagcctgcgg cagaacggtt tttcgcgaaa gacgaatcgg tgaacgtcct  11640
gttcaagatg actctgcgaa gccttcagca gcgatggaat cgcatctttg aaggtttcgc  11700
ggccaagatc gccccggagt tcgtcaatcg ggccgacgaa gccgcgaccg ctgcgactct  11760
acacagcctg tcggtggccg gcgtcgatca gccgcgagct tcatacaatg agagcgtcag  11820
gaacaccctg gaagccgcga ctacttacaa ccataccctc atcaccaaca ttcaagagga  11880
agtccacgag aaaatttaca catctgtaat gttgtctctg acttccccaa acccagagga  11940
acaaggaact tctggaataa caaatgcact tcgagaagtc ggaaagtttt ctgaaaaccg  12000
aatcgaactc atcgcaagag atcaaaccag taaactttac agttcgttga gtgatgagag  12060
aatggcagag aatggagtcg aagagttcga atggatgcac tcttcggcag ggaagacgcc  12120
tcgccatacc cacctggaaa aggacgggaa aagattcaaa ctgaatgacc ctagactttg  12180
ggaaggtcca aaggccgacc aaggaccgcc aggttgggcg attaactgcc ggtgcagaaa  12240
aatcccgatc atttagtcat cgataggagt gcgatatgcc gttagtccat ggaacttcca  12300
atgaagcccg ttctgaaaac atcaagcggg agattgaagc agggaaagac ccgaaacagg  12360
cagtcgccat agcctattcc gtccagcgca gcgagaaaga gaagaaggcg aaagattgtt  12420
cgcatgaact cgtcgctgat cttcgcgccc tggtagactc gctgtcgagg ctcgtgaaat  12480
gaaccgaaag acatgcatac gccgactcgc gaccgatgtg atcaaggcca atattaacgg  12540
cggattcttc agcctgaagt ttgccgcagt tgatctggcc atcatcggcg tctcaatcct  12600
gattgctttc ggcggatgat gccgcgagaa tccggattct gactaaaaat tctggtccgg  12660
atagccgcaa attaccgttt ctgggaaata gcggtaattt ggaaatccta ctgccgcaag  12720
gctttaacag gctaaattcc taatttccga tttcgccgca tgccgcaaaa gtatatagca  12780
tgggaaatta ggaataacgt tctaatagaa ttcatctata agtaacgtta taatataacg  12840
ttaatcgata tgctctatac gcattgaaat tcaattttta atcggtaaat tggtaatttg  12900
gattagttta aagattgaaa gtcttgcggc agtaggccta gacaaatccc gtcaaatttc  12960
cgaaaccaat ttaccagttt tcgcggctga ggaagtccgg taattaggtc acaatacaga  13020
ttctagtgta aattaacagt cgcggctaca tcgaattatt gttccgctta tttaccctta  13080
gatgtcctgc gtatataata cagccatagt ccacgactct tcgaattaac gatggcaaag  13140
tcgaaaagaa aaattgacga aaatggatat atgaccatcg agggctgtcc aatcagctct  13200
tatggcattt tccaatattc tgccggtcaa ctcggtcttc cgggcgatcc gatgcggatt  13260
gtcaacgtgt atcgtccgga gtctgccgtt agcgatcctg agtacatcga atctctgaag  13320
aatctcccgc tgatcgacga gcacgaaatg ctgtcgggat tcgacggcga tgacgatggc  13380
gtggctcccg aagacaaagg cgtggaaggc atcatcacag ccaacgccta ctacgaagct  13440
ccatgggctc gcggcgatat ccgcatctat tcccgcaaca tgcagaatca gctggaaagg  13500
ggcaaggaag atctgtccct aggctatagt tgccgctaca ctgagcaacc cggcatctgg  13560
aatggaacgc cttatgaagt cgtccaggac aagatgcgcg gcaaccacat cgccctggta  13620
aaagagggtc gtgtgccggg ggccagagta ttggatggtc tgtgctttga ccatctcagt  13680
tttgatttca gaccatccga tgagggtaat gaaatgggtc tcaagaaagc caagcagaag  13740
actcctgtcc agcgcgcagg acaagctgct gattcggcgg tcgaagagtt gcgcgccctg  13800
tggccgaagc tctctgcatc tgtccagaag ttcctgggcg aagaggcgca ggagccggag  13860
catcaggaag gcgcaaccgc tccggccgaa ccgaccgaca gcgagcacat gaccgagcat  13920
```

-continued

```
ccgactctgg aaggcgctca ggaagacgac gaagagcacg aagaagcgcc gtccgttgtc  13980
gatccggccg tggtcgccgt cgagccggaa cagcaagaag gtgccgcatc cgaaatgtcc  14040
ggtgaaggcg aagtcgccga actgatctcc caggtcaagg ccattctggc tcgactggaa  14100
ggcacggtag ccgaagaggc ggacgaagaa catggcgaag gtcaagatgt cgtcgagggc  14160
ttggaagaac agagcatcct ctgcggcgcg caaaccgcca gcgacgatgg tggtgagggc  14220
aaggataaca gcgaggaact tcctgaaatg gcacaaaaga acgcgcaaga tgctgcaatt  14280
cgtggtctct atcgcgacat tgctgctaaa gatcgcctct acaagcgtct tagttccgtg  14340
gttggtgcgt tcgaccaccg agctatggac tcggctgaag tcgctgttta cggcgtgaag  14400
aagctggcga tcagctgtga gaagggccag gaagttctgg cgctcgacat gtacctgaaa  14460
ggcgtcgaag ctgctcgtgg cgcggccagc cgtcaatcga aagcccagga ttcggccagt  14520
tctgctccgc agtgcgccga gctggacagt tacctgaagg gggagtaacc catgttccag  14580
aaacaagtct atcgccagta cactcctggt tttcctggtg atctgatcga ggacggcccg  14640
aagcgtgcgc ggccgggtcg gatcatggcg ttggcatcgg tcactccggc cgcgactgcc  14700
accggcccca accgcatcag tcgcgcgttt ggttacgcag gtgatgtcgg ctccctcggt  14760
gaaggccagc cgaagaccgt tgccgcgcgc gcttctgaag tcgtggtcgg cggcgcgacc  14820
ttcttcggca tcctcggtca cccgaagcat tatgctctgt acgggtcggc cggcgattcc  14880
ctggctccca gttatgacct gcccgacggt tccgaaggcg agttcttcga catggccacc  14940
ggcctggtcg tcgaaatctt caacggcgca gaagccgctc tggatttgag ctacggcgat  15000
ccggtggcat atgtaccgaa caacctgcct accgccgaca acgccctggg cctgccggcc  15060
ggcgccctgg tcggtttcaa ggccggcgcc atgccaaccg gcctggttca aatccccaac  15120
gcgcgtatcg tcaatgccat cagcctgcct gcccagtcgg cgggaaatct ggtagctggc  15180
gttaccatcg tccagctcac gcagtaagga ggcgtcatga gccatatcag taagacccat  15240
tcgcgcctcg caggccgtca cgcaaaacca ttcgacctga agaacgtcac ccacgaagcc  15300
gtggccgccc tgagtcgcat cggcctggta ttcgatcacg ccgtcgtcca ggaccagatc  15360
aaggccttgg cgaaggccgg cgcattccgt tccggctcgg ccatggacag caacttcacc  15420
gccccggtga ccacgccgtc catcccgacc cccatccagt tccttcagac ctggttgcct  15480
gggttcgtga aggtcatgac cgccgcgcgg aaaatcgatg agatcatcgg catcgacacc  15540
gttggctcct gggaagacca ggaaatcgtt cagggtatcg ttgagccggc cggcactgcg  15600
gtggaatacg gtgaccacac caacatcccg ctgaccagct ggaacgccaa cttcgagcgc  15660
cgcaccatcg ttcgtggtga gctgggtctg ctcgtgggta ctctggaaga gggccgcgct  15720
tcggccattc gcctgaacag cgcagaggcc aagcgtcagc aggcggccat cggtctggaa  15780
atcttccgca acgccatcgg tttttacggc tggcagagcg gcctgggcaa ccgcacctat  15840
ggtttcctga atgaccccaa cctgccgcca ttccagactc cgccgagcca gggctgggcc  15900
actgccgact gggcaggcat catcggcgat atccgtgagg ccgtccgcca gctgcgcatc  15960
cagagccaag accagatcga cccgaaggcc gagaagatca ccatggccct ggccaccagc  16020
aaagtggact acctgtcggt gaccacgcct tacggcattt cggtttctga ctggatcgaa  16080
cagacctatc cgaagatgcg gatcgtgtcg gctccggagc tgtccggcgt ccagatgcag  16140
ggccaaacgc cggaagacgc cctggtcctc ttcgtcgaag aagtggacgc gtccgtcgat  16200
ggcagcaccg atggcggcag cgtgttcagc cagctggttc agagcaagtt catcaccctt  16260
ggcgtcgaaa agcgggcgaa gtcgtatgtg gaggatttct ccaacggcac cgccggtgct  16320
```

ctttgcaaac gcccttgggc tgtggtgcgc tacctcggca tctaaccgat gctgactcac 16380
caaaggccgg gcttccggcc tttgttcact ctgactctga ctcggttgta ggggccggtt 16440
agggcataat taataggact acgccaatga ctgtttacat cgtttccgca atgactcaat 16500
ccgtgtctta caatgcgtat gacacctctg atccgtccaa tcctcgcctc cagagaaagg 16560
tgctgattcg cggccgcgct ggtatcgcat ccgaaacctc cggcttcggc gacatgattt 16620
ccgacgcatc cgggcgcccg atctggacgc cgcagggcga ttgcacggcg gtgagcgatt 16680
ccgatttcga actgcttcag tccaacaaaa tcttcatgcg acacatggag aagggatatc 16740
tgcgagtcgt gaaaaccgac atcaccaatg accaccagcg gattgcgaaa gagactcgca 16800
ccatggagcg cgatggcttc caacctctgg attctactcg cctgaagcag aagatcaaag 16860
tgactactgc cagcgcttcc caggaacaag agttccgggt ttaaccgagg gtttcggtat 16920
ggtaattttc gacgagcaaa agtttcgaac gctgtttccg gagtttactg atccggcttc 16980
ctatccggat gtgcgcctgc agctgtactt cgacattgcg tgcgaattca tttctgatcg 17040
ggattctcca taccgaattc tcaatggcaa agccttggag gcctgtctgt atctgctgac 17100
ggcccacctc ctttcgctgt cgacgatgca agttcagggc gcggccggtg gcggggtcac 17160
agcaggcggg actcaaggcg gtttcatcac tagcgctacg gtcggcgagg tcagcgttgc 17220
caagctcgcg ccccctgcca agaacggttg gcagtggtgg ctttccggga cgccttacgg 17280
tcaggaactg tgggcgctcc tgagtgtcaa ggcagttggc ggattctaca tcggcggcct 17340
tccagaacgt cgaggattcc gtaaggttgg agggacgttc tggtgatccc tggagcgaat 17400
ctgctgcgta tggcatttag cgtcatagga acgcagttcg ttcagtatcg caaattcgag 17460
cagaggacga agaatagcca ggcgcagtac gtttctgtgt ttggcgagcc attccaattg 17520
gccgcttcca tccaaagggt tcgtcgcgat cagtatgtcc agttcaatct ggagtttcaa 17580
cgaaattacg tcatgatctt tgccaacttt gagatggttg acttggatcg agatttggcc 17640
ggcgaccagt tcatctggac cggaagagtt tttcaactag agtctcaagg ctcttggttt 17700
tatcaggacg gctggggagt ctgcttagcc gtggatatcg gtacagccaa actagctgaa 17760
gacggaaccc tgactttcta ggtggcttat gttcgacggc gaactgatag aaaaattggt 17820
ggtcgagctt acttccgcca tgacgtcagc caaagaaact ttgcagtttc ctgattttga 17880
ggttgtgcag aaagcccagc cgacccaaca gggcacgtca accaagccta ccatcttctt 17940
ccagaagcta tttgacatcc ctcgcggctg gccggcaacc gattggtatc tggacaacgt 18000
cgccagaaaa tatgtagaaa ttactcgaca gcatgtcgag acgacttttc agataagttc 18060
ccttcattgg cagaatcctg agatggatca cgtagtcacg gcagccgata tcgccaatta 18120
cgtgagagct tatttccagg ctcggtccac cattcagcga gtcaaggaac tggacttcct 18180
tatccttcgc gtgtctcata tatccaacga ggcattcgaa aatgacaatc atcagttcga 18240
attccaccca agttttgaca tggttgtaac ttacaatcag tatattcgtc tgcacgaaaa 18300
cgcagcatat tcagccgatg gggcgctgat aggcatatga tcctgagacg cgattcagaa 18360
ctgatcgccg cgcacctgca gatgttaaga gccatgcgcg gcaggtccgt ttcggccgga 18420
tggtattcca ccgctcgata tcctgataag gcgggcggat cggtcggaat acaagtcgcg 18480
agaatcgcgc gcctcaatga gtacggcgga actatcgacc atccgggcgg gaccaggtat 18540
attagggacg ccattgttcg gggtcggttt gttggcgttc ggttcgtcag aaacgatttt 18600
ccgggagaaa ccgaggtaac aaaacctcac aggattacaa tcccggctcg accgtttatg 18660

-continued

```
cgatatgctt ggaacttatt ttccgcagat cgcgccgcaa tccagaatcg aatagccatg  18720
aggctggcca gaggacaaat cacgccggat caagcgcttg cccagatcgg cctggcgttg  18780
gaaggataca tagccagaag cataaggacc gggccatggg tggctaactc agcatctacg  18840
gtcaggagaa agggtttcaa cagaccgctg gtcgatacgg ctcacatgct ccagtcgatt  18900
agcagcagag taacataaac caggagatca tccagtgatc agtcagagcc gttatatccg  18960
gatcatttcc ggcgtaggcg caggcgctcc ggtcgcaggc cgaaagctga ttctgcgcgt  19020
catgaccacc aacaacgtca ttccgcctgg aatcgtcatc gagttcgaca atgccaacgc  19080
ggtgatgtct tacttcggcg cccagtctga agaatatcag cgcgctgcgg cctacttcaa  19140
gttcatcagc aagagcgtca attccccgtc cagcatcagc ttcgctcgct gggtcaacac  19200
cgccatcgcg ccgatggtag ttggcgacaa cctgccgaag accatcgccg atttcgccgg  19260
cttttccgca ggcgttctga ccatcatggt cggcgcgtct gagcagaaca tcacggccat  19320
cgatacgtcc gccgcgacct ccatggacaa cgtggcgtcg atcattcaga ccgaaatccg  19380
caagaatacc gatccgcagt tggcccaagc caccgtcacc tggaatccga ataccaacca  19440
gttcaccttg gtcggcgcta ccatcggcac cggcgttctg gccgtggcga aatcggccga  19500
tccgcaggac atgtccaccg ccctcggctg gtccacctcc aacgtcgtga acgtcgccgg  19560
tcaggctgcc gacctcccag acgcggccgt ggccaagagc accaatgtca gcaacaactt  19620
cggctcgttc ctgttcgccg gggcgaccct cgacaacgat cagatcaagg ccgtgtcggc  19680
ctggaacgcg gctcagaaca accagttcat ctatacggtt gcgacctctc tggcgaatct  19740
cggcgctctt ttcgacttgg tgaagggcaa ctccggaacc gcgctgaacg ttctgtctgc  19800
gactgcctcc aacgacttcg ttgagcagtg tcccagcgaa atcctggccg ccaccaacta  19860
tgacgagccg ggcgcttcgc agaactacat gtactatcag ttccctggcc gcaacatcac  19920
cgtgtccgac gataccgttg cgaacaccgt cgacaagagc cggggcaact acatcggcgt  19980
cacccaggcc aacggccaac agctcgcgtt ctaccagcgc ggcattctgt gcggcggtcc  20040
gaccgatgcg gtggacatga acgtctacgc caacgaaatc tggctgaagt ccgccatcgc  20100
ccaggccctt ctggatctgt tcttgaacgt gaacgccgtt ccggccagca tggtcggcga  20160
agcgatgact ctggccgtcc tccagccggt tctggacaag gcgacttcca acggcacttt  20220
cacctatggc aaggacatca gcgccgtcca acagcagtac atcacccaaa tcaccggtga  20280
tcgtcgcgcc tggcgtcaag tccaaacctt gggttattgg atcaacatca ccttctccag  20340
ctataccaac agcaacaccg gcttgaccga gtggaaggcc aactacaccc tgatctattc  20400
gaagggcgac gcaatccgct tcgtcgaagg atcggatgta atgatctaac ggtttgcggc  20460
ggactcgacc gccgcaacct tccatgaatg gagtgaggaa taagcaatga tcaacatttc  20520
tgcgttcggc tcgattgccc aattcacggc aagcagaacc ttcccgaacg gattcacggt  20580
gaccgagttc gctgatgatg cggaccccat cgacagcccg ccgttcactg cggctgatac  20640
cggcgtcggc ctcaatggcg atatggtggt ttggaaccgg gccaacatcc tggaagtcgt  20700
cgtcaacgtc atcccgaaca ccgagggtga gcgcaacttg gccgtcctgc tggatgccaa  20760
ccgcaccgga aaagacaagt cgggtgctcg tgatgtcatc ggtctggtcg tggcgatgcc  20820
ggacggtagc aaaatcacct gtaccaacgg cactcccatc gacggcgttc tgatcaatgc  20880
ggtggcgagc gttggccgcc tgaagacgaa gccgtatcga ttccgtttcg agaaagtagt  20940
caaagccggt actagctgat gaagaagatt ccgctgacag cagtcccgaa tcaggcgatc  21000
tcatttaacg ccggcagcag ctattggaag attcgtctgt accagaatct ggatatgatg  21060
```

-continued

```
aatgccgata tcagccgcga cggcgtgatc gtttgtcatg gggtccgctg cttcggcgga  21120
attccgcttc tccagtatag ccaccagtat cgacccgact atggcaattt cgttttcgac  21180
cgtgacgccg attggacgtt gttcggcgac ggcataaacc tgttctatct ggacggtgtc  21240
gagttcgcag aatatcaggc gctggccacg aggaaagaat gagcacatca acgatcagaa  21300
ccggggtgaa caatgacatc cttttggacg acaatggaaa catggtcatt ctcagggatg  21360
tagaagcgtg cgcccaggac gttcgggcgg cgatgctcat gcgcaccggc gaaaacattt  21420
tcgatgtgga cgccggtgtg ggatattttg aatatatctt ctcgccgcag aagagctatg  21480
atgatgctcg caaatccatc gcggatgcaa ttttgtcatc gccggacgtg accggcatcg  21540
agcaacttga catcgacatc accggtgaag tcttcggcgt cgatgcgaaa gtcatcacca  21600
tccacgggcc tgtaactgca ggagtttgaa atgagtacca tccgcatcca atacgccaac  21660
ggcacccaac tattcttgga cggcaaaaac ccgccgctcc tggacccgct gccttctttc  21720
aacccgtcgg tcgaagacct ggaaggcctg gaccgcgaaa agaacactgg caagggcaac  21780
tcttcgtcgg ccggtattcc cgttccccg gtgaacgtcg atccgaatgt cgacaacggc  21840
ggtgccatcc cagctccggc atcgaccggc acccctgcgg ccggatcgac cccggaaagc  21900
gcccaggaag cccctgcaga gggccaaggc gacgagaaag ggtccgagac gcccccgact  21960
actaccaagg aagaaaagac cgaggtagag gcctctgcag ccgctaaaga ggccaccgcc  22020
actaccaagc ccacggctcg caaaaccacc agcaagtaag gactcgacat gatcaacgtc  22080
agcggcttcg gcacgggaat tgtgatagtt tcaacctcgt cgttcccgat ggggttttcc  22140
ttgtcgaagt tcgctgatga tgagagtccg atatcatcca aagagctgga gccgttcggg  22200
tatgagatgc tttatgatgg cggtctgttt gccttcgata aggcggcccc tttggaagtg  22260
tccatatccg taatcgcagg gagcgaagat gatattaatc ttcgcatcct tctaaattcc  22320
aaaaagggat catttcgatt ccttccaggc gtcattccag acatgacgac tcttgttgca  22380
actcttcccg atggcggccg cactgttctg tccaacggaa ctatcatcaa gggtccggcc  22440
atagatacca tccagaacac cggacggcgc aaaggcaaca cgtatacttt tgttttcggc  22500
aactatctcg gcgcccagac tgcgcgtcaa gctatttcta acgttattca atcggttctg  22560
gaggtgatct gatgttaggg attttcacca gcctcctaag ctcgcggtct ttttcgattg  22620
tagatcagaa tacaaaccag ctagttgctg cggatttgag gataagccgg gttaacaccc  22680
ggttttcttc tgtagggcag cgccacatgc tggaagacgg tacgacaaag atggactcca  22740
gaacggtcca tcctatggag ataatcgttg aggtattctg cccttcaatt gatgtcgtag  22800
atcagattaa tcaactgctc ctggatcgtg atacgctgta caaagtcatc actcgcggca  22860
tggtattcga acggatgatg tgtaccagcg aagcgcttaa tcagacgcca gaaatgatat  22920
cggcaactcc tgcgcggctg acattttccc aagtgctcgt tcagaatccc aaaccaatca  22980
tgttcaggaa tgctggagac tcttccataa tcgaccgagg gttggccctg gccgaagacg  23040
ttgtgggctc ggccagtgac ctgttcgact acgcagtgaa cggcgtccag aacgccgcag  23100
acttgttctg aggtgccaat tgaactcttt cctcaaggcc attctcaaca cgcctactct  23160
caccatccgt gatgatttaa ccaaacttcc cgtttggaag agtctccaag tcaagaaagt  23220
ggaaatttac tcaccggctt ccgtagtgtc gaagcctttg gcgacgaaag accagacgga  23280
agctcaggtg tataccgaag cgctggacgt tgatgtgaag aacgggaaga tcattcagcc  23340
agtgcggctt cgcatcaatg ccatctgtcc agacttgtcc acagttgaaa gtatcatgaa  23400
```

-continued tgcttttaat gacaatacct cgactttcgc catcacttcc aagtcgatat tggctgataa 23460
aatggccatc atgacgctcg atgtagatca atctcctgac atgctaaatg cggctgagat 23520
caacatggaa ttcgagcagg ttgagcctcc agtattgaat gaatttgatc cggctttccc 23580
tcaagatcgc ccaacttatg gcgtgcagat tcagtccctt tccgatgcaa atttgctaga 23640
cttgggagcc accggcgatt cgatatcttc ggccgcaaaa tcgctatata atcgcgtgac 23700
cagttatttc tgaggatgta tcatgcttga aatcaacctt cccgatggcc gccaaactcg 23760
cgtacaaatc gaggcgtggt cggcattgga cggctgggaa ctccagcgcc gtttcgtcga 23820
gttcgcagtc agcaaggatg ccgacttccg ccgcgctttc accatggaaa tcctgagcta 23880
tgccaaagtc attctcggta acgatgattc cgaaattccg ttgactactg ctgcggtcat 23940
caacaaccac ctcggcaact ggaagaacgt tgaattcgtc ttcgattccg tcctcaagca 24000
caacggcatc gatccgacaa cgcacgccga ccgcccggac tattgggagc aagccggttc 24060
gcagatggca atcgcatttc tggccgaggc gtccaagctc attgggccag ctatgaaaat 24120
cgccgaagga ctcgccagca agccggagta attcatgtct agtgatttgg atgaattcat 24180
acttcggtat gaggccgaca cggccagagc cgaacgaaat ctggaacgtc tccagaatca 24240
gatcaggcgc gtaaacagcg catcgactag tggccttcaa gatttgcgcc acttcgcaga 24300
cggcgctgca accgaactcg gccgcgtggt tccgcaggtg gacgccgtaa cgagcgcgat 24360
tcgcgggatg aacgcccagc tcgcgatagg cgctactggc gtggccctgg tcgcggccgg 24420
cgtcaaggcg ttcatgaaca ccagggacca gtacaaccag cagcgcatcc aggcgatgga 24480
tatcggcatc gccccggcgc ggctggaaga gtaccagcgg aaactggccc gccagtctgg 24540
aggaacgatc agccgcgagc agggcgcgga aatgaccaaa aatctggccg acactttccg 24600
gcgagcttat cgcgatatcg gacgggtcgg cccagaggcg cggattctgc gcatggccgg 24660
cgtagatgtc ggaagcttcc agaaaggcat gaggccgctc aacgacatca tcactgagct 24720
ggccacgaag atggccaagt tgaaaccgga cgagatttcg gcatatgctg atgccctcgg 24780
cgtctcgcgg gactatctga gcaccctggc gaagatcggc ccggcaatgg gcaaagtcac 24840
tgagatgacg tcagaagagc ttcaggctag ggtcaggggc gagtcaaaca ttcagaagtt 24900
caatgatgct ttggcaaacc tcaaccaaac gttcacgact ctggaaaacc gcgttggcga 24960
aaaactcgcg cctgcattca ccaagttgat cgaaatcatc gacaaaattg tccaggccat 25020
tcccaatgaa gtggaagaat tcgccaagga cacgaaagcc cgctgggacg atggaatcac 25080
cggaaaggcc actgtgggcg gcgatatcct gtcccttctc agtcctggtg ctctgctagg 25140
tcgtctggcc tcctggggca ctcggcgcgg catggaagag gccggattaa tcgacaagtc 25200
aaaggtccca ggctcccaag gccaaaccag cgaagacctg gccaagaaac aggaagacca 25260
ggacaaagct acgaagtcca tgaaagagct ggagaaattg gccgaccaga ctacgaagtc 25320
aacgaatgat ttcgcggtgg cgatcaacat gttcagcgga gccgtgtcat cgttcgccaa 25380
tgccgttgac gagcgtcaag catgggcggc atgggcgggg gaaatcgggc gcgcagtggg 25440
catgggaagc accgcaccga cttcgcgagc aacaggggtt tatccgcacg cgatctacga 25500
tcagtcgaag agtggcgcgg ccggtcaagt attcggcgag cctattggcg cccagtctct 25560
gcgaaacagg atgttctcgc cgcagcgcaa ggccgagccg atcaacgtgc catcgtacat 25620
caatgacatc atcaaagatg catctaagat gtacaacatt cctgagatgg acatcaagaa 25680
gctcatatac actgaaagcc gattcaacgc tagggcgacc agcgaagccg gggcgaaagg 25740
cctcatgcag ctgatgccgg aaattgccaa ggcgtatgga atcaccgatg tgtatgaccc 25800

```
acgccaaaac atcctcggtg gaacgcgcct attgcgggaa aacctggacc gggccaaagg  25860
cgacatgcga ttggcgttga cctactacca tggcggcctc gacccgaaga actgggggcc  25920
aaggactcgc gcatatcctg gtttggtgat gagcgcacca attgaactga tggaggaagc  25980
ccagcgcaag cagaaggccg cggccatgac ggtcgccaac gagacgttcg cgccagaagg  26040
tggcgacatg gacattcgcc cctatgacgg cggaaggctg gaagctccgg accagggcag  26100
gaaggaggat gatcgccgcg aagctcgtcg atatgacgac agagttgtcc ggccggagat  26160
tcgcatcatc gaccgcatgc cagaccgcag tgacggcgaa attcttaaaa tgtctcagcg  26220
ccaagacgcc gaccgggcgg actctggatt ccggaaattc ccgaaccagg ttcgtggcga  26280
gacaaagcag aacatccagg cccaactcac tgccggagct attgcccaag tcatcggtgt  26340
taatcctaac caaattatgc gccgcgaaat cagccgttcc gacttgctgt tcggatacaa  26400
ccaggccatc ttgggcaaac agcaggaaat caaagccgct gcgacagagg ccaacaatgt  26460
attcctttct ccagccaagc tcgccgaagc tactgccaag gttaacgccg catcgcgaga  26520
aatggatatt ctcaggacgt atggggagaa gcttctgaag agcgctccag agcgcggcca  26580
ggaactgaca atcggtcgaa ttgatatgtt ggtaaacgtc accggcgcga attctccaga  26640
agaggctcgc gaaatcttca gcaggcaaac cgcagaacag ctgaccactg ccatccagga  26700
ctcccaaaac gattctgcaa ctaagatact ctactgatga aaaagagaat tctgcgagtc  26760
acattcaata tgccctatgg acccgaaatc atccgtgaag acctggatgt tcgggtccgg  26820
attatgaagg ctgcattgcg aattcaaaac cgagctaccc tggaaatctt tggactcacg  26880
acgcaattgc gcgagtctct tctgtcgcag ttcacagcgt ggaagcaccg gcagcgtcaa  26940
gtaggcatgg aagacgaact gatgatcaga gtatcggttg aggccggtta ttccgatcag  27000
ggccgcgaac aagtttccag agtatttgtc ggcgaagtgg caattgtcga tgtcatttcg  27060
ccgccaccgg atattggaat tcgcatccaa tgctacacaa ggcaaatcga taggacgaag  27120
actattcgaa atatgccgcc agccaacacg acgtttgtaa agttcgtcga atggggcgca  27180
aatgaaatgg ggcttaactt catctgcgac accagctaca atgatcaagt tttgaagaat  27240
ccgggccggt cgatcactgt cgcgtcggca atcctggcat cgattcagga tatgtacatg  27300
ccggatgtgg ccgcgttcgt cgatgatgac attctggtcg tgaaggaccg ggataaggtc  27360
attcgtcctg atgaagttgc caacatcaac tcattcgtcg gcatcccttc atggtcggaa  27420
tggggcgtgg aatttcagtg tctgtttgaa ccgtcgattc gcgtggctgg cggtgtcgcg  27480
gtcgaatctc tcatgaatcc aagcgtcaac ggcaactatg tgatcaccgc tctagagtat  27540
gatttggcca gccgggatcg gccgttctat atcaaagtca tggggagccc agcagcgtaa  27600
tggccaggga aatcaaatca ttcaatatgt tcggcgtgca ctacaactcg cggcaattct  27660
ctgcggtcga tggactcagg atgatgtcgg gaatccatga tgttcctccg gaagaattgc  27720
tcaaagggac cgacgtgttg gcccatacgg aggaacaacc ggaaggcgtt tggcttccct  27780
tgaccgctgc gaacataaat ctttatgtaa ttgaccgggc gaacgtaata gctcccgtac  27840
aagtgcttgc gcttttgtct gaactggtca tagattggaa ctttggcttc ctcaaagatt  27900
ggacaggggt caaaattcca tcaagatttg tagaagatat caaaagcgtg aagacggccc  27960
attcgccttc cgtggtcgca agtttggtgg cgaatgggtc agcttctatg cgcgagctgg  28020
aagagtatta ttcgactcaa gatgccttta agatgattga catcatgact gcgaagagcg  28080
tgaatgaggc tctagcgtcc gaagcatcac agaacagaat caaaaaggga taattcctaa  28140
```

-continued

```
gcgagcctgg gaaggctata ctagaccggc caaatcagag gctttcccat gtccaatatt  28200
ccgctaacat ccgcaaaatc taccgacaga acgcgactga tcgccgctct tgacgctcgg  28260
tcgcggcggg atgcgctcga ctttgaagtc atgattcccg cccaggttgt tcaatatgat  28320
cgggcagaaa acatcgctac cattcaacct ctcatcacct gggttgatac ggaacacaat  28380
gccgtccagc ggcatcagct ggttgacatc ccggtgattt ccatgggcgc tggcggcttc  28440
cacataagtt tcccgatcca gcagggggat atcggctgga tttacgcggc cgaccgcgat  28500
acttcccagt tcttggagtc gctatcgatg tcgaagccga acaccggccg catccacaaa  28560
tttgaacatg gtatgttcat accggacgta ttccgccgat acaccatcaa ttctgaagac  28620
tcggacgcga tggtcatcca atcgactagt ggagcgacca ggatatccat tcgcggagac  28680
aacatcaaga tcactgcgcc gtcgaatgta acagtggata ctccgcaggc gaatttcact  28740
ggagatgtga ctatcgccaa caccctggtt gtaaacggcg tcaacgtgaa caaccacggt  28800
cacctcgaaa acaatccgcc tgatacccgg actaaaggcg gcatgattgc ctaaggagaa  28860
tttcatggct agttttgatt tttctgattt aacagcgggg gggggttgta atggctaatt  28920
atgactacat agtagatact ggagtcatag tcgccgatac tgctgatatt ctgaaggacg  28980
ttgaagcgga attcagggca gccctcggcg ccaatatcaa cctggcggcc tcaacgcccc  29040
agggaactct ggtcgcggct gaaaccattg cgcgttctag cgtgatgagg aatgaagctc  29100
gcatcgccaa taccatcaac ccaaacgtgt ctttcggaac gttcctggac gccatctgtg  29160
cgctgatggg aatcgagcgc ggctctgatc tttcgacgtt cggctatggc gtccaggtga  29220
ccggccgcag ccagacccga atttccaccg ggtcgcgtgt gcagactccg gccggagcga  29280
ttttcacggt catgagtgac gttctgattc cggcaaccgg agtcgccacc atcgacgtaa  29340
aatcgcagga ctatggaaac atccctcttc ccgtaggaaa tctgatcatc atcgatggaa  29400
ccatcggttg ggccggggcg aaagtcatcg cttcaactcg cgtcgatcct ggcagccgcc  29460
aaatgaccga tgcagaattg aagaatgctc gcgtcaatcg tctggcgatc caaggccgca  29520
actcgacttt ggccattaaa gcgtatgtca gcgccgtgcc caacgttacc tcggtcaacg  29580
tcatcgaaaa caacaccggc acggttcaag ttgtcaacgg cgtatcattc acccttccgt  29640
atgcggtctg ggtctgcgtc gccggaaatc cggataagca ggctgtcgca gatgctctgt  29700
gggcggccca caacggcggg actccctggg actatggcgc ggccgacaac ggcgtccctg  29760
tggatgggcc tactggcgtt cctgttcgcg acccggcatc cggtcggaag tatgtggtga  29820
agtggactac tccgatcatg tatgacggat atgtaaacgt caccgttcag caaggctctt  29880
cctcggtcgc tccggaagca atccaaaacg cagttgtaaa ttacgcccag gggaaagtgg  29940
agggcgaaga gggattggtc gtcggcgcga gtctgtctgc ctttgaagtg gccggggcca  30000
tcgctcgcga gattcccgga atctacatta aactatgcca ggtggcttgc gtcccggctg  30060
gatcgccggc cccggccccc ggcgacttct cgcctgagta cgtcatgagc gcattcggtc  30120
aggctaccat ttcggttggc aacgttaggg tgactttcgt atgactctgc ccgcgtacaa  30180
ttctgatatt caacaggcgc tgaagtggct ccataaccag gcccctggga tcaccggctt  30240
ggttcagcga aaagctcaat ggtatgaccg tttcagtcgt cagttttggg ttaactggga  30300
gcgcgacgtt ttcaacctga agaccgccaa cccgttcggc ctcatggtgt ggtgcatcat  30360
cctcggcacg ccgtcgaaag gattcggcct atatccaaaa aacagttctt gggcattcgg  30420
tcggctacgc cagaacttca tctatagcgg tacacaagtt ccgccaccgg cagacgcatc  30480
gccgggcggc aacttctacg gtggcggcaa tgccgaaatt ctcaacttgg acgaaatcag  30540
```

gaaagtgctt cagctaagat atgtagcgct gatttcgaac ggctcgattg catatatcaa 30600
tcgcatgctt cgctacatat tcaatgatga tgagccgtgg gacgaggcga ccggtctgta 30660
cttctatctc atggactcaa ccggcgagga tggccctgtg gagaacttgg ccatatatcg 30720
gaaagattgg gaaggtatgg tgctgttgtc cagttcgccc agaacgaacc atgtgctgac 30780
atcgacccct gccagcgacg ccgattggcc gggagtcgat ccggccgcga gcggtcttcc 30840
ggtaacggtc gaaacggcgt ccgctacggc cccggacggc tccgctacgg tgtgcaagct 30900
tactaagccg gccgggagta ccgcttacgt ctccgcgccg atagatgggc cgctggggtc 30960
cggtagcact gtaacgttct cgttcttcgc gaaagccggc tccacccgtt tcattgcaat 31020
tcagtcggct gccgatttcc ccagtcgagc cgatgccgtt ttcgacctgg attccgggca 31080
cgtgatcagc gatcagatgt tggacagcag cgtggtaagc gcccgaatga ttcgtctgga 31140
gaatggctgg tggcgttgcg ttctcacgac caagaccgtc agctcttcgt tccgcgcggc 31200
ttacatcgct ccggcagaaa ccaacttcag ctggattgat tcgaattcca gcgcggcgat 31260
tgatgtgctt atctggggcg ctcagatcga actgggtgat actccaaccg gatacttgga 31320
gactaccgga acgcccgtaa ccatcaccga ttacgttctg cagagcgccc agaccggaac 31380
ggtcaagttc acacagcctc ttccgaccgg agtagaagcg tattggactg gagactggaa 31440
aggtgggtct gcgaccgagc cggccagatt cgcagtaggg gatgggactc aagatacatt 31500
caatctgtcc agccctgcat acatcggcct acccactagt ggggcgttca agctagaata 31560
cagagttggt ccggcgctta atttgtcgcc gcaattgatc aacctcatga atgaccgggc 31620
ggtcggtatc atgccgactt gcgccggttg cgatgtaaaa gtcattcagg agtaatgacg 31680
tgatcacacc cgaactgata cccagtccgt ttgctgcgca gggcgacaaa gacccgatcc 31740
cgcagacctc ttccactggc tttgccaacc ttcgcgacgg ctacacgccg gactacgaaa 31800
tcagtctggc gtcgaacaac ccgcaggcca aagcggtcga gcggaaaatt caaaaccaac 31860
tcttcttcat cgcgacccag aacgcacagg cttggcagcg gcaaatggcg ccgccgtggt 31920
ttcagggcat gcctggcggc tacgaacaga atgcagaagt cgtgcgagtc ggcaatgacg 31980
gcataatgcg gcgttatcgt tccatggtga atgccaatgc gagcgaccct ctcagcagca 32040
cgacttggga agaacaaccc gcatggtcgg tgatgcgctc caacataccg atgccagctg 32100
gaggcccagg cctatcttct ggcggagaag tcatcacgac cggccgcaac ttcaatgacc 32160
tgttgaatgg gacgtgggag ttcttctctg attcagtggt cgtcgcttct cagaacgccc 32220
ccgtatatcc cgcttcggct ggtgcagcag ctggaatgtt ggaggcgaaa tcctggatat 32280
ccgggtccaa tacattctgc gttcaacgct acactgaccg cgtcgggaac gtcgctgtgc 32340
gcgggcttaa tgccggggcc tggaccaact ggatgtacgc agtaaatgtc atggccctcc 32400
aacaaggccg tgtgacctat ggggtcgcgg ctggctcggc gaacgcttac acgttgacgc 32460
tcgttccgca gctccaaggc ggcctggtgg acggcatgat ccttcgggtc aagttcaaca 32520
ccgttaacac cggcgcctcc accatcaacg tctccggatt tggcgccaag gccatcgtcg 32580
gcgcggcaaa cttcccgttg actggtggag aactcggtca aggactcatt gctgagcttg 32640
tattcgacgc caccggcgac cgttggagga ttctcgcagg cgcgccgcgc atccaagtag 32700
gcaacgccga tcaagattat caggctccca gctggaaaca ggttaaggac tatgtcgcgt 32760
cccaaaagtt gactgaagtg gactgggctg acgtcgtcaa caagccgaac gtcgccatcc 32820
aagacaccac accgtggttc gccaatctgg agttgtctga cgctcgtcct ttcatcgatt 32880

```
tccacttcaa caacaaccgc gccaaagact tcgactatcg ctttatctct gaagctgatg  32940
ggtcgatggc gttctattct cgccaggggt ccgctggtcc tacccaggat atcctgttca  33000
gcaggtcgaa tgttacattc ctccagccgc gactggatgt tgcgaaaaac ctcgcgtaca  33060
tcgcgaactc tggccccctt tggcagaaca caactgccga tcagcccggt tggaaattca  33120
ccttcgcaca aggtgtggac gccaacaaca acgcggttat cgcagtcaat accaccaacc  33180
cggacggctc ttatcgctcg caggtcatgc gatgggactg ggcgtccacg aacgtcatat  33240
tcaacaatcg ccctctgttt gctggacaat atgttccgtg ggactccgga aactttgatc  33300
cggccaccaa gctcactgtc ggtactacca acaatatttc ggggccgacc ggaattcgta  33360
ataccaccag caataccgga aatatgaaca cctggggctc cagctccaca actgcatcgt  33420
atggaaacgc agctcttcaa atcttcggta gagggggtgg cgagcctgcg gccatctact  33480
tcgacaactc ccaaaccggc tggtatttgg gaatggacaa ggacggccaa ttgaagcgag  33540
caggctggtc gctcggcaat aactcctatg tggtcactga cgagtcgaat attcggaatc  33600
acgtcaatgg aatgtctggc gctcctgttt ggggaggtca atggttctgg ggtgaatgga  33660
acttcaaccc gaacacaaag ctaaccatca aagccggcac gcaggagact agcagcactg  33720
cgatattcag cggaaccctg ccgtttgcac caatcgcgtc tctgtccgac tattcccagg  33780
cgcccctgac gatttataac tcgccgactg ggccatctgc taagcctgct gtgatcgcgt  33840
ttattcgccc tgggaactgg ggcgcgttct tcggcatcga taccgacaac aagctgaaat  33900
ggggcggcgg atcgctcggc aacaactcca gggaaatcgc cgattccagc aacatcatga  33960
atctttgggc gtccaacccg accgcgccgt cctggaacgg ccaaaccgtc tggcgatccg  34020
gaaactttga tccggcgacg aaagtggatt tgaacgccgc gaacgccacc aacggcaaca  34080
tgatcttcaa ccgcatttcg ggtactggta gcggcatcgc ttcgtccggt cgagttggtg  34140
ccatcaacct acagaatggc gcgcattcag ggcaagcggc cgcagtcact ttcgagcgtg  34200
gtggaagtat cttcgtcaac ttcggcttgg ataccgacaa cgttctcaaa gtaggtggtg  34260
gaaacctggg ggcaaacgcc tacccagtca tccacgccgg gaactacaac aactacatca  34320
accaggcgtt ggttcaggtc ggtctgggcg gagtcggttc ctatggcatt ttcgcggttc  34380
tggataatgc cgctccaatc gcaaccgttc aacccggagt ggtagtggac ggttccattc  34440
tcatctactc gtcttgcgcc gcaaactaca atagcggtca aaaacctgcc ggaacttggc  34500
gctgcatggg atatgtagtc aacagagacg ccaacacccc tgactccgcg accctttcc   34560
agcgagtgac gtaaaatgag atggacgcgg atcagaaacc cacgttggct ggacgcagta  34620
aacatccacg ccatggtgac tttcgaggga atcggtgaag tgccgttcac cgccaatccg  34680
caagacgtgg aggcccacgg aagggccata tacgctgcga ttctatctgg ggagcacggg  34740
cctatcgccc cggtcgattc gaagcgggag aaggccttgc aggacgctat acgagccagg  34800
gaaaagcggg ctatccttcg ggatacccgc tggcccatag atcgtcacga cgagcagaga  34860
cggctgggta tcgaaaccac ggacggccct gggctgatcg cagccctcgt tcactggagg  34920
cagcagattc gcgactggaa tagcggggat cggccgcgac ttcccatggc tctgaaaaca  34980
atgttcaaaa atcaggagta ctgatgaaaa taacgaagga tattttgatc accggaaccg  35040
ggtgtaccac ggatcgggcg atcaagtggc tggatgacat ccaggcggcc atggataaat  35100
tccagatcga gtcgccgcga gccatcgcgg cttacctcgc caacatcggt gtcgaatccg  35160
gtggactggt gagtctggtg gagaatctca actacagcgc tcaaggactg gccaacactt  35220
ggccgcgccg atatgccgtg gacccgcgtg tccgtccgta tgtaccgaac gctctggcga  35280
```

-continued accgcctggc tcgcaatccg gtcgccatcg ccaacaacgt gtacgctgac cgcatgggta 35340
atggatgcga gcaggacggg gacggctgga agtatcgcgg tcgcggactg attcagctga 35400
ccgggaaatc gaactatgcc ctgtttgccg aagactccgg catggacgtt ctggagaagc 35460
cggagctgct ggaaactcct gccggcgcgt cgatgtcttc ggcatggttc ttctggcgca 35520
atcgctgcat acccatggcg gaatccaaca acttctctat ggtcgtgaag accatcaacg 35580
gcgctgcgcc gaacgatgcg aaccacggtc agctccggat aaaccgatat gtgaagaccg 35640
tcgccgcgat caatcaaggc tcctgatctt ctccgaaaag aaaggccgct tattcagcgg 35700 ccttttttgct ttccggcttt gcctcttcaa tctttctgac ttcagtaggc gcgacggact 35760
cttcctgggt aactgagtcc acatagttcc ctagcgaact caaaacgccg attaacagcg 35820
ctcttaccac tttatcctta actgtctcgc ctatgatctt tgtcagaacg gatatcaact 35880
cttcccggag ccttgggctt attcttggcc gaaagcgctt gcgatgctct ttgcgtttca 35940
tgtttagtcc tctgtttgcg gtcttctcct caccccgata atggcttggg gatgcgctgt 36000
gttaatcgga agggtcgggc gctattataa ctcgacgaaa atgctcgcgc ttaactgttt 36060
aacgatacgc accgcgatat taaatcgcct tctttctggc caaggaactc tggcggccga 36120
gtccggtcta aggcttaatt tgtcgacatt aaaacgagaa aacccggatc gcctttaggg 36180
taaggagtcc gggttttctt cgctctagtg tacgctagaa tcagtggctg gcaccccatc 36240
cgtccagcca gcagtcgaag acagcgtgtc gtggcttatc cttggcgcca tgggagaagt 36300
gcttaaatcg gatgacctgg cgcttgagat gttccctgtc attccagagc cgtttttttct 36360 cgtcgtgggt caggctggac gccgacacat tgaaggtaac tccaggccac aaaacctcgt 36420
tgcggcagac gaatgctcca accatgcctg atggggccag attttccgca tggctggagc 36480
gggccgtgcg acctagctca tccgtgaatg cttcgttgtt gttgtgcatc agctcttcga 36540
cgtcaacaat ctctgcttca tcatagtcat agcgcttaac cttgacacag taaccttcct 36600
tggcagtaga gcgcccgaac ttgtatgcgc catcagcgcg cttgcccatg gagccttcga 36660
atccaagtcc tgtgtggcga cgttcgactt cgctgaactg ttcgatggag gtgaccagtt 36720
cctgctcgac taggtgaatc ctctcatagc cgatgcagtt cttcagaaag ctgacgcgct 36780
cggcagctct ggccagtcgc tcttcggtcg gcgcgcgcgg atcggtgaaa tcgtcaaaca 36840
cgtggaaaga ccaatccggt tcaccgtcgc gacggcgaag gtcgccggac gacttctgga 36900
atactttcgg gtctctgatg tcgccgcaga ccagttcgcc atccaggcca tcgaacattg 36960
catcgctgag atattcacgg atggactggt tggtctgcgg ctttaggctt cgcgtcaagg 37020
cttcgccttc aaatatgaaa cagcgaaaac catcgatctt cggagaaaag tacatcggca 37080
actggccgtc cagaagttcc gggtcatagt tcgatgcgag catgggtttc atacagtact 37140
ccagaaagaa gcccggcgaa ccgggctgaa tggcggtaag ccggatcaga tggtttcgtt 37200
ggcgtgattc agctcggcca tgatcgatgc atagcgctca tccgactcct tgatgaacac 37260
gccgttgtac attacgccct tgcgatcctt gatggtgtcg taggccgcct ggtagcattc 37320
gagcatgctg gtgtcgtgct cttctgccgc gtcgaacagg gatgcgactg ccatgaccaa 37380
gctcttgatg gcaagccact gatttccgcg agccagcgag ccggccaggt cgccgagtaa 37440
tttcagatct tcgccgtagg acgggcggcg ctcgaccgcc aagacgaagg ctgacatatg 37500
gtcgagcaga ttttcgccga gctgcgcggc catgatggtg gccacgacca tgacatcgcc 37560
gatgccgtct ttcacttcgg cggtgtcatt ctggatgtag gcttcgcaaa cttctgcgaa 37620

-continued

```
ttcttctacc agcttgagaa actgatcttt ggccgaagag cctttgatca ggttacggtc  37680
ggcaccccat tttaccacca ggtcatggag ttcgctattc atgattcgtt cgatgatcat  37740
tctttcgatt ccttctgtat ttgggatttg actgcgttga tgatggacgc cgtgctctgg  37800
cgcgatccgt ccttagtggt gccgaagtaa aaggccataa cagacttcag ttcggcaaac  37860
caatagccga tgatagtgcc gatggcgaca gaggaagtcg ggtccatcag cgcctcgcgg  37920
ccgaatgtga aaattgcgat gatgatgaga atggaaccgg tcagaagagc gaaggttatc  37980
gccgggcgaa cgaagtcatt ttgttgcgcg gcaagccttc tcgccgaatc tctgtctgcc  38040
gcctcggcgg cgaactggct gagttcggcc tggagctggt tctgctcaga ctgaagacgg  38100
ttttgttcgg cctggatggc cagttcctgg agacgaacac gctcggcgct ctggagttct  38160
gcgaggcgcg ctagagcctc cggattcgcg tctagagcgc tcgcgaccga tgctgggtcg  38220
gccttcgacc ctagagccgt cgcgacgata gcgccaacgg cggcgcctgc aggcccaccc  38280
aggagcgacc ccagggccgg ggcagcagcg ccgatcttac tacctatgtc cttccagtcc  38340
attttcgatt cctcaaaaga aaggcgccat tacagcgcct ttctctggcc gttgacgtta  38400
gaactcttcg gcttcggtag cgccgccaac gccgccggtg tcgccgcgag gctgttcctg  38460
cttgctgtag tccaccttca cttcgccgcc gacgaacgac ttgtacagat cggccgcagc  38520
cttgaagtga tccgggtttt tcaccaggcc ttccagttcg aactggacgc cggaccagct  38580
gcccttgtcg ttcgacagac cgacggtggt catgcggacc aggttggcga aagtcggcgg  38640
ggtgcgcagg ccctgcggag tctggacttt cttctgggac agcgcggtca tgagcttctt  38700
cgaggccttg atctgcgaag acgacaggga gatcagggcc tggccgaaat cgccggtttc  38760
cggatcgatg acgatgacgt aatggccacg ggtgtcggcg aagtaatcag atttcttgtc  38820
gcttaccgaa ccgtcttcgt tcggcgcgta cagtcgccct tctacttcct tcaccttggt  38880
cgggtctttc atcatttcct tgaagtcttc gacgctgatg gaccctttga aaccgccttc  38940
ggcatcgcgg ccggcccagc gaatgaactc gcgacgatac gcggccggga tgatcagcag  39000
accggttttg ccgtcgtaaa tcttgccggt gacggtattc aggaacatgc cggccttcgc  39060
gccctcgatg tatttcgggt cgtcttcatc gacctgcggc gacatctttt gcagcacttg  39120
gatgaaggga atggcatagg aatctgcgtc agccccttcg aaaccagcgc cgtcatacgc  39180
gcccaggtcc atgaagtcgg gaacgtcagt agtcgcgacg gcgccgccgt tggccactgc  39240
aacggccttg gtttcttcgg ttgcttcgga agtctcggtt ttcttgccag ccatgttagg  39300
ctccttgttt gtcgaatttc agttatcgct aactgtgggt ttataataac ggaagttgca  39360
gcgaagtaaa gcaaattaca tgttaagatt tgctcttttt caccttcggc ttcgtgatct  39420
tggcctcttt atattcgtgg acgccgatga aatctggcaa ctcttcgccc ttctccaggt  39480
actcgcgacc gaacgcctgg agggtctggt agtgaacatc gcggttgatg gtggcgtcat  39540
agccggcttc gatgatcgct tcggccgcct tcttcgcatc ttccatttct ccgcgaccga  39600
attctgccag aactttggtc ttgatgatgc cgtcgttgtc tgtgtcttcc agccacttcc  39660
agaacttcga cttgttctct tccttgacgg aaatgatggc tttcggctcg acttttaccg  39720
tgcggccatc agccagagtc gtggtcttct ggccgagttc ctccagaagt tcaggaatgg  39780
tattgcgctt gagggtcttc agctcttctt ctttttcggc cagcgccttt tgcaattcga  39840
ggatttcgcc gtccagctgc gaagccttgt ccaccaagtt cagcagtcga tggccgatgt  39900
cggtagcttc gactgccatt tcatccatga cgccgaaata gtcaatttcg cccggcgcat  39960
tgtccttcag atactccgga acttccaatt cttgctcgct catgtcagcc tccaacttag  40020
```

tgatgttccc ttacttgaac taagtattga gtagatatta tgccgcatct tccttgatac 40080
ggctactgat ttacatatta aatttcgtcg cgagtgctaa cgtcagcctc gaacactcca 40140
tcgacgacat aactcgcaag attgcgcttc cactccaagc taacctggat tttctcgtcg 40200
atggagtcca gacagatgag gtcgaagtac aggacagagt tgatggtccc gatgcgatgg 40260
tttctgtctt cggactgcat ccgcaactcg ttgtcttcgt cggtcgtgta gtaaattgcc 40320
acgtctgcgg cagtgagcgt gattccgatc ccagcagcgg ccgggtttcc caggaagact 40380
tggacgcgct ttgcctgaaa atcatcgatc agtttttctc gttctgcctc tttggtctcg 40440
ccataatagg ctccaaacga aattccttgg gcctcaagat acgcagcgat ctggccgatt 40500
tcgtgaatcc gcatggccca gatgatgata gaccgttccg ggtcttcctc caacagaccc 40560
tccagaaggt cggtgaatac cgcgaatcgc gggttgtctt cgggcggcag gatcaccggt 40620
tccccataga cgttgatata gccggacgcc acttgcttga gtttcgaacg cgctgctgct 40680
gcatcgaacg atacatccag catgaaatct tcgttcttga gcacgaaatg gtagtcctct 40740
tcaacgcgct gataaatctt cctttgctcc ggcgacattt cgaaatatat gcgcttgtaa 40800
accttttctg gcaggaatgg caatgcctct ttcttcgtga cccggaagct gtgcggctcg 40860
atcagggacc gcagtttgtc aagatttcgg aatactggtc gcccaaaatc gtctttttcg 40920
acgagctgag gtggaacagt gctcttccca tccaatttgc gcatgatggc gaccattcgc 40980
gggtcgtcac ttggaaccag aacggaaaat tcagccacga acgcgcgata ggatttcgtc 41040
cccagaattc catcacgcag gaattgaaac tgcataaaca aatccgtagg cgctcgcgtc 41100
agaggcgtac cagagagtat gcggcgcgcc acggccttct cgcccagctt tacgatcttt 41160
ttcgctcgtt tggcctgtgg gttcttgatc ctcgttgatt catccacaat tgcgcagact 41220
ttgaacgtct taaggaatcg ctccacttcg tcatagccag actgatggtt gatggcatcg 41280
acgtttatgg caaagacccg aagaactttt tcatcagcga atgtctcggc atacagacga 41340
tccagacgcg ccctggcctt tttggaagtc ggtcggccgc gccaatccac gcacagagtc 41400
ttgatagcaa cgtgggtggg aatctcgcgc agaatccagt tcgtgtgtac gcccttgggg 41460
gcgacgatga gcagcgcgtc aacccttcct tgcaggaaga gcctaactga gtctgccaaa 41520
gtagtccagg tcttcccggt gccttgctcc atcaggtatg cgaaattcct tttgttaagg 41580
gaagcctcca gggcattgaa ctggtgttgc atcgcctcgg tcttcatgcc cttgactgga 41640
aaggttttgg ctttcatttg ttctccagat cggcgagaaa ttgaatgatg ttgtccagtc 41700
cttctgcatg actcgcgact tccaccaggt cgcggctgtt aagatcgaac agatcgagca 41760
ttggattcag gagcagccaa tcggttccga ttttcaccag aacgaagccg cgaccacccc 41820
agccgatccg ctcccgaagg aaagggattt gcccaggctc gaaacagcgc gccattgggc 41880
aggtagaggt gcgctttggc caagcttcca gagccttgaa ctcgacccaa aactggacac 41940
cgtgacgatt caggcatatc gaatcggaca tgccggaccg gcgcgtctcc aggaaatcga 42000
ccaggattct gcctagcgag cgttgcttaa acgcattcgc ggctttcgtt tcgcgatcat 42060
tcatcgccat tcccctcttc ggaatctttc tctgcttgcg ctgccaactt tgctttctcg 42120
cgttcggtca atatccgctt gacggccttc acgatgaaca tatcgattcc gctgagcttc 42180
catcctttga tgaggaacca agagccggta ggcgtacctt cggcgatatt cttaccgtac 42240
tgaagatatt tttcagggcg aatcctgaaa cgaatcggtt ggtcaaccga gtcatccacg 42300
cacatcaaat cgaggaactg cgactggcct ttgtacaccg gattctttcc ttggtcagcc 42360

-continued

```
ctcttcttct ggcggatcgg ttcattctca tccgacagaa ctttctttac cagcttgacg  42420
ataactaggc catcgtcgcc atcgcggata tcacgaatgt tctgaatggg atttccggaa  42480
gtcaccccaa ccaactcagg attgtcatag gcatgacccc agagcgtatg agattcattc  42540
aaatccgcga attgaacctc agaattcgac aaactcgcgg caactttctc ccaatcctga  42600
agcgttttaa gatgggagcc ggccagctct ttatattgcg ccttcaactc cttcagttca  42660
gctttcaact ccttgagatc agctttgagt agcttctcca gttctttgtc tctgcttact  42720
ttcgccgaaa gaatctgggc ttccagcgcg gcaacgtcat cggccttatc ctctacatcc  42780
tgcgccgaaa tcgggcaatt ggccagggcg atcctcgcgg ccttgacttc ctcgcgaaga  42840
cgcaagaatc gctcggcctt agccgggccg aagcctttgg cgttcatgat gccgccgatc  42900
aggcgtccgt ccgctacaac ccagttgagt tcggaatgct ccgggtccag ggccgtatat  42960
tctacgcctt ctttggccaa ttcgcgaagg atagacacag tttgctggtc gtccttcgcc  43020
gcccgaaggc acgcggccgc gtattccagg cgatgatacc gcttcatgta gcaagtccag  43080
tacgtcacca cggcatagct tacagagtgg gagcggttga atccccaggc gccgaatgtc  43140
accatttcct gccaaactcg gtgagcgtct tccggggcga cgcctatggt cttggcgccc  43200
tcgatgaaca attctcggcg cttgttgaag aactcttcgc ccttccgcgc cgacatcgct  43260
ttccggatcg ccgacgtttg ttcccagtcg aactgaccaa tgtccttaac aattgacatg  43320
atctgttctt ggtacaggaa cacgccatac gtccccgaca aatactgctc gacctgcgga  43380
atggtatagg tcacaggctc gcgaccggct acgcgctcga tgtatttcgt ggccatgccc  43440
gaagacaacg gacccggacg agcgagcgcc gtgatgtggt cgatgttttc gaacgcggtg  43500
atgtttatcg cattggcgac cgagcggacg gcctggcctt cgaactggaa gatgcctgac  43560
atcttgtctt cgttgagaac atccaaaacc gccttgtcgt tcagcggcaa gtcgtacaac  43620
tcttgcgccg tcacgcaatt cgcatcttga attacgccca gcgttcgaag acctagcgcg  43680
tcaatcttga gaagattcaa atattccgaa tcaggcttgt cgagctgcgc gacgccttca  43740
gaagtaaccg tacagaaatc gattacttca tcgttgcaga ccaggatgcc tgccgcgtgg  43800
acgccggagt gggatgggtg aatttcgagg tcgcccatgc aggcggacgc aatctcatac  43860
ttttcgcgga agtcgcggcc gggttgagtc ttttcgaaag tgtcctccaa tccttttcca  43920
tatcgttcgt ccgccgaagt atattcgatg atcgagtttt tgatgttgtc ggtgtcatgg  43980
aatggaatgc cgaagcgctt tccgacgtga gcgataaccg acgcggcctt tagtgtgttg  44040
atgttcccaa gctttaccac gttccaagtg ccgtatttct gctggagata ttcgaacact  44100
agatagcgat gggtatcggc gaagtcgata tctatatcgg gaagatcgga acgggaaatg  44160
tcgataaagc gctggaagag aaggcgatgc gggagcggat cgacctcggt aattcccagc  44220
aggtagcaga ccaaagagcc ggccgaagag ccgcgagccg gaccgaccag catatgcttc  44280
ttggcgaagg caaccagatc ggccacaacc agaaagtagc tgtcgaagtc tttcagctga  44340
atctgcttga tttcttcctg gaaccgatct tcgtaaactt gggtccattc cttgatgtgg  44400
ccgcgactga gacggtaggc ttggccctcg cgagccaggg cgacgatatc accatccagg  44460
tggatcatcg gcgctttcgc cagctttacg tcgaccagct gctcgaccac cgcatgcgta  44520
ttggcaacgg ctttgtcgaa ctcttcgcgg gtcatgatat ggcgaagacg ggcccacaac  44580
tcttcctcag tcgcgatgtg gcgaaggccg accgattccc gaaccttcca ggccgaagca  44640
aaatctgcat ggtcgatgga cggcatgtcg ttgtaggagg taatcaccac aggcttgccg  44700
aacgccctgg ccgtctccat agcgccgtgt gcggctacca tcgacgcagg attgatgtca  44760
```

atgtaatcga ttccggccaa gtccaagtag gcataggcct cgccggcgaa cttgatgacg 44820
ccgtcagcat cctggaattc ttggggagac aatccttgat tctggacagt tttggacgtc 44880
aggcgataga actttctggt atctttggct agcgcccagg ctttcagttt cagctctttg 44940
tcaccatcat cggcgcattt gatcgggatt tccatgccga atccgcgagg aagttctgcc 45000
ttggtggcag cctgctccca gcggacgtgg ccccatgtcc catcatcgac gatggcgaca 45060
aagggcgatt cgatttcttt ggcgcgctca atgatttccg gaaacctgcc atatgcggcg 45120
ccgtatgagt agccggagcg aacgcggagt tgagggaaag acattatgcg gcctccattg 45180
cttgatatgc tcgatatact cccatgcgct tgcaaacttc gtggagcagc cgcacgtcgt 45240
ccaatgcccg gtgcttctga acataagggc cgcagtagtg ctcatacaga tgctgcagcc 45300
gcatgcggtg gccgaacaat ggcgccgact cttctacagt acagatatcg agcgatggga 45360
agttgacttc ttccaggccg agctttccgc gagccaaatc gcaggtaagc atgaatttat 45420
cgaatggaag gttgtgggca atatttgcgt cggccttcga aaagaaatcg cgaactttct 45480
ggcgttgatc gaggaacgat gggtgtttga ttaagtcttc attcttcagg cctgtgatct 45540
ttgtaatgat ttcttctatc acaatcccag ggttgcaaat gaactcgact tcatccaaaa 45600
tcgtctcgcc atcggtgatc actccggcga attcaatgat cctcggttgc tttctcagac 45660
ttaccctctg gtggaacggg agtcctgtgg tctcagtatc ccatacggcg aatctcatgt 45720
ctgttccctc ttatgtcgaa aggccggctg ctttcgcgac cggcctgaag agtataccgc 45780
aacggcgcag ggtttatgcc ttctgtccgt ctttcggcgt gatgcggccg gagtgcatgg 45840
tggcgtggac gaacgctgaa tagttgatca agtcaaatac cgaatcgtca tcctcaaacc 45900
cactattcgc caggcgagtg agtttgccaa ctgtatgcat cacgaacagg gcgagccgat 45960
gatcatctgc ggtcttcgcc accatgccat tcgggaagag gatttccatg atcttgccat 46020
acatcagatc atttcgacca taagcgctct ggcggtcgcg gaaaatttct gcggctgagg 46080
acaggttgtt gagaacatcc tccacgaaat catcgggatc ggcatcaccg tcaccaggcc 46140
aggcggattc catggcgaac ggcgctgctg cgtcttcggt cggctcttcg gccggctctt 46200
cggctggctc ttcggccggt gcttcgtaga gcggagacgg ggcctgcgca aacgcctcgt 46260
cgagggtagg ggcggagtcc ggggcgaccg ggaacggctc gcctgctatg tcgttgggcg 46320
cgctaccggg atcgctatcg gccgcgacgg cgaagaacgg cgcatcgcag ccttccaggt 46380
ccaggatata ggcgtcgatg cccaggccct tgtaggcgtc gatgatatcc tggcggtcat 46440
cgaatgccgc gacgatcttt gtcaggccgt cgatcttctt caaaatatct agcgcgactg 46500
agcgcttgaa ctccggcgcc ggctgggtgc ttccatactc ccgcatgatg agctcatatt 46560
cgcgatgttc ggcgataccc aggtcgcgat ggattttcgc cctggtctgg aaatagttgt 46620
tgtcggttcg gccggtgatg aagaaaatca tcaggtcggc gtcgatggcg ttacggattc 46680
gtgctactgc atgcggattg agcttgtcct tgtcgaggcg ggaatggtac tcgtcccatt 46740
gcttttccag ggcgaagctt ttacggtggc tatcgtcgaa gacgcatccg tccagatcga 46800
agatcatgat gccattcttg ggttttcgtg ccatattcag atttcctcgc tttctgcttt 46860
ctgggtgatg gttttctcga tgaaagcgcc atcggaagtt agacggaaca gctcaccgtt 46920
ctggaccaga tcgaacgatt tcacgttcat ggtgacgcga attgattcgc cgccgttggt 46980
cacttcgact tgtgcgacat caccaacctt ctcgatgatg atcttcatgc tacattgact 47040
tcccattgac cgctacagga ttggcctctt gtttctccga tccccagaac tcgcggcgca 47100

-continued

```
gctcttcctg ctcggccgag cgatccatcc atggacgata gaacttgcac tgatagatcg  47160
gtttcaccgg caactcaaca acaggaatct ggccgggctt cgtctccaga gcggacatga  47220
agcggtcaca ggattgctca tgaatctcat cttcattcag aaccttcgat ccatagcgcg  47280
ggaaggcaca ggagccagtg gcgacgcagt gcggctggag cagactatcg aacataggat  47340
agacttccag aaccagtcgg cgcatttcgc ggaaggcttc ctgatactca ccttgcgtac  47400
gaacacacag gcgaactttc gccatgtcgc tcagagtgcg cagattgaat ttggccgcga  47460
tcttcgtttc catgttggaa gggatgatgg cacgagcatc ctgaagcgat gcgccggcct  47520
ccaagagctt ctggtaactg gtctgcgcgt cggcgattgc atcatgccac aggcggttca  47580
gctcttcacg agcgtgatag gtcgggtccg gctcaccatt ggccgtagcc ttctcatcga  47640
aatcccagcg gaacgcttcc ggctgaacaa cggcgctaac ctccagagcg cgactggttt  47700
cctgctggta agccccggtc cgagtccgaa cgagttgatg agtgaaattc ttgctgacgc  47760
cctcgatctg gaagatgaag tccacgaatt cgaatggcga gcgaatggtg tccagcatgt  47820
acttccagtg gtcgagcttt tcggcttcgg tcatggtcgc cgggtcttgg ccgcgcatgc  47880
gggtggattt tgtgcccagg agaagttccc aggcgttctg agtataactg atcagagaaa  47940
ttttcatcag aaatcttccg gaattggcgt gaaagtgaat ttctccgtca gcgcaatggc  48000
caacgcttgt gcatcttcct tgtgtagacc gtatctgtcg atctcttcgg ccagcaattt  48060
gcacgcctcc agacggtctt catactcttc ggcgtggcac atggacgaga agatagtgcc  48120
atcagaggtc cggtacacca gttcaatgga cattactgta atcctcagta gcagcggatg  48180
atttcggcgc gaatatcgcg acggtccagg taatgctcaa taatcttgtc gcgggcgcgc  48240
tcggcctctt cgcgactgcc gaacgacagg ttgaacgaag tgaaaggctt atcgtccagg  48300
cgtccatcgc caatcaggta caggatgcct accagcacga aagacggcgc tgtctgtcgc  48360
gtttgcggcg ggtcgatttg catttcgagg aaagacatag gaacctcttc aggatggtct  48420
ggtgcgtaca ttaatagcgc tcctgctgag cagccaccgt ctccggttcg tagatgatca  48480
tatccacgat ttccgggcac tggcttttca cccagtcgat ggccgcaacc aacgttgtag  48540
cggcgccgaa ggtgaaagtg cggtaagact catggatgta cggcgcaccc atggagtcgc  48600
gctcggtcgt gcgagaaatg actactttga tgttaacgat ccggcccatc ttcggcctcc  48660
actttagcga tgatatcgga caggctcagc ttctcgccat tcaggaaata actggcgcga  48720
agcttcctgt cgccttctgg cccgacgatc cgggccgtta ttgtgagact cccgccgcca  48780
agggcatctg tggccctgaa gaaagccagc agcgcccgct tgagcgctgc ctcgcgagga  48840
tcgactgcca ttaacctatc acattccagc cgtgctgggc gcaccacacc gcgccagctc  48900
ccgcaggaag gctgttaaga aggaacactg gggtcaggcg gccatcctcg gtcatgtgga  48960
tgaagtagcg tgcactttca ccgagccatt cggccttggc gatggcgcgt tcgagattgg  49020
ccttggtggc gtaggtcttg gtggtgtttt tgtcggtgga gaaggttact tcgcgggcca  49080
ttttgtcgat tccttttggt tgaagggttt cgcgtttcga tgagggaata ctactctcac  49140
ctggctcaga agtaaagcac tttgtgtaaa ttatttcacg aacatcttct tggccttctg  49200
ataagacgaa gaagtcatca ggcgctcgat gacgtccatg tccgaaacca gatcgtccag  49260
aaggacgttt cgccaggtcg cgaaccgacc gagcgagaag atgccggctt catgggtgag  49320
attccagatc atggattcgc gctcgtcgcg gccgagcgga atgattttac ccttggtctg  49380
gacggtcggc tcgccgtccg gaatgagatt cttcttcctg atgccgaagg ccgagcaaac  49440
ttcatccagg tcccagttgc tgtcccattc gatggtttcg atttcaccag ccgcagtctc  49500
```

-continued cacgatgccc ttagtaacgg attcgacgat aagggtgtcg ccggtgatgg acgctcgaaa 49560
cgttcccact tcgggaccag ggaaatacac cgtctggaag acatcacaag gaatggaaag 49620
cttgtaccga ctcacgacga tggaggttcc ttcgccgaat gacgggtcga tccccaggtc 49680
cagccctgcc gcagccagat tggcgcggaa tggtgctgtg ctgatgatat taacgtgatc 49740
atcttgccgg cgaaggaact ggaagaaaga ggcgtcgaaa ggcctgcccc agctgatgcg 49800
attcgctagc ttagcgacca gctgctcata gtagtctgcc ggcgcgatcc aacgcttttc 49860
ggtcgccata ttccagatgg accgatccga caggccgccc gttactttcc tggagtacat 49920
gttgcagtag tcgatgcgcg gctgggaaac gaactcgccg tcaatgtaga tggccttgtg 49980
tacggtgact tcgcggaacg ggatgccggt gagttggccg atgactggtg agcggaaccg 50040
caagagcgcg ttgtggcgtt ccttgctcgt cggcgtcgcc gcgtcgatga tttgggcttg 50100
agggaaacga tgcgcggcga tcaggccggc gagtccggct cccacgatga taactttgtg 50160
atcaggaatc atgagatgtt ccttatgagt gtacagaact tgggaggata aaaaagggac 50220
ccattttcat gagtcccttg aagagctaga cgattcggtc tcagaagagc ggcggcttac 50280
tcttcttcac catcggaacc gtcggcgccc tgaccttcac cgtcgtgctc ctggccttca 50340
tcggccttct cgtcatcgcc ctggccagct tcgtcttcct tcgaagcgat ggcaaccaga 50400
tcgacccagc ccatgatttc cagcttgctc aggtagctgc gaaccgaggt gccgtacagc 50460
aagtgggcca ccttctcgcc gaaggattcg atttcgaccg gctcaccaac ggtgcagtgc 50520
tcgttgatgt aagcgaacac cttgccgcga gtcgagaagg cctgcggggt tccatgaccg 50580
tcgccggtcg ggatgaagtg ggtggcacgc ggacggcgcg aaccattgga cttcaggtct 50640
tcgcgacggg cttctgcctt cgcgcggcgc tcttcctgct cttccttgcg acgcttcttc 50700
tcggcttcgc gctctgcctt cttctcttcg gccaggcgct tgcgctcttc ttcgcgggct 50760
gctttctggg cttcctgcgc ggctttcttc tcttcggcct tcctggcgcg ctcggcttcc 50820
ttctcggcct tcttctgctc gcgctcggct tccttcgcct tggccttctc ggcctgctca 50880
gcttccttgg ccttggcctt ttcagcacgc tcggcttcct tggcggcggc cttttccttc 50940
gccttctcgg cgcgctcggc ttccttcttc tcgcgctcgg ccttgcgctt ctcttcgcgc 51000
tcggctttct tctgctcggc ttccttggcc ttggcctcgg ccttctcggc gcgctcgcgc 51060
tctttacgtt ggcgctcagc ggccttctcg gccttgcgca gggtagctgc ttgttccttg 51120
gtcagctctt cgccttgggt ctgttcgttc tggtccttct gttccatgtt cttactccgg 51180
gaatgttcaa agggatggct tattggcctg tgcggggatt atctctaaac taattgaaga 51240
agggaatacc cttagcctga actttcctaa atattttctt tcgggaaagt ccaaactcta 51300
gggaacttat ttatgttcga gaagttccta gcttttacgc aagaacagta agtattcgat 51360
tgcgcgagtt atcccagtat acatcaactg actataaggg atggacggca agttttcttc 51420
taacatggcg acccgtttcc attctgatcc ctgcgacttg tggaacgtca tcgcccatcc 51480
gaagtcgaat ccgccaatgg ccttctgcgc ctccagccgc acgtcttcct cgaccgaaaa 51540
actcagagga ttgaacttaa cccagcgttc aaagttcgta ccgataatgc gaactttggc 51600
gaacaacatt tcatcaggct cgtcatcatc ttcttgccct tcaggaaccg gcttgaagtc 51660
cagcagaatg gcttgttcgc cgttcatgat tccatattcg tgctggttcc cagtgcatac 51720
cagcttctcg ccgattcccg gctgcgcacc tttgtagccg aggattcggc gagcgcgtgc 51780
gttcaagcga cggcgagtat tgttgtaagc acaaagaatc acgccatcat cgtccaggaa 51840

-continued

```
cgtccgcatt tcatcatccg acatatcgaa gccggcccgg accaatatgt cgtcatactc  51900
gcggcagggc aggcgctttc cctggcggac gaacatcgac gcccgaacga tattgccagc  51960
gttgcgctcg atttcggtca tgatggtgtc acagctgttc tcgtggaaaa tctggacgcc  52020
gcgtacagga ggaacttggc caaagtcgcc aatctccaga accggaattc ggtgcgacaa  52080
caggcgctct tcatcccact cgccgatcat ggacgactcg tcgagaacta ccaacttcgg  52140
tttctcgtcg agcgagtctt tgttggcaaa catgatttcg ccgtcttcat cttcaccaat  52200
cggtcgatag ataaagctgt gaagagtccg ggcattgacg caacctttct cacgaagccg  52260
cgcggcggcc tttccggtcg gcgcgatgaa gactgtccag tccatcgagc agcaaagttc  52320
ggcgatgatc ttcgcaatag aagtcttacc agttcctgca aaaccggcga gtcgatagac  52380
ctgacggcgg tgcgctcgat cacaccaacc gcgataccag ttaacgacgg aatttatcgc  52440
gtcgatctgc tggctattag gtcggaagcc gaatcgctct tcgatctgat cgacggtgaa  52500
gttagatgct gacatatttg cgttctccaa cgctaggttt aattgaattg agactcagtt  52560
taagcagacc gtccacagac cacccagtat cacgacgata tttgcggccg tgcggatcga  52620
catagaagtt tttcgtgcgc cgcaacagga catagtgcca agcagcaccg agcgcatgga  52680
cccttccttt ataagggaag gccttaagtt gctctgcggc cttcttcgcc ccagggagcc  52740
agcggacggt cgaaaggacc aagaccgcac ccttgacagc ctgggaagcg gcgcggccgt  52800
cctgtgggct atagcgatgt ctatcggggt ctacccagtg gtggttgcca cgccggagct  52860
tcaccgtccg ggaccggccc tcaaacacca cagtaccttc gtgagtaaaa atatgttccg  52920
ccatggaatg ttccttataa cgtacagttc tgctttacct ctgcgcaaga agagtatact  52980
atcagctgac tcgtcaaagc gagctaattt aatccgactt tacttcggca ggaaagtggc  53040
cgatactagc gccgccgcct gtactgccct ccaaaacaga ggatacatta aatgcaagaa  53100
tgcaagattt cccgcgacca actcccggtc ggcaatccga atcccaatgt cgacaagact  53160
cgcgacccga acctaaagcc cggctacctg cgtcgcagtc gcgagctgga cccggctctg  53220
gccgttcgca tccgtcgcga gctgatccat gcggaagcct ccgacttggc catggccggg  53280
tgggtcaatt cccagtccag cctctatgga tcgaaagcgt tcccgcgcca ttccgtcgtt  53340
cgcgtgactg ggatggcgga atctgaaacg aacgtcggaa tgctcatcgg attcatcgag  53400
caccgcaagc acggtgaatg ggcagttctg gaaactggga cgaaagaagg cggcgcgatc  53460
accatcccag tcgagagcat catgcgtgcg tcattcgcag aggccgaaga attcgccgag  53520
aaatggaagc gtaacctggg gtggcgcctc ctgcgtcagc ttcgtgaatg cggcgccctg  53580
gccgggactg aagacgaatt cctgcggcgg ataatcaatc gatatgttcg cgatctcacg  53640
atactcgccc accacaaagc cggcgcagac aaaagctata ccgatgcagt gctcaaaagt  53700
atcggcgaag catggccgca gattcctgcc ggaacattcg tcggccaccg agtcgcgcaa  53760
ctcctgatca atcacaaact aggccgagct ggcaccatct tgaatgacct ggtggacttc  53820
ctggagaggt tcgcggccgg tcgtgataaa gtgctcaata tcgccatttg taattgaggt  53880
tagtgatatg ccagatttga tgaagctgag tcataggcaa gttgaagctc tgctagggct  53940
gtctaggaat tcttacaatt ggattcacgg tccttcgact gattcaacct tgaaggctct  54000
gagacgaatg ggactcgtaa atttgtcctg ggatgattct gtagctggat acatgttcgg  54060
cagtcagcct tgttggagca taactgacgc cgggaaaaaa cgaatcctgg caatgcagga  54120
aactctgaca gaagagcctg aacagcaatt taatcccagc ccatgccgcc atgagccagg  54180
taagtccgat tctgatcgac ttgctaagca actagaaacc atcgctcgtc tggaaaagga  54240
```

-continued

```
acttgaagca tcggaaaagc gcgggagcga actggcagca agctattgcg acggcgtggt  54300
cggtgatgaa tacggccaca cttattgccg ttataaggcg gaacgcgata cagctctggc  54360
cagggtcgct gagctggaag gaaagttgac tgattgggta cacgaaggat tccggctcaa  54420
cgaagcactg gcagcggcac agaccgccca cgaatgtacc atgggcgtag gcgacggcga  54480
cggcaagttg ctagttcatg gtgaccacgc cagcatcaaa gctgcccaga agatcgtcat  54540
agagcgcgac gccgcgttgg tcaggatagc ggagcttgaa tctaagcttg cggagacgca  54600
accctacaaa caacacccgc aaatcatagg gtacgcccgc aaaaaggaac ttgcgccatt  54660
gctcgatcca agccaacccg gtggaagcta catctatatt ggactggacc atccggcctg  54720
ctgggcggaa gagccacctt acgaattctt gacccctttg tataccggtc ctgtggcgag  54780
tcacagcgtg ccggatggtt acgccctaat tccggttaag gagactgagg cgatgcacga  54840
tgccgtaatg gcgctgttgt acaacggcat agcccgcacc gatacacaaa agctgctgga  54900
tgcgtacatc aacgccgcga ctaacaagga gtccgtgtaa tggaaccgaa gaaaccttca  54960
ccagtagatg gagtcatcat gaccagcctc gacgttctca ggaaggcaaa gcctgaagcg  55020
caggacgagt atgctctgtc catgttcgca acggcgatcc gccagaagtt gcagcgctcc  55080
cgcgacaagg gccgaggcgg atggatcgat tgcgacgaaa atgttctgct ggatggattc  55140
gccgaacatg cgctgaaggg caatgagaac aatctcctgg acctggcgac gttcctgatg  55200
ttcatgtggg ttcgcggcat cgatgatgcg aagattcccc cggcgctaga aaaggcgcgg  55260
cagcacaagg tcactgaagc ttgggaccag atcaacgaag gaaggacaag ctatgccggt  55320
aaggccggcg gcaagcgaca attcgtggaa gtgcctcgac gcaaagggcg cccggagcgg  55380
ctcgcatgaa gcctcacgaa ataagattgg cccaggccga agaattcctg agagaactcg  55440
gccgagggat tccggaagac gaacgggtga tggtcggcta cgctgaagag gccacagtcc  55500
agaccgacga aaacggccgc aagctcaacg caggctggtg gcccgtgccc tggaaggaag  55560
gcaagtacat caattccaga tccaacgctt atgcctgtat atcgtcatcc atcaagacgc  55620
ccaacccgaa gactggccag atgcgatact ggcgcggcga ggcctctttc ggccacggac  55680
tggcgttaat ggtcgatgac atcggctccg gcaaagggtc caagggcgac ttcaaccgcg  55740
acgagttccg cgagcgcctg gagccgaccg cgattgtgga gacttcgccg aacaactacc  55800
agttctggta tttcttcaaa gagccgatgt cccacatgct ccagtttaag gcattgctct  55860
attcgttcgt ggaccaggtg ctaaagaaag gcggcgacaa caccgtcaaa gacgtaagcc  55920
gttatggtcg catgccattc ggcttcaaca ataagcgcgg ggaagacggc aacttcaagt  55980
atgccgacga aaacggcaag cccgaactcg tgcgtttgta tcacgcagac tattccaagc  56040
gctactcgcc agaggaaatc gcccaggcct tcggcgtccg catcatcatg ccacagatga  56100
agaaggtgga gataaaccgc gacgattggg tttatgacca ggtgtggcta aagtatgccg  56160
agcacatctg cacgaaatac aaaatgggcg aggcagcggg cggccaagtc caacagaata  56220
tgtccggtaa atatcgcatc cgctgcccat ggggagacga gcatacaaat ggcgatccat  56280
ttggcgccta ctttcgcgga ccgatccctg gagccgagca cgaatatgtg ttcggttgcg  56340
gccacgatac ctgccgcaaa gagcatcgcc ggacgtgggc ggccttcacg gatgaagtcg  56400
tgctacccta tatcgtcgaa caattggaaa gaatcaaccg ccgtcacatc ggtgaggagt  56460
agacaatatg caaaacgatc ctggaatcct gatcacagcc attggcttgc tgttcctcgg  56520
ccttatcatc ttcttcgaag gcctaaaggg atggaaaata caagtcgcaa acttcctcgc  56580
```

-continued

```
gtcgcttctg tgcttcttct tcggcctttc tgctttgacg ttctggttcg tcgtggcgtt  56640
tgacgtattt taatcgacga acggtacaga aattttcgga tggggacgga acttattagc  56700
tatgccggtt taggtaggag ataatagccg tccctttcgc ctcaatatgt agaggcaatg  56760
ttgaatccga tcatgtaaag cagaaggcgg caaacctaac atgattatcg acgaagataa  56820
tatttttgat gatgacgaat cagggtccag tgagttcgat ctcacacaga tagaagatgc  56880
tggaatggac cctttgatga ccgccgcgag caaggcggcc gatgatgcga ttgcgaggaa  56940
cgaaacgcac cgcgcacaaa aggcggcaag atacgccgag gcgtatgcgg aaccagactt  57000
gagaaagcga gcgcgattgt tgatgctcga ccaggcgttc gatcttccgg tcagccgggt  57060
ggtgaaaggg ccgttcgatg acttcatcac taaatacagc tcgacttccg acagcaacta  57120
tctcgcggtg tacgatactt tgttctgcaa gggtgatgga accgtcccgc atccgcactt  57180
cgacgagttt cgcggacggc tggtggacca tcgcggcgtg gcgttcaaca acaagaccct  57240
cgacccgatt gacctgatgg gcgccctcgc ggctgcggcc ttggacgatc cctcgattaa  57300
gaagacgatt gagacttgct gcgtttgggc gcgtcgatac cgccgcaact cgctgataga  57360
gacgttcgag aagaagatac cggagtggga cggcgaagag cgaattagca cgttgctgat  57420
cgatcttttt aagccattcg acaccgaatt gaaccggatg gtgagcaagt atttctggct  57480
gagcctgtac tgccgcatca actatcctgg aatctcggcg ccgatctcgc tggcgttgat  57540
tggtgggcag gatgcgggga aatcctattt cggcctgctg atctgcaagg aactgtcggg  57600
cggtcgcgat ctggctcccg tccagctcga cctgagccga cacgaccaga caccattcct  57660
gcgcaacatc accggcaact cggtcattgc gaacgtcggg gaaatgtccg gcttcaaaaa  57720
gggcgacatg gaacgcatca aggagttctt ggtgcggtct tctgatacat tcgaccagaa  57780
gtttgagccg ggcgaaacga tcaagcgaca atggatcacc atcatggacg gcaacggcta  57840
cgatggactc cagcgggacg actctggtaa ccgacgtttc tatcctatgt ttgttgcgca  57900
actgcccgat gaggatggaa agccgaactg ggttaagccg ggcgatggca atgaaccgtt  57960
caaggtggac ttcaccgact tcggccgcaa attctggcaa gcgatggctg aatgccgcgc  58020
atggatcgaa gagcacggcg tcgatggcta cctgaatatg gtgtcggaag caaaccgcga  58080
agtccagaac ttctctattt cggaaatgga gaatgcgcgc ggcgtggttc gcgacgatac  58140
gattgatatg tatctgatca atgtcctgat cagttgtgag ttcgaagagg ttaagcctgg  58200
tgggaattcc aagactcctg ggtggagggc agacaccgtt tccattctga agtggttcga  58260
tattctcgcc aggaagaagc cgatttctcg ccatttaact ccacacctga aagcgctggg  58320
attcattccg aataagaacg gcctgaatgg atggtgcctg cctgtggata aggtcgcgcc  58380
tgactggtcg aagaatatgc agacgacgct gccgccattc aatgatgcgc tggtgtatct  58440
gttgagaaag ggcgatccgg atatgaccga tgaggctgcc atggcaaaaa ttcgagcagt  58500
acgggcagag cgagccaaga tattgggcga ggatttctga taggtcgatt gagttggagt  58560
ggattaggcc gccttcgggc ggtcttttct ttgtcgcgga gaacattaat ttagcttgtg  58620
aacgggtgag gcttgaaagc tatgtgggaa ttaggttggc gtggcgatgg cgtattatgg  58680
gaagttaata gatttcggta ttggtctgga gtgtatgatg gttggatttt gcgtgaaatg  58740
ttgagaaatt gtgggtttga ggtggatttt tgtgtggaaa tagccgcaaa ttcctggatt  58800
gctattctga ctgggaagat gggaggccta ctgccgcgcg ggtttgcggc catattccct  58860
aattcccggg tttttcgagc atggtttaaa actattctac agcgaaaatc gattgcacaa  58920
tcctaataga aaaaatctat cacggacgtt acctatcttt aaaattaata aaattaatgg  58980
```

-continued

```
taatttggta atttggaata gtttagtctt tgaaagcctc gcggcactaa gccggtacac  59040
tacccgtcga gtttccgatt ccactcaact cgcggcaggg tcgccggaaa cttccgtcct  59100
tccaaaccat gggcagcggc aacaccacgg cggactaagc ggcaggggcc aaaactcgac  59160
gagcggaacc ggaaatttgg tcacagggca gaatcgctca cctggacata ttcctaacat  59220
ccgatttaac attcaatcca aacactcacc gccaccatcg cccgccaccc accaatccga  59280
ccctcacccg ccagcagacc gcccatataa catcctataa caccacctaa cactcattca  59340
ccatcaaacc cacccagacc tacaggccac ccacaagcag cccatagacg cgctccctgg  59400
ccccatagta caatcgcgcc atactcagtg tcgcggcaag caccaggtcc cagccaccta  59460
cccagccacc gcgacggtcc aagaatcgaa ctccagggac gcagcaacaa atgaccgcca  59520
aatattacag ccccgacgat ttagtcacgc cacaggaatt cgctgatccg cagttcgcgg  59580
cgatcaacca gaagcgtttc gatctgtaca tcgacctgcg cgttcaaggc tatagctcct  59640
ggcgggtctt cagagcgatc tggggcgaag agcacatgga tggcccggcc caggcccgca  59700
tcttcgcgat ggagtccaac ccgtactatc gcaagcaatt caaagccaag ctgaatgcga  59760
ccagaacgtc cgatctatgg aatccaaaga cggcgcttca cgaacttctc cagatggttc  59820
gtgatcccac cgtcaaggac tccagccgtc tgtcggccat caaggaattg aacgttctgg  59880
ccgaaatcac gttcgttgac gagtctggta agaccagggt aggtcgcgga ttggccgact  59940
tctacgcatc agaagccgag gctcagaccg ccaccgtcgc tgctgcggcc gaagccaatg  60000
gctatgtgca ggacggcgaa gagggcgatt tcccgtcccc gacgccggag ccgaccgagg  60060
aagaccgcgc caaccccatt cagacataaa ataacatcgt tctaggcccg aatcggaccg  60120
aactaaggcg acggtagcgg gttgggacga aaaacgattc tagggctgtt ctaggaagcc  60180
gaccaataac aatcagaaac gacaaagccc cggactctag ttcagaatcc ggggctttct  60240
ttttgggttt cttattctcc agcttcgatg atttcgaagt tgtatttgac gccttcgtgc  60300
tcgaaagtca acttgccggc ttccttcagc tgcatgcgga agcggatgtg cttcgaagag  60360
ggcaggccga actcgatgaa tgctgcgttg gtggaccgga actcaccgcg cttgcctttg  60420
acggtaacgg caactccatg acgctgagtg cgctttctgg agacttccgg gtctttccag  60480
gagttggcga tggctgccga caggtctttg gcctctttgg ccttctctgg agcgttcttc  60540
gcctcttcgc gcatcttcct gatttcttcc agcgcttcct cttcggtgat ttcctcttcc  60600
ggcttcaggc tctcttcctc ggccttctct tcttccttct tcttggaagt gcgggttttg  60660
taaaccttgg ccggggcttc ctcttcctgg aaggcttctt cctcggccgg cagagcgttc  60720
aggatggcga ggcagcgacg ctcggcggtc ttgcggtcgg agaagcgctt tacagtcgca  60780
tcggcgttgt gagagttgta gaaggcgacc agttctttca tttctgcgtt ctggatgtcg  60840
ccgaaggttt tgatggagtt ggtcatttct gcgatcctct gttttggaag atttctttcg  60900
ggcttcggtt tgtcgccccg ttgaaagaga ttatgcctag atcgatgctg cgtgtctaca  60960
tttattttag cagaatgatg atgaacccga cgaacggttg tcggatgtga aaacaccgca  61020
ggacaggctg cggtgttttc tggacgatgg tgcgacggtc agaaagtcgg gaccgtgatc  61080
ggctcgattg gtaggtcgcc gggcttgtcg ttgtccgacg cgggtgacga acttgacggt  61140
atggctccgg accgaagacc cagcggttca ggccgcctgc ttacctgcgg aggtggcgga  61200
gcttttggcg ctttcggaac tggaggtact ggaggcgccg gcggagacat cggccccttct  61260
ggaagatcgg gaaggctcgg cgctttcggt tcgtggtaaa ccgtcgtgtc gttgcctggt  61320
```

-continued

```
tctgcgggat cgacgcccat gaatggagtg gtgacgcagc gcatgttcgg atagttcggc  61380
agcgttttca aagcgatgga gtctgcccag acatacggat tcttgtgatt accagggccg  61440
tggctgatga tctcggcagg catgtggccg ttgaggttca gccactccgc cgccccttgc  61500
cgagacagcg ggcttaccac gatctggcca gtggcctctt cggcaacagc gaacagatcg  61560
ccgagtttga atccgatgat caaatagttg gacctggcct cgccgacgaa tgcgacagtt  61620
tcagtgccgt gatggatatc ttgatcttcc catatgtata gcatgatgcg ccctcagtaa  61680
ggttgcttga tgtgatcgac cagggacatt ccggccggaa ttttgaagcg tatgtactcg  61740
atcataatcg cagttcggcg acgattcgtt cctgcctcgt cattcacgaa gagttcgcac  61800
tggttcggaa tgactcgcgt caccagagct tcgcctttcg agccgtagaa cttgatgtag  61860
gctgcgacgc ctcgcgtcat gttcagttgg atcgtttcgc agagtcgctg cgcggccgac  61920
gcgctggaca gatctgtcgg actgaccgtc acccagtaat gagcatttgc tgtttgttct  61980
ttgtcagaca tcaatggtct ccagtgagaa agccctgccg agtcgcagag gctggttgct  62040
gttagtcgcg cttcaacaga acgactttgt catatgcgcg atatttaccg cgccagtctt  62100
cccagtagtc gccggccggg caggtgagct ccagggtgat ttcgtcgcgc cagcattcga  62160
cagaaagtac aatagccttg ttccttgctg cggcatctgc tctgagctta atcagaattt  62220
cgtcgccagt tttcagctca tcaactctca caactttggc catgacacac tcctgtttga  62280
agaggcgcga ccggaaccaa cccagccgcg ccgatggatt aacgtttgtg aaggatggac  62340
acggcgtcca cgtcgaggat gctgatggta cggcgacggc gcggattgct gcgttcatgg  62400
atgcgaatca ggtcagcaga tgtagcttcg tgcaccaccc atacatcttc tggcttctgc  62460
gtccggagca ggatcgttac ctctgtgttc tgggcgaggc cgttgcagat gaacgtgaac  62520
ttggacgagg gagttctgta catttctaga ttcctttttg gactttgggt ccgacttctc  62580
agccggtgaa gagattatgc ccttattttg gccgccgagt aaagcatttg tgtatcaatt  62640
ctcccgtcag gtggaaccaa agtgcggtat cgcttatggc tacgctaccg cgccatggcc  62700
cttcttgctc gcacactgcg aaccacaggc tgatttccat ccttgccagg actcggccga  62760
aagattcgaa cctgcgccga ctggacagga tgtcgacatt cactcgtcga ttgacctcgt  62820
accggcgacc gttgatgacg aagaccagcc gcagggtttg tccgtcaaga cactcccagt  62880
atctggtttc atatcggagc caatagcgct tgcctgtcgg ccctaccata gtcatccttc  62940
tatgctcctg gccgctccac ggggaccggg cggtggagtc ggatcgaatc gacccaggat  63000
gtaatcgggc cgacgcgctt cctgcggaca aacggcgaga aggcgccatc ctgcgtccag  63060
ggcatgctgg agttcgtccg tgcagcagtc ttccttgagc aggagacggt tgacgctctg  63120
gagattcgga ccagggatgg ccgagctggt gtgcgagttc caaccttcga tgccgtccac  63180
catctgtggt tggttgatgt agccttcgga cctgccagcc aaccggctcg cggccagctc  63240
caggcgctcc agcattggcc gcagagcggc ttccgggtca acatcgtccc agagaaggac  63300
caagctgatg atggtgtacg gatagtcctt gtccagatcc caggccgaag cggtcagacg  63360
gcccaggccg atttcattac acatcacggg aacgtcgttg ctccatgtgg acggctccca  63420
gttccgctca ccaggattcc cgattgttac gccttccagg ttccccagga ggacgtggag  63480
tttgctgatg tattccgcct ccagcgcttt ccgctcttcg tcggtctggt tgtggcgata  63540
gaaggatgga gggctgactt ttgcatggta gagtttcatg gcggttcctc ggtttttgaa  63600
ggcttgaacg ttagaaaatg gtgtcgcagt atttctcgaa aggactctgg cgcttcttct  63660
cgcagatcgc gcaggtgact tccaggtcgg gcagctcgct gtaagtcttg ccgagataca  63720
```

-continued

```
gccagcgctt gcacagactg cggccgtccg acgtgaagaa gtggactttg cgagcattgc  63780

cgggttgcgc ccagccgcct tgatcgtttt tgcgcttgct catggcgata tttcctttgg  63840

atctggaatc catgccgtcc gttcgctcac ccaaactccg tctacataga tcaggactga  63900

cagagcagtc gcgccaaacc cgaagcctac atagaatgaa ccgggatcga tttccatggt  63960

ggcgctattg gtggcgctat tgaaatcgac ttcaaagtcg aacatcgaat ggccgctcat  64020

accatcacca tgtcgatttc attgatgaag aaatgaacat cgacaccatc ggcgcgaccg  64080

gtgtaacgca gccgagtcgt cccatcaatg tgggcttcct cgacgccgat gacttccagg  64140

atggtgtcgt tgcagtaaag cttgacgaac atcttgatgc cggagccaat cgccgcgaag  64200

gcgatctgct tgtacaggtc ttgcttgatc atgctttgcg ctcctgtttg ctggtgtaga  64260

tggcttcgac ttcggcctca agcttcgccc aaagttcgtt gtccaccgga ccccatggtc  64320

cggtctgggt gccgtcaacc ggcgcgaact tcccaccggc gcgacgatat ttggaacggg  64380

tctggagttc gatgattagc cgttcgtagg cgttgaattg agatgtcatt tcacaatcct  64440

cttttggacg ttcgcgtttc gatgaggtga ctatatctaa gtcgcctcat cgagtaaagc  64500

acttctgcga aattatttga tattctgtaa ggtcaggaag ccggacgatt tggtcagtcg  64560

atggagccga ggctccaccc gttgcgggcg aaggccgagc gacccgacag cttgcggcac  64620

tgaatggagc ttccatcgtc gaaagtatag gctgtggccc agtcaaggcg ctcacgacgt  64680

actgccgcat tggcgatgtc ttccagacgg gctttaagga gttgctcggc tttagtcatc  64740

tcacacctct ttggtttatt cactcgatga ggtgactata cctcagacac ctcatcgagt  64800

aaagcacttt tgagagaatt atctgaaatt tctggaagcc aggaactgtc gccagagcca  64860

gtcaatgtga tcgttcagat agcgctcgcc atcggatgac agagacaggc agccgtcatt  64920

gatgccgagt ttggaactgg caatccgttc gaattcgaac tggagcgttc cgggccgagg  64980

gatatggtgc aggcaatatt tctgcacgat cagcagtcct cgaaaggttt gcggttcgca  65040

atttccgcga tcctttgcat gccgatgcga tagaactcgg catcctcgcg cgcccgcgac  65100

aatgcttcgc gcgcttcgca agccaacttg tattgattgt tggcattggc gatgcttccg  65160

tccaggcttc tgtcagactc ttcccggagc gccttttggg actccagctc ggcctccagc  65220

tcgcggattc gaagggcgag ctggctattc gtttcggcag ctttgttttc cagatcgatg  65280

gccgatttcg ctgctgtttc gagcctgtct ttgtcggcca tgagggtttc caggctcttg  65340

tcgagtgctt ccagaagagt cttcttggac tccagctcca gcgaaaattc gacgttctgc  65400

gcggacaagt tctgcgagtg cttcagcagt tcgtcgattc ttctttgatg gcccttgatg  65460

gccgagttct tcgtttcgac ttcggcctcc aaatctctga ttctgagttg aagctggcga  65520

ttcacctcgg ccgtcttgtc ttcgcgagcg atggagtttt gcaggcattc gtccagacgc  65580

gagttctccc gatcaagctc catggccgtc aggctttcgt cagaagtcac gccttcggat  65640

tcgtctttcc gtccctgatc ggcccgcaga taatactgtc cagcggcgaa cgccaggagg  65700

gcgcggttgg aaaactcagt agcgccctgc aagtaagaag atttgtatcg aggaacgaac  65760

tcgg                                                                65764
```

```
<210> SEQ ID NO 2
<211> LENGTH: 578
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 2
cggactaaag gcggcatgat tgcctaaaag gagattcaac atggtcttca cactcgaaga 60
tttcgttggg gactggcgac agacagccgg ctacaacctg gaccaagtcc ttgaacaggg 120
aggtgtgtcc agtttgtttc agaatctcgg ggtgtccgta actccgatcc aaaggattgt 180
cctgagcggt gaaaatgggc tgaagatcga catccatgtc atcatcccgt atgaaggtct 240
gagcggcgac caaatgggcc agatcgaaaa aatttttaag gtggtgtacc ctgtggatga 300
tcatcacttt aaggtgatcc tgcactatgg cacactggta atcgacgggg ttacgccgaa 360
catgatcgac tatttcggac ggccgtatga aggcatcgcc gtgttcgacg gcaaaaagat 420
cactgtaaca gggaccctgt ggaacggcaa caaaattatc gacgagcgcc tgatcaaccc 480
cgacggctcc ctgctgttcc gagtaaccat caacggagtg accggctggc ggctgtgcga 540
acgcattctg gcgtaataag gagaatttca tggctagt 578

<210> SEQ ID NO 3
<211> LENGTH: 66293
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
ccttctcttc gtcccagcag aggctatctg ctatcggcca gaactttcga aactgggagg 60
tgctgacgct tacatccact aggacgattt ctgcttcacc cacgacttcg agcttgaact 120
tgacgtcacc gtcgatgctg ttgaaaggga ttggcttgga cacgacaatt ctcctgtgaa 180
tggcgcgacc aaccggccgc gcctgatgat tactcttcgc cttcgtccgc gctcagccac 240
tcttcgaagg cgaaattgac cttagactcg acccaatctt gaagctcatc ggcgaactcg 300
tcactgtcga tgtccatcgg aatgcccaga gtctcttcgt tccacagttc ggcattcagt 360
tcgaactgga tagccggttc gccatccaca ttcagcagga tgcggtctgc gacttcatag 420
tcgtcgacat cgaagaggaa accgccgctg atgatgtgct ggatgaaagc ttcgtcgaag 480
ttgctgacgc cgatattgat ctgcttagtc atttttctgg ccccttattt ggcgagtttg 540
tactgagctt tgagggtggt cagcttagct ttcagggcga tcatagcctg gccgcgcagg 600
ccttccattt ctgcctcgct gatggcgatc ttggcggagc ggatttgatc gttgatctgg 660
gatttggtca tttctgcgtt cctctgtttt ggagtgtttc gcgtttcgat gaagagatta 720
tgacgctatt cagaatggaa gtaaagcaga attgtgaaat atttctcaaa gtggacgagc 780
ggtctgttcg tcaggaatat ttcctcccat ggaaggcgtg tccgcatccg aagactgaca 840
ggtatccgtt gacttcggat tgtctctttt cggagtcgat ttcgattctt agcatttcca 900
gctcataccg ggccaggccg ccccactccc tttcgatgcg ttcatactcg gcttctaatc 960
ggcgcagacg ttcaatcatg ggaatctcct ttggattgtt atagctagca tcattacgga 1020
caaacagtct ttcgtttcgc tgaagagatt atgccgttgg tcagaatgga agtaaagtgt 1080
attaacaata aaattatgtt caccgacgaa cggttgtgct cgaccgtctg ttgcggcgtc 1140
gatatactcg acctattgct gacaccggat tgattagaat gtacaaactc aaccctgcac 1200
tgcgagcggt ctggcgaact cgcgcccgtt acaaagtcat ttatggcggc cgggcgtctt 1260
cgaagtcaca cgacgcaggc ggtatcgccg tttacctcgc ggccaactat agactcaagt 1320
tcctctgtgc tcgccagttt cagaaccgca tcagcgaatc ggtctacacg ttgatcaagg 1380

```
acaagattga gaattctgag tacaacggcg agttcatttt cacgaagaac tcgatcaagc   1440
acaagaggac aggatcagaa ttcttattct atgggatcgc ccgtaacctg tcggaaatca   1500
agtccaccga aggcattgac attctctggc ttgaggaagc tcactacctt acccaggaac   1560
agtgggaagt cattgagccg accattcgga aagagaactc agaaatctgg atcatcttca   1620
acccgaacga agtaacagac ttcgtgtatc agaacttcgt ggtgaagcca cccaaagacg   1680
ccttcgtcaa gatgatcaac tggaacgaaa atccgtttct cagtgagacg atgctcaagg   1740
tcatccacga agcttatgag cgcgacaagg accaggccga gcacatatat ggagggattc   1800
cgaagacggg cggcgacaaa tccgtcatca acctcaagtt catccttgct gccattgatg   1860
cccacaaaaa actcggctgg gagccggccg ggtcgaagcg catcggcttc gacgttgcgg   1920
atgacggcga ggatgcgaac gccacgactc tcatgcacgg caacgtcatc atggaagtgg   1980
acgaatggga tggtctggaa gatgagttgc tcaagtcgtc cagtcgcgtt tacaatctgg   2040
caaagatgaa aggcgcctcg gtcacttatg actccatcgg cgtcggcgct cacgtcgggt   2100
ctaagttcgc cgaattgaat gactccagcc cagacttcaa actgacctat gatccattca   2160
acgcgggcgg cgctgtagat aagcctgatg atatttacat gaagctgccg cacactacga   2220
tcaagaacaa agatcacttt agcaacatca aggcgcaaaa gtgggaagaa gtcgcgacaa   2280
gattccggaa gacttacgag gcggttgtcc atggaaaggt ttatccattc gacgaattga   2340
tttcgatcaa ctctgaaaca attcacccgg acaaactaaa tcagctatgt atcgagcttt   2400
cctcgccgcg caaagacttg gatatgaacg gccgattcaa agtcgagtcc aagaaggata   2460
tgcgcgagaa gcgtaagatc aagtcgccga acatcgctga ttcggtgatc atgtcggcca   2520
ttctgccgat caggaagccc aaaggtttct tcgacttcta aacacagaaa agcccggagc   2580
gatccgggct tctggtctta ctcggtgcgg ttcctggcgc tgagtgtcga cgcaacggcc   2640
tcgccgactt ccagagcttt ctggcctgct gcgagcgctt cggtttccga ctcgacgatg   2700
aagtcatcgc cttgtccgtc gccgggcggc acctcgacca gcacggcttc ttcgccctcg   2760
aaacgcaggt cataagtctt ctcgacggac aggccgtaac gggcgttgag cgcatcccat   2820
agctgagctt cataggttcg aaggtcttgc agagatttct ggtgactgag catcgccatg   2880
tcgacggccc gttgcagggt ttcgtccagg acgttgagtc gcatgcgaag agaacgaatc   2940
cgctcgacga cttccgcatc cacaatgtgt ctttcgatca tcgcttttca cctttgctga   3000
atgttacgtt atagccgtta tcggccaaat aggtcagggc accttcgaat gaagttccga   3060
cgaggtgcct gagctgcatt tcgcgttgcg cagcgatcca aaatgcagtt ccggagaact   3120
ctgcgcggcc ttccgacaga acctttccgt caggtccgtc gattcgaacg tgaacggaag   3180
atagcttcag agtcattagt gaatccctcc actggcttgc gacggcattc tttctgcgcg   3240
agcggatgcg cagtccgggc acgggcaggc ctggcggacg cgctccaact cgtcggcgtc   3300
catgacatag agcttcccat cggaagtgtc gtgcgccatg gcgatgttcg ggaagtcggt   3360
ggcactcagg ccggcgacag cgcggatttc gccccagagc gcttcattct cggcattcag   3420
acgagcggcg agcgcttcgt gctctttcgc tacacgcgcc atgaactcgt ccatccggaa   3480
tgcgaattcc gcatcgatgg cgcgggccga ggccatagag ctgaggtgaa tcggttcttt   3540
cttcatggta attctctttt ggctgggggt ttgtggtcta cccaggccta ttcaaagcct   3600
ggtcgtcttg atgaagatga acaagaagac tgcaaacgcc aatagcgttc cagccaacat   3660
aaatactgca aatgccaata gcgttcctga gagcatgctc gcttgattct gcagctcagc   3720
```

```
gtactccttg gttgacagcc cttgctgcgc cgcctcggcc gcgaagcggg ttttcgcctc   3780
gataacttcc gggcgcagcg acaggacata ttctaaggcc tcttcccgcg ctttttcggc   3840
ctcgaccaac ctagggtcgc gggccgagac ttcgctgtgc cctggcctcg cgggatgggc   3900
ctgcagcgat ggaggaagtt cggcggccac gactccatag tcggagcagg cccaagcgat   3960
cccgatgagg atcgcgagga tggactggac gattcgcagc atcactttgt cgctaggaag   4020
actcatggtt aatcctccac cgaccgaacg atttccatat tgcgtccggc attggttccg   4080
gcagcgtagg cgcgccgacc gtcactgtct tccagacgca tgagtttggt aacattagac   4140
ttcttgtaac ccggatcgcc gaaatgttcg tggaccgcag cttccttaac caccaccaga   4200
gacgttccgg ccgaagaaac cagctccata cgtttccggg tgatggatct gaggcgatag   4260
ctgatttcct gggtcgcggc gagcttaaat tgcgcggcga ccttgacgtt gaaccgctcg   4320
aaaccttgag ccttctgata ttcccggcac agacggtcta ctgcctcgac cagggagttg   4380
aacatgttca ccgctagctc aacgtcagat ttgtagcctt taaagcggac ggcatggccc   4440
cagcgcttgg tggtgctgcc gtcgcgagcg ctcctggacg ccttcgccga tgctcggtga   4500
ttgttgatgc caccgacgaa atccatgatg caatcattgt acgtcgccac tgccacagag   4560
aagaacttca tccagttcgg gattgcggaa tagtagcgag tagcaatttg ctcgtcgaat   4620
tcttcgcgaa tctcgccggt cacttcgaag tcgtgaaggt catatttatc cttcagcttc   4680
ttcacgcgtt ctgccgcgat ggcagcttcg tgcggactgg aagagtcggc cgccatcgca   4740
gtcagcttgc gaatgcgatc tttcgccttc tcgatggctt caggagtgaa ttcgttctgg   4800
tcggtcatgg tcggttcctt ttgtctgaag gtttcgcgtt tcgatggagc tattctgcct   4860
tcatccagaa tggaagtaaa gcattttctt ccactatttc ggaagagcct ggaaatagct   4920
ccagatccaa tcgcctgcgg ccaggacaac gatgagaact gcgaagaaca cgactgcaga   4980
gaccaattgc gcgccaggct tcagcttggg atgactgagt ttgtgctcta ccggattcgc   5040
cggggcgctg gcgctgggcc cggcgtcttc tggaccaaag ccggcgccgc gctcgcgtgc   5100
ctggatagac gctatggatt tcaaatactc ggtctgcttt tgcgactctt cgtagatgcc   5160
ggcgacggcg aaccagagtg cgaacactac ggccgtgcag acgacccagg ctccggtcag   5220
aaggatggcc agcggaccga tgaggaagac ggaagccgcc aggatgatgg cgccgcccca   5280
gatgatgaag ccggccagac cattggtgat gtcgatacag aatttcttca ttttttggt    5340
tccttcggtc aagggatgga tgggatttgg aattcggcgc cgccgaggac atcaatgacg   5400
acctcccaga gcgtcggaac cgaccactga taacggtcga agtcggtttc aggatcgact   5460
cccagggtta cataggaagt ggccggccat ttgtgaacgg cgccttttcg catgagagcg   5520
gccacgcgac cgtcaccgag cggattcgtc ctgtgaggaa cataagccga catcgaatat   5580
tgctgtccag caccaatgat gaattcttgc ctctggcgca gacatacaga gcctacaggc   5640
tcccaaccgc gaccgccgca ggcctggcga gccgaagaat gctcataccc ttcatgagtc   5700
aattcaccga gacgcgccga acggtccacg taataatttg tattctccag agacccaacc   5760
agaaccaagg actcgaaatc gaatcgatga tcgtggatgg aagagtgatg gaaacaaagc   5820
cggcgcggca gctccggatg ccacacatgg aggcgcccgg ccgggagctg gacctggatg   5880
aagcccaggc cgtgcagcgt gattctgtcc ttcatcggat cagggacggt gtccatggat   5940
aatcctcagt agcagaagtg gatggtaaag gttacgatgg ccaagccggt cgcccatagg   6000
agggcgaacc aggccatggc tttgattgta aggtggatca tccgaagaac tttccggcgc   6060
agatggggcc gatgcccatt tcgatggatg cgtgattggt caactcgcga ccgcagcagg   6120
```

agcattgacc agtcttccga ccgtaggcga ctgccgattc cattggcttt tcgaacatct 6180
tcaggatatc gccatactct gtgtcggtgc agtcgcggct cttgatgaat ttgccgttag 6240
tgatccggcc gaggtagatg tcgcccagga catacagact cccggcgttc cggctgttag 6300
cgctagcctc tttgaccaca acgatgagag gctcctcacc ttcgccagcc agacgcattt 6360
tcgggcgctt gatgccagag tctttcgcct tctcaaacgc cttctcgatt ccggaaatgt 6420
ccagagtcgg cgcagcagcc tcctgcgcgg ccactttctc gcgatgtttg gcgaggtttt 6480
cgatagctcg tttcgcagca gcgatctgat tttcggtcaa ggagccatat ctgtaaagag 6540
aatccttaag gctctgggca aaactgaaag agttgtcggt ccaccactcg atgatgtccg 6600
ggtgagcggc ttcgaaagcc tgaattttaa ggccgcgata ttgctcggcc ttctggactt 6660
tctcgatgcg cttttctgca gccttagcac gactcttggc gcgttgctcc gggctgctct 6720
tgtactcttt atatccaacg ccgccgcagg caaagcaggc gcgaccataa gacgaaggac 6780
cacggtacag gccagtgcct gcgcatttgg ggcacttttc gcgatacagc ttcggttcct 6840
tccaggagtt cgggcgggca cccatggaca cctcttccag ggtcttcggc gcttcgttgt 6900
tgacctctac ggtagcgaag tcatcgccca ggtcttcgaa gccgttgaac agattctctg 6960
ctgcgttcat atcgattctc ctgtttggaa agttcgtttc gatgggttga ctatactcca 7020
taaatggaaa cgcggtagca cttcacgcta ccgttcgtcg ggttgctgac gatcaataaa 7080
tgtcgctgct gatcttaaac ccatgctcag cgccgtcgtt gtagtcatac tcagcatagc 7140
tgtcgcagta gtcattcaga tgctggatga ttccaagaac gtcgttagcg accctgtgac 7200
gcttcgccgc gatggtcttg gcaatgctgt cgccgacttc cagagtttcg gcggtccggc 7260
gatgaatcag caaacggctc caaagataga gtcggacccg gcgaatcatg tcatgatggc 7320
gcctcagtcg gctctgcaac ttttcaattt cgaattcgcg agacttgact actcgtcgaa 7380
gctgctgaac ttccaattcc aaatcggcct tagtagccat attcacctca gaaagggaaa 7440
tcgtctgagg ctccaggaag ctcgacaatt gttgttgagc ctgagcggtc gagtatgcac 7500
ccgaccgatc ctgccctatg gggataatgc ctgcacgaac cgtaacaagt aacttctttg 7560
acgattcgcc atgtcgatcc tccacaccac ctacatgctg gtgggcgctt cgacttcagt 7620
tttcgttcgt ccaggacggc tcgtctgtcg caggaaaggc agcgagcctt aaccgacgta 7680
accatgagtg tagtcgatca tgcgaatgag ttcgtcatcc accgattctc tcgacttcaa 7740
accgttcaac gaatccgact ggccgttgca atttccatta atatccatgg aagacagaaa 7800
gcctgccgac accactgtga tgtcaacttt atcgccagcc ttcttgaagc cttcgcattc 7860
ggcgtcgagg gccaccaacg cactcgcggc catgttgacg tgactgatta agtcggggaa 7920
gattacggga acttcacgag acattccccg gaccgtcatc ttcatcacta catatttcat 7980
actcactatc ctttttgtgt gtgaggaaag aatttgctgt tttccggatg gtggaaacgc 8040
tcggccgcag gcggtctttc ttccggacac tgaatcgtcg aaggcgggaa aaccgcgcta 8100
gagattatcg ccgcgagcag cgcagcggat gtcgacatcc acagggcagt ttccagactg 8160
acccgcactt ccggtcggcg cggcttcatt cgctccaacc ccttcccggc tcataagacg 8220
ggatgctgcc gccgcgaatc caactgtccc acatatggtt cagaccagtg ggcggctggg 8280
gcggcggact gtaaaagccg ggaacttctg tactgctgag gaaataaggc gtgcaaacgg 8340
cccgaacaac cagttgatgt cgctcccaca tcttatcaat cgctcttagc atgacgtctt 8400
cgcactgagc tttgctgtcg aaccgtctgc tggtatgatc cggcatctgg acacagccat 8460

-continued

```
cgccagtaca aaggaaagca gtggcgatcc atactgtgat gcttgccatt tcttcaccct   8520
ctttggtaga tgagcagatt ttattccatc tgctcttcag aagtaaagcg cttttcgtcg   8580
ggataaatgc cgatgatgtc tgcgtcgagc atccaaatgt ccacggacgg atcgtcgcta   8640
ttgatctgat acaggtggta caattctttc tcgtcacgcg ccgattcacc gcgaggttcg   8700
acagccaata tgcggccgtg cccttcgccg tgctcatcgc gatacatgac gtgatctccg   8760
acttcatagc actcttttct gacaaggcgc gagcgcgagc tgttcggcga ttccactacc   8820
caggaatcca caactgcgtc tttcacattg ctgtaccact tcgcagattt gtcgcagtcg   8880
aacacgccca gaacttcgcc gtccttcaac acgatatgta cgataggaag aagaggattc   8940
atgttaatct ccattggttg ataattagag tctaatctgc cgaaaagttc ccgtaaagaa   9000
ttattttctc ataactgatt agttgcgact gttaatgtga tgtatctgtt tgaatctctt   9060
ttgaacgttt gatgtttccc ctataataag tgcacacaac cagcaaccgc atggaattaa   9120
aatgtttaaa ctttcctgga tattcgggcg caaaaaggaa taatgttgcc tgttctgaat   9180
cggcgccgga gaaagtcgca cgaatccctc aacacgatcc gctcgaccct atgattaagc   9240
tggggaagat tcgcggctgg aatgtcgagc cggagaaagc cccggtcatc cgtagcgtga   9300
aggatttcct ggagccgggc ctatccgtcg caatggacag tgcgtatggt gacggaccca   9360
ccccagccgc gaaagctgcc gctggcggcc agaatcccta tgtagttccg accatgctgc   9420
aggactggta taactcccaa ggattcatcg gataccaagc ttgcgccatc atttctcaac   9480
actggttggt cgacaaagct tgctccatgt caggcgaaga cgccgcgcgg aacggatggg   9540
aactcaaatc ggatggccgg aagctgtctg atgaacaaag cgcgctgatc gctcggcgcg   9600
acatggagtt tcgcgtcaaa gacaacctcg tcgaattgaa ccgattcaaa aacgtcttcg   9660
gcgttcgaat cgctctgttc gtcgttgagt ctgacgatcc ggactactat gagaagccat   9720
tcaacccaga cggaatagcg cccggctcgt acaagggaat ttcccagata gatccatatt   9780
gggcaatgcc tcagctgacc gcagagtcca cggcagaccc gtctgccgaa cacttctatg   9840
agcccgattt ttggatcatc agcgggaaga agtatcatcg cagccatctg gtggtcgttc   9900
gtgggccgca gccgccagat atcctgaagc cgacatacat tttcggaggc atcccgctca   9960
cccagcgcat ttacgagcgc gtgtatgctg ccgagcgaac tgcgaacgaa gcgccgttgc  10020
tggcgatgtc gaagcgaacc agcaccattc acgttgacgt ggaaaaggcc atcgcgaatg  10080
aggatgcctt caacgcccgt ctggcgttct ggatcgccaa tcgagacaac catggcgtga  10140
aagttattgg tattgatgaa accatggagc agttcgatac gaacctgtcc gatttcgaca  10200
gcgtcatcat gaaccaatat cagctggttg cggccatcgc caagactcct gcgacgaagc  10260
tactcggcac ttctcccaaa ggattcaacg cgactggtga gcacgagacg atttcttatc  10320
acgaagagtt ggaatcgatt caagagcata tattcgaccc gctgcttgag cgtcattatt  10380
tgctgctggc aaaatcggaa gcaatcgatg tacagctgga aatcgtctgg aaccctgtgg  10440
attccacaac cagccagcaa caagccgagc tgaacaacaa gaaggctgct actgatgaaa  10500
tttatatcaa ttccggcgtc gtgtctccgg atgaagtccg cgagcgcctg cgtgatgatc  10560
cgcgctccgg ctataatcga ctcaccgacg atcaggccga aaccgagccg ggcatgtctc  10620
cggaaaacct ggccgaactc gaaaaggccg gtgcacagtc ggcgaaggcg aaaggcgagg  10680
ccgagcgagc cgaagcccaa gcgggcgccg tagaaggcgc aggcgaccca gttccggccg  10740
ctccacgcgg tactaagccc ctcgcgaaag cggccgagga aggggccggc gaggccgcta  10800
caccgccgtc gcggccgaac cccagggccg agcttcggaa cctgctgtcc gatctactgt  10860
```

-continued

```
cgaaactcga agccctggac gacgcgcagg ctccggacgg cgtggacata gagcaggatg  10920
acgcgccagg tctgaagaga acgtcaaagc cgagcgtatc gggtatggag ccttcggtgt  10980
tttcgtccaa ccgcatcgtc ggccctcgtg atcattctga actccagagg atcaaggtca  11040
atggaattac taccttgatc gaaaatccgc gcggaagtat ccggcaaggg aaggacggga  11100
gctggcgagt ccagatgaag caccactatg gattcatcaa aggtacgaag ggggctgatg  11160
gggatgaggt cgattgcttc gtaggcccga accttggttc gaaacgggtc ttcgtcgtca  11220
accaggtgaa caaagatggg caattcgacg agcacaagtg catgctcggt ttcaacaaca  11280
ttaacgacgc caagtctgga tatctgtctt gcttccgtcc gggctgggat ggactcggct  11340
ccatccatga agttgatctg cccgccttcc gtcgttggct ggcaaatggc gacacgacga  11400
agccatttgg aggcaagtga tggcgttcaa agcctccaag aaacgcgaac gccgggggcc  11460
tcttccagtc ggaagaggca agcccataat tccttctgct ggaatcgaag cctggtatcg  11520
aaagcaaatg aaggatatgg ccagactcat gatcgccgat tatcgaagtg aaatcgagaa  11580
ggccatatcc cagcctgcgg cagaacggtt tttcgcgaaa gacgaatcgg tgaacgtcct  11640
gttcaagatg actctgcgaa gccttcagca gcgatggaat cgcatctttg aaggtttcgc  11700
ggccaagatc gccccggagt tcgtcaatcg ggccgacgaa gccgcgaccg ctgcgactct  11760
acacagcctg tcggtggccg gcgtcgatca gccgcgagct tcatacaatg agagcgtcag  11820
gaacaccctg gaagccgcga ctacttacaa ccataccctc atcaccaaca ttcaagagga  11880
agtccacgag aaaatttaca catctgtaat gttgtctctg acttccccaa acccagagga  11940
acaaggaact tctggaataa caaatgcact tcgagaagtc ggaaagtttt ctgaaaaccg  12000
aatcgaactc atcgcaagag atcaaaccag taaactttac agttcgttga gtgatgagag  12060
aatggcagag aatggagtcg aagagttcga atggatgcac tcttcggcag ggaagacgcc  12120
tcgccatacc cacctggaaa aggacgggaa aagattcaaa ctgaatgacc ctagactttg  12180
ggaaggtcca aaggccgacc aaggaccgcc aggttgggcg attaactgcc ggtgcagaaa  12240
aatcccgatc atttagtcat cgataggagt gcgatatgcc gttagtccat ggaacttcca  12300
atgaagcccg ttctgaaaac atcaagcggg agattgaagc agggaaagac ccgaaacagg  12360
cagtcgccat agcctattcc gtccagcgca gcgagaaaga gaagaaggcg aaagattgtt  12420
cgcatgaact cgtcgctgat cttcgcgccc tggtagactc gctgtcgagg ctcgtgaaat  12480
gaaccgaaag acatgcatac gccgactcgc gaccgatgtg atcaaggcca atattaacgg  12540
cggattcttc agcctgaagt ttgccgcagt tgatctggcc atcatcggcg tctcaatcct  12600
gattgctttc ggcggatgat gccgcgagaa tccggattct gactaaaaat tctggtccgg  12660
atagccgcaa attaccgttt ctgggaaata gcggtaattt ggaaatccta ctgccgcaag  12720
gctttaacag gctaaattcc taatttccga tttcgccgca tgccgcaaaa gtatatagca  12780
tgggaaatta ggaataacgt tctaatagaa ttcatctata agtaacgtta taatataacg  12840
ttaatcgata tgctctatac gcattgaaat tcaattttta atcggtaaat tggtaatttg  12900
gattagttta aagattgaaa gtcttgcggc agtaggccta gacaaatccc gtcaaatttc  12960
cgaaaccaat ttaccagttt tcgcggctga ggaagtccgg taattaggtc acaatacaga  13020
ttctagtgta aattaacagt cgcggctaca tcgaattatt gttccgctta tttaccctta  13080
gatgtcctgc gtatataata cagccatagt ccacgactct tcgaattaac gatggcaaag  13140
tcgaaaagaa aaattgacga aaatggatat atgaccatcg agggctgtcc aatcagctct  13200
```

-continued

```
tatggcattt tccaatattc tgccggtcaa ctcggtcttc cgggcgatcc gatgcggatt  13260
gtcaacgtgt atcgtccgga gtctgccgtt agcgatcctg agtacatcga atctctgaag  13320
aatctcccgc tgatcgacga gcacgaaatg ctgtcgggat tcgacggcga tgacgatggc  13380
gtggctcccg aagacaaagg cgtggaaggc atcatcacag ccaacgccta ctacgaagct  13440
ccatgggctc gcggcgatat ccgcatctat tcccgcaaca tgcagaatca gctggaaagg  13500
ggcaaggaag atctgtccct aggctatagt tgccgctaca ctgagcaacc cggcatctgg  13560
aatggaacgc cttatgaagt cgtccaggac aagatgcgcg gcaaccacat cgccctggta  13620
aaagagggtc gtgtgccggg ggccagagta ttggatggtc tgtgctttga ccatctcagt  13680
tttgatttca gaccatccga tgagggtaat gaaatgggtc tcaagaaagc caagcagaag  13740
actcctgtcc agcgcgcagg acaagctgct gattcggcgg tcgaagagtt gcgcgccctg  13800
tggccgaagc tctctgcatc tgtccagaag ttcctgggcg aagaggcgca ggagccggag  13860
catcaggaag gcgcaaccgc tccggccgaa ccgaccgaca gcgagcacat gaccgagcat  13920
ccgactctgg aaggcgctca ggaagacgac gaagagcacg aagaagcgcc gtccgttgtc  13980
gatccggccg tggtcgccgt cgagccggaa cagcaagaag gtgccgcatc cgaaatgtcc  14040
ggtgaaggcg aagtcgccga actgatctcc caggtcaagg ccattctggc tcgactggaa  14100
ggcacggtag ccgaagaggc ggacgaagaa catggcgaag gtcaagatgt cgtcgagggc  14160
ttggaagaac agagcatcct ctgcggcgcg caaaccgcca gcgacgatgg tggtgagggc  14220
aaggataaca gcgaggaact tcctgaaatg gcacaaaaga acgcgcaaga tgctgcaatt  14280
cgtggtctct atcgcgacat tgctgctaaa gatcgcctct acaagcgtct tagttccgtg  14340
gttggtgcgt tcgaccaccg agctatggac tcggctgaag tcgctgttta cggcgtgaag  14400
aagctggcga tcagctgtga gaagggccag gaagttctgg cgctcgacat gtacctgaaa  14460
ggcgtcgaag ctgctcgtgg cgcggccagc cgtcaatcga aagcccagga ttcggccagt  14520
tctgctccgc agtgcgccga gctggacagt tacctgaagg gggagtaacc catgttccag  14580
aaacaagtct atcgccagta cactcctggt tttcctggtg atctgatcga ggacggcccg  14640
aagcgtgcgc ggccgggtcg gatcatggcg ttggcatcgg tcactccggc cgcgactgcc  14700
accggcccca accgcatcag tcgcgcgttt ggttacgcag gtgatgtcgg ctccctcggt  14760
gaaggccagc cgaagaccgt tgccgcgcgc gcttctgaag tcgtggtcgg cggcgcgacc  14820
ttcttcggca tcctcggtca cccgaagcat tatgctctgt acgggtcggc cggcgattcc  14880
ctggctccca gttatgacct gcccgacggt tccgaaggcg agttcttcga catggccacc  14940
ggcctggtcg tcgaaatctt caacggcgca gaagccgctc tggatttgag ctacggcgat  15000
ccggtggcat atgtaccgaa caacctgcct accgccgaca acgccctggg cctgccggcc  15060
ggcgccctgg tcggtttcaa ggccggcgcc atgccaaccg gcctggttca aatccccaac  15120
gcgcgtatcg tcaatgccat cagcctgcct gcccagtcgg cgggaaatct ggtagctggc  15180
gttaccatcg tccagctcac gcagtaagga ggcgtcatga gccatatcag taagacccat  15240
tcgcgcctcg caggccgtca cgcaaaacca ttcgacctga agaacgtcac ccacgaagcc  15300
gtggccgccc tgagtcgcat cggcctggta ttcgatcacg ccgtcgtcca ggaccagatc  15360
aaggccttgg cgaaggccgg cgcattccgt tccggctcgg ccatggacag caacttcacc  15420
gccccggtga ccacgccgtc catcccgacc cccatccagt tccttcagac ctggttgcct  15480
gggttcgtga aggtcatgac cgccgcgcgg aaaatcgatg agatcatcgg catcgacacc  15540
gttggctcct gggaagacca ggaaatcgtt cagggtatcg ttgagccggc cggcactgcg  15600
```

-continued

```
gtggaatacg gtgaccacac caacatcccg ctgaccagct ggaacgccaa cttcgagcgc  15660
cgcaccatcg ttcgtggtga gctgggtctg ctcgtgggta ctctggaaga gggccgcgct  15720
tcggccattc gcctgaacag cgcagaggcc aagcgtcagc aggcggccat cggtctggaa  15780
atcttccgca acgccatcgg tttttacggc tggcagagcg gcctgggcaa ccgcacctat  15840
ggtttcctga atgaccccaa cctgccgcca ttccagactc cgccgagcca gggctgggcc  15900
actgccgact gggcaggcat catcggcgat atccgtgagg ccgtccgcca gctgcgcatc  15960
cagagccaag accagatcga cccgaaggcc gagaagatca ccatggccct ggccaccagc  16020
aaagtggact acctgtcggt gaccacgcct tacggcattt cggtttctga ctggatcgaa  16080
cagacctatc cgaagatgcg gatcgtgtcg gctccggagc tgtccggcgt ccagatgcag  16140
ggccaaacgc cggaagacgc cctggtcctc ttcgtcgaag aagtggacgc gtccgtcgat  16200
ggcagcaccg atggcggcag cgtgttcagc cagctggttc agagcaagtt catcaccctt  16260
ggcgtcgaaa agcgggcgaa gtcgtatgtg gaggatttct ccaacggcac cgccggtgct  16320
ctttgcaaac gcccttgggc tgtggtgcgc tacctcggca tctaaccgat gctgactcac  16380
caaaggccgg gcttccggcc tttgttcact ctgactctga ctcggttgta ggggccggtt  16440
agggcataat taataggact acgccaatga ctgtttacat cgtttccgca atgactcaat  16500
ccgtgtctta caatgcgtat gacacctctg atccgtccaa tcctcgcctc cagagaaagg  16560
tgctgattcg cggccgcgct ggtatcgcat ccgaaacctc cggcttcggc gacatgattt  16620
ccgacgcatc cgggcgcccg atctggacgc cgcagggcga ttgcacggcg gtgagcgatt  16680
ccgatttcga actgcttcag tccaacaaaa tcttcatgcg acacatggag aagggatatc  16740
tgcgagtcgt gaaaaccgac atcaccaatg accaccagcg gattgcgaaa gagactcgca  16800
ccatggagcg cgatggcttc caacctctgg attctactcg cctgaagcag aagatcaaag  16860
tgactactgc cagcgcttcc caggaacaag agttccgggt ttaaccgagg gtttcggtat  16920
ggtaattttc gacgagcaaa agtttcgaac gctgtttccg gagtttactg atccggcttc  16980
ctatccggat gtgcgcctgc agctgtactt cgacattgcg tgcgaattca tttctgatcg  17040
ggattctcca taccgaattc tcaatggcaa agccttggag gcctgtctgt atctgctgac  17100
ggcccacctc ctttcgctgt cgacgatgca agttcagggc gcggccggtg gcggggtcac  17160
agcaggcggg actcaaggcg gtttcatcac tagcgctacg gtcggcgagg tcagcgttgc  17220
caagctcgcg ccccctgcca agaacggttg gcagtggtgg ctttccggga cgccttacgg  17280
tcaggaactg tgggcgctcc tgagtgtcaa ggcagttggc ggattctaca tcggcggcct  17340
tccagaacgt cgaggattcc gtaaggttgg agggacgttc tggtgatccc tggagcgaat  17400
ctgctgcgta tggcatttag cgtcatagga acgcagttcg ttcagtatcg caaattcgag  17460
cagaggacga agaatagcca ggcgcagtac gtttctgtgt ttggcgagcc attccaattg  17520
gccgcttcca tccaaagggt tcgtcgcgat cagtatgtcc agttcaatct ggagtttcaa  17580
cgaaattacg tcatgatctt tgccaacttt gagatggttg acttggatcg agatttggcc  17640
ggcgaccagt tcatctggac cggaagagtt tttcaactag agtctcaagg ctcttggttt  17700
tatcaggacg gctggggagt ctgcttagcc gtggatatcg gtacagccaa actagctgaa  17760
gacggaaccc tgactttcta ggtggcttat gttcgacggc gaactgatag aaaaattggt  17820
ggtcgagctt acttccgcca tgacgtcagc caaagaaact ttgcagtttc ctgattttga  17880
ggttgtgcag aaagcccagc cgacccaaca gggcacgtca accaagccta ccatcttctt  17940
```

ccagaagcta tttgacatcc ctcgcggctg gccggcaacc gattggtatc tggacaacgt 18000
cgccagaaaa tatgtagaaa ttactcgaca gcatgtcgag acgacttttc agataagttc 18060
ccttcattgg cagaatcctg agatggatca cgtagtcacg gcagccgata tcgccaatta 18120
cgtgagagct tatttccagg ctcggtccac cattcagcga gtcaaggaac tggacttcct 18180
tatccttcgc gtgtctcata tatccaacga ggcattcgaa aatgacaatc atcagttcga 18240
attccaccca agttttgaca tggttgtaac ttacaatcag tatattcgtc tgcacgaaaa 18300
cgcagcatat tcagccgatg gggcgctgat aggcatatga tcctgagacg cgattcagaa 18360
ctgatcgccg cgcacctgca gatgttaaga gccatgcgcg gcaggtccgt ttcggccgga 18420
tggtattcca ccgctcgata tcctgataag gcgggcggat cggtcggaat acaagtcgcg 18480
agaatcgcgc gcctcaatga gtacggcgga actatcgacc atccgggcgg gaccaggtat 18540
attagggacg ccattgttcg gggtcggttt gttggcgttc ggttcgtcag aaacgatttt 18600
ccgggagaaa ccgaggtaac aaaacctcac aggattacaa tcccggctcg accgtttatg 18660
cgatatgctt ggaacttatt ttccgcagat cgcgccgcaa tccagaatcg aatagccatg 18720
aggctggcca gaggacaaat cacgccggat caagcgcttg cccagatcgg cctggcgttg 18780
gaaggataca tagccagaag cataaggacc gggccatggg tggctaactc agcatctacg 18840
gtcaggagaa agggtttcaa cagaccgctg gtcgatacgg ctcacatgct ccagtcgatt 18900
agcagcagag taacataaac caggagatca tccagtgatc agtcagagcc gttatatccg 18960
gatcatttcc ggcgtaggcg caggcgctcc ggtcgcaggc cgaaagctga ttctgcgcgt 19020
catgaccacc aacaacgtca ttccgcctgg aatcgtcatc gagttcgaca atgccaacgc 19080
ggtgatgtct tacttcggcg cccagtctga agaatatcag cgcgctgcgg cctacttcaa 19140
gttcatcagc aagagcgtca attccccgtc cagcatcagc ttcgctcgct gggtcaacac 19200
cgccatcgcg ccgatggtag ttggcgacaa cctgccgaag accatcgccg atttcgccgg 19260
cttttccgca ggcgttctga ccatcatggt cggcgcgtct gagcagaaca tcacggccat 19320
cgatacgtcc gccgcgacct ccatggacaa cgtggcgtcg atcattcaga ccgaaatccg 19380
caagaatacc gatccgcagt tggcccaagc caccgtcacc tggaatccga ataccaacca 19440
gttcaccttg gtcggcgcta ccatcggcac cggcgttctg gccgtggcga aatcggccga 19500
tccgcaggac atgtccaccg ccctcggctg gtccacctcc aacgtcgtga acgtcgccgg 19560
tcaggctgcc gacctcccag acgcggccgt ggccaagagc accaatgtca gcaacaactt 19620
cggctcgttc ctgttcgccg gggcgaccct cgacaacgat cagatcaagg ccgtgtcggc 19680
ctggaacgcg gctcagaaca accagttcat ctatacggtt gcgacctctc tggcgaatct 19740
cggcgctctt ttcgacttgg tgaagggcaa ctccggaacc gcgctgaacg ttctgtctgc 19800
gactgcctcc aacgacttcg ttgagcagtg tcccagcgaa atcctggccg ccaccaacta 19860
tgacgagccg ggcgcttcgc agaactacat gtactatcag ttccctggcc gcaacatcac 19920
cgtgtccgac gataccgttg cgaacaccgt cgacaagagc cggggcaact acatcggcgt 19980
cacccaggcc aacggccaac agctcgcgtt ctaccagcgc ggcattctgt gcggcggtcc 20040
gaccgatgcg gtggacatga acgtctacgc caacgaaatc tggctgaagt ccgccatcgc 20100
ccaggccctt ctggatctgt tcttgaacgt gaacgccgtt ccggccagca tggtcggcga 20160
agcgatgact ctggccgtcc tccagccggt tctggacaag gcgacttcca acggcacttt 20220
cacctatggc aaggacatca gcgccgtcca acagcagtac atcacccaaa tcaccggtga 20280
tcgtcgcgcc tggcgtcaag tccaaacctt gggttattgg atcaacatca ccttctccag 20340

```
ctataccaac agcaacaccg gcttgaccga gtggaaggcc aactacaccc tgatctattc  20400
gaagggcgac gcaatccgct tcgtcgaagg atcggatgta atgatctaac ggtttgcggc  20460
ggactcgacc gccgcaacct tccatgaatg gagtgaggaa taagcaatga tcaacatttc  20520
tgcgttcggc tcgattgccc aattcacggc aagcagaacc ttcccgaacg gattcacggt  20580
gaccgagttc gctgatgatg cggaccccat cgacagcccg ccgttcactg cggctgatac  20640
cggcgtcggc ctcaatggcg atatggtggt ttggaaccgg gccaacatcc tggaagtcgt  20700
cgtcaacgtc atcccgaaca ccgagggtga gcgcaacttg gccgtcctgc tggatgccaa  20760
ccgcaccgga aaagacaagt cgggtgctcg tgatgtcatc ggtctggtcg tggcgatgcc  20820
ggacggtagc aaaatcacct gtaccaacgg cactcccatc gacggcgttc tgatcaatgc  20880
ggtggcgagc gttggccgcc tgaagacgaa gccgtatcga ttccgtttcg agaaagtagt  20940
caaagccggt actagctgat gaagaagatt ccgctgacag cagtcccgaa tcaggcgatc  21000
tcatttaacg ccggcagcag ctattggaag attcgtctgt accagaatct ggatatgatg  21060
aatgccgata tcagccgcga cggcgtgatc gtttgtcatg gggtccgctg cttcggcgga  21120
attccgcttc tccagtatag ccaccagtat cgacccgact atggcaattt cgttttcgac  21180
cgtgacgccg attggacgtt gttcggcgac ggcataaacc tgttctatct ggacggtgtc  21240
gagttcgcag aatatcaggc gctggccacg aggaaagaat gagcacatca acgatcagaa  21300
ccggggtgaa caatgacatc cttttggacg acaatggaaa catggtcatt ctcagggatg  21360
tagaagcgtg cgcccaggac gttcgggcgg cgatgctcat gcgcaccggc gaaaacattt  21420
tcgatgtgga cgccggtgtg ggatattttg aatatatctt ctcgccgcag aagagctatg  21480
atgatgctcg caaatccatc gcggatgcaa ttttgtcatc gccggacgtg accggcatcg  21540
agcaacttga catcgacatc accggtgaag tcttcggcgt cgatgcgaaa gtcatcacca  21600
tccacgggcc tgtaactgca ggagtttgaa atgagtacca tccgcatcca atacgccaac  21660
ggcacccaac tattcttgga cggcaaaaac ccgccgctcc tggacccgct gccttctttc  21720
aacccgtcgg tcgaagacct ggaaggcctg gaccgcgaaa agaacactgg caagggcaac  21780
tcttcgtcgg ccggtattcc cgttcccccg gtgaacgtcg atccgaatgt cgacaacggc  21840
ggtgccatcc cagctccggc atcgaccggc acccctgcgg ccggatcgac cccggaaagc  21900
gcccaggaag cccctgcaga gggccaaggc gacgagaaag ggtccgagac gcccccgact  21960
actaccaagg aagaaaagac cgaggtagag gcctctgcag ccgctaaaga ggccaccgcc  22020
actaccaagc ccacggctcg caaaaccacc agcaagtaag gactcgacat gatcaacgtc  22080
agcggcttcg gcacgggaat tgtgatagtt tcaacctcgt cgttcccgat ggggttttcc  22140
ttgtcgaagt tcgctgatga tgagagtccg atatcatcca aagagctgga gccgttcggg  22200
tatgagatgc tttatgatgg cggtctgttt gccttcgata aggcggcccc tttggaagtg  22260
tccatatccg taatcgcagg gagcgaagat gatattaatc ttcgcatcct tctaaattcc  22320
aaaaagggat catttcgatt ccttccaggc gtcattccag acatgacgac tcttgttgca  22380
actcttcccg atggcggccg cactgttctg tccaacggaa ctatcatcaa gggtccggcc  22440
atagatacca tccagaacac cggacggcgc aaaggcaaca cgtatacttt tgttttcggc  22500
aactatctcg gcgcccagac tgcgcgtcaa gctatttcta acgttattca atcggttctg  22560
gaggtgatct gatgttaggg attttcacca gcctcctaag ctcgcggtct ttttcgattg  22620
tagatcagaa tacaaaccag ctagttgctg cggatttgag gataagccgg gttaacaccc  22680
```

-continued

```
ggttttcttc tgtagggcag cgccacatgc tggaagacgg tacgacaaag atggactcca  22740
gaacggtcca tcctatggag ataatcgttg aggtattctg cccttcaatt gatgtcgtag  22800
atcagattaa tcaactgctc ctggatcgtg atacgctgta caaagtcatc actcgcggca  22860
tggtattcga acggatgatg tgtaccagcg aagcgcttaa tcagacgcca gaaatgatat  22920
cggcaactcc tgcgcggctg acattttccc aagtgctcgt tcagaatccc aaaccaatca  22980
tgttcaggaa tgctggagac tcttccataa tcgaccgagg gttggccctg gccgaagacg  23040
ttgtgggctc ggccagtgac ctgttcgact acgcagtgaa cggcgtccag aacgccgcag  23100
acttgttctg aggtgccaat tgaactcttt cctcaaggcc attctcaaca cgcctactct  23160
caccatccgt gatgatttaa ccaaacttcc cgtttggaag agtctccaag tcaagaaagt  23220
ggaaatttac tcaccggctt ccgtagtgtc gaagcctttg gcgacgaaag accagacgga  23280
agctcaggtg tataccgaag cgctggacgt tgatgtgaag aacgggaaga tcattcagcc  23340
agtgcggctt cgcatcaatg ccatctgtcc agacttgtcc acagttgaaa gtatcatgaa  23400
tgcttttaat gacaatacct cgactttcgc catcacttcc aagtcgatat tggctgataa  23460
aatggccatc atgacgctcg atgtagatca atctcctgac atgctaaatg cggctgagat  23520
caacatggaa ttcgagcagg ttgagcctcc agtattgaat gaatttgatc cggctttccc  23580
tcaagatcgc ccaacttatg gcgtgcagat tcagtccctt tccgatgcaa atttgctaga  23640
cttgggagcc accggcgatt cgatatcttc ggccgcaaaa tcgctatata atcgcgtgac  23700
cagttatttc tgaggatgta tcatgcttga aatcaacctt cccgatggcc gccaaactcg  23760
cgtacaaatc gaggcgtggt cggcattgga cggctgggaa ctccagcgcc gtttcgtcga  23820
gttcgcagtc agcaaggatg ccgacttccg ccgcgctttc accatggaaa tcctgagcta  23880
tgccaaagtc attctcggta acgatgattc cgaaattccg ttgactactg ctgcggtcat  23940
caacaaccac ctcggcaact ggaagaacgt tgaattcgtc ttcgattccg tcctcaagca  24000
caacggcatc gatccgacaa cgcacgccga ccgcccggac tattgggagc aagccggttc  24060
gcagatggca atcgcatttc tggccgaggc gtccaagctc attgggccag ctatgaaaat  24120
cgccgaagga ctcgccagca agccggagta attcatgtct agtgatttgg atgaattcat  24180
acttcggtat gaggccgaca cggccagagc cgaacgaaat ctggaacgtc tccagaatca  24240
gatcaggcgc gtaaacagcg catcgactag tggccttcaa gatttgcgcc acttcgcaga  24300
cggcgctgca accgaactcg gccgcgtggt tccgcaggtg gacgccgtaa cgagcgcgat  24360
tcgcgggatg aacgcccagc tcgcgatagg cgctactggc gtggccctgg tcgcggccgg  24420
cgtcaaggcg ttcatgaaca ccagggacca gtacaaccag cagcgcatcc aggcgatgga  24480
tatcggcatc gccccggcgc ggctggaaga gtaccagcgg aaactggccc gccagtctgg  24540
aggaacgatc agccgcgagc agggcgcgga aatgaccaaa aatctggccg acactttccg  24600
gcgagcttat cgcgatatcg gacgggtcgg cccagaggcg cggattctgc gcatggccgg  24660
cgtagatgtc ggaagcttcc agaaaggcat gaggccgctc aacgacatca tcactgagct  24720
ggccacgaag atggccaagt tgaaaccgga cgagatttcg gcatatgctg atgccctcgg  24780
cgtctcgcgg gactatctga gcaccctggc gaagatcggc ccggcaatgg gcaaagtcac  24840
tgagatgacg tcagaagagc ttcaggctag ggtcaggggc gagtcaaaca ttcagaagtt  24900
caatgatgct ttggcaaacc tcaaccaaac gttcacgact ctggaaaacc gcgttggcga  24960
aaaactcgcg cctgcattca ccaagttgat cgaaatcatc gacaaaattg tccaggccat  25020
tcccaatgaa gtggaagaat tcgccaagga cacgaaagcc cgctgggacg atggaatcac  25080
```

```
cggaaaggcc actgtgggcg gcgatatcct gtcccttctc agtcctggtg ctctgctagg  25140
tcgtctggcc tcctggggca ctcggcgcgg catggaagag gccggattaa tcgacaagtc  25200
aaaggtccca ggctcccaag gccaaaccag cgaagacctg gccaagaaac aggaagacca  25260
ggacaaagct acgaagtcca tgaaagagct ggagaaattg gccgaccaga ctacgaagtc  25320
aacgaatgat ttcgcggtgg cgatcaacat gttcagcgga gccgtgtcat cgttcgccaa  25380
tgccgttgac gagcgtcaag catgggcggc atgggcgggg gaaatcgggc gcgcagtggg  25440
catgggaagc accgcaccga cttcgcgagc aacaggggtt tatccgcacg cgatctacga  25500
tcagtcgaag agtggcgcgg ccggtcaagt attcggcgag cctattggcg cccagtctct  25560
gcgaaacagg atgttctcgc cgcagcgcaa ggccgagccg atcaacgtgc catcgtacat  25620
caatgacatc atcaaagatg catctaagat gtacaacatt cctgagatgg acatcaagaa  25680
gctcatatac actgaaagcc gattcaacgc tagggcgacc agcgaagccg gggcgaaagg  25740
cctcatgcag ctgatgccgg aaattgccaa ggcgtatgga atcaccgatg tgtatgaccc  25800
acgccaaaac atcctcggtg gaacgcgcct attgcgggaa aacctggacc gggccaaagg  25860
cgacatgcga ttggcgttga cctactacca tggcggcctc gacccgaaga actgggggcc  25920
aaggactcgc gcatatcctg gtttggtgat gagcgcacca attgaactga tggaggaagc  25980
ccagcgcaag cagaaggccg cggccatgac ggtcgccaac gagacgttcg cgccagaagg  26040
tggcgacatg gacattcgcc cctatgacgg cggaaggctg gaagctccgg accagggcag  26100
gaaggaggat gatcgccgcg aagctcgtcg atatgacgac agagttgtcc ggccggagat  26160
tcgcatcatc gaccgcatgc cagaccgcag tgacggcgaa attcttaaaa tgtctcagcg  26220
ccaagacgcc gaccgggcgg actctggatt ccggaaattc ccgaaccagg ttcgtggcga  26280
gacaaagcag aacatccagg cccaactcac tgccggagct attgcccaag tcatcggtgt  26340
taatcctaac caaattatgc gccgcgaaat cagccgttcc gacttgctgt tcggatacaa  26400
ccaggccatc ttgggcaaac agcaggaaat caaagccgct gcgacagagg ccaacaatgt  26460
attcctttct ccagccaagc tcgccgaagc tactgccaag gttaacgccg catcgcgaga  26520
aatggatatt ctcaggacgt atggggagaa gcttctgaag agcgctccag agcgcggcca  26580
ggaactgaca atcggtcgaa ttgatatgtt ggtaaacgtc accggcgcga attctccaga  26640
agaggctcgc gaaatcttca gcaggcaaac cgcagaacag ctgaccactg ccatccagga  26700
ctcccaaaac gattctgcaa ctaagatact ctactgatga aaaagagaat tctgcgagtc  26760
acattcaata tgccctatgg acccgaaatc atccgtgaag acctggatgt tcgggtccgg  26820
attatgaagg ctgcattgcg aattcaaaac cgagctaccc tggaaatctt tggactcacg  26880
acgcaattgc gcgagtctct tctgtcgcag ttcacagcgt ggaagcaccg gcagcgtcaa  26940
gtaggcatgg aagacgaact gatgatcaga gtatcggttg aggccggtta ttccgatcag  27000
ggccgcgaac aagtttccag agtatttgtc ggcgaagtgg caattgtcga tgtcatttcg  27060
ccgccaccgg atattggaat tcgcatccaa tgctacacaa ggcaaatcga taggacgaag  27120
actattcgaa atatgccgcc agccaacacg acgtttgtaa agttcgtcga atggggcgca  27180
aatgaaatgg ggcttaactt catctgcgac accagctaca atgatcaagt tttgaagaat  27240
ccgggccggt cgatcactgt cgcgtcggca atcctggcat cgattcagga tatgtacatg  27300
ccggatgtgg ccgcgttcgt cgatgatgac attctggtcg tgaaggaccg ggataaggtc  27360
attcgtcctg atgaagttgc caacatcaac tcattcgtcg gcatcccttc atggtcggaa  27420
```

tggggcgtgg aatttcagtg tctgtttgaa ccgtcgattc gcgtggctgg cggtgtcgcg 27480
gtcgaatctc tcatgaatcc aagcgtcaac ggcaactatg tgatcaccgc tctagagtat 27540
gatttggcca gccgggatcg gccgttctat atcaaagtca tggggagccc agcagcgtaa 27600
tggccaggga aatcaaatca ttcaatatgt tcggcgtgca ctacaactcg cggcaattct 27660
ctgcggtcga tggactcagg atgatgtcgg gaatccatga tgttcctccg gaagaattgc 27720
tcaaagggac cgacgtgttg gcccatacgg aggaacaacc ggaaggcgtt tggcttccct 27780
tgaccgctgc gaacataaat ctttatgtaa ttgaccgggc gaacgtaata gctcccgtac 27840
aagtgcttgc gcttttgtct gaactggtca tagattggaa ctttggcttc ctcaaagatt 27900
ggacaggggt caaaattcca tcaagatttg tagaagatat caaaagcgtg aagacggccc 27960
attcgccttc cgtggtcgca agtttggtgg cgaatgggtc agcttctatg cgcgagctgg 28020
aagagtatta ttcgactcaa gatgccttta agatgattga catcatgact gcgaagagcg 28080
tgaatgaggc tctagcgtcc gaagcatcac agaacagaat caaaaaggga taattcctaa 28140
gcgagcctgg gaaggctata ctagaccggc caaatcagag gctttcccat gtccaatatt 28200
ccgctaacat ccgcaaaatc taccgacaga acgcgactga tcgccgctct tgacgctcgg 28260
tcgcggcggg atgcgctcga ctttgaagtc atgattcccg cccaggttgt tcaatatgat 28320
cgggcagaaa acatcgctac cattcaacct ctcatcacct gggttgatac ggaacacaat 28380
gccgtccagc ggcatcagct ggttgacatc ccggtgattt ccatgggcgc tggcggcttc 28440
cacataagtt tcccgatcca gcagggggat atcggctgga tttacgcggc cgaccgcgat 28500
acttcccagt tcttggagtc gctatcgatg tcgaagccga acaccggccg catccacaaa 28560
tttgaacatg gtatgttcat accggacgta ttccgccgat acaccatcaa ttctgaagac 28620
tcggacgcga tggtcatcca atcgactagt ggagcgacca ggatatccat tcgcggagac 28680
aacatcaaga tcactgcgcc gtcgaatgta acagtggata ctccgcaggc gaatttcact 28740
ggagatgtga ctatcgccaa caccctggtt gtaaacggcg tcaacgtgaa caaccacggt 28800
cacctcgaaa acaatccgcc tgatacccgg actaaaggcg gcatgattgc ctaaaaggag 28860
attcaacatg gtcttcacac tcgaagattt cgttggggac tggcgacaga cagccggcta 28920
caacctggac caagtccttg aacagggagg tgtgtccagt ttgtttcaga atctcggggt 28980
gtccgtaact ccgatccaaa ggattgtcct gagcggtgaa aatgggctga agatcgacat 29040
ccatgtcatc atcccgtatg aaggtctgag cggcgaccaa atgggccaga tcgaaaaaat 29100
ttttaaggtg gtgtaccctg tggatgatca tcactttaag gtgatcctgc actatggcac 29160
actggtaatc gacggggtta cgccgaacat gatcgactat ttcggacggc cgtatgaagg 29220
catcgccgtg ttcgacggca aaaagatcac tgtaacaggg accctgtgga acggcaacaa 29280
aattatcgac gagcgcctga tcaaccccga cggctccctg ctgttccgag taaccatcaa 29340
cggagtgacc ggctggcggc tgtgcgaacg cattctggcg taaggagaat ttcatggcta 29400
gttttgattt ttctgattta acagcggggg ggggttgtaa tggctaatta tgactacata 29460
gtagatactg gagtcatagt cgccgatact gctgatattc tgaaggacgt tgaagcggaa 29520
ttcagggcag ccctcggcgc caatatcaac ctggcggcct caacgcccca gggaactctg 29580
gtcgcggctg aaaccattgc gcgttctagc gtgatgagga atgaagctcg catcgccaat 29640
accatcaacc caaacgtgtc tttcggaacg ttcctggacg ccatctgtgc gctgatggga 29700
atcgagcgcg gctctgatct ttcgacgttc ggctatggcg tccaggtgac cggccgcagc 29760
cagacccgaa tttccaccgg gtcgcgtgtg cagactccgg ccggagcgat tttcacggtc 29820

-continued

```
atgagtgacg ttctgattcc ggcaaccgga gtcgccacca tcgacgtaaa atcgcaggac  29880
tatggaaaca tccctcttcc cgtaggaaat ctgatcatca tcgatggaac catcggttgg  29940
gccggggcga aagtcatcgc ttcaactcgc gtcgatcctg gcagccgcca aatgaccgat  30000
gcagaattga agaatgctcg cgtcaatcgt ctggcgatcc aaggccgcaa ctcgactttg  30060
gccattaaag cgtatgtcag cgccgtgccc aacgttacct cggtcaacgt catcgaaaac  30120
aacaccggca cggttcaagt tgtcaacggc gtatcattca cccttccgta tgcggtctgg  30180
gtctgcgtcg ccggaaatcc ggataagcag gctgtcgcag atgctctgtg ggcggcccac  30240
aacggcggga ctccctggga ctatggcgcg gccgacaacg gcgtccctgt ggatgggcct  30300
actggcgttc ctgttcgcga cccggcatcc ggtcggaagt atgtggtgaa gtggactact  30360
ccgatcatgt atgacggata tgtaaacgtc accgttcagc aaggctcttc ctcggtcgct  30420
ccggaagcaa tccaaaacgc agttgtaaat tacgcccagg ggaaagtgga gggcgaagag  30480
ggattggtcg tcggcgcgag tctgtctgcc tttgaagtgg ccggggccat cgctcgcgag  30540
attcccggaa tctacattaa actatgccag gtggcttgcg tcccggctgg atcgccggcc  30600
ccggcccccg gcgacttctc gcctgagtac gtcatgagcg cattcggtca ggctaccatt  30660
tcggttggca acgttagggt gactttcgta tgactctgcc cgcgtacaat tctgatattc  30720
aacaggcgct gaagtggctc cataaccagg cccctgggat caccggcttg gttcagcgaa  30780
aagctcaatg gtatgaccgt ttcagtcgtc agttttgggt taactgggag cgcgacgttt  30840
tcaacctgaa gaccgccaac ccgttcggcc tcatggtgtg gtgcatcatc ctcggcacgc  30900
cgtcgaaagg attcggccta tatccaaaaa acagttcttg ggcattcggt cggctacgcc  30960
agaacttcat ctatagcggt acacaagttc cgccaccggc agacgcatcg ccgggcggca  31020
acttctacgg tggcggcaat gccgaaattc tcaacttgga cgaaatcagg aaagtgcttc  31080
agctaagata tgtagcgctg atttcgaacg gctcgattgc atatatcaat cgcatgcttc  31140
gctacatatt caatgatgat gagccgtggg acgaggcgac cggtctgtac ttctatctca  31200
tggactcaac cggcgaggat ggccctgtgg agaacttggc catatatcgg aaagattggg  31260
aaggtatggt gctgttgtcc agttcgccca gaacgaacca tgtgctgaca tcgacccctg  31320
ccagcgacgc cgattggccg ggagtcgatc cggccgcgag cggtcttccg gtaacggtcg  31380
aaacggcgtc cgctacggcc ccggacggct ccgctacggt gtgcaagctt actaagccgg  31440
ccgggagtac cgcttacgtc tccgcgccga tagatgggcc gctggggtcc ggtagcactg  31500
taacgttctc gttcttcgcg aaagccggct ccacccgttt cattgcaatt cagtcggctg  31560
ccgatttccc cagtcgagcc gatgccgttt tcgacctgga ttccgggcac gtgatcagcg  31620
atcagatgtt ggacagcagc gtggtaagcg cccgaatgat tcgtctggag aatggctggt  31680
ggcgttgcgt tctcacgacc aagaccgtca gctcttcgtt ccgcgcggct tacatcgctc  31740
cggcagaaac caacttcagc tggattgatt cgaattccag cgcggcgatt gatgtgctta  31800
tctggggcgc tcagatcgaa ctgggtgata ctccaaccgg atacttggag actaccggaa  31860
cgcccgtaac catcaccgat tacgttctgc agagcgccca gaccggaacg gtcaagttca  31920
cacagcctct tccgaccgga gtagaagcgt attggactgg agactggaaa ggtgggtctg  31980
cgaccgagcc ggccagattc gcagtagggg atgggactca agatacattc aatctgtcca  32040
gccctgcata catcggccta cccactagtg gggcgttcaa gctagaatac agagttggtc  32100
cggcgcttaa tttgtcgccg caattgatca acctcatgaa tgaccgggcg gtcggtatca  32160
```

-continued

```
tgccgacttg cgccggttgc gatgtaaaag tcattcagga gtaatgacgt gatcacaccc  32220
gaactgatac ccagtccgtt tgctgcgcag ggcgacaaag acccgatccc gcagacctct  32280
tccactggct ttgccaacct tcgcgacggc tacacgccgg actacgaaat cagtctggcg  32340
tcgaacaacc cgcaggccaa agcggtcgag cggaaaattc aaaaccaact cttcttcatc  32400
gcgacccaga acgcacaggc ttggcagcgg caaatggcgc cgccgtggtt tcagggcatg  32460
cctggcggct acgaacagaa tgcagaagtc gtgcgagtcg gcaatgacgg cataatgcgg  32520
cgttatcgtt ccatggtgaa tgccaatgcg agcgaccctc tcagcagcac gacttgggaa  32580
gaacaacccg catggtcggt gatgcgctcc aacataccga tgccagctgg aggcccaggc  32640
ctatcttctg gcggagaagt catcacgacc ggccgcaact tcaatgacct gttgaatggg  32700
acgtgggagt tcttctctga ttcagtggtc gtcgcttctc agaacgcccc cgtatatccc  32760
gcttcggctg gtgcagcagc tggaatgttg gaggcgaaat cctggatatc cgggtccaat  32820
acattctgcg ttcaacgcta cactgaccgc gtcgggaacg tcgctgtgcg cgggcttaat  32880
gccggggcct ggaccaactg gatgtacgca gtaaatgtca tggccctcca acaaggccgt  32940
gtgacctatg gggtcgcggc tggctcggcg aacgcttaca cgttgacgct cgttccgcag  33000
ctccaaggcg gcctggtgga cggcatgatc cttcgggtca agttcaacac cgttaacacc  33060
ggcgcctcca ccatcaacgt ctccggattt ggcgccaagg ccatcgtcgg cgcggcaaac  33120
ttcccgttga ctggtggaga actcggtcaa ggactcattg ctgagcttgt attcgacgcc  33180
accggcgacc gttggaggat tctcgcaggc gcgccgcgca tccaagtagg caacgccgat  33240
caagattatc aggctcccag ctggaaacag gttaaggact atgtcgcgtc ccaaaagttg  33300
actgaagtgg actgggctga cgtcgtcaac aagccgaacg tcgccatcca agacaccaca  33360
ccgtggttcg ccaatctgga gttgtctgac gctcgtcctt tcatcgattt ccacttcaac  33420
aacaaccgcg ccaaagactt cgactatcgc tttatctctg aagctgatgg gtcgatggcg  33480
ttctattctc gccaggggtc cgctggtcct acccaggata tcctgttcag caggtcgaat  33540
gttacattcc tccagccgcg actggatgtt gcgaaaaacc tcgcgtacat cgcgaactct  33600
ggcccccttt ggcagaacac aactgccgat cagcccggtt ggaaattcac cttcgcacaa  33660
ggtgtggacg ccaacaacaa cgcggttatc gcagtcaata ccaccaaccc ggacggctct  33720
tatcgctcgc aggtcatgcg atgggactgg gcgtccacga acgtcatatt caacaatcgc  33780
cctctgtttg ctggacaata tgttccgtgg gactccggaa actttgatcc ggccaccaag  33840
ctcactgtcg gtactaccaa caatatttcg gggccgaccg gaattcgtaa taccaccagc  33900
aataccggaa atatgaacac ctggggctcc agctccacaa ctgcatcgta tggaaacgca  33960
gctcttcaaa tcttcggtag agggggtggc gagcctgcgg ccatctactt cgacaactcc  34020
caaaccggct ggtatttggg aatggacaag gacggccaat tgaagcgagc aggctggtcg  34080
ctcggcaata actcctatgt ggtcactgac gagtcgaata ttcggaatca cgtcaatgga  34140
atgtctggcg ctcctgtttg gggaggtcaa tggttctggg gtgaatggaa cttcaacccg  34200
aacacaaagc taaccatcaa agccggcacg caggagacta gcagcactgc gatattcagc  34260
ggaaccctgc cgtttgcacc aatcgcgtct ctgtccgact attcccaggc gcccctgacg  34320
atttataact cgccgactgg gccatctgct aagcctgctg tgatcgcgtt tattcgccct  34380
gggaactggg gcgcgttctt cggcatcgat accgacaaca agctgaaatg gggcggcgga  34440
tcgctcggca acaactccag ggaaatcgcc gattccagca acatcatgaa tctttgggcg  34500
tccaacccga ccgcgccgtc ctggaacggc caaaccgtct ggcgatccgg aaactttgat  34560
```

```
ccggcgacga aagtggattt gaacgccgcg aacgccacca acggcaacat gatcttcaac  34620
cgcatttcgg gtactggtag cggcatcgct tcgtccggtc gagttggtgc catcaaccta  34680
cagaatggcg cgcattcagg gcaagcggcc gcagtcactt tcgagcgtgg tggaagtatc  34740
ttcgtcaact tcggcttgga taccgacaac gttctcaaag taggtggtgg aaacctgggg  34800
gcaaacgcct acccagtcat ccacgccggg aactacaaca actacatcaa ccaggcgttg  34860
gttcaggtcg gtctgggcgg agtcggttcc tatggcattt tcgcggttct ggataatgcc  34920
gctccaatcg caaccgttca acccggagtg gtagtggacg gttccattct catctactcg  34980
tcttgcgccg caaactacaa tagcggtcaa aaacctgccg gaacttggcg ctgcatggga  35040
tatgtagtca acagagacgc caacacccct gactccgcga ccctttttcca gcgagtgacg  35100
taaaatgaga tggacgcgga tcagaaaccc acgttggctg gacgcagtaa acatccacgc  35160
catggtgact ttcgagggaa tcggtgaagt gccgttcacc gccaatccgc aagacgtgga  35220
ggcccacgga agggccatat acgctgcgat tctatctggg gagcacgggc ctatcgcccc  35280
ggtcgattcg aagcgggaga aggccttgca ggacgctata cgagccaggg aaaagcgggc  35340
tatccttcgg gatacccgct ggcccataga tcgtcacgac gagcagagac ggctgggtat  35400
cgaaaccacg gacggccctg ggctgatcgc agccctcgtt cactggaggc agcagattcg  35460
cgactggaat agcggggatc ggccgcgact tcccatggct ctgaaaacaa tgttcaaaaa  35520
tcaggagtac tgatgaaaat aacgaaggat attttgatca ccggaaccgg gtgtaccacg  35580
gatcgggcga tcaagtggct ggatgacatc caggcggcca tggataaatt ccagatcgag  35640
tcgccgcgag ccatcgcggc ttacctcgcc aacatcggtg tcgaatccgg tggactggtg  35700
agtctggtgg agaatctcaa ctacagcgct caaggactgg ccaacacttg gccgcgccga  35760
tatgccgtgg acccgcgtgt ccgtccgtat gtaccgaacg ctctggcgaa ccgcctggct  35820
cgcaatccgg tcgccatcgc caacaacgtg tacgctgacc gcatgggtaa tggatgcgag  35880
caggacgggg acggctggaa gtatcgcggt cgcggactga ttcagctgac cgggaaatcg  35940
aactatgccc tgtttgccga agactccggc atggacgttc tggagaagcc ggagctgctg  36000
gaaactcctg ccggcgcgtc gatgtcttcg gcatggttct tctggcgcaa tcgctgcata  36060
cccatggcgg aatccaacaa cttctctatg gtcgtgaaga ccatcaacgg cgctgcgccg  36120
aacgatgcga accacggtca gctccggata aaccgatatg tgaagaccgt cgccgcgatc  36180
aatcaaggct cctgatcttc tccgaaaaga aaggccgctt attcagcggc ctttttgctt  36240
tccggctttg cctcttcaat ctttctgact tcagtaggcg cgacggactc ttcctgggta  36300
actgagtcca catagttccc tagcgaactc aaaacgccga ttaacagcgc tcttaccact  36360
ttatccttaa ctgtctcgcc tatgatcttt gtcagaacgg atatcaactc ttcccggagc  36420
cttgggctta ttcttggccg aaagcgcttg cgatgctctt tgcgtttcat gtttagtcct  36480
ctgtttgcgg tcttctcctc accccgataa tggcttgggg atgcgctgtg ttaatcggaa  36540
gggtcgggcg ctattataac tcgacgaaaa tgctcgcgct taactgttta acgatacgca  36600
ccgcgatatt aaatcgcctt ctttctggcc aaggaactct ggcggccgag tccggtctaa  36660
ggcttaattt gtcgacatta aaacgagaaa acccggatcg cctttagggt aaggagtccg  36720
ggttttcttc gctctagtgt acgctagaat cagtggctgg caccccatcc gtccagccag  36780
cagtcgaaga cagcgtgtcg tggcttatcc ttggcgccat gggagaagtg cttaaatcgg  36840
atgacctggc gcttgagatg ttccctgtca ttccagagcc gtttttttctc gtcgtgggtc  36900
```

-continued

```
aggctggacg ccgacacatt gaaggtaact ccaggccaca aaacctcgtt gcggcagacg  36960
aatgctccaa ccatgcctga tggggccaga ttttccgcat ggctggagcg ggccgtgcga  37020
cctagctcat ccgtgaatgc ttcgttgttg ttgtgcatca gctcttcgac gtcaacaatc  37080
tctgcttcat catagtcata gcgcttaacc ttgacacagt aaccttcctt ggcagtagag  37140
cgcccgaact tgtatgcgcc atcagcgcgc ttgcccatgg agccttcgaa tccaagtcct  37200
gtgtggcgac gttcgacttc gctgaactgt tcgatggagg tgaccagttc ctgctcgact  37260
aggtgaatcc tctcatagcc gatgcagttc ttcagaaagc tgacgcgctc ggcagctctg  37320
gccagtcgct cttcggtcgg cgcgcgcgga tcggtgaaat cgtcaaacac gtggaaagac  37380
caatccggtt caccgtcgcg acggcgaagg tcgccggacg acttctggaa tactttcggg  37440
tctctgatgt cgccgcagac cagttcgcca tccaggccat cgaacattgc atcgctgaga  37500
tattcacgga tggactggtt ggtctgcggc tttaggcttc gcgtcaaggc ttcgccttca  37560
aatatgaaac agcgaaaacc atcgatcttc ggagaaaagt acatcggcaa ctggccgtcc  37620
agaagttccg ggtcatagtt cgatgcgagc atgggtttca tacagtactc cagaaagaag  37680
cccggcgaac cgggctgaat ggcggtaagc cggatcagat ggtttcgttg gcgtgattca  37740
gctcggccat gatcgatgca tagcgctcat ccgactcctt gatgaacacg ccgttgtaca  37800
ttacgccctt gcgatccttg atggtgtcgt aggccgcctg gtagcattcg agcatgctgg  37860
tgtcgtgctc ttctgccgcg tcgaacaggg atgcgactgc catgaccaag ctcttgatgg  37920
caagccactg atttccgcga gccagcgagc cggccaggtc gccgagtaat ttcagatctt  37980
cgccgtagga cgggcggcgc tcgaccgcca agacgaaggc tgacatatgg tcgagcagat  38040
tttcgccgag ctgcgcggcc atgatggtgg ccacgaccat gacatcgccg atgccgtctt  38100
tcacttcggc ggtgtcattc tggatgtagg cttcgcaaac ttctgcgaat tcttctacca  38160
gcttgagaaa ctgatctttg gccgaagagc ctttgatcag gttacggtcg gcaccccatt  38220
ttaccaccag gtcatggagt tcgctattca tgattcgttc gatgatcatt ctttcgattc  38280
cttctgtatt tgggatttga ctgcgttgat gatggacgcc gtgctctggc gcgatccgtc  38340
cttagtggtg ccgaagtaaa aggccataac agacttcagt tcggcaaacc aatagccgat  38400
gatagtgccg atggcgacag aggaagtcgg gtccatcagc gcctcgcggc cgaatgtgaa  38460
aattgcgatg atgatgagaa tggaaccggt cagaagagcg aaggttatcg ccgggcgaac  38520
gaagtcattt tgttgcgcgg caagccttct cgccgaatct ctgtctgccg cctcggcggc  38580
gaactggctg agttcggcct ggagctggtt ctgctcagac tgaagacggt tttgttcggc  38640
ctggatggcc agttcctgga gacgaacacg ctcggcgctc tggagttctg cgaggcgcgc  38700
tagagcctcc ggattcgcgt ctagagcgct cgcgaccgat gctgggtcgg ccttcgaccc  38760
tagagccgtc gcgacgatag cgccaacggc ggcgcctgca ggcccaccca ggagcgaccc  38820
cagggccggg gcagcagcgc cgatcttact acctatgtcc ttccagtcca ttttcgattc  38880
ctcaaaagaa aggcgccatt acagcgcctt tctctggccg ttgacgttag aactcttcgg  38940
cttcggtagc gccgccaacg ccgccggtgt cgccgcgagg ctgttcctgc ttgctgtagt  39000
ccaccttcac ttcgccgccg acgaacgact tgtacagatc ggccgcagcc ttgaagtgat  39060
ccgggttttt caccaggcct tccagttcga actggacgcc ggaccagctg cccttgtcgt  39120
tcgacagacc gacggtggtc atgcggacca ggttggcgaa agtcggcggg gtgcgcaggc  39180
cctgcggagt ctggactttc ttctgggaca gcgcggtcat gagcttcttc gaggccttga  39240
tctgcgaaga cgacagggag atcagggcct ggccgaaatc gccggtttcc ggatcgatga  39300
```

cgatgacgta atggccacgg gtgtcggcga agtaatcaga tttcttgtcg cttaccgaac 39360
cgtcttcgtt cggcgcgtac agtcgccctt ctacttcctt caccttggtc gggtctttca 39420
tcatttcctt gaagtcttcg acgctgatgg accctttgaa accgccttcg gcatcgcggc 39480
cggcccagcg aatgaactcg cgacgatacg cggccgggat gatcagcaga ccggttttgc 39540
cgtcgtaaat cttgccggtg acggtattca ggaacatgcc ggccttcgcg ccctcgatgt 39600
atttcgggtc gtcttcatcg acctgcggcg acatcttttg cagcacttgg atgaagggaa 39660
tggcatagga atctgcgtca gccccttcga aaccagcgcc gtcatacgcg cccaggtcca 39720
tgaagtcggg aacgtcagta gtcgcgacgg cgccgccgtt ggccactgca acggccttgg 39780
tttcttcggt tgcttcggaa gtctcggttt tcttgccagc catgttaggc tccttgtttg 39840
tcgaatttca gttatcgcta actgtgggtt tataataacg gaagttgcag cgaagtaaag 39900
caaattacat gttaagattt gctctttttc accttcggct tcgtgatctt ggcctcttta 39960
tattcgtgga cgccgatgaa atctggcaac tcttcgccct tctccaggta ctcgcgaccg 40020
aacgcctgga gggtctggta gtgaacatcg cggttgatgg tggcgtcata gccggcttcg 40080
atgatcgctt cggccgcctt cttcgcatct tccatttctc cgcgaccgaa ttctgccaga 40140
actttggtct tgatgatgcc gtcgttgtct gtgtcttcca gccacttcca gaacttcgac 40200
ttgttctctt ccttgacgga aatgatggct ttcggctcga cttttaccgt gcggccatca 40260
gccagagtcg tggtcttctg gccgagttcc tccagaagtt caggaatggt attgcgcttg 40320
agggtcttca gctcttcttc tttttcggcc agcgcctttt gcaattcgag gatttcgccg 40380
tccagctgcg aagccttgtc caccaagttc agcagtcgat ggccgatgtc ggtagcttcg 40440
actgccattt catccatgac gccgaaatag tcaatttcgc ccggcgcatt gtccttcaga 40500
tactccggaa cttccaattc ttgctcgctc atgtcagcct ccaacttagt gatgttccct 40560
tacttgaact aagtattgag tagatattat gccgcatctt ccttgatacg gctactgatt 40620
tacatattaa atttcgtcgc gagtgctaac gtcagcctcg aacactccat cgacgacata 40680
actcgcaaga ttgcgcttcc actccaagct aacctggatt ttctcgtcga tggagtccag 40740
acagatgagg tcgaagtaca ggacagagtt gatggtcccg atgcgatggt ttctgtcttc 40800
ggactgcatc cgcaactcgt tgtcttcgtc ggtcgtgtag taaattgcca cgtctgcggc 40860
agtgagcgtg attccgatcc cagcagcggc cgggtttccc aggaagactt ggacgcgctt 40920
tgcctgaaaa tcatcgatca gtttttctcg ttctgcctct ttggtctcgc cataataggc 40980
tccaaacgaa attccttggg cctcaagata cgcagcgatc tggccgattt cgtgaatccg 41040
catggcccag atgatgatag accgttccgg gtcttcctcc aacagaccct ccagaaggtc 41100
ggtgaatacc gcgaatcgcg ggttgtcttc gggcggcagg atcaccggtt ccccatagac 41160
gttgatatag ccggacgcca cttgcttgag tttcgaacgc gctgctgctg catcgaacga 41220
tacatccagc atgaaatctt cgttcttgag cacgaaatgg tagtcctctt caacgcgctg 41280
ataaatcttc ctttgctccg gcgacatttc gaaatatatg cgcttgtaaa ccttttctgg 41340
caggaatggc aatgcctctt tcttcgtgac ccggaagctg tgcggctcga tcagggaccg 41400
cagtttgtca agatttcgga atactggtcg cccaaaatcg tctttttcga cgagctgagg 41460
tggaacagtg ctcttcccat ccaatttgcg catgatggcg accattcgcg ggtcgtcact 41520
tggaaccaga acggaaaatt cagccacgaa cgcgcgatag gatttcgtcc ccagaattcc 41580
atcacgcagg aattgaaact gcataaacaa atccgtaggc gctcgcgtca gaggcgtacc 41640

-continued

```
agagagtatg cggcgcgcca cggccttctc gcccagcttt acgatctttt tcgctcgttt  41700
ggcctgtggg ttcttgatcc tcgttgattc atccacaatt gcgcagactt tgaacgtctt  41760
aaggaatcgc tccacttcgt catagccaga ctgatggttg atggcatcga cgtttatggc  41820
aaagacccga agaacttttt catcagcgaa tgtctcggca tacagacgat ccagacgcgc  41880
cctggccttt ttggaagtcg gtcggccgcg ccaatccacg cacagagtct tgatagcaac  41940
gtgggtggga atctcgcgca gaatccagtt cgtgtgtacg cccttggggg cgacgatgag  42000
cagcgcgtca acccttcctt gcaggaagag cctaactgag tctgccaaag tagtccaggt  42060
cttcccggtg ccttgctcca tcaggtatgc gaaattcctt ttgttaaggg aagcctccag  42120
ggcattgaac tggtgttgca tcgcctcggt cttcatgccc ttgactggaa aggttttggc  42180
tttcatttgt tctccagatc ggcgagaaat tgaatgatgt tgtccagtcc ttctgcatga  42240
ctcgcgactt ccaccaggtc gcggctgtta agatcgaaca gatcgagcat tggattcagg  42300
agcagccaat cggttccgat tttcaccaga acgaagccgc gaccacccca gccgatccgc  42360
tcccgaagga aagggatttg cccaggctcg aaacagcgcg ccattgggca ggtagaggtg  42420
cgctttggcc aagcttccag agccttgaac tcgacccaaa actggacacc gtgacgattc  42480
aggcatatcg aatcggacat gccggaccgg cgcgtctcca ggaaatcgac caggattctg  42540
cctagcgagc gttgcttaaa cgcattcgcg gctttcgttt cgcgatcatt catcgccatt  42600
cccctcttcg gaatctttct ctgcttgcgc tgccaacttt gctttctcgc gttcggtcaa  42660
tatccgcttg acggccttca cgatgaacat atcgattccg ctgagcttcc atcctttgat  42720
gaggaaccaa gagccggtag gcgtaccttc ggcgatattc ttaccgtact gaagatattt  42780
ttcagggcga atcctgaaac gaatcggttg gtcaaccgag tcatccacgc acatcaaatc  42840
gaggaactgc gactggcctt tgtacaccgg attctttcct tggtcagccc tcttcttctg  42900
gcggatcggt tcattctcat ccgacagaac tttctttacc agcttgacga taactaggcc  42960
atcgtcgcca tcgcggatat cacgaatgtt ctgaatggga tttccggaag tcaccccaac  43020
caactcagga ttgtcatagg catgacccca gagcgtatga gattcattca aatccgcgaa  43080
ttgaacctca gaattcgaca aactcgcggc aactttctcc caatcctgaa gcgttttaag  43140
atgggagccg gccagctctt tatattgcgc cttcaactcc ttcagttcag ctttcaactc  43200
cttgagatca gctttgagta gcttctccag ttctttgtct ctgcttactt tcgccgaaag  43260
aatctgggct tccagcgcgg caacgtcatc ggccttatcc tctacatcct gcgccgaaat  43320
cgggcaattg gccagggcga tcctcgcggc cttgacttcc tcgcgaagac gcaagaatcg  43380
ctcggcctta gccgggccga agcctttggc gttcatgatg ccgccgatca ggcgtccgtc  43440
cgctacaacc cagttgagtt cggaatgctc cgggtccagg gccgtatatt ctacgccttc  43500
tttggccaat tcgcgaagga tagacacagt ttgctggtcg tccttcgccg cccgaaggca  43560
cgcggccgcg tattccaggc gatgataccg cttcatgtag caagtccagt acgtcaccac  43620
ggcatagctt acagagtggg agcggttgaa tccccaggcg ccgaatgtca ccatttcctg  43680
ccaaactcgg tgagcgtctt ccggggcgac gcctatggtc ttggcgccct cgatgaacaa  43740
ttctcggcgc ttgttgaaga actcttcgcc cttccgcgcc gacatcgctt tccggatcgc  43800
cgacgtttgt tcccagtcga actgaccaat gtccttaaca attgacatga tctgttcttg  43860
gtacaggaac acgccatacg tccccgacaa atactgctcg acctgcggaa tggtataggt  43920
cacaggctcg cgaccggcta cgcgctcgat gtatttcgtg gccatgcccg aagacaacgg  43980
acccggacga gcgagcgccg tgatgtggtc gatgttttcg aacgcggtga tgtttatcgc  44040
```

-continued

```
attggcgacc gagcggacgg cctggccttc gaactggaag atgcctgaca tcttgtcttc  44100
gttgagaaca tccaaaaccg ccttgtcgtt cagcggcaag tcgtacaact cttgcgccgt  44160
cacgcaattc gcatcttgaa ttacgcccag cgttcgaaga cctagcgcgt caatcttgag  44220
aagattcaaa tattccgaat caggcttgtc gagctgcgcg acgccttcag aagtaaccgt  44280
acagaaatcg attacttcat cgttgcagac caggatgcct gccgcgtgga cgccggagtg  44340
ggatgggtga atttcgaggt cgcccatgca ggcggacgca atctcatact tttcgcggaa  44400
gtcgcggccg ggttgagtct tttcgaaagt gtcctccaat ccttttccat atcgttcgtc  44460
cgccgaagta tattcgatga tcgagttttt gatgttgtcg gtgtcatgga atggaatgcc  44520
gaagcgcttt ccgacgtgag cgataaccga cgcggccttt agtgtgttga tgttcccaag  44580
ctttaccacg ttccaagtgc cgtatttctg ctggagatat tcgaacacta gatagcgatg  44640
ggtatcggcg aagtcgatat ctatatcggg aagatcggaa cgggaaatgt cgataaagcg  44700
ctggaagaga aggcgatgcg ggagcggatc gacctcggta attcccagca ggtagcagac  44760
caaagagccg gccgaagagc cgcgagccgg accgaccagc atatgcttct tggcgaaggc  44820
aaccagatcg gccacaacca gaaagtagct gtcgaagtct ttcagctgaa tctgcttgat  44880
ttcttcctgg aaccgatctt cgtaaacttg ggtccattcc ttgatgtggc cgcgactgag  44940
acggtaggct tggccctcgc gagccagggc gacgatatca ccatccaggt ggatcatcgg  45000
cgctttcgcc agctttacgt cgaccagctg ctcgaccacc gcatgcgtat tggcaacggc  45060
tttgtcgaac tcttcgcggg tcatgatatg gcgaagacgg gcccacaact cttcctcagt  45120
cgcgatgtgg cgaaggccga ccgattcccg aaccttccag gccgaagcaa aatctgcatg  45180
gtcgatggac ggcatgtcgt tgtaggaggt aatcaccaca ggcttgccga acgccctggc  45240
cgtctccata gcgccgtgtg cggctaccat cgacgcagga ttgatgtcaa tgtaatcgat  45300
tccggccaag tccaagtagg cataggcctc gccggcgaac ttgatgacgc cgtcagcatc  45360
ctggaattct tggggagaca atccttgatt ctggacagtt ttggacgtca ggcgatagaa  45420
ctttctggta tctttggcta gcgcccaggc tttcagtttc agctctttgt caccatcatc  45480
ggcgcatttg atcgggattt ccatgccgaa tccgcgagga agttctgcct tggtggcagc  45540
ctgctcccag cggacgtggc cccatgtccc atcatcgacg atggcgacaa agggcgattc  45600
gatttctttg gcgcgctcaa tgatttccgg aaacctgcca tatgcggcgc cgtatgagta  45660
gccggagcga acgcggagtt gagggaaaga cattatgcgg cctccattgc ttgatatgct  45720
cgatatactc ccatgcgctt gcaaacttcg tggagcagcc gcacgtcgtc caatgcccgg  45780
tgcttctgaa cataagggcc gcagtagtgc tcatacagat gctgcagccg catgcggtgg  45840
ccgaacaatg gcgccgactc ttctacagta cagatatcga gcgatgggaa gttgacttct  45900
tccaggccga gctttccgcg agccaaatcg caggtaagca tgaatttatc gaatggaagg  45960
ttgtgggcaa tatttgcgtc ggccttcgaa aagaaatcgc gaactttctg gcgttgatcg  46020
aggaacgatg ggtgtttgat taagtcttca ttcttcaggc ctgtgatctt tgtaatgatt  46080
tcttctatca caatcccagg gttgcaaatg aactcgactt catccaaaat cgtctcgcca  46140
tcggtgatca ctccggcgaa ttcaatgatc ctcggttgct ttctcagact taccctctgg  46200
tggaacggga gtcctgtggt ctcagtatcc catacggcga atctcatgtc tgttccctct  46260
tatgtcgaaa ggccggctgc tttcgcgacc ggcctgaaga gtataccgca acggcgcagg  46320
gtttatgcct tctgtccgtc tttcggcgtg atgcggccgg agtgcatggt ggcgtggacg  46380
```

aacgctgaat agttgatcaa gtcaaatacc gaatcgtcat cctcaaaccc actattcgcc 46440
aggcgagtga gtttgccaac tgtatgcatc acgaacaggg cgagccgatg atcatctgcg 46500
gtcttcgcca ccatgccatt cgggaagagg atttccatga tcttgccata catcagatca 46560
tttcgaccat aagcgctctg gcggtcgcgg aaaatttctg cggctgagga caggttgttg 46620
agaacatcct ccacgaaatc atcgggatcg gcatcaccgt caccaggcca ggcggattcc 46680
atggcgaacg gcgctgctgc gtcttcggtc ggctcttcgg ccggctcttc ggctggctct 46740
tcggccggtg cttcgtagag cggagacggg gcctgcgcaa acgcctcgtc gagggtaggg 46800
gcggagtccg gggcgaccgg gaacggctcg cctgctatgt cgttgggcgc gctaccggga 46860
tcgctatcgg ccgcgacggc gaagaacggc gcatcgcagc cttccaggtc caggatatag 46920
gcgtcgatgc ccaggccctt gtaggcgtcg atgatatcct ggcggtcatc gaatgccgcg 46980
acgatctttg tcaggccgtc gatcttcttc aaaatatcta gcgcgactga gcgcttgaac 47040
tccggcgccg gctgggtgct tccatactcc cgcatgatga gctcatattc gcgatgttcg 47100
gcgataccca ggtcgcgatg gattttcgcc ctggtctgga aatagttgtt gtcggttcgg 47160
ccggtgatga agaaaatcat caggtcggcg tcgatggcgt tacggattcg tgctactgca 47220
tgcggattga gcttgtcctt gtcgaggcgg gaatggtact cgtcccattg cttttccagg 47280
gcgaagcttt tacggtggct atcgtcgaag acgcatccgt ccagatcgaa gatcatgatg 47340
ccattcttgg gttttcgtgc catattcaga tttcctcgct ttctgctttc tgggtgatgg 47400
ttttctcgat gaaagcgcca tcggaagtta gacggaacag ctcaccgttc tggaccagat 47460
cgaacgattt cacgttcatg gtgacgcgaa ttgattcgcc gccgttggtc acttcgactt 47520
gtgcgacatc accaaccttc tcgatgatga tcttcatgct acattgactt cccattgacc 47580
gctacaggat tggcctcttg tttctccgat ccccagaact cgcggcgcag ctcttcctgc 47640
tcggccgagc gatccatcca tggacgatag aacttgcact gatagatcgg tttcaccggc 47700
aactcaacaa caggaatctg gccgggcttc gtctccagag cggacatgaa gcggtcacag 47760
gattgctcat gaatctcatc ttcattcaga accttcgatc catagcgcgg gaaggcacag 47820
gagccagtgg cgacgcagtg cggctggagc agactatcga acataggata gacttccaga 47880
accagtcggc gcatttcgcg gaaggcttcc tgatactcac cttgcgtacg aacacacagg 47940
cgaactttcg ccatgtcgct cagagtgcgc agattgaatt tggccgcgat cttcgtttcc 48000
atgttggaag ggatgatggc acgagcatcc tgaagcgatg cgccggcctc caagagcttc 48060
tggtaactgg tctgcgcgtc ggcgattgca tcatgccaca ggcggttcag ctcttcacga 48120
gcgtgatagg tcgggtccgg ctcaccattg gccgtagcct tctcatcgaa atcccagcgg 48180
aacgcttccg gctgaacaac ggcgctaacc tccagagcgc gactggtttc ctgctggtaa 48240
gccccggtcc gagtccgaac gagttgatga gtgaaattct tgctgacgcc ctcgatctgg 48300
aagatgaagt ccacgaattc gaatggcgag cgaatggtgt ccagcatgta cttccagtgg 48360
tcgagctttt cggcttcggt catggtcgcc gggtcttggc cgcgcatgcg ggtggatttt 48420
gtgcccagga gaagttccca ggcgttctga gtataactga tcagagaaat tttcatcaga 48480
aatcttccgg aattggcgtg aaagtgaatt tctccgtcag cgcaatggcc aacgcttgtg 48540
catcttcctt gtgtagaccg tatctgtcga tctcttcggc cagcaatttg cacgcctcca 48600
gacggtcttc atactcttcg gcgtggcaca tggacgagaa gatagtgcca tcagaggtcc 48660
ggtacaccag ttcaatggac attactgtaa tcctcagtag cagcggatga tttcggcgcg 48720
aatatcgcga cggtccaggt aatgctcaat aatcttgtcg cgggcgcgct cggcctcttc 48780

```
gcgactgccg aacgacaggt tgaacgaagt gaaaggctta tcgtccaggc gtccatcgcc  48840
aatcaggtac aggatgccta ccagcacgaa agacggcgct gtctgtcgcg tttgcggcgg  48900
gtcgatttgc atttcgagga aagacatagg aacctcttca ggatggtctg gtgcgtacat  48960
taatagcgct cctgctgagc agccaccgtc tccggttcgt agatgatcat atccacgatt  49020
tccgggcact ggcttttcac ccagtcgatg gccgcaacca acgttgtagc ggcgccgaag  49080
gtgaaagtgc ggtaagactc atggatgtac ggcgcaccca tggagtcgcg ctcggtcgtg  49140
cgagaaatga ctactttgat gttaacgatc cggcccatct tcggcctcca ctttagcgat  49200
gatatcggac aggctcagct tctcgccatt caggaaataa ctggcgcgaa gcttcctgtc  49260
gccttctggc ccgacgatcc gggccgttat tgtgagactc ccgccgccaa gggcatctgt  49320
ggccctgaag aaagccagca gcgcccgctt gagcgctgcc tcgcgaggat cgactgccat  49380
taacctatca cattccagcc gtgctgggcg caccacaccg cgccagctcc cgcaggaagg  49440
ctgttaagaa ggaacactgg ggtcaggcgg ccatcctcgg tcatgtggat gaagtagcgt  49500
gcactttcac cgagccattc ggccttggcg atggcgcgtt cgagattggc cttggtggcg  49560
taggtcttgg tggtgttttt gtcggtggag aaggttactt cgcgggccat tttgtcgatt  49620
ccttttggtt gaagggtttc gcgtttcgat gagggaatac tactctcacc tggctcagaa  49680
gtaaagcact ttgtgtaaat tatttcacga acatcttctt ggccttctga taagacgaag  49740
aagtcatcag gcgctcgatg acgtccatgt ccgaaaccag atcgtccaga aggacgtttc  49800
gccaggtcgc gaaccgaccg agcgagaaga tgccggcttc atgggtgaga ttccagatca  49860
tggattcgcg ctcgtcgcgg ccgagcggaa tgattttacc cttggtctgg acggtcggct  49920
cgccgtccgg aatgagattc ttcttcctga tgccgaaggc cgagcaaact tcatccaggt  49980
cccagttgct gtcccattcg atggtttcga tttcaccagc cgcagtctcc acgatgccct  50040
tagtaacgga ttcgacgata agggtgtcgc cggtgatgga cgctcgaaac gttcccactt  50100
cgggaccagg gaaatacacc gtctggaaga catcacaagg aatggaaagc ttgtaccgac  50160
tcacgacgat ggaggttcct tcgccgaatg acgggtcgat ccccaggtcc agccctgccg  50220
cagccagatt ggcgcggaat ggtgctgtgc tgatgatatt aacgtgatca tcttgccggc  50280
gaaggaactg gaagaaagag gcgtcgaaag gcctgcccca gctgatgcga ttcgctagct  50340
tagcgaccag ctgctcatag tagtctgccg gcgcgatcca acgcttttcg gtcgccatat  50400
tccagatgga ccgatccgac aggccgcccg ttactttcct ggagtacatg ttgcagtagt  50460
cgatgcgcgg ctgggaaacg aactcgccgt caatgtagat ggccttgtgt acggtgactt  50520
cgcggaacgg gatgccggtg agttggccga tgactggtga gcggaaccgc aagagcgcgt  50580
tgtggcgttc cttgctcgtc ggcgtcgccg cgtcgatgat ttgggcttga gggaaacgat  50640
gcgcggcgat caggccggcg agtccggctc ccacgatgat aactttgtga tcaggaatca  50700
tgagatgttc cttatgagtg tacagaactt gggaggataa aaaagggacc cattttcatg  50760
agtcccttga agagctagac gattcggtct cagaagagcg gcggcttact cttcttcacc  50820
atcggaaccg tcggcgccct gaccttcacc gtcgtgctcc tggccttcat cggccttctc  50880
gtcatcgccc tggccagctt cgtcttcctt cgaagcgatg gcaaccagat cgacccagcc  50940
catgatttcc agcttgctca ggtagctgcg aaccgaggtg ccgtacagca agtgggccac  51000
cttctcgccg aaggattcga tttcgaccgg ctcaccaacg gtgcagtgct cgttgatgta  51060
agcgaacacc ttgccgcgag tcgagaaggc ctgcggggtt ccatgaccgt cgccggtcgg  51120
```

gatgaagtgg gtggcacgcg gacggcgcga accattggac ttcaggtctt cgcgacgggc 51180
ttctgccttc gcgcggcgct cttcctgctc ttccttgcga cgcttcttct cggcttcgcg 51240
ctctgccttc ttctcttcgg ccaggcgctt gcgctcttct tcgcgggctg ctttctgggc 51300
ttcctgcgcg gctttcttct cttcggcctt cctggcgcgc tcggcttcct tctcggcctt 51360
cttctgctcg cgctcggctt ccttcgcctt ggccttctcg gcctgctcag cttccttggc 51420
cttggccttt tcagcacgct cggcttcctt ggcggcggcc ttttccttcg ccttctcggc 51480
gcgctcggct tccttcttct cgcgctcggc cttgcgcttc tcttcgcgct cggctttctt 51540
ctgctcggct tccttggcct tggcctcggc cttctcggcg cgctcgcgct ctttacgttg 51600
gcgctcagcg gccttctcgg ccttgcgcag ggtagctgct tgttccttgg tcagctcttc 51660
gccttgggtc tgttcgttct ggtccttctg ttccatgttc ttactccggg aatgttcaaa 51720
gggatggctt attggcctgt gcggggatta tctctaaact aattgaagaa gggaataccc 51780
ttagcctgaa ctttcctaaa tattttcttt cgggaaagtc caaactctag ggaacttatt 51840
tatgttcgag aagttcctag cttttacgca agaacagtaa gtattcgatt gcgcgagtta 51900
tcccagtata catcaactga ctataaggga tggacggcaa gttttcttct aacatggcga 51960
cccgtttcca ttctgatccc tgcgacttgt ggaacgtcat cgcccatccg aagtcgaatc 52020
cgccaatggc cttctgcgcc tccagccgca cgtcttcctc gaccgaaaaa ctcagaggat 52080
tgaacttaac ccagcgttca aagttcgtac cgataatgcg aactttggcg aacaacattt 52140
catcaggctc gtcatcatct tcttgccctt caggaaccgg cttgaagtcc agcagaatgg 52200
cttgttcgcc gttcatgatt ccatattcgt gctggttccc agtgcatacc agcttctcgc 52260
cgattcccgg ctgcgcacct ttgtagccga ggattcggcg agcgcgtgcg ttcaagcgac 52320
ggcgagtatt gttgtaagca caaagaatca cgccatcatc gtccaggaac gtccgcattt 52380
catcatccga catatcgaag ccggcccgga ccaatatgtc gtcatactcg cggcagggca 52440
ggcgctttcc ctggcggacg aacatcgacg cccgaacgat attgccagcg ttgcgctcga 52500
tttcggtcat gatggtgtca cagctgttct cgtggaaaat ctggacgccg cgtacaggag 52560
gaacttggcc aaagtcgcca atctccagaa ccggaattcg gtgcgacaac aggcgctctt 52620
catcccactc gccgatcatg gacgactcgt cgagaactac caacttcggt ttctcgtcga 52680
gcgagtcttt gttggcaaac atgatttcgc cgtcttcatc ttcaccaatc ggtcgataga 52740
taaagctgtg aagagtccgg gcattgacgc aacctttctc acgaagccgc gcggcggcct 52800
ttccggtcgg cgcgatgaag actgtccagt ccatcgagca gcaaagttcg gcgatgatct 52860
tcgcaataga agtcttacca gttcctgcaa aaccggcgag tcgatagacc tgacggcggt 52920
gcgctcgatc acaccaaccg cgataccagt taacgacgga atttatcgcg tcgatctgct 52980
ggctattagg tcggaagccg aatcgctctt cgatctgatc gacggtgaag ttagatgctg 53040
acatatttgc gttctccaac gctaggttta attgaattga gactcagttt aagcagaccg 53100
tccacagacc acccagtatc acgacgatat ttgcggccgt gcggatcgac atagaagttt 53160
ttcgtgcgcc gcaacaggac atagtgccaa gcagcaccga gcgcatggac ccttccttta 53220
taagggaagg ccttaagttg ctctgcggcc ttcttcgccc cagggagcca gcggacggtc 53280
gaaaggacca agaccgcacc cttgacagcc tgggaagcgg cgcggccgtc ctgtgggcta 53340
tagcgatgtc tatcggggtc tacccagtgg tggttgccac gccggagctt caccgtccgg 53400
gaccggccct caaacaccac agtaccttcg tgagtaaaaa tatgttccgc catggaatgt 53460
tccttataac gtacagttct gctttacctc tgcgcaagaa gagtatacta tcagctgact 53520

```
cgtcaaagcg agctaattta atccgacttt acttcggcag gaaagtggcc gatactagcg  53580
ccgccgcctg tactgccctc caaaacagag gatacattaa atgcaagaat gcaagatttc  53640
ccgcgaccaa ctcccggtcg gcaatccgaa tcccaatgtc gacaagactc gcgacccgaa  53700
cctaaagccc ggctacctgc gtcgcagtcg cgagctggac ccggctctgg ccgttcgcat  53760
ccgtcgcgag ctgatccatg cggaagcctc cgacttggcc atggccgggt gggtcaattc  53820
ccagtccagc ctctatggat cgaaagcgtt cccgcgccat tccgtcgttc gcgtgactgg  53880
gatggcggaa tctgaaacga acgtcggaat gctcatcgga ttcatcgagc accgcaagca  53940
cggtgaatgg gcagttctgg aaactgggac gaaagaaggc ggcgcgatca ccatcccagt  54000
cgagagcatc atgcgtgcgt cattcgcaga ggccgaagaa ttcgccgaga aatggaagcg  54060
taacctgggg tggcgcctcc tgcgtcagct tcgtgaatgc ggcgccctgg ccgggactga  54120
agacgaattc ctgcggcgga taatcaatcg atatgttcgc gatctcacga tactcgccca  54180
ccacaaagcc ggcgcagaca aaagctatac cgatgcagtg ctcaaaagta tcggcgaagc  54240
atggccgcag attcctgccg gaacattcgt cggccaccga gtcgcgcaac tcctgatcaa  54300
tcacaaacta ggccgagctg gcaccatctt gaatgacctg gtggacttcc tggagaggtt  54360
cgcggccggt cgtgataaag tgctcaatat cgccatttgt aattgaggtt agtgatatgc  54420
cagatttgat gaagctgagt cataggcaag ttgaagctct gctagggctg tctaggaatt  54480
cttacaattg gattcacggt ccttcgactg attcaacctt gaaggctctg agacgaatgg  54540
gactcgtaaa tttgtcctgg gatgattctg tagctggata catgttcggc agtcagcctt  54600
gttggagcat aactgacgcc gggaaaaaac gaatcctggc aatgcaggaa actctgacag  54660
aagagcctga acagcaattt aatcccagcc catgccgcca tgagccaggt aagtccgatt  54720
ctgatcgact tgctaagcaa ctagaaacca tcgctcgtct ggaaaaggaa cttgaagcat  54780
cggaaaagcg cgggagcgaa ctggcagcaa gctattgcga cggcgtggtc ggtgatgaat  54840
acggccacac ttattgccgt tataaggcgg aacgcgatac agctctggcc agggtcgctg  54900
agctggaagg aaagttgact gattgggtac acgaaggatt ccggctcaac gaagcactgg  54960
cagcggcaca gaccgcccac gaatgtacca tgggcgtagg cgacggcgac ggcaagttgc  55020
tagttcatgg tgaccacgcc agcatcaaag ctgcccagaa gatcgtcata gagcgcgacg  55080
ccgcgttggt caggatagcg gagcttgaat ctaagcttgc ggagacgcaa ccctacaaac  55140
aacacccgca aatcataggg tacgcccgca aaaaggaact tgcgccattg ctcgatccaa  55200
gccaacccgg tggaagctac atctatattg gactggacca tccggcctgc tgggcggaag  55260
agccacctta cgaattcttg accccttttgt ataccggtcc tgtggcgagt cacagcgtgc  55320
cggatggtta cgccctaatt ccggttaagg agactgaggc gatgcacgat gccgtaatgg  55380
cgctgttgta caacggcata gcccgcaccg atacacaaaa gctgctggat gcgtacatca  55440
acgccgcgac taacaaggag tccgtgtaat ggaaccgaag aaaccttcac cagtagatgg  55500
agtcatcatg accagcctcg acgttctcag gaaggcaaag cctgaagcgc aggacgagta  55560
tgctctgtcc atgttcgcaa cggcgatccg ccagaagttg cagcgctccc gcgacaaggg  55620
ccgaggcgga tggatcgatt gcgacgaaaa tgttctgctg gatggattcg ccgaacatgc  55680
gctgaagggc aatgagaaca atctcctgga cctggcgacg ttcctgatgt tcatgtgggt  55740
tcgcggcatc gatgatgcga agattccccc ggcgctagaa aaggcgcggc agcacaaggt  55800
cactgaagct tgggaccaga tcaacgaagg aaggacaagc tatgccggta aggccggcgg  55860
```

```
caagcgacaa ttcgtggaag tgcctcgacg caaagggcgc ccggagcggc tcgcatgaag  55920
cctcacgaaa taagattggc ccaggccgaa gaattcctga gagaactcgg ccgagggatt  55980
ccggaagacg aacgggtgat ggtcggctac gctgaagagg ccacagtcca gaccgacgaa  56040
aacggccgca agctcaacgc aggctggtgg cccgtgccct ggaaggaagg caagtacatc  56100
aattccagat ccaacgctta tgcctgtata tcgtcatcca tcaagacgcc caacccgaag  56160
actggccaga tgcgatactg gcgcggcgag gcctctttcg gccacggact ggcgttaatg  56220
gtcgatgaca tcggctccgg caaagggtcc aagggcgact tcaaccgcga cgagttccgc  56280
gagcgcctgg agccgaccgc gattgtggag acttcgccga acaactacca gttctggtat  56340
ttcttcaaag agccgatgtc ccacatgctc cagtttaagg cattgctcta ttcgttcgtg  56400
gaccaggtgc taaagaaagg cggcgacaac accgtcaaag acgtaagccg ttatggtcgc  56460
atgccattcg gcttcaacaa taagcgcggg gaagacggca acttcaagta tgccgacgaa  56520
aacggcaagc ccgaactcgt gcgtttgtat cacgcagact attccaagcg ctactcgcca  56580
gaggaaatcg cccaggcctt cggcgtccgc atcatcatgc cacagatgaa gaaggtggag  56640
ataaaccgcg acgattgggt ttatgaccag gtgtggctaa agtatgccga gcacatctgc  56700
acgaaataca aaatgggcga ggcagcgggc ggccaagtcc aacagaatat gtccggtaaa  56760
tatcgcatcc gctgcccatg gggagacgag catacaaatg gcgatccatt tggcgcctac  56820
tttcgcggac cgatccctgg agccgagcac gaatatgtgt tcggttgcgg ccacgatacc  56880
tgccgcaaag agcatcgccg gacgtgggcg gccttcacgg atgaagtcgt gctaccctat  56940
atcgtcgaac aattggaaag aatcaaccgc cgtcacatcg gtgaggagta gacaatatgc  57000
aaaacgatcc tggaatcctg atcacagcca ttggcttgct gttcctcggc cttatcatct  57060
tcttcgaagg cctaaaggga tggaaaatac aagtcgcaaa cttcctcgcg tcgcttctgt  57120
gcttcttctt cggcctttct gctttgacgt tctggttcgt cgtggcgttt gacgtatttt  57180
aatcgacgaa cggtacagaa attttcggat ggggacggaa cttattagct atgccggttt  57240
aggtaggaga taatagccgt ccctttcgcc tcaatatgta gaggcaatgt tgaatccgat  57300
catgtaaagc agaaggcggc aaacctaaca tgattatcga cgaagataat atttttgatg  57360
atgacgaatc agggtccagt gagttcgatc tcacacagat agaagatgct ggaatggacc  57420
ctttgatgac cgccgcgagc aaggcggccg atgatgcgat tgcgaggaac gaaacgcacc  57480
gcgcacaaaa ggcggcaaga tacgccgagg cgtatgcgga accagacttg agaaagcgag  57540
cgcgattgtt gatgctcgac caggcgttcg atcttccggt cagccgggtg gtgaaagggc  57600
cgttcgatga cttcatcact aaatacagct cgacttccga cagcaactat ctcgcggtgt  57660
acgatacttt gttctgcaag ggtgatggaa ccgtcccgca tccgcacttc gacgagtttc  57720
gcggacggct ggtggaccat cgcggcgtgg cgttcaacaa caagaccctc gacccgattg  57780
acctgatggg cgccctcgcg gctgcggcct tggacgatcc ctcgattaag aagacgattg  57840
agacttgctg cgtttgggcg cgtcgatacc gccgcaactc gctgatagag acgttcgaga  57900
agaagatacc ggagtgggac ggcgaagagc gaattagcac gttgctgatc gatcttttta  57960
agccattcga caccgaattg aaccggatgg tgagcaagta tttctggctg agcctgtact  58020
gccgcatcaa ctatcctgga atctcggcgc cgatctcgct ggcgttgatt ggtgggcagg  58080
atgcggggaa atcctatttc ggcctgctga tctgcaagga actgtcgggc ggtcgcgatc  58140
tggctcccgt ccagctcgac ctgagccgac acgaccagac accattcctg cgcaacatca  58200
ccggcaactc ggtcattgcg aacgtcgggg aaatgtccgg cttcaaaaag ggcgacatgg  58260
```

aacgcatcaa ggagttcttg gtgcggtctt ctgatacatt cgaccagaag tttgagccgg 58320
gcgaaacgat caagcgacaa tggatcacca tcatggacgg caacggctac gatggactcc 58380
agcgggacga ctctggtaac cgacgtttct atcctatgtt tgttgcgcaa ctgcccgatg 58440
aggatggaaa gccgaactgg gttaagccgg gcgatggcaa tgaaccgttc aaggtggact 58500
tcaccgactt cggccgcaaa ttctggcaag cgatggctga atgccgcgca tggatcgaag 58560
agcacggcgt cgatggctac ctgaatatgg tgtcggaagc aaaccgcgaa gtccagaact 58620
tctctatttc ggaaatggag aatgcgcgcg gcgtggttcg cgacgatacg attgatatgt 58680
atctgatcaa tgtcctgatc agttgtgagt tcgaagaggt taagcctggt gggaattcca 58740
agactcctgg gtggagggca gacaccgttt ccattctgaa gtggttcgat attctcgcca 58800
ggaagaagcc gatttctcgc catttaactc cacacctgaa agcgctggga ttcattccga 58860
ataagaacgg cctgaatgga tggtgcctgc ctgtggataa ggtcgcgcct gactggtcga 58920
agaatatgca gacgacgctg ccgccattca atgatgcgct ggtgtatctg ttgagaaagg 58980
gcgatccgga tatgaccgat gaggctgcca tggcaaaaat tcgagcagta cgggcagagc 59040
gagccaagat attgggcgag gatttctgat aggtcgattg agttggagtg gattaggccg 59100
ccttcgggcg gtcttttctt tgtcgcggag aacattaatt tagcttgtga acgggtgagg 59160
cttgaaagct atgtgggaat taggttggcg tggcgatggc gtattatggg aagttaatag 59220
atttcggtat tggtctggag tgtatgatgg ttggattttg cgtgaaatgt tgagaaattg 59280
tgggtttgag gtggattttt gtgtggaaat agccgcaaat tcctggattg ctattctgac 59340
tgggaagatg ggaggcctac tgccgcgcgg gtttgcggcc atattcccta attcccgggt 59400
ttttcgagca tggtttaaaa ctattctaca gcgaaaatcg attgcacaat cctaatagaa 59460
aaaatctatc acggacgtta cctatcttta aaattaataa aattaatggt aatttggtaa 59520
tttggaatag tttagtcttt gaaagcctcg cggcactaag ccggtacact acccgtcgag 59580
tttccgattc cactcaactc gcggcagggt cgccggaaac ttccgtcctt ccaaaccatg 59640
ggcagcggca acaccacggc ggactaagcg gcaggggcca aaactcgacg agcggaaccg 59700
gaaatttggt cacagggcag aatcgctcac ctggacatat tcctaacatc cgatttaaca 59760
ttcaatccaa acactcaccg ccaccatcgc ccgccaccca ccaatccgac cctcacccgc 59820
cagcagaccg cccatataac atcctataac accacctaac actcattcac catcaaaccc 59880
acccagacct acaggccacc cacaagcagc ccatagacgc gctccctggc cccatagtac 59940
aatcgcgcca tactcagtgt cgcggcaagc accaggtccc agccacctac ccagccaccg 60000
cgacggtcca agaatcgaac tccagggacg cagcaacaaa tgaccgccaa atattacagc 60060
cccgacgatt tagtcacgcc acaggaattc gctgatccgc agttcgcggc gatcaaccag 60120
aagcgtttcg atctgtacat cgacctgcgc gttcaaggct atagctcctg gcgggtcttc 60180
agagcgatct ggggcgaaga gcacatggat ggcccggccc aggcccgcat cttcgcgatg 60240
gagtccaacc cgtactatcg caagcaattc aaagccaagc tgaatgcgac cagaacgtcc 60300
gatctatgga atccaaagac ggcgcttcac gaacttctcc agatggttcg tgatcccacc 60360
gtcaaggact ccagccgtct gtcggccatc aaggaattga acgttctggc cgaaatcacg 60420
ttcgttgacg agtctggtaa gaccagggta ggtcgcggat tggccgactt ctacgcatca 60480
gaagccgagg ctcagaccgc caccgtcgct gctgcggccg aagccaatgg ctatgtgcag 60540
gacggcgaag agggcgattt cccgtccccg acgccggagc cgaccgagga agaccgcgcc 60600

-continued

```
aaccccattc agacataaaa taacatcgtt ctaggcccga atcggaccga actaaggcga  60660
cggtagcggg ttgggacgaa aaacgattct agggctgttc taggaagccg accaataaca  60720
atcagaaacg acaaagcccc ggactctagt tcagaatccg gggctttctt tttgggtttc  60780
ttattctcca gcttcgatga tttcgaagtt gtatttgacg ccttcgtgct cgaaagtcaa  60840
cttgccggct tccttcagct gcatgcggaa gcggatgtgc ttcgaagagg gcaggccgaa  60900
ctcgatgaat gctgcgttgg tggaccggaa ctcaccgcgc ttgcctttga cggtaacggc  60960
aactccatga cgctgagtgc gctttctgga gacttccggg tctttccagg agttggcgat  61020
ggctgccgac aggtctttgg cctctttggc cttctctgga gcgttcttcg cctcttcgcg  61080
catcttcctg atttcttcca gcgcttcctc ttcggtgatt tcctcttccg gcttcaggct  61140
ctcttcctcg gccttctctt cttccttctt cttggaagtg cgggttttgt aaaccttggc  61200
cggggcttcc tcttcctgga aggcttcttc ctcggccggc agagcgttca ggatggcgag  61260
gcagcgacgc tcggcggtct tgcggtcgga gaagcgcttt acagtcgcat cggcgttgtg  61320
agagttgtag aaggcgacca gttctttcat ttctgcgttc tggatgtcgc cgaaggtttt  61380
gatggagttg gtcatttctg cgatcctctg ttttggaaga tttctttcgg gcttcggttt  61440
gtcgccccgt tgaaagagat tatgcctaga tcgatgctgc gtgtctacat ttattttagc  61500
agaatgatga tgaacccgac gaacggttgt cggatgtgaa aacaccgcag gacaggctgc  61560
ggtgttttct ggacgatggt gcgacggtca gaaagtcggg accgtgatcg gctcgattgg  61620
taggtcgccg ggcttgtcgt tgtccgacgc gggtgacgaa cttgacggta tggctccgga  61680
ccgaagaccc agcggttcag gccgcctgct tacctgcgga ggtggcggag cttttggcgc  61740
tttcggaact ggaggtactg gaggcgccgg cggagacatc ggcccttctg gaagatcggg  61800
aaggctcggc gctttcggtt cgtggtaaac cgtcgtgtcg ttgcctggtt ctgcgggatc  61860
gacgcccatg aatggagtgg tgacgcagcg catgttcgga tagttcggca gcgttttcaa  61920
agcgatggag tctgcccaga catacggatt cttgtgatta ccagggccgt ggctgatgat  61980
ctcggcaggc atgtggccgt tgaggttcag ccactccgcc gcccccttgcc gagacagcgg  62040
gcttaccacg atctggccag tggcctcttc ggcaacagcg aacagatcgc cgagtttgaa  62100
tccgatgatc aaatagttgg acctggcctc gccgacgaat gcgacagttt cagtgccgtg  62160
atggatatct tgatcttccc atatgtatag catgatgcgc cctcagtaag gttgcttgat  62220
gtgatcgacc agggacattc cggccggaat tttgaagcgt atgtactcga tcataatcgc  62280
agttcggcga cgattcgttc ctgcctcgtc attcacgaag agttcgcact ggttcggaat  62340
gactcgcgtc accagagctt cgcctttcga gccgtagaac ttgatgtagg ctgcgacgcc  62400
tcgcgtcatg ttcagttgga tcgtttcgca gagtcgctgc gcggccgacg cgctggacag  62460
atctgtcgga ctgaccgtca cccagtaatg agcatttgct gtttgttctt tgtcagacat  62520
caatggtctc cagtgagaaa gccctgccga gtcgcagagg ctggttgctg ttagtcgcgc  62580
ttcaacagaa cgactttgtc atatgcgcga tatttaccgc gccagtcttc ccagtagtcg  62640
ccggccgggc aggtgagctc cagggtgatt tcgtcgcgcc agcattcgac agaaagtaca  62700
atagccttgt tccttgctgc ggcatctgct ctgagcttaa tcagaatttc gtcgccagtt  62760
ttcagctcat caactctcac aactttggcc atgacacact cctgtttgaa gaggcgcgac  62820
cggaaccaac ccagccgcgc cgatggatta acgtttgtga aggatggaca cggcgtccac  62880
gtcgaggatg ctgatggtac ggcgacggcg cggattgctg cgttcatgga tgcgaatcag  62940
gtcagcagat gtagcttcgt gcaccaccca tacatcttct ggcttctgcg tccggagcag  63000
```

gatcgttacc tctgtgttct gggcgaggcc gttgcagatg aacgtgaact tggacgaggg 63060
agttctgtac atttctagat tcctttttgg actttgggtc cgacttctca gccggtgaag 63120
agattatgcc cttattttgg ccgccgagta aagcatttgt gtatcaattc tcccgtcagg 63180
tggaaccaaa gtgcggtatc gcttatggct acgctaccgc gccatggccc ttcttgctcg 63240
cacactgcga accacaggct gatttccatc cttgccagga ctcggccgaa agattcgaac 63300
ctgcgccgac tggacaggat gtcgacattc actcgtcgat tgacctcgta ccggcgaccg 63360
ttgatgacga agaccagccg cagggtttgt ccgtcaagac actcccagta tctggtttca 63420
tatcggagcc aatagcgctt gcctgtcggc cctaccatag tcatccttct atgctcctgg 63480
ccgctccacg gggaccgggc ggtggagtcg gatcgaatcg acccaggatg taatcgggcc 63540
gacgcgcttc ctgcggacaa acggcgagaa ggcgccatcc tgcgtccagg gcatgctgga 63600
gttcgtccgt gcagcagtct tccttgagca ggagacggtt gacgctctgg agattcggac 63660
cagggatggc cgagctggtg tgcgagttcc aaccttcgat gccgtccacc atctgtggtt 63720
ggttgatgta gccttcggac ctgccagcca accggctcgc ggccagctcc aggcgctcca 63780
gcattggccg cagagcggct tccgggtcaa catcgtccca gagaaggacc aagctgatga 63840
tggtgtacgg atagtccttg tccagatccc aggccgaagc ggtcagacgg cccaggccga 63900
tttcattaca catcacggga acgtcgttgc tccatgtgga cggctcccag ttccgctcac 63960
caggattccc gattgttacg ccttccaggt tccccaggag gacgtggagt ttgctgatgt 64020
attccgcctc cagcgctttc cgctcttcgt cggtctggtt gtggcgatag aaggatggag 64080
ggctgacttt tgcatggtag agtttcatgg cggttcctcg gtttttgaag gcttgaacgt 64140
tagaaaatgg tgtcgcagta tttctcgaaa ggactctggc gcttcttctc gcagatcgcg 64200
caggtgactt ccaggtcggg cagctcgctg taagtcttgc cgagatacag ccagcgcttg 64260
cacagactgc ggccgtccga cgtgaagaag tggactttgc gagcattgcc gggttgcgcc 64320
cagccgcctt gatcgttttt gcgcttgctc atggcgatat ttcctttgga tctggaatcc 64380
atgccgtccg ttcgctcacc caaactccgt ctacatagat caggactgac agagcagtcg 64440
cgccaaaccc gaagcctaca tagaatgaac cgggatcgat ttccatggtg gcgctattgg 64500
tggcgctatt gaaatcgact tcaaagtcga acatcgaatg gccgctcata ccatcaccat 64560
gtcgatttca ttgatgaaga aatgaacatc gacaccatcg gcgcgaccgg tgtaacgcag 64620
ccgagtcgtc ccatcaatgt gggcttcctc gacgccgatg acttccagga tggtgtcgtt 64680
gcagtaaagc ttgacgaaca tcttgatgcc ggagccaatc gccgcgaagg cgatctgctt 64740
gtacaggtct tgcttgatca tgctttgcgc tcctgtttgc tggtgtagat ggcttcgact 64800
tcggcctcaa gcttcgccca aagttcgttg tccaccggac cccatggtcc ggtctgggtg 64860
ccgtcaaccg gcgcgaactt cccaccggcg cgacgatatt tggaacgggt ctggagttcg 64920
atgattagcc gttcgtaggc gttgaattga gatgtcattt cacaatcctc ttttggacgt 64980
tcgcgtttcg atgaggtgac tatatctaag tcgcctcatc gagtaaagca cttctgcgaa 65040
attatttgat attctgtaag gtcaggaagc cggacgattt ggtcagtcga tggagccgag 65100
gctccacccg ttgcgggcga aggccgagcg acccgacagc ttgcggcact gaatggagct 65160
tccatcgtcg aaagtatagg ctgtggccca gtcaaggcgc tcacgacgta ctgccgcatt 65220
ggcgatgtct tccagacggg ctttaaggag ttgctcggct ttagtcatct cacacctctt 65280
tggtttattc actcgatgag gtgactatac ctcagacacc tcatcgagta aagcactttt 65340

-continued

```
gagagaatta tctgaaattt ctggaagcca ggaactgtcg ccagagccag tcaatgtgat  65400

cgttcagata gcgctcgcca tcggatgaca gagacaggca gccgtcattg atgccgagtt  65460

tggaactggc aatccgttcg aattcgaact ggagcgttcc gggccgaggg atatggtgca  65520

ggcaatattt ctgcacgatc agcagtcctc gaaaggtttg cggttcgcaa tttccgcgat  65580

cctttgcatg ccgatgcgat agaactcggc atcctcgcgc gcccgcgaca atgcttcgcg  65640

cgcttcgcaa gccaacttgt attgattgtt ggcattggcg atgcttccgt ccaggcttct  65700

gtcagactct tcccggagcg ccttttggga ctccagctcg gcctccagct cgcggattcg  65760

aagggcgagc tggctattcg tttcggcagc tttgttttcc agatcgatgg ccgatttcgc  65820

tgctgtttcg agcctgtctt tgtcggccat gagggtttcc aggctcttgt cgagtgcttc  65880

cagaagagtc ttcttggact ccagctccag cgaaaattcg acgttctgcg cggacaagtt  65940

ctgcgagtgc ttcagcagtt cgtcgattct tctttgatgg cccttgatgg ccgagttctt  66000

cgtttcgact tcggcctcca aatctctgat tctgagttga agctggcgat tcacctcggc  66060

cgtcttgtct tcgcgagcga tggagttttg caggcattcg tccagacgcg agttctcccg  66120

atcaagctcc atggccgtca ggctttcgtc agaagtcacg ccttcggatt cgtctttccg  66180

tccctgatcg gcccgcagat aatactgtcc agcggcgaac gccaggaggg cgcggttgga  66240

aaactcagta gcgccctgca agtaagaaga tttgtatcga ggaacgaact cgg         66293
```

<210> SEQ ID NO 4
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4

```
cggactaaag gcggcatgat tgcctaaaag gagattcaac atggtcttca cactcgaaga     60

tttcgttggg gactggcgac agacagc                                          87
```

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5

```
tgaccggctg gcggctgtgc gaacgcattc tggcgtaa                              38
```

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

```
cggactaaag gcggcatgat tgcctaaaag gagattcaac atggtcttca c               51
```

<210> SEQ ID NO 7
<211> LENGTH: 42
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 7
actagccatg aaattctcct tattacgcca gaatgcgttc gc 42

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcataccgga cgtattccgc 20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcgatgcga gcttcattc 19

<210> SEQ ID NO 10
<211> LENGTH: 324
<212> TYPE: DNA
<213> ORGANISM: Pseudomonas phage PB1

<400> SEQUENCE: 10
gcgaatttca ctggagatgt gactatcgcc aacaccctgg ttgtaaacgg cgtcaacgtg 60
aacaaccacg gtcacctcga aaacaatccg cctgataccc ggactaaagg cggcatgatt 120
gcctaaggag aatttcatgg ctagttttga tttttctgat ttaacagcgg ggggggttg 180 taatggctaa ttatgactac atagtagata ctggagtcat agtcgccgat actgctgata 240
ttctgaagga cgttgaagcg gaattcaggg cagccctcgg cgccaatatc aacctggcgg 300
cctcaacgcc ccagggaact ctgg 324

<210> SEQ ID NO 11
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cccggactaa aggcggcatg attgcctaaa aggagattca acatggtctt cacactcgaa 60
gatttcgttg gggactggcg acagacagc 89

<210> SEQ ID NO 12
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)

-continued

```
<223> OTHER INFORMATION: a, c, t, g, unknown or other
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 12

ngnnggcatg attgcntaaa aggagattca acatggtctt cacactcgaa gatttcgttg     60

gggactggcg acagacagc                                                  79


<210> SEQ ID NO 13
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 13

nnnnatgatt gcctaaaagg ngattcaaca tggtcttcac actcgaagat ttcgttgggg     60

actggcgaca gacagc                                                     76


<210> SEQ ID NO 14
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

gtgaccggct ggcggctgtg cgaacgcatt ctggcgtaat aaggagaatt tcatggctag     60

ttttgatttt tctgatttaa cagcggggg                                       89
```